United States Patent
Jones et al.

(10) Patent No.: US 12,256,934 B2
(45) Date of Patent: Mar. 25, 2025

(54) METHODS OF FORMING AN ANASTOMOSIS BETWEEN ORGANS WITH AN EXPANDABLE PATTERN

(71) Applicant: Cilag GmbH International, Zug (CH)

(72) Inventors: Shannon L. Jones, Cincinnati, OH (US); Gregory J. Bakos, Mason, OH (US); Chad P. Boudreaux, Cincinnati, OH (US); John S. Kimsey, Walton, KY (US); Yvan D. Nguetio Tchoumkeu, Blue Ash, OH (US); John K. Bruce, Morrow, OH (US); Frederick E. Shelton, IV, Hillsboro, OH (US); Jason L. Harris, Lebanon, OH (US); Bradley A. Arnold, Mason, OH (US); Gregory G. Scott, Cincinnati, OH (US); Cory G. Kimball, Hamilton, OH (US); Nichole Y. Kwee, Cincinnati, OH (US); Jeffrey L. Aldridge, Lebanon, OH (US)

(73) Assignee: Cilag GmbH International, Zug (CH)

( * ) Notice: Subject to any disclaimer, the term of this patent is extended or adjusted under 35 U.S.C. 154(b) by 726 days.

(21) Appl. No.: 17/401,391

(22) Filed: Aug. 13, 2021

(65) Prior Publication Data

US 2023/0051305 A1 Feb. 16, 2023

(51) Int. Cl.
*A61B 17/115* (2006.01)
*A61B 17/3205* (2006.01)

(52) U.S. Cl.
CPC ...... *A61B 17/1155* (2013.01); *A61B 17/3205* (2013.01)

(58) Field of Classification Search
CPC ............ A61B 17/1155; A61B 17/3205; A61B 2017/07228; A61B 2017/1157; A61B 17/115; A61B 17/0644; A61B 17/0643
See application file for complete search history.

(56) References Cited

U.S. PATENT DOCUMENTS

| 2,277,931 | A | 3/1942 | Moe |
| 4,047,654 | A | 9/1977 | Alvarado |

(Continued)

FOREIGN PATENT DOCUMENTS

| EP | 1875870 A1 | 1/2008 |
| EP | 2157918 | 3/2010 |

(Continued)

OTHER PUBLICATIONS

U.S. Appl. No. 17/401,444.

(Continued)

*Primary Examiner* — Tan-Uyen T Ho
*Assistant Examiner* — Cherie M Poland
(74) *Attorney, Agent, or Firm* — Frost Brown Todd LLP

(57) ABSTRACT

A method of creating an anastomosis is provided using a stapling assembly including a body extending distally along a longitudinal axis and a deck member defining a deck surface. The deck surface includes a first array of staple openings comprising a herringbone pattern, and each staple opening of the first array of staple openings has a same size. The method includes positioning an anvil within a first lumen of a patient and positioning the stapling assembly within a second lumen of the patient. The method also includes releasably coupling the anvil with the stapling assembly and compressing tissue of the first and second lumens between the anvil and the deck member. The method further includes actuating a plurality of staple drivers to drive a first plurality of staples distally and parallel to the longitudinal axis from the first array of staple openings into the tissue to define the anastomosis.

18 Claims, 99 Drawing Sheets

(56) References Cited

U.S. PATENT DOCUMENTS

| | | |
|---|---|---|
| 4,407,286 A | 10/1983 | Noiles et al. |
| 4,505,273 A | 3/1985 | Braun et al. |
| 4,669,647 A | 6/1987 | Storace |
| 4,848,328 A | 7/1989 | Laboureau et al. |
| 4,874,122 A | 10/1989 | Froelich et al. |
| 4,899,745 A | 2/1990 | Laboureau et al. |
| 5,292,053 A | 3/1994 | Bilotti et al. |
| 5,309,927 A | 5/1994 | Welch |
| 5,333,773 A | 8/1994 | Main et al. |
| 5,342,396 A * | 8/1994 | Cook ............. A61B 17/0644 227/19 |
| 5,350,104 A | 9/1994 | Main et al. |
| 5,425,489 A | 6/1995 | Shichman et al. |
| 5,533,661 A | 7/1996 | Main et al. |
| 5,713,505 A | 2/1998 | Huitema |
| 5,725,554 A | 3/1998 | Simon et al. |
| 5,732,872 A | 3/1998 | Bolduc et al. |
| 5,993,468 A | 11/1999 | Rygaard |
| 6,352,541 B1 | 3/2002 | Kienzle et al. |
| 6,425,903 B1 | 7/2002 | Voegele |
| 6,616,686 B2 | 9/2003 | Coleman et al. |
| 6,629,630 B2 | 10/2003 | Adams |
| 6,767,356 B2 | 7/2004 | Kanner et al. |
| 6,769,590 B2 | 8/2004 | Vresh et al. |
| 6,915,937 B2 | 7/2005 | Lat et al. |
| 6,978,922 B2 | 11/2005 | Bilotti et al. |
| 7,056,330 B2 | 6/2006 | Gayton |
| 7,422,138 B2 | 9/2008 | Bilotti et al. |
| 7,722,643 B2 | 5/2010 | Schaller et al. |
| 7,824,426 B2 | 11/2010 | Racenet et al. |
| 7,934,630 B2 | 5/2011 | Shelton, IV et al. |
| 8,062,330 B2 | 11/2011 | Prommersberger et al. |
| 8,143,870 B2 | 3/2012 | Ng et al. |
| 8,231,042 B2 | 7/2012 | Hessler et al. |
| 8,267,301 B2 | 9/2012 | Milliman et al. |
| 8,328,062 B2 | 12/2012 | Viola |
| 8,328,063 B2 | 12/2012 | Milliman et al. |
| 8,393,516 B2 | 3/2013 | Kostrzewski |
| 8,413,870 B2 | 4/2013 | Pastorelli et al. |
| 8,590,762 B2 * | 11/2013 | Hess ............. F02D 11/105 227/176.1 |
| 8,613,384 B2 | 12/2013 | Pastorelli et al. |
| 8,684,254 B2 | 4/2014 | Kostrzewski |
| 8,789,738 B2 | 7/2014 | Knodel et al. |
| 8,801,732 B2 | 8/2014 | Harris et al. |
| 8,910,847 B2 | 12/2014 | Nalagatla et al. |
| 8,978,954 B2 | 3/2015 | Shelton, IV et al. |
| 9,016,541 B2 | 4/2015 | Viola et al. |
| 9,113,885 B2 | 8/2015 | Hodgkinson et al. |
| 9,161,803 B2 | 10/2015 | Yates et al. |
| 9,192,387 B1 | 11/2015 | Holsten et al. |
| 9,265,500 B2 | 2/2016 | Sorrentino et al. |
| 9,402,628 B2 | 8/2016 | Beardsley |
| 9,629,624 B2 | 4/2017 | Hessler et al. |
| 9,713,469 B2 | 7/2017 | Leimbach et al. |
| 9,730,694 B2 | 8/2017 | Scirica et al. |
| 9,782,171 B2 | 10/2017 | Viola |
| 9,848,874 B2 | 12/2017 | Kostrzewski |
| 9,907,552 B2 | 3/2018 | Measamer et al. |
| 9,936,949 B2 | 4/2018 | Measamer et al. |
| 9,987,013 B2 | 6/2018 | Eckert et al. |
| 10,080,565 B2 | 9/2018 | Pastorelli et al. |
| 10,105,134 B2 | 10/2018 | Biedermann et al. |
| 10,117,675 B2 | 11/2018 | Cabrera et al. |
| 10,130,359 B2 | 11/2018 | Hess et al. |
| 10,136,888 B2 | 11/2018 | Chen et al. |
| 10,166,026 B2 | 1/2019 | Shelton, IV et al. |
| 10,285,705 B2 | 5/2019 | Shelton, IV et al. |
| 10,327,776 B2 | 6/2019 | Harris et al. |
| 10,433,849 B2 | 10/2019 | Shelton, IV et al. |
| 10,603,041 B2 | 3/2020 | Miller et al. |
| 10,611,060 B2 | 4/2020 | Stopek et al. |
| 10,639,040 B2 | 5/2020 | Penna et al. |
| 10,709,452 B2 | 7/2020 | DiNardo et al. |
| 10,758,237 B2 | 9/2020 | Williams |
| 10,856,867 B2 | 12/2020 | Shelton, IV et al. |
| 10,869,663 B2 | 12/2020 | Shelton, IV et al. |
| 10,925,607 B2 | 2/2021 | Penna et al. |
| 11,065,022 B2 | 7/2021 | Ebner |
| 11,147,559 B2 | 10/2021 | Wise et al. |
| 11,241,232 B2 | 2/2022 | Guerrera |
| 11,284,890 B2 | 3/2022 | Nalagatla et al. |
| 11,291,450 B2 | 4/2022 | Nalagatla et al. |
| 11,523,821 B2 | 12/2022 | Harris et al. |
| 11,653,926 B2 | 5/2023 | Jones et al. |
| 11,666,339 B2 | 6/2023 | Bruce et al. |
| 11,819,212 B2 | 11/2023 | Jones et al. |
| 11,911,039 B2 | 2/2024 | Boudreaux et al. |
| 11,944,310 B2 | 4/2024 | Shelton, IV et al. |
| 2002/0185517 A1 * | 12/2002 | Vresh ............. A61B 17/115 227/176.1 |
| 2003/0009193 A1 | 1/2003 | Corsaro |
| 2004/0073237 A1 | 4/2004 | Leinsing |
| 2006/0291981 A1 | 12/2006 | Viola et al. |
| 2008/0082126 A1 | 4/2008 | Murray et al. |
| 2008/0294179 A1 | 11/2008 | Balbierz et al. |
| 2009/0188964 A1 | 7/2009 | Orlov |
| 2010/0191262 A1 | 7/2010 | Harris et al. |
| 2011/0011916 A1 | 1/2011 | Levine |
| 2011/0017800 A1 * | 1/2011 | Viola ............. A61B 17/115 227/175.1 |
| 2012/0080498 A1 | 4/2012 | Shelton, IV et al. |
| 2012/0193395 A1 | 8/2012 | Pastorelli et al. |
| 2014/0027493 A1 | 1/2014 | Jankowski |
| 2014/0158747 A1 | 6/2014 | Measamer et al. |
| 2015/0083772 A1 | 3/2015 | Miller et al. |
| 2016/0278768 A1 | 9/2016 | Johnson et al. |
| 2017/0119397 A1 | 5/2017 | Harris et al. |
| 2018/0132849 A1 | 5/2018 | Miller et al. |
| 2018/0168637 A1 * | 6/2018 | Harris ............. A61B 17/0682 |
| 2018/0235626 A1 * | 8/2018 | Shelton, IV ..... A61B 17/07292 |
| 2018/0235635 A1 | 8/2018 | Rekstad et al. |
| 2018/0242974 A1 | 8/2018 | Guerrera et al. |
| 2018/0325508 A1 | 11/2018 | Aronhalt et al. |
| 2020/0038017 A1 | 2/2020 | Hess et al. |
| 2020/0054339 A1 | 2/2020 | Scirica et al. |
| 2020/0229814 A1 | 7/2020 | Amariglio et al. |
| 2021/0290225 A1 | 9/2021 | Shi et al. |
| 2023/0049242 A1 | 2/2023 | Jones et al. |
| 2023/0102965 A1 | 3/2023 | Wise et al. |

FOREIGN PATENT DOCUMENTS

| | | |
|---|---|---|
| EP | 2649949 A1 | 10/2013 |
| EP | 3225176 A1 | 10/2017 |
| EP | 3225179 A1 | 10/2017 |
| EP | 3245958 A1 | 11/2017 |
| EP | 3130292 B1 | 8/2018 |
| EP | 3173030 B1 | 10/2019 |
| EP | 3643252 A1 | 4/2020 |
| WO | WO 2001/054594 A1 | 8/2001 |
| WO | WO 2002/009595 A1 | 2/2002 |
| WO | WO 2005/115254 A2 | 12/2005 |
| WO | WO 2008/141288 A1 | 11/2008 |
| WO | WO 2020/249487 A1 | 12/2020 |

OTHER PUBLICATIONS

U.S. Appl. No. 17/401,451; and.
U.S. Appl. No. 17/401,460.
U.S. Appl. No. 17/401,428, entitled, "Staple Forming Features for Circular Surgical Stapler," filed Aug. 13, 2021.
U.S. Appl. No. 17/401,430, entitled, "Non-Circular End Effector Features for Surgical Stapler," filed Aug. 13, 2021.
U.S. Appl. No. 17/401,439, entitled, "Circular Surgical Stapler End Effector Having Staple Line Alignment Feature," filed Aug. 13, 2021.
U.S. Appl. No. 17/401,444, entitled, "Circular Surgical Stapler for Forming Pattern of Non-Tangential Staples," filed Aug. 13, 2021.
U.S. Appl. No. 17/401,451, entitled, "Circular Surgical Stapler Having Staples with Expandable Crowns," filed Aug. 13, 2021.
U.S. Appl. No. 17/401,460, entitled, "Circular Surgical Stapler for Forming Cross-Pattern of Staples," filed Aug. 13, 2021.

(56) References Cited

OTHER PUBLICATIONS

International Search Report and Written Opinion dated Nov. 14, 2022 for Application No. PCT/IB2022/057444, 12 pgs.
International Search Report and Written Opinion dated Jan. 27, 2023 for Application No. PCT/IB2022/057446, 19 pgs.
International Search Report and Written Opinion dated Nov. 23, 2022 for Application No. PCT/IB2022/057449, 15 pgs.
International Search Report and Written Opinion dated Jan. 25, 2023 for Application No. PCT/IB2022/057442, 20 pgs.
International Search Report and Written Opinion dated Nov. 14, 2022 for Application No. PCT/IB2022/057443, 12 pgs.
International Search Report and Written Opinion dated Nov. 24, 2022 for Application No. PCT/IB2022/057451, 13 pgs.
U.S. Appl. No. 17/401,428.
U.S. Appl. No. 17/401,430.
U.S. Appl. No. 17/401,439.
U.S. Appl. No. 17/401,451.
U.S. Appl. No. 17/489,965.

\* cited by examiner

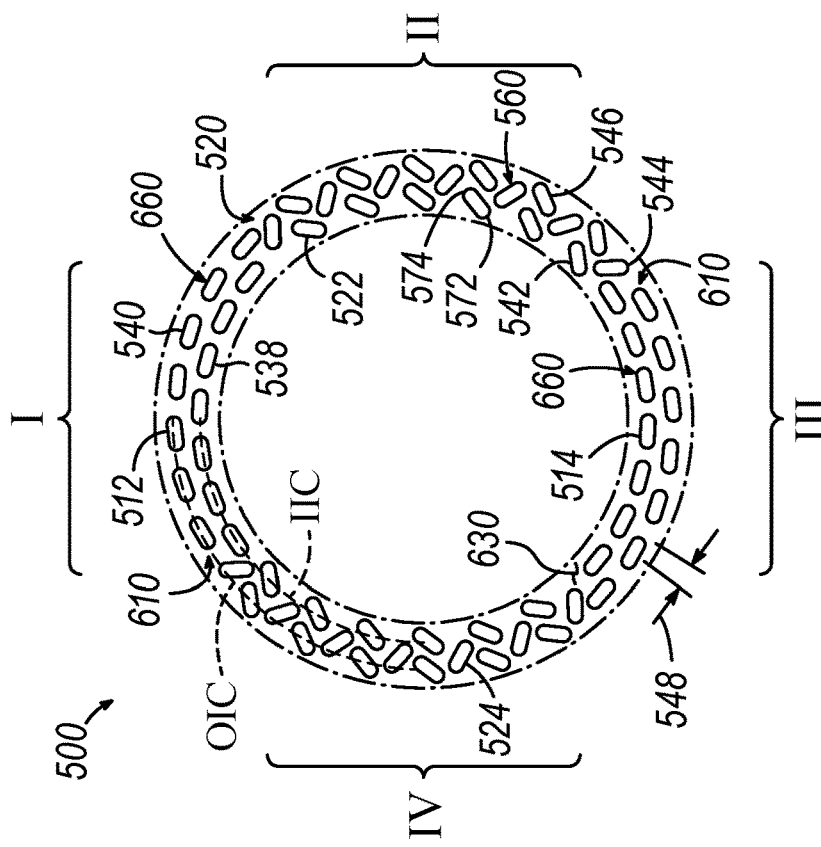
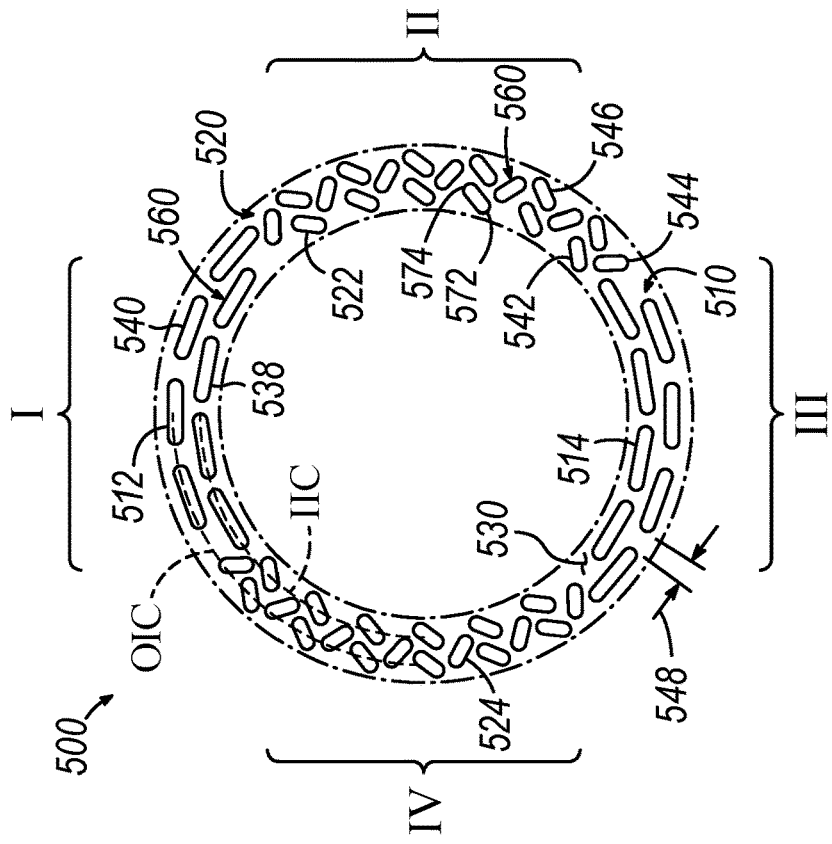

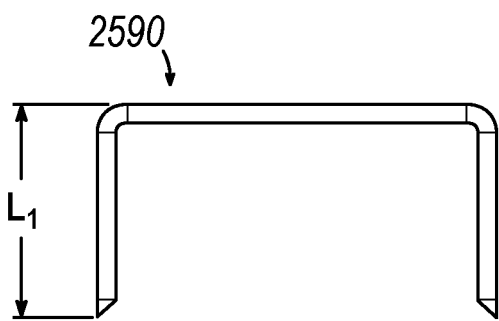
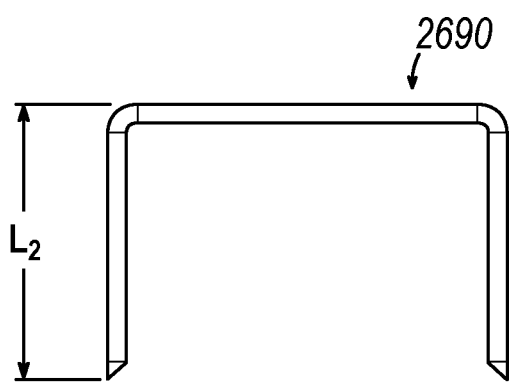
FIG. 35A  FIG. 35B
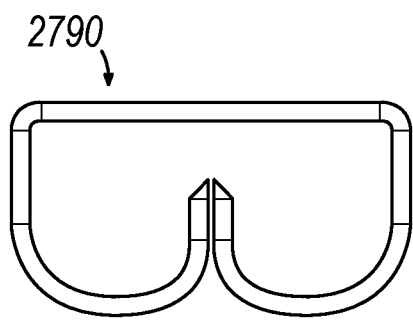
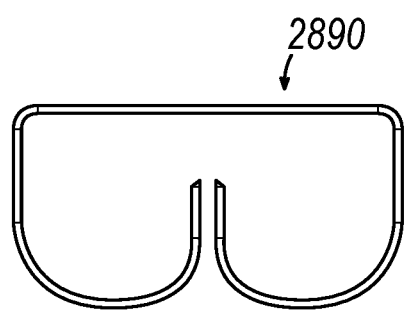
FIG. 36A  FIG. 36B
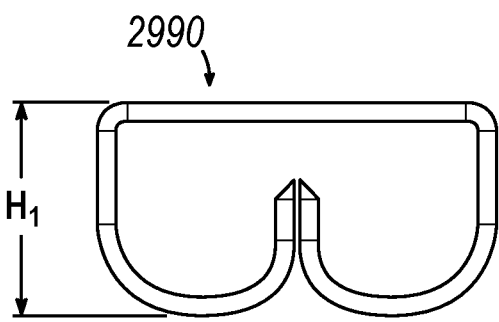
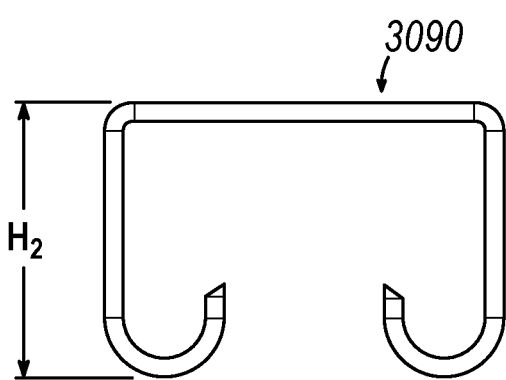
FIG. 37A  FIG. 37B

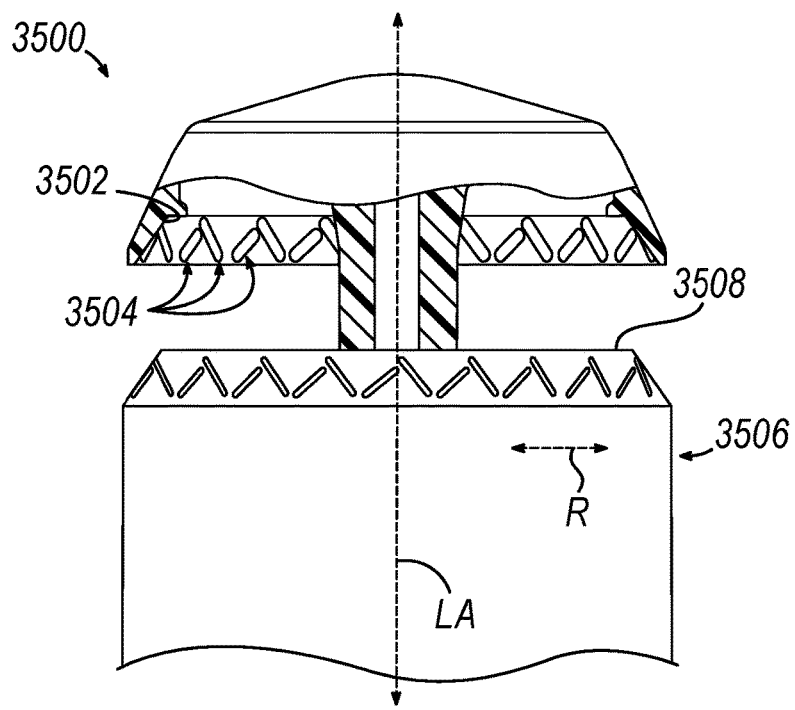
FIG. 57
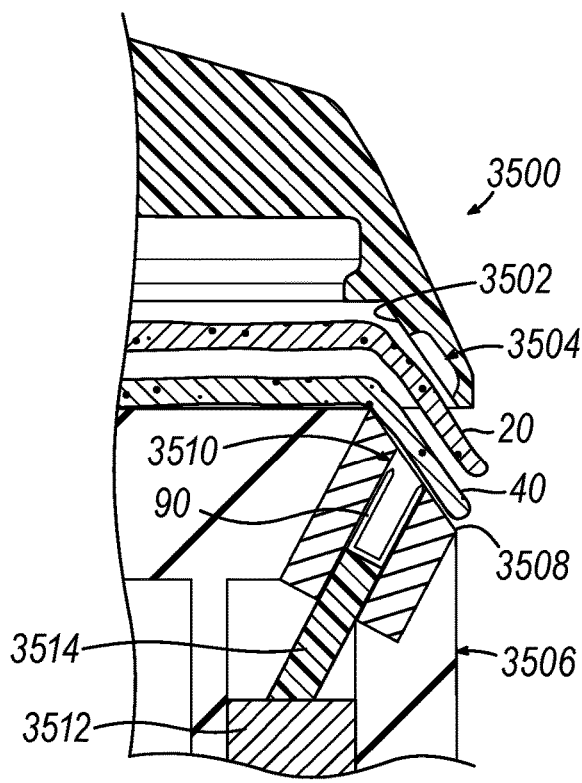 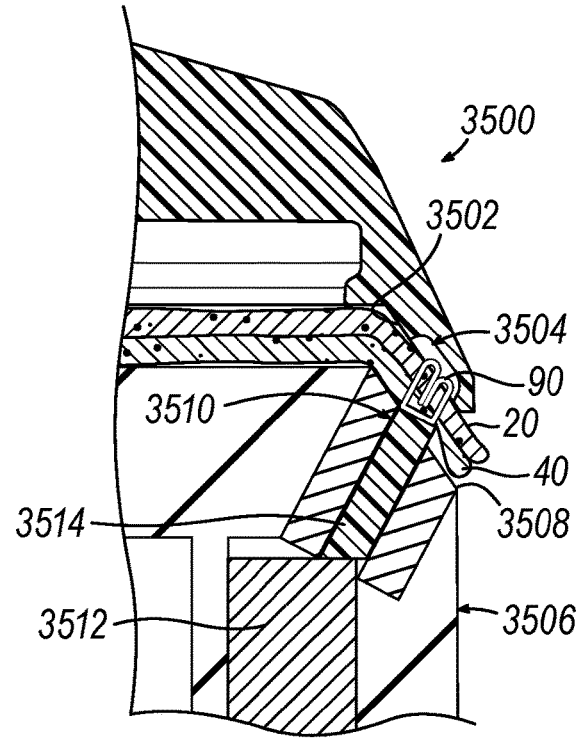
FIG. 58A  FIG. 58B

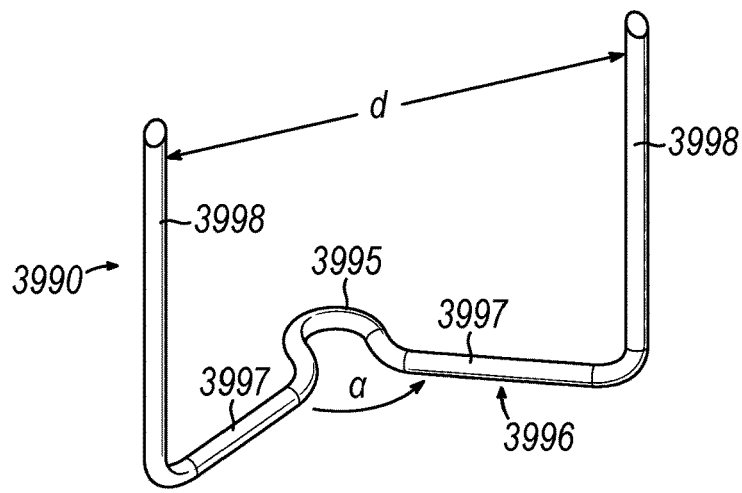
FIG. 82
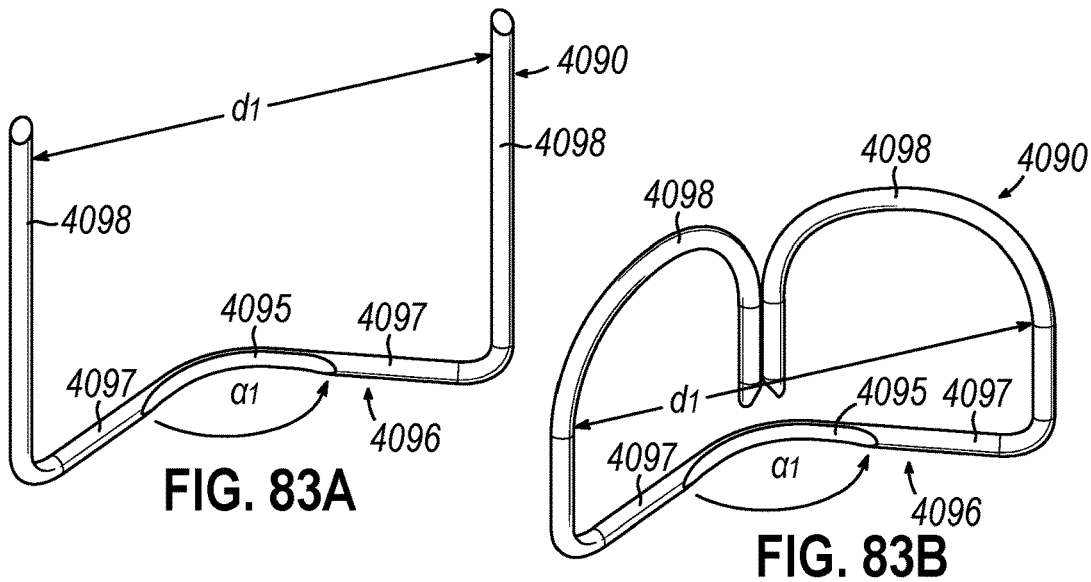
FIG. 83A
FIG. 83B
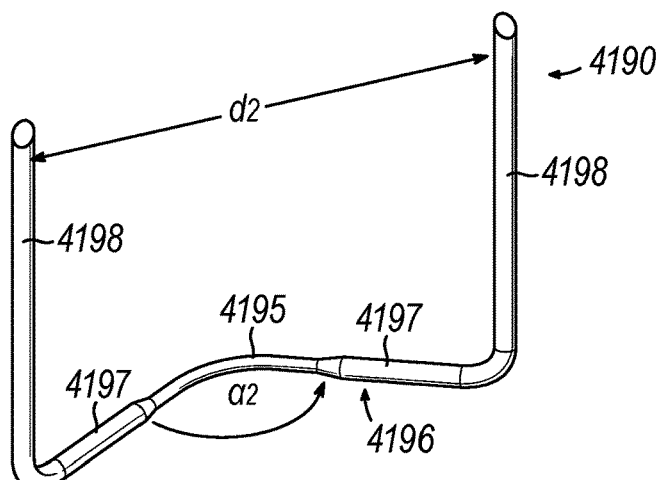
FIG. 84

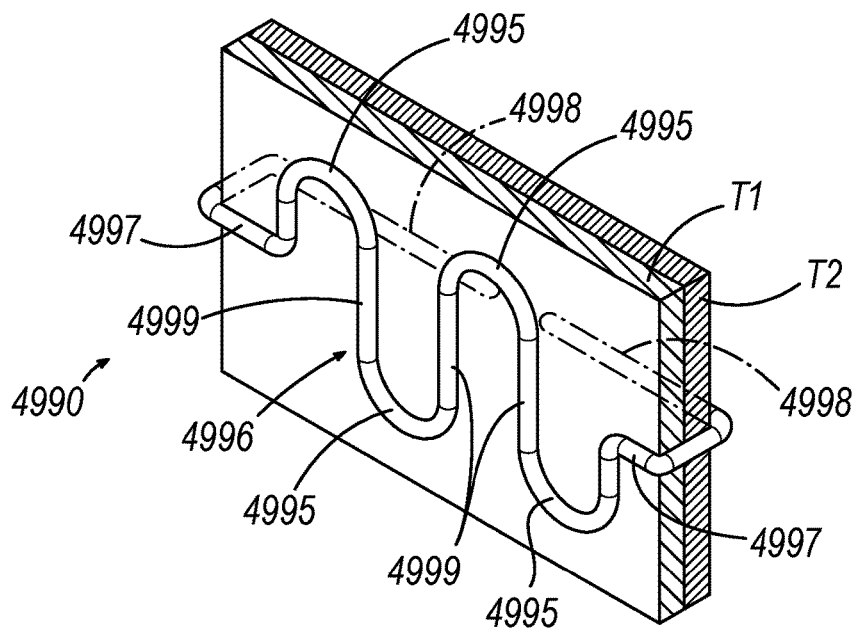
FIG. 93
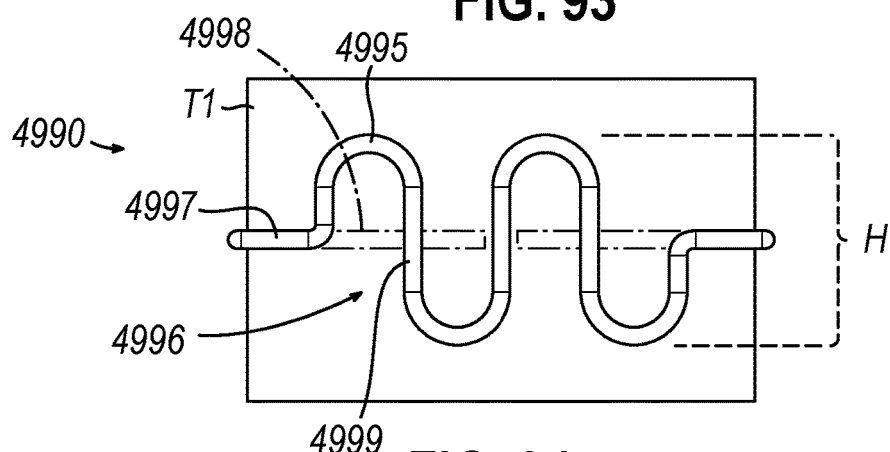
FIG. 94
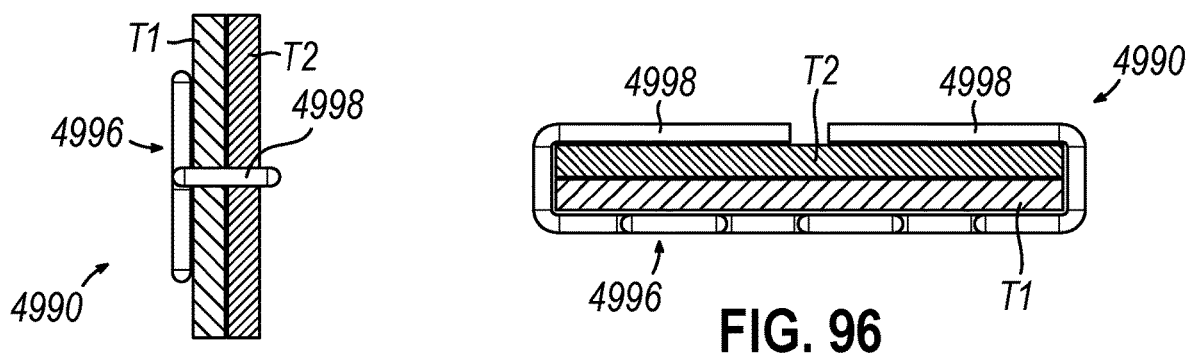
FIG. 95
FIG. 96

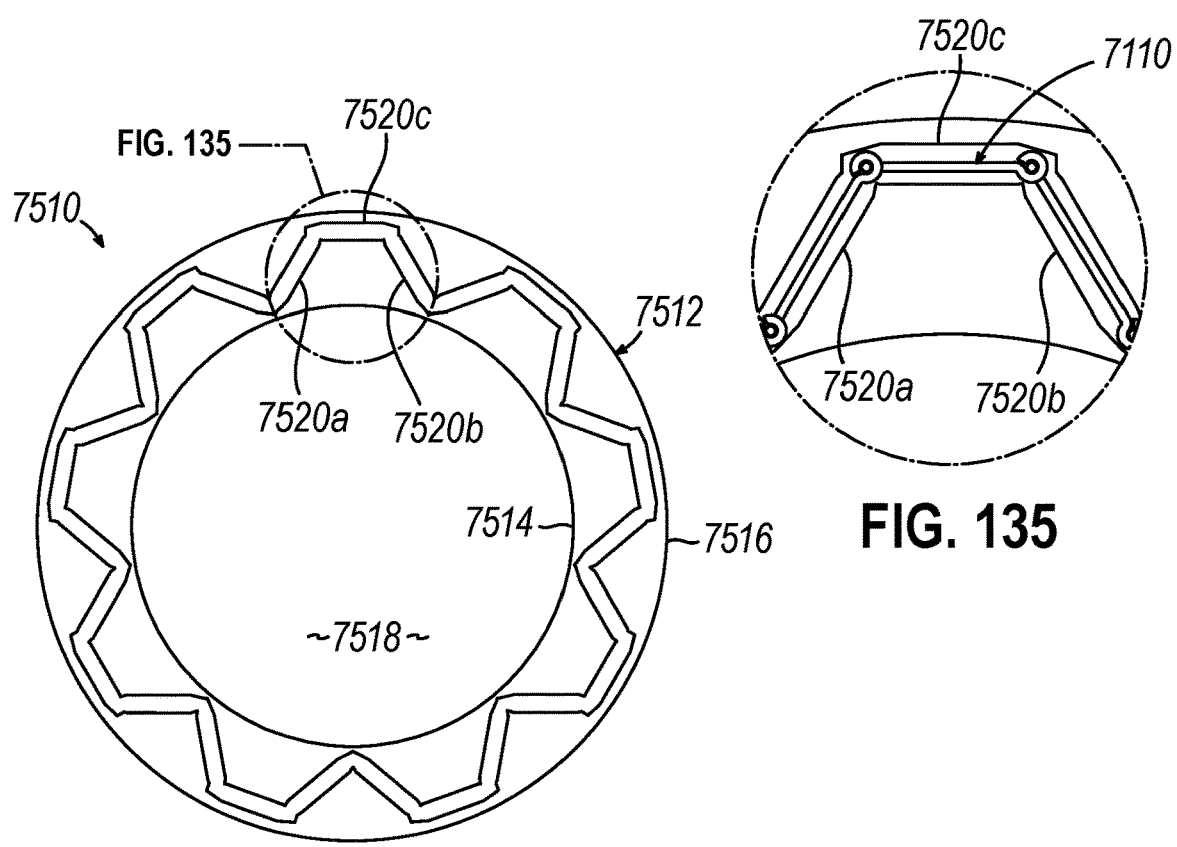
FIG. 134
FIG. 135
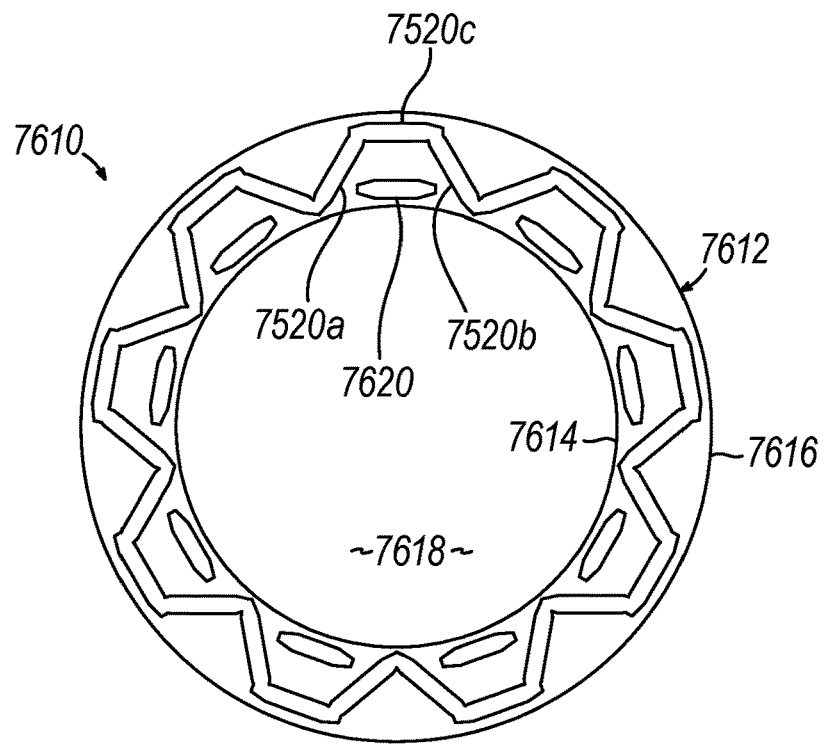
FIG. 136

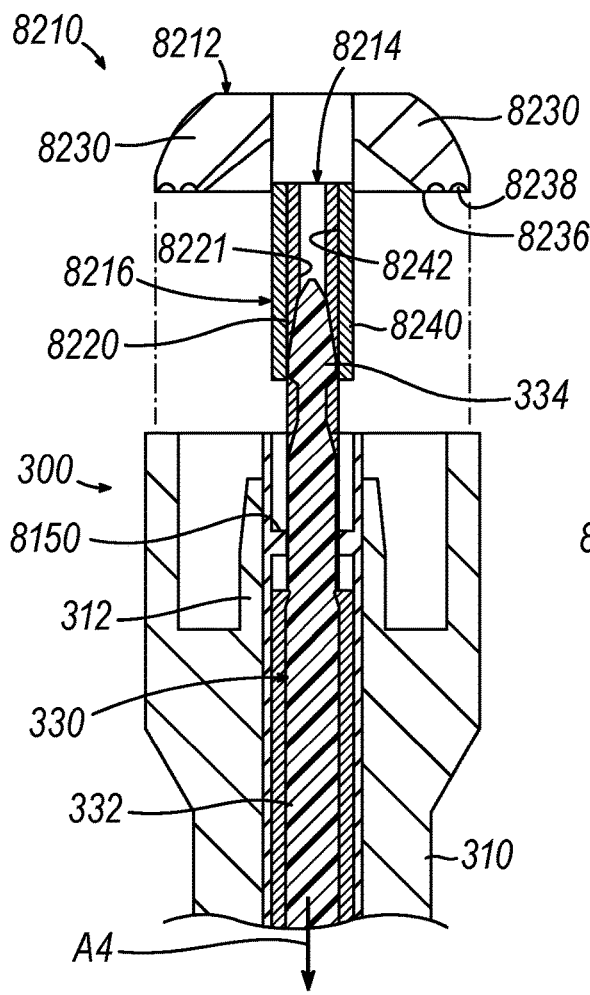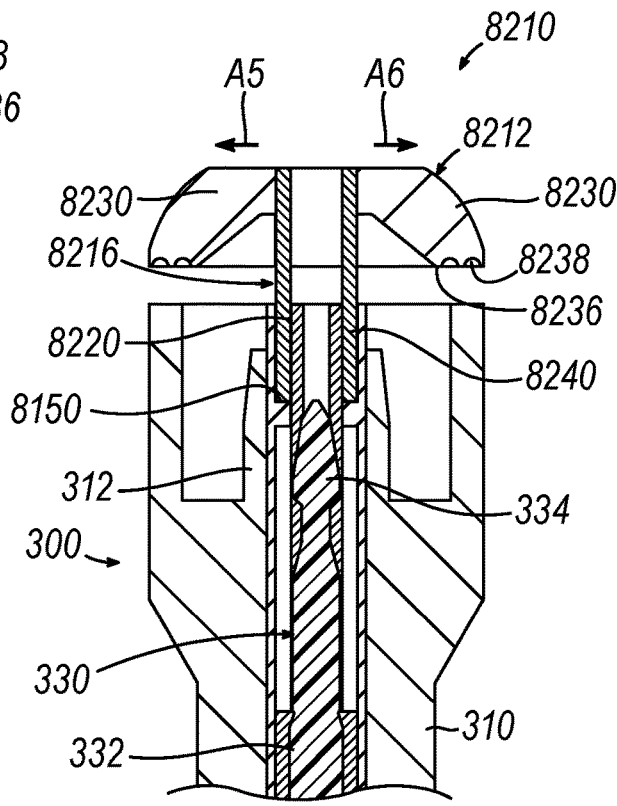
FIG. 143A   FIG. 143B
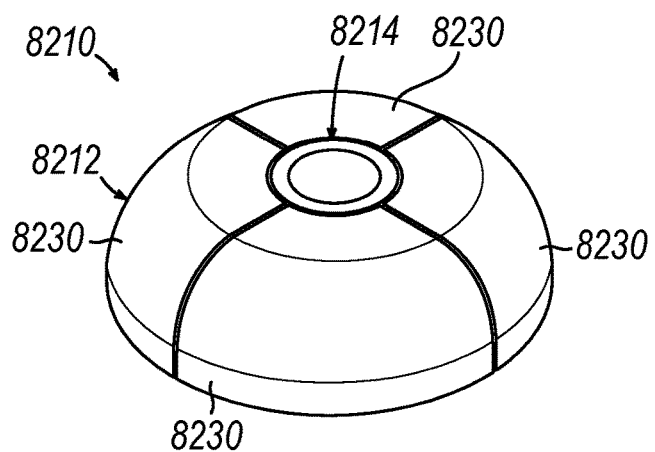
FIG. 144

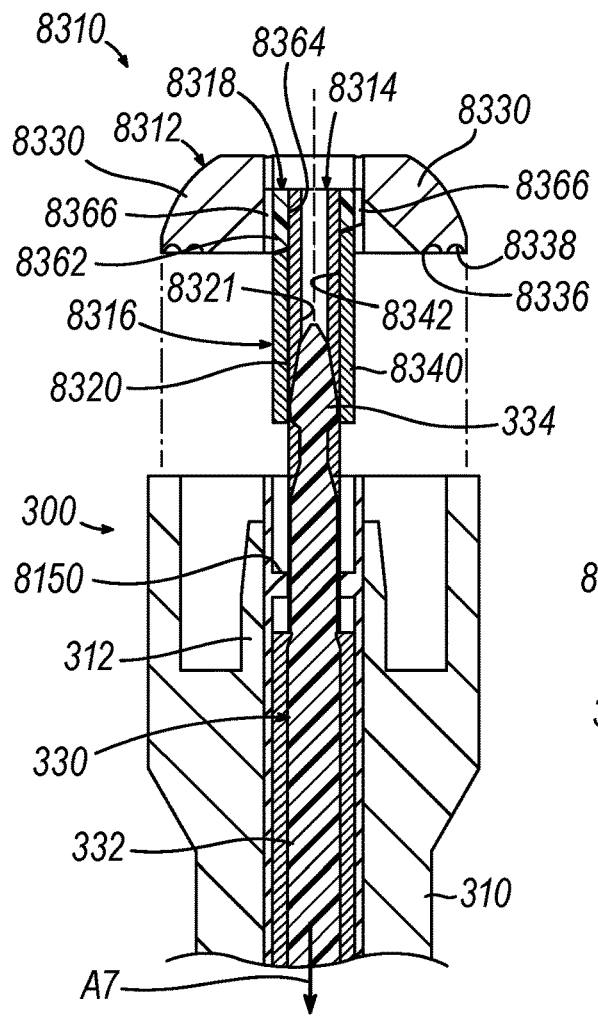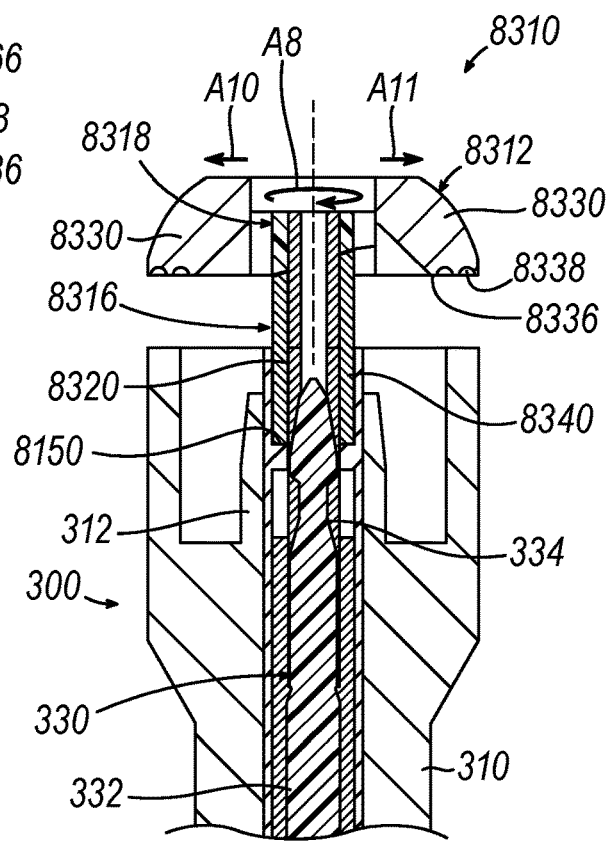
FIG. 145A    FIG. 145B
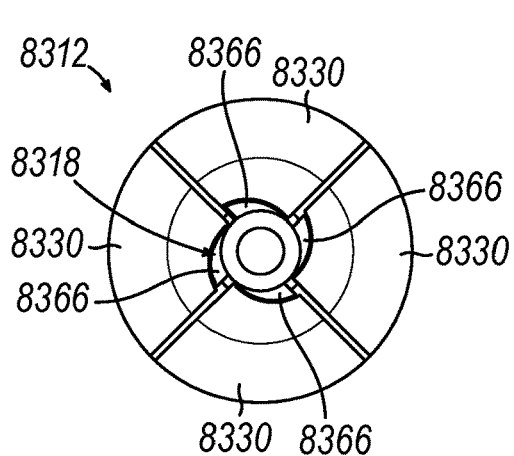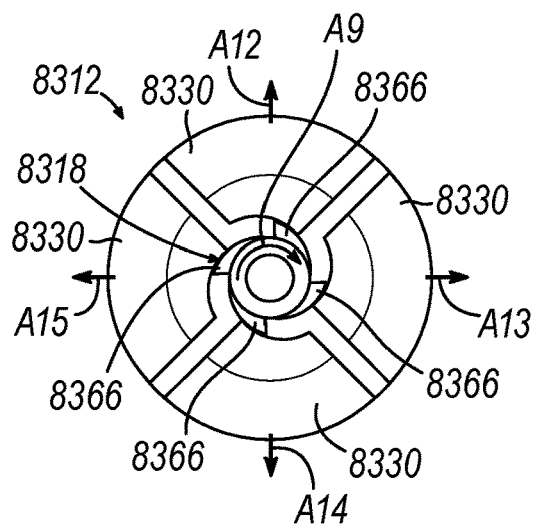
FIG. 146A    FIG. 146B

METHODS OF FORMING AN ANASTOMOSIS BETWEEN ORGANS WITH AN EXPANDABLE PATTERN

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018, now abandoned; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 9 depicts a top plan view of a deck surface of the stapling head assembly of FIG. 8;

FIG. 10 depicts a top plan view of a second exemplary deck surface configured for use with the stapling head assembly of FIG. 8;

FIG. 35A depicts a front view of an exemplary staple having a first staple leg length, the staple usable with the various stapling head assemblies described herein;

FIG. 35B depicts a front view of another exemplary staple having a second staple leg length, the staple usable with the various stapling head assemblies described herein;

FIG. 36A depicts a front view of an exemplary staple having a first wire diameter, the staple usable with the various stapling head assemblies described herein;

FIG. 36B depicts a front view of an exemplary staple having a second wire diameter, the staple usable with the various stapling head assemblies described herein;

FIG. 37A depicts a front view of an exemplary staple having a first formed staple height, the staple usable with the various stapling head assemblies described herein;

FIG. 37B depicts a front view of an exemplary staple having a second formed staple height, the staple usable with the various stapling head assemblies described herein;

FIG. 57 depicts a front elevational view of an alternative exemplary anvil and an alternative exemplary stapling head assembly that may be incorporated into the circular stapler of FIG. 1;

FIG. 58A depicts a cross-sectional view of the anvil and stapling head assembly of FIG. 57 initially grasping tissue and in a pre-fired position;

FIG. 58B depicts a cross-sectional view of the anvil and stapling head assembly of FIG. 57 grasping tissue an in a fired position;

FIG. 82 depicts a perspective view of an exemplary staple having a "V" shape and a spring feature;

FIG. 83A depicts a perspective view of an exemplary staple having a "V" shape and a notch feature;

FIG. 83B depicts a perspective view of the staple of FIG. 83A, but shown in the formed state;

FIG. 84 depicts a perspective view of an exemplary staple having a "V" shape and reduced diameter feature;

FIG. 92B depicts a perspective view of the staple of FIG. 92A, shown in an expanded state;

FIG. 93 depicts a perspective view of another exemplary staple fastening two tissues together, with the staple having a crown with curved portions;

FIG. 94 depicts a bottom view of the staple and tissues of FIG. 93;

FIG. 95 depicts a side view of the staple and tissues of FIG. 93;

FIG. 96 depicts a front view of the staple and tissues of FIG. 93;

FIG. 97 depicts bottom views of exemplary staples with curved crown portions in various states as well as a top view of exemplary staple patters associated with each of the exemplary staples;

FIG. 98A depicts a top view of exemplary "S" shaped staples in a horizontal nested arrangement in a relaxed state;

FIG. 98B depicts an enlarged view of the staples of FIG. 98A;

FIG. 98C depicts the staples of FIG. 98B, showing the nested arrangement in an expanded state;

FIG. 98D depicts the staples of FIG. 98C, showing the staples themselves in an expanded state.

FIG. 99 depicts a top view of exemplary "S" shaped staples in a slightly angled nested arrangement in a relaxed state;

FIG. 100 depicts a top view of exemplary "C" shaped staples in a two-row nested arrangement;

Figure 1:
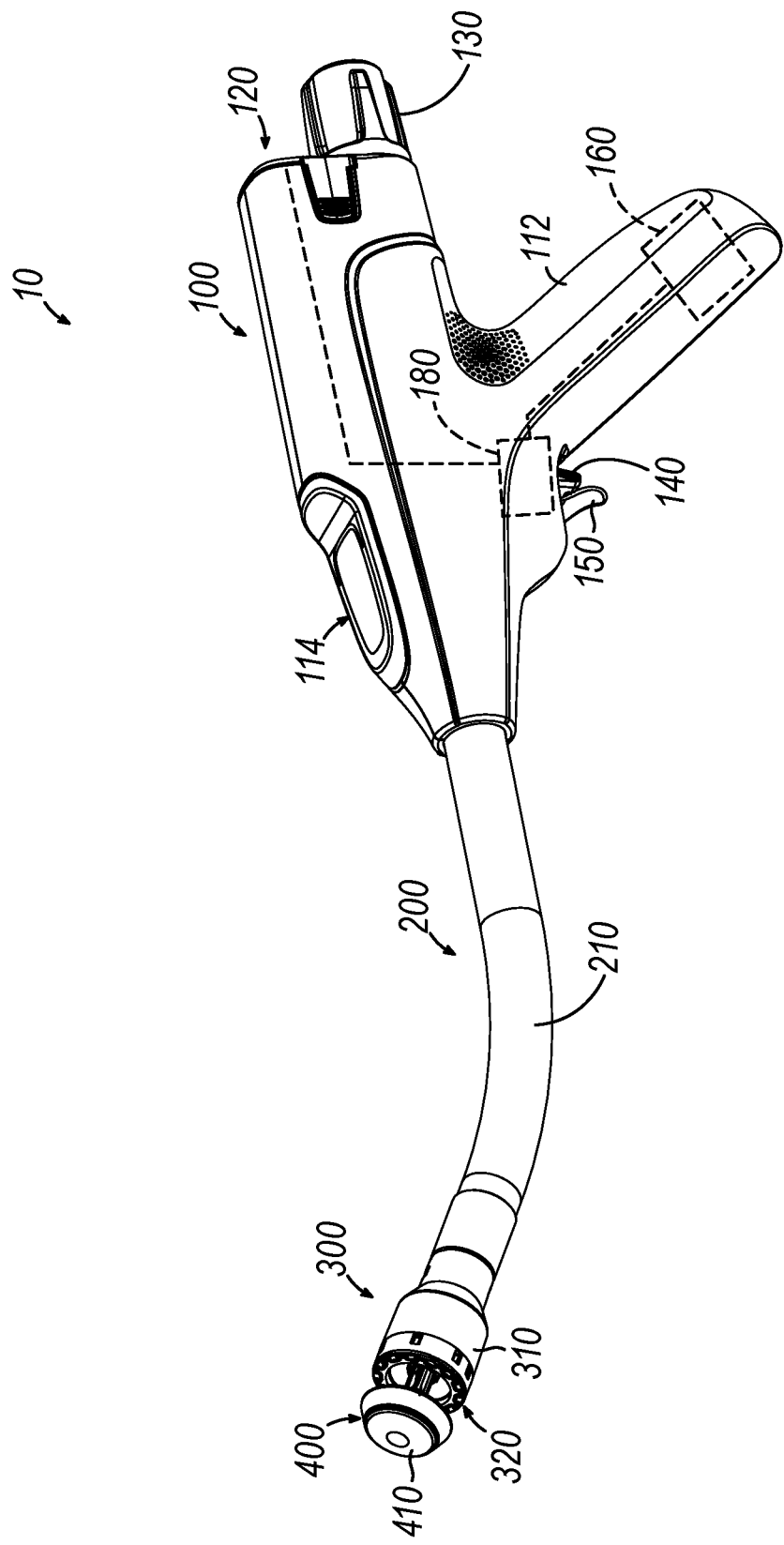
FIG. 1 depicts a perspective view of an exemplary circular surgical stapler that includes a handle assembly, a shaft assembly, and an end effector having a stapling head assembly and an anvil.
Figure 4:
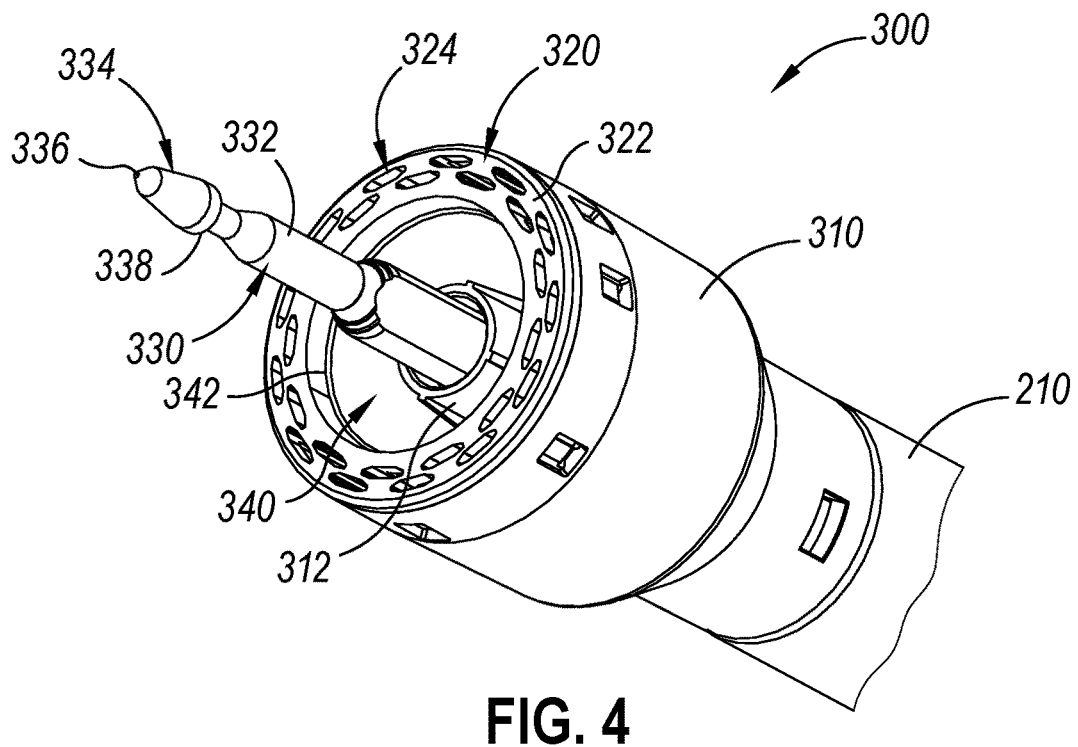
FIG. 4 depicts a perspective view of the stapling head assembly of the circular stapler of FIG. 1.
Figure 7A:
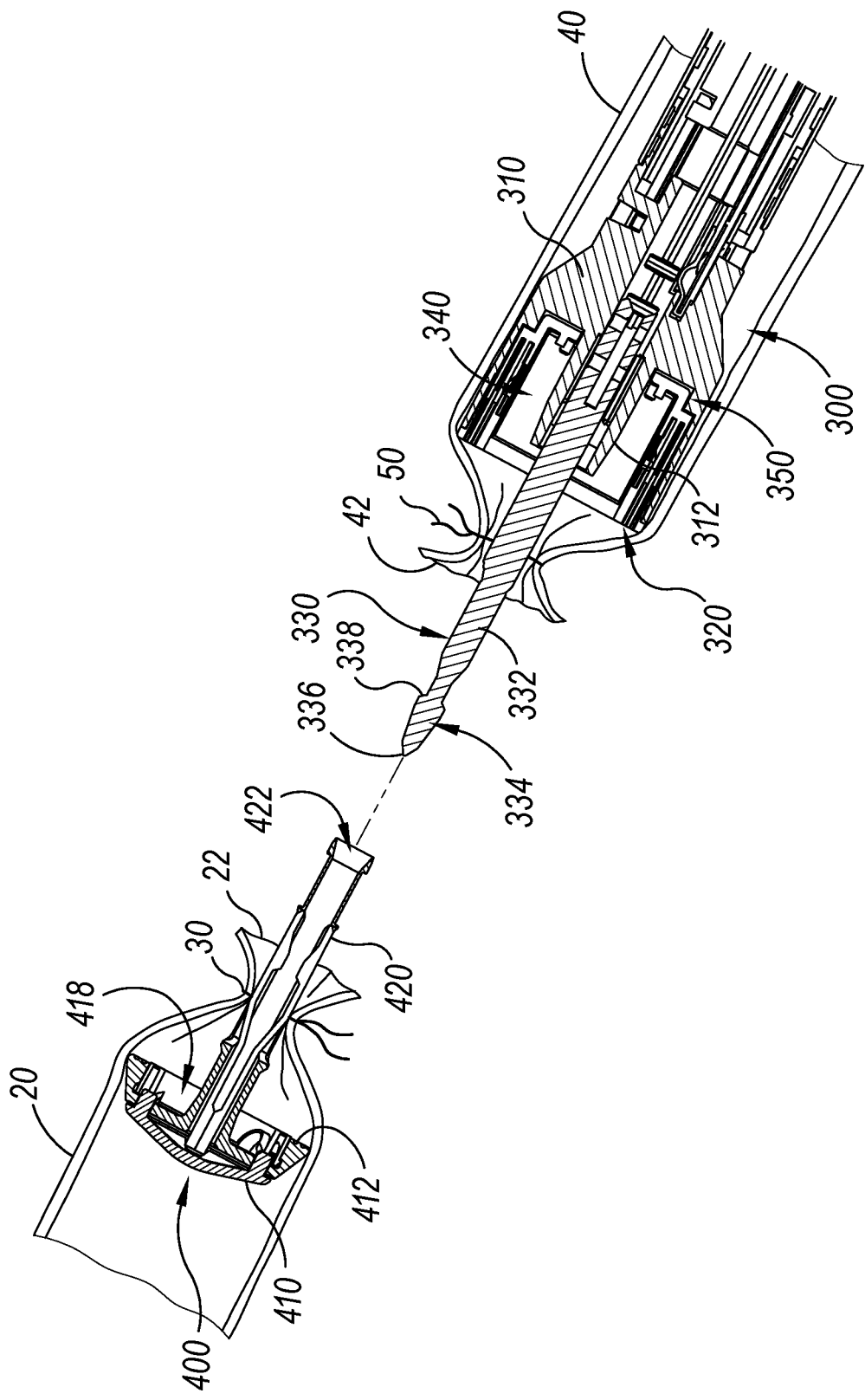
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.
Figure 101:
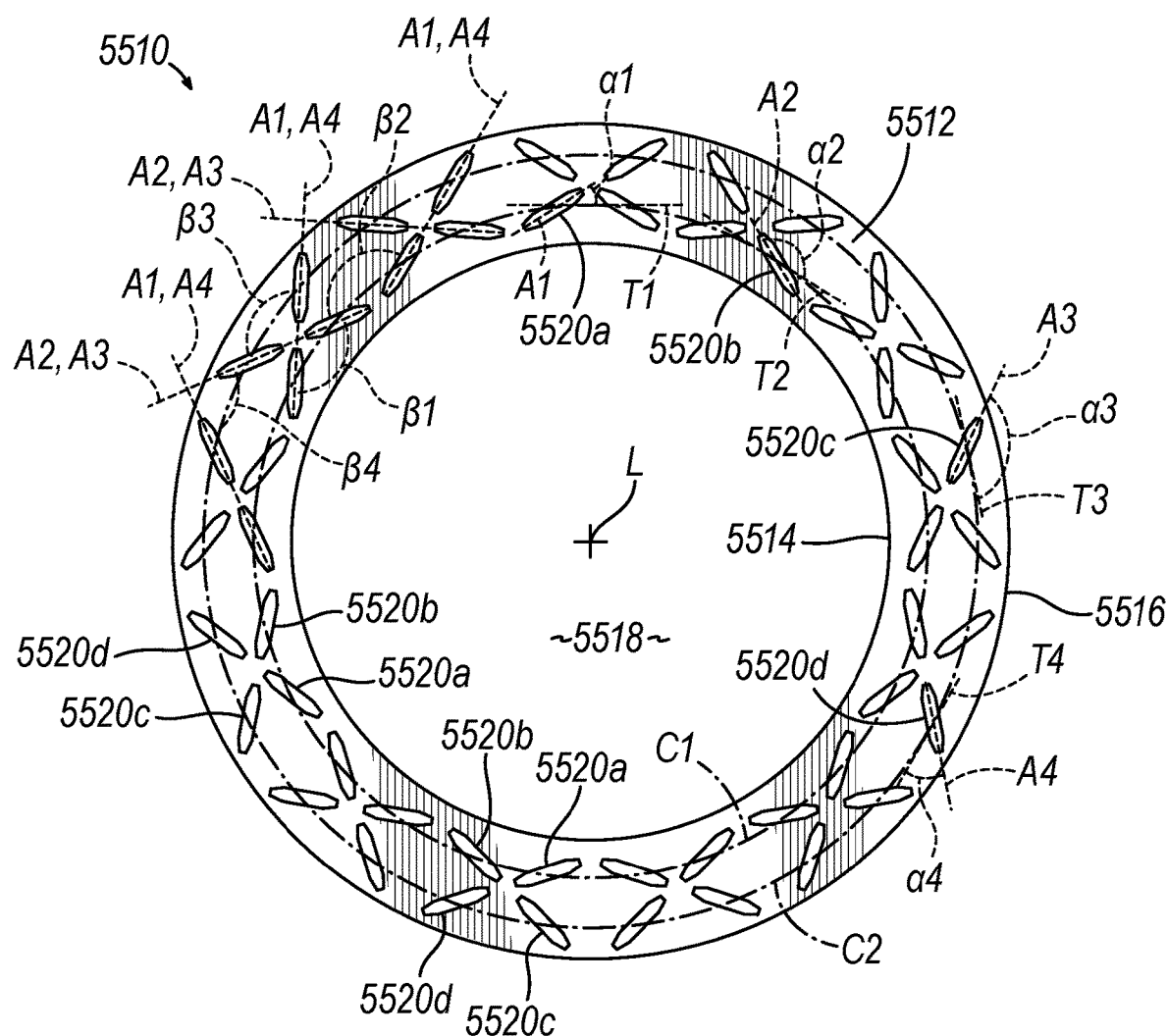
Figure 102A:
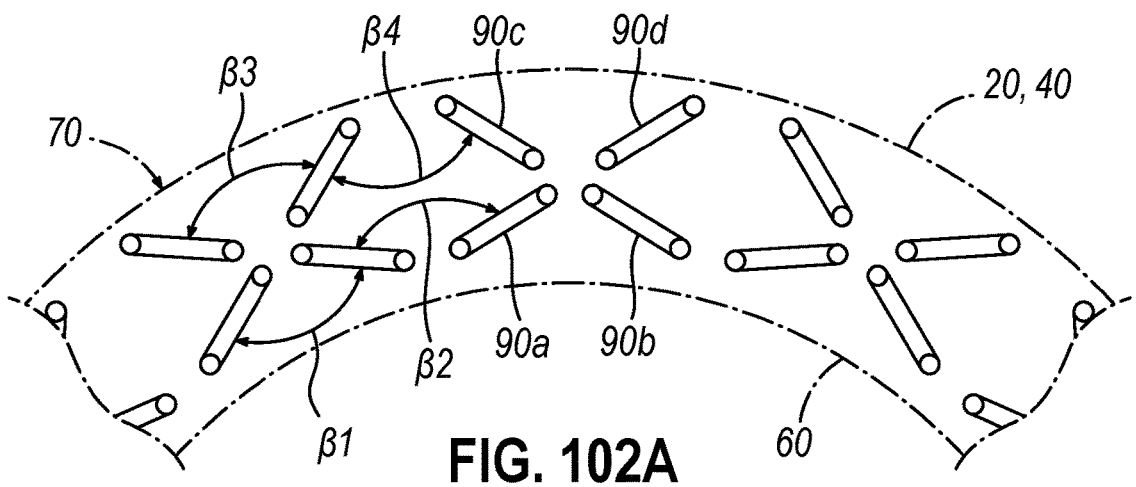
Figure 102B:
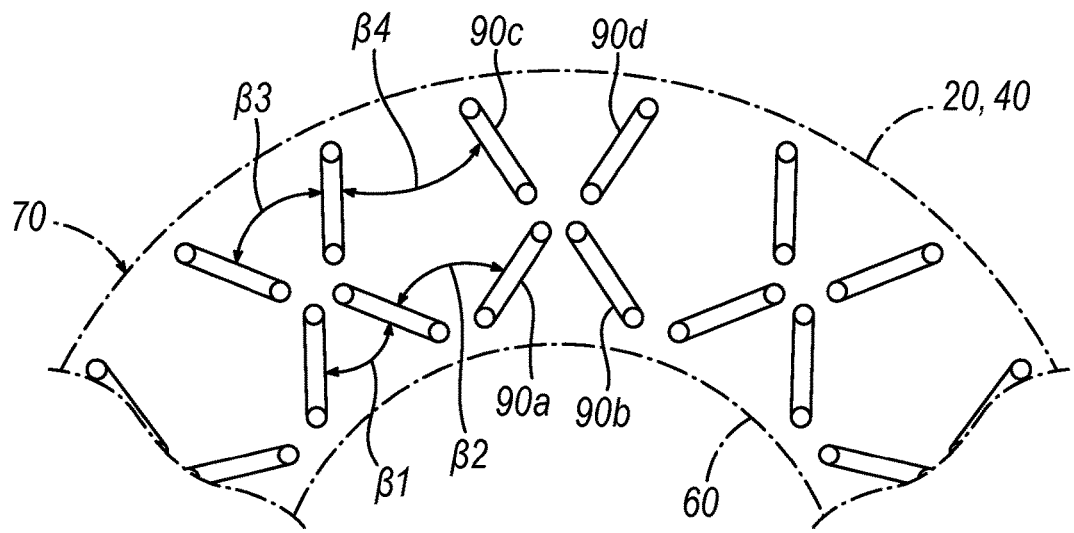
Figure 102C:
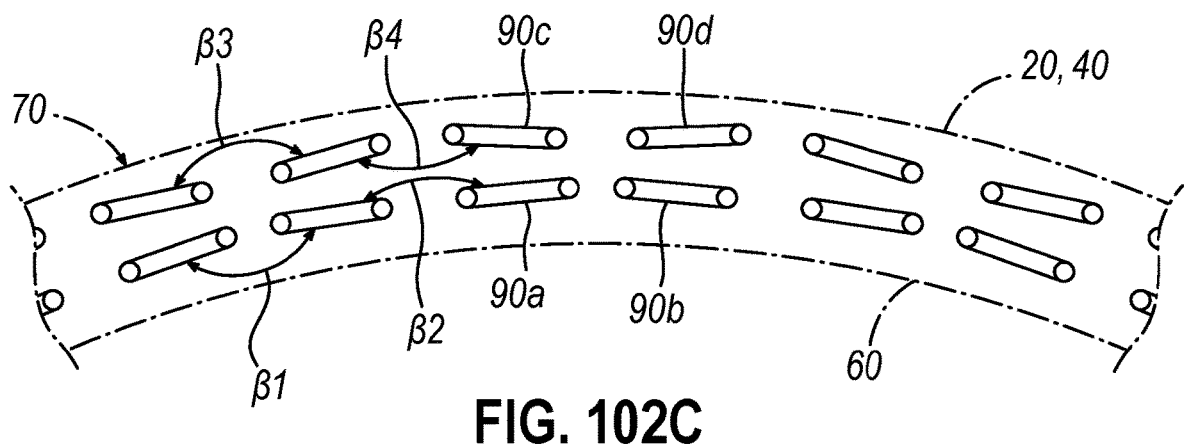
Figure 103:
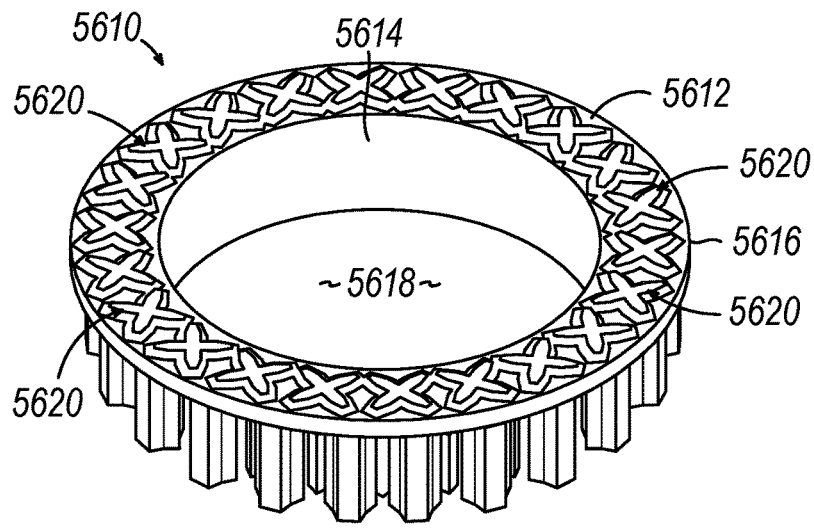
Figure 104:
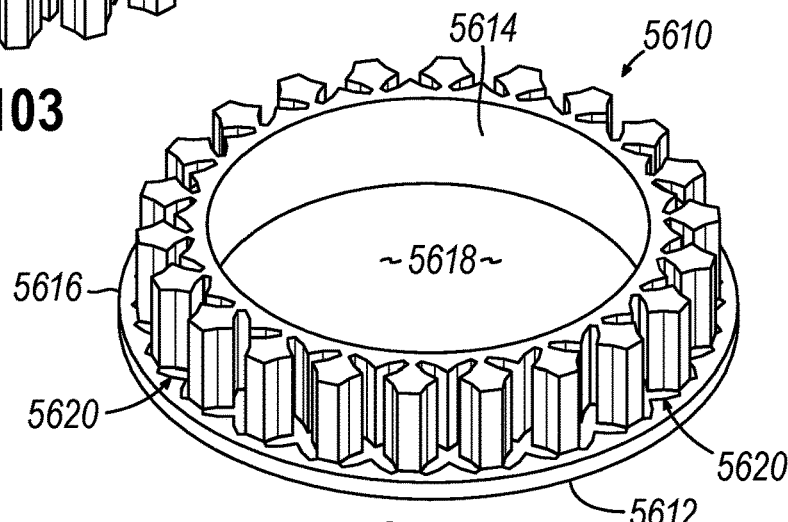
Figure 105:
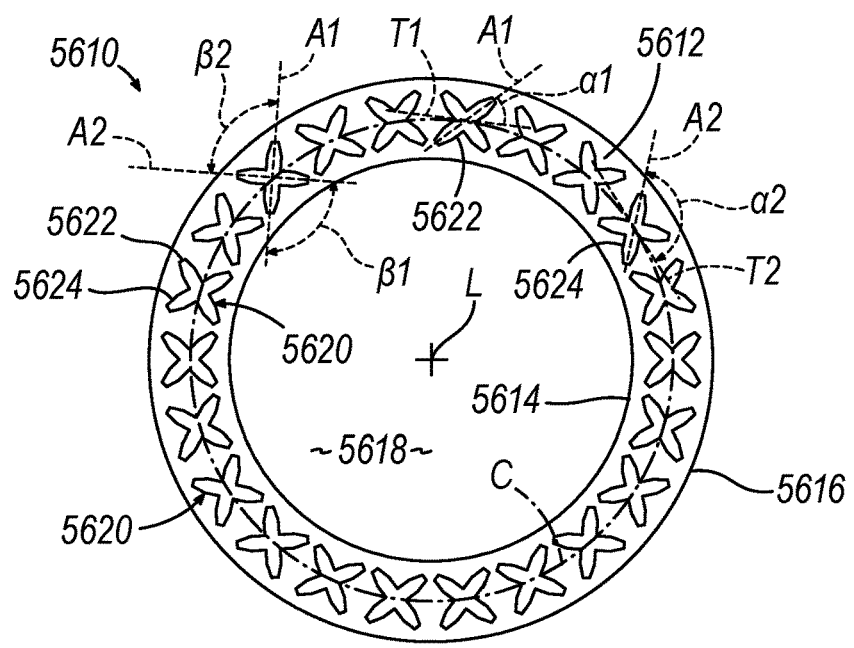
Figure 106:
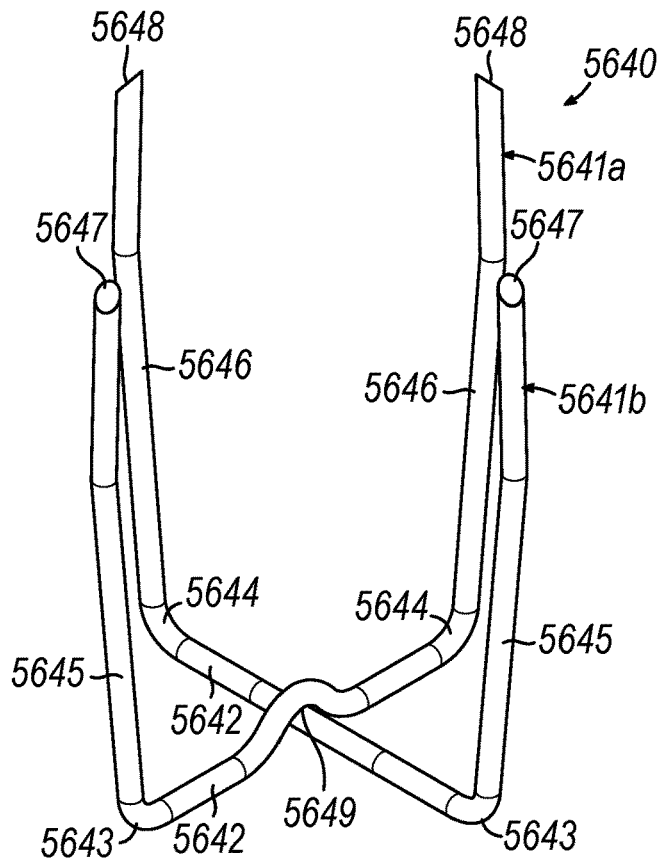
Figure 107:
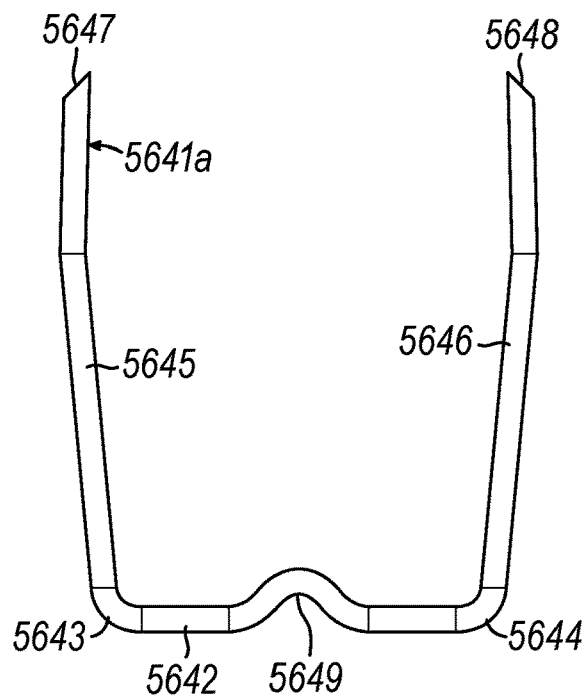
Figure 108A:
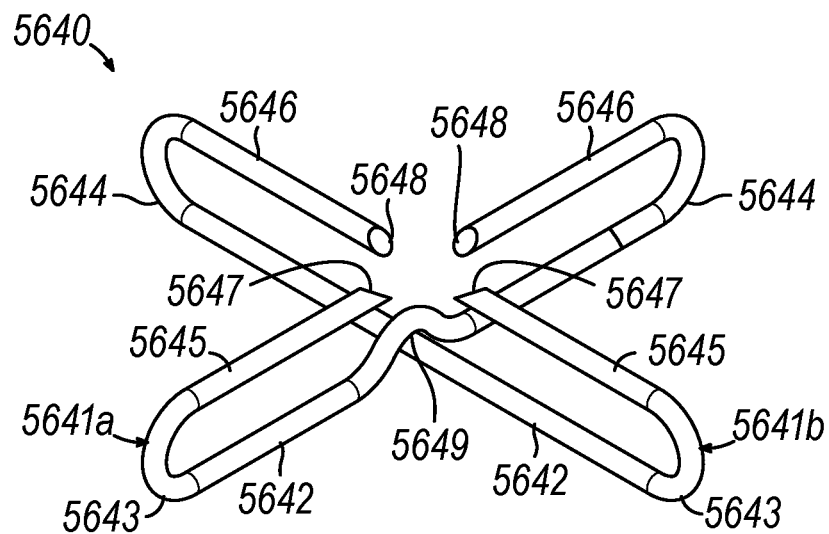
Figure 108B:
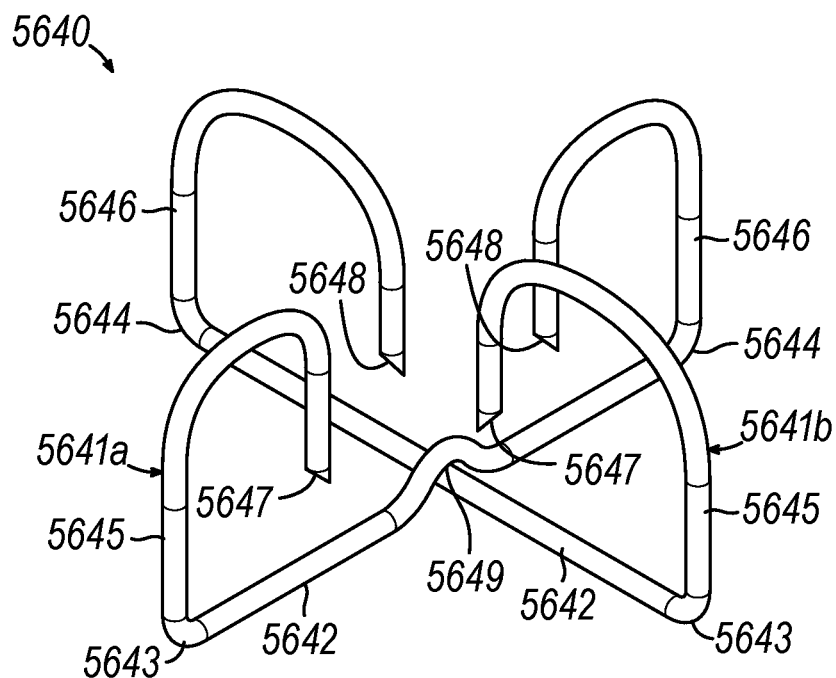
Figure 109A:
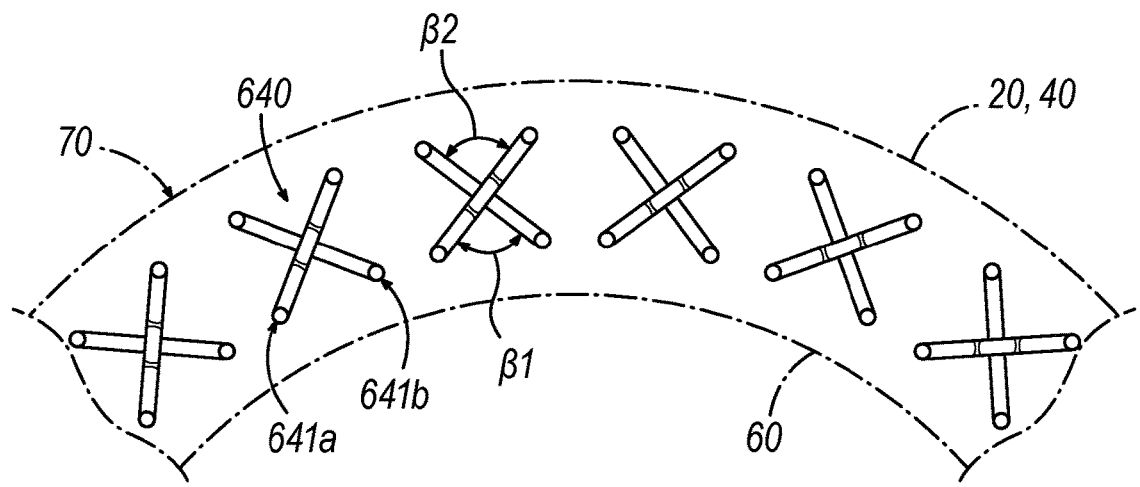
Figure 109B:
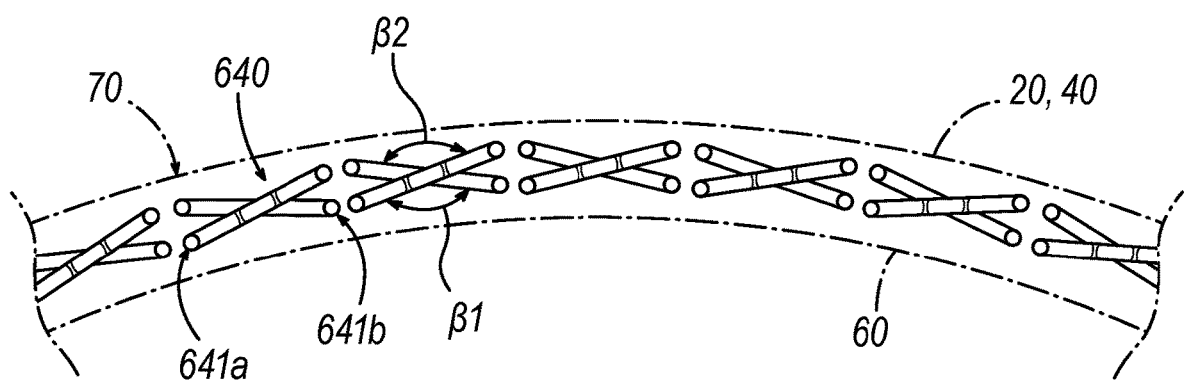
Figure 110:
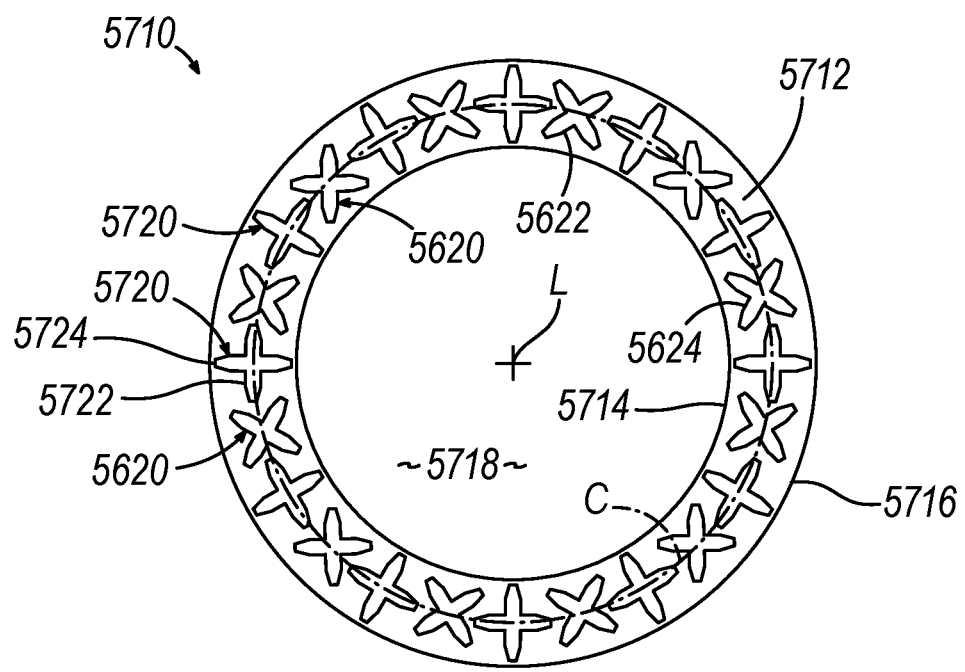
Figure 111:
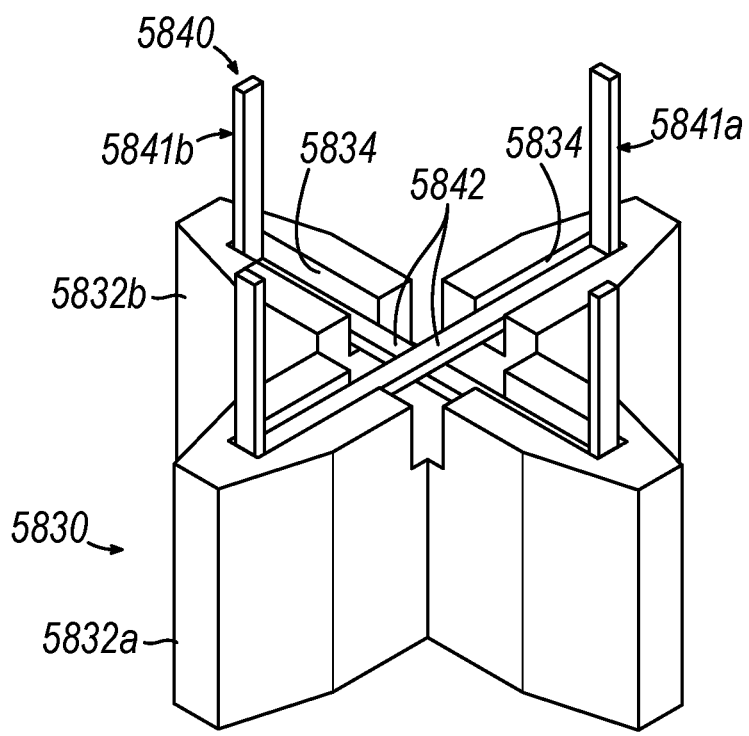
Figure 112:
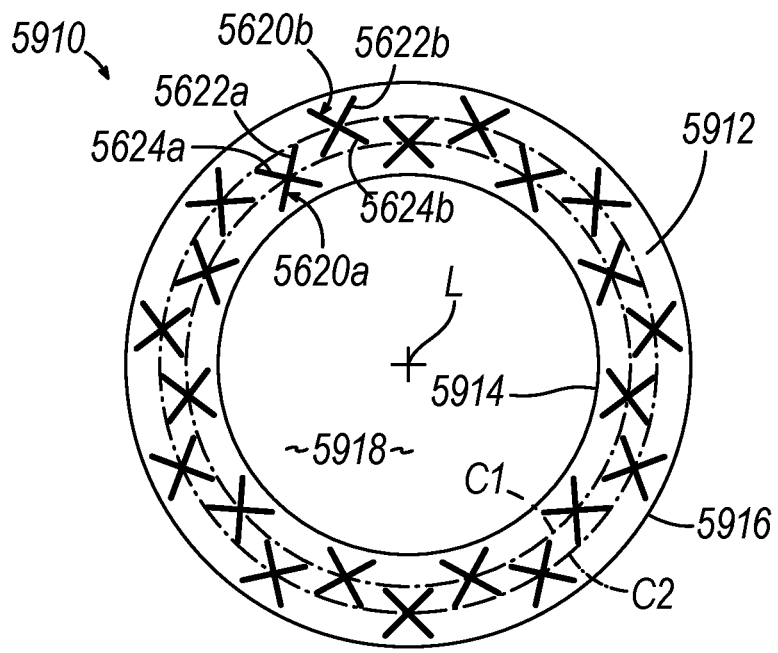
Figure 113:
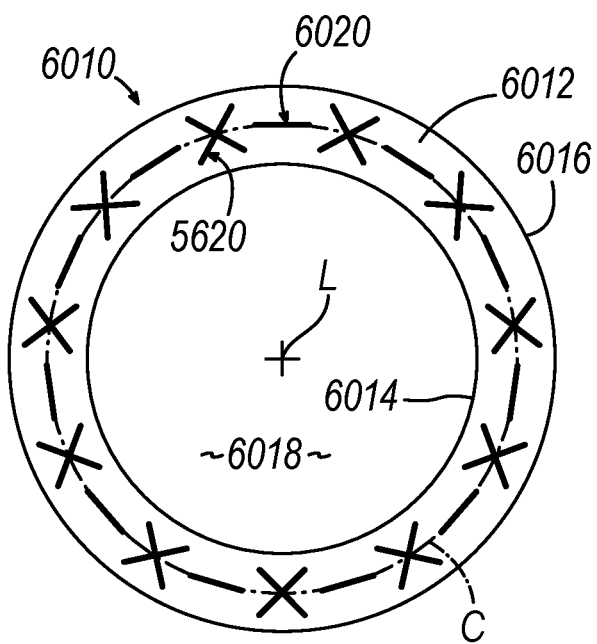
Figure 114:
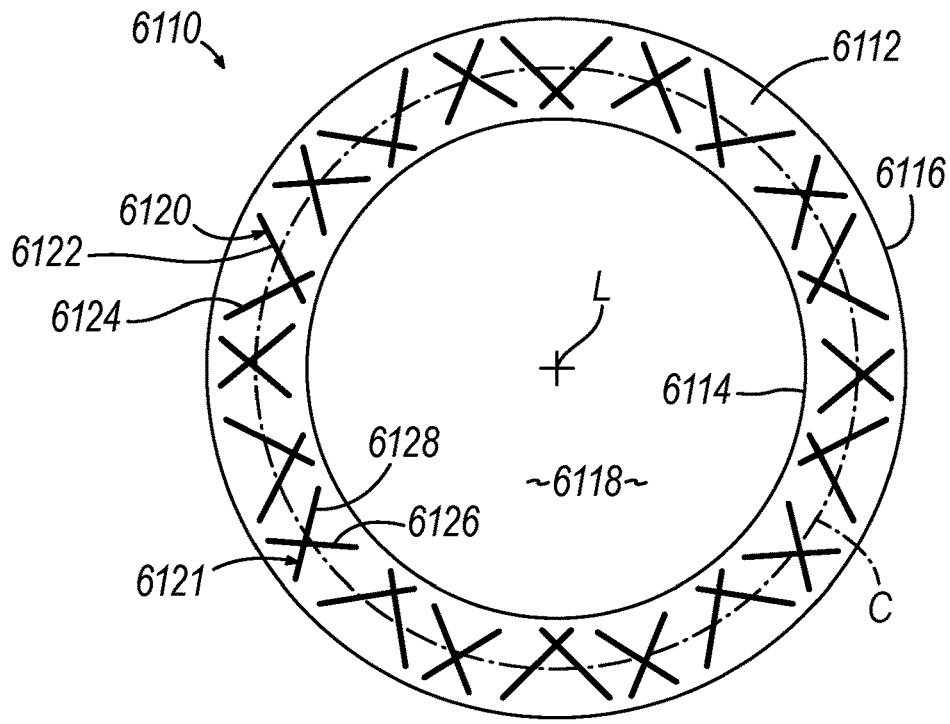
Figure 115:
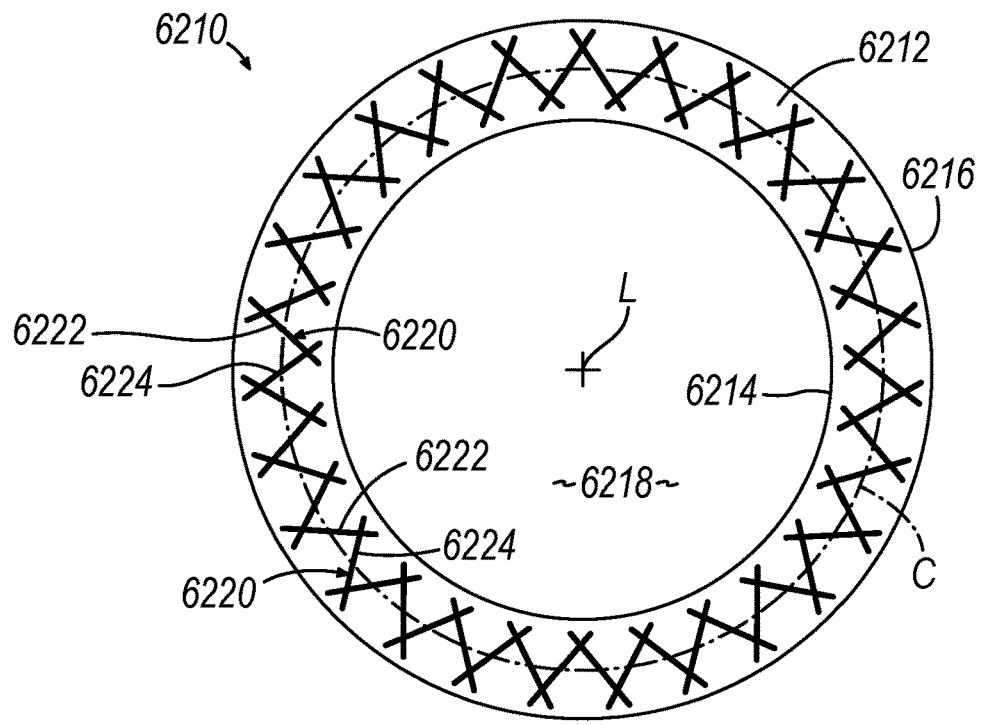
Figure 116:
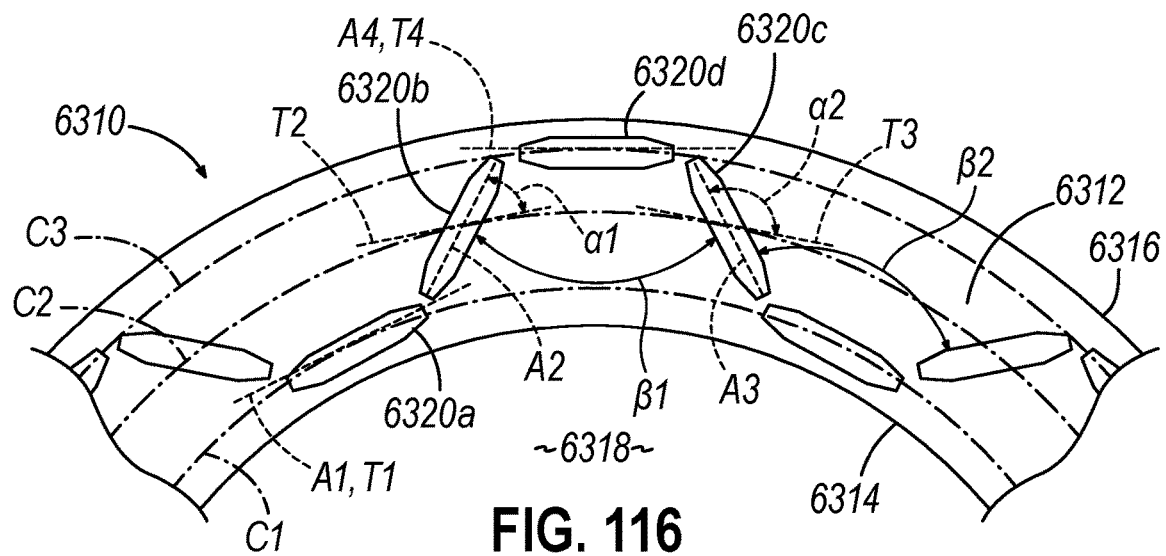
Figure 117A:
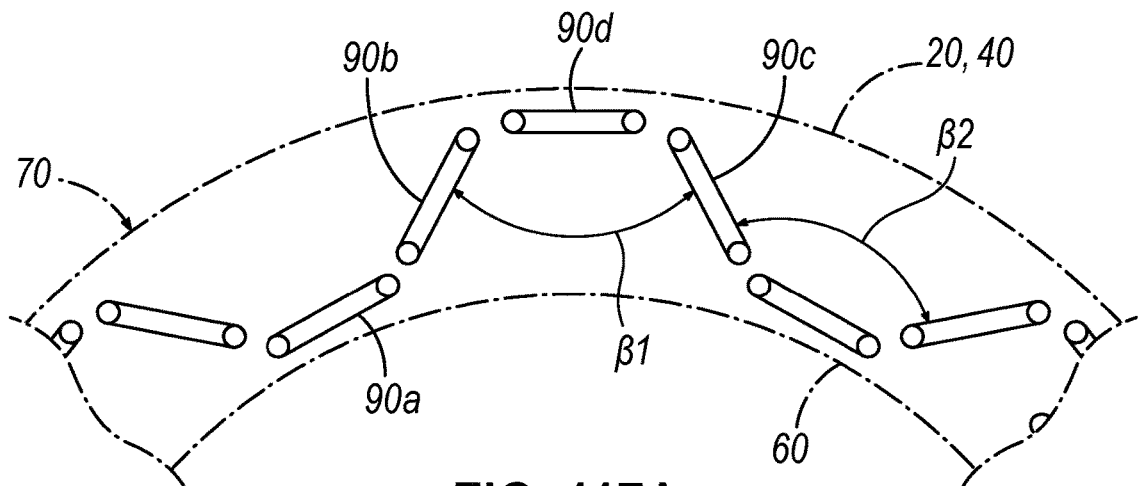
Figure 117B:
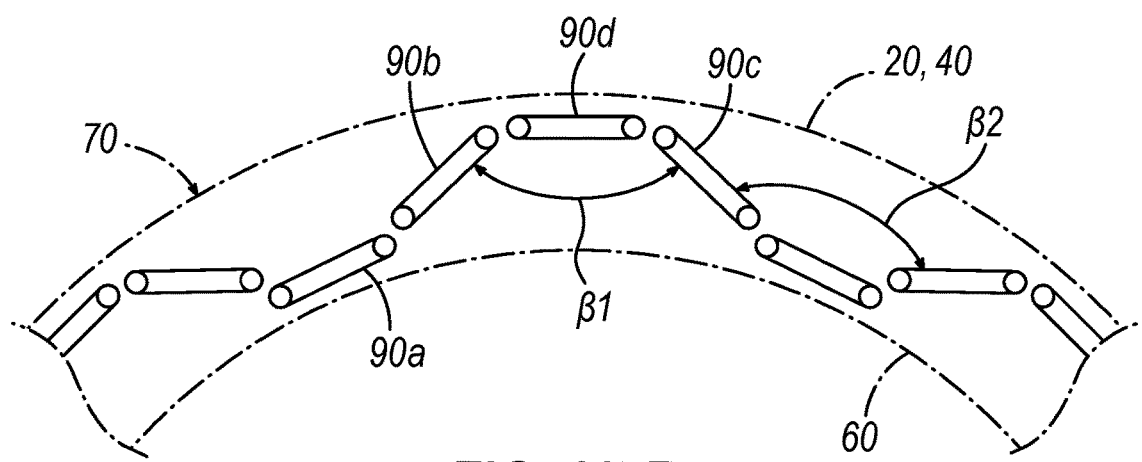
Figure 118:
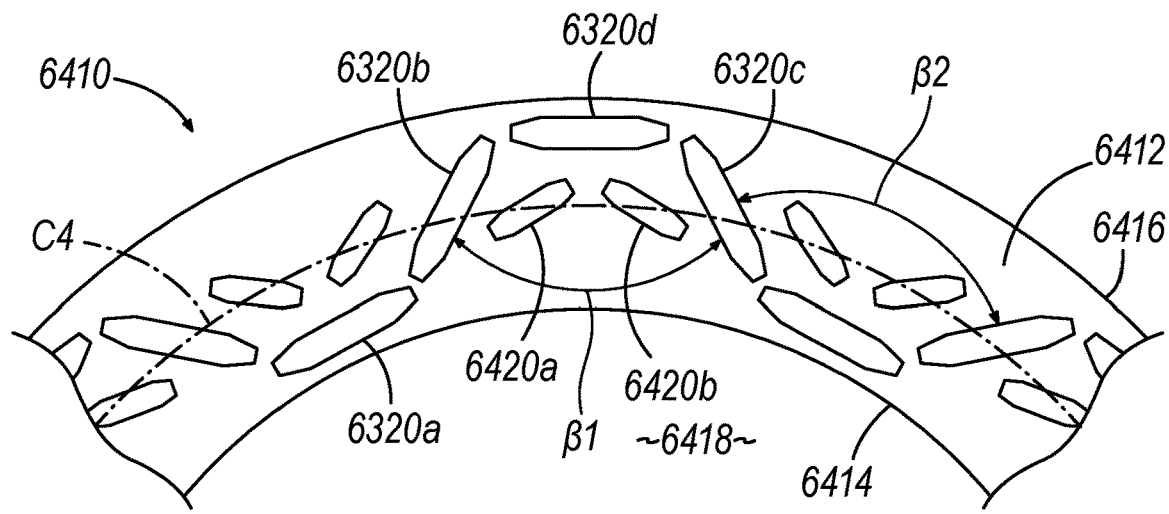
Figure 119:
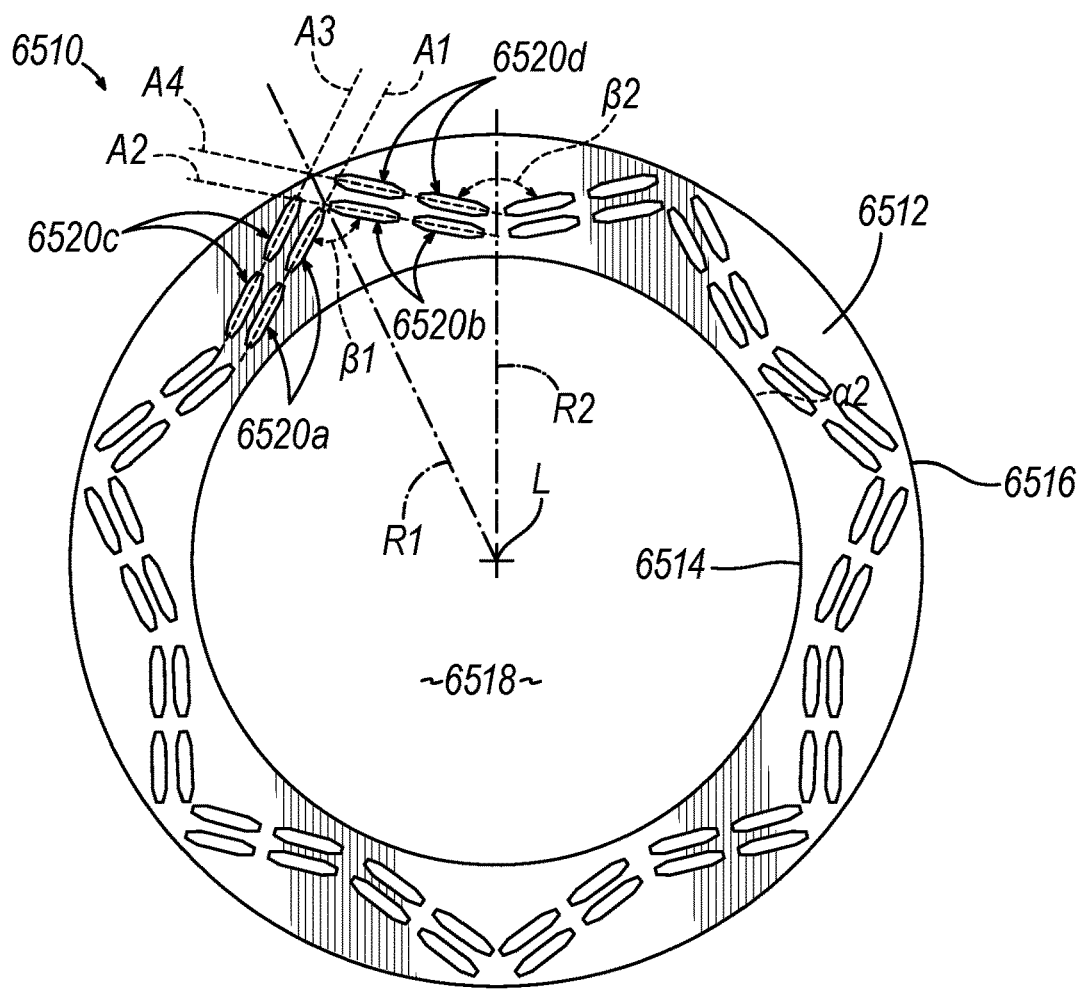
Figure 120A:
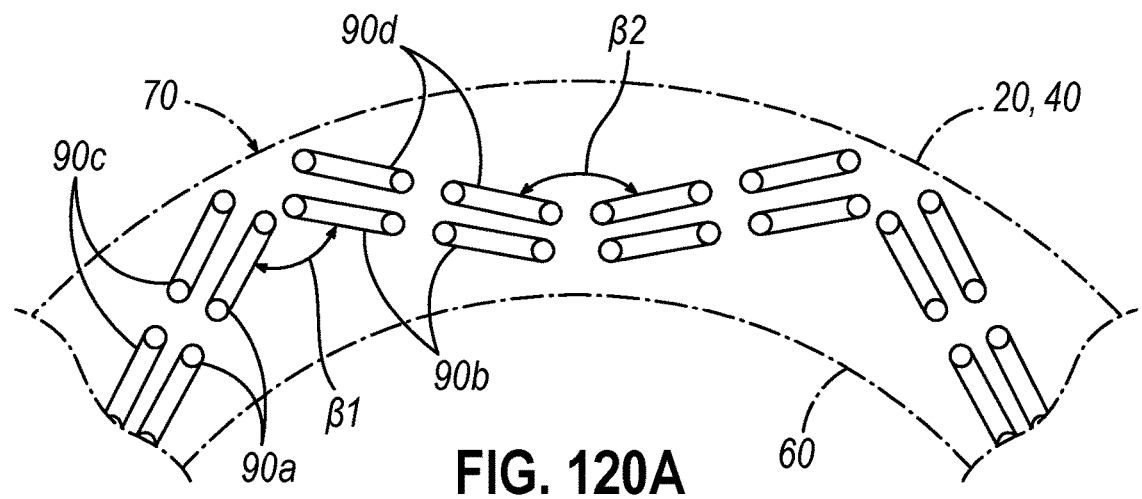
Figure 120B:
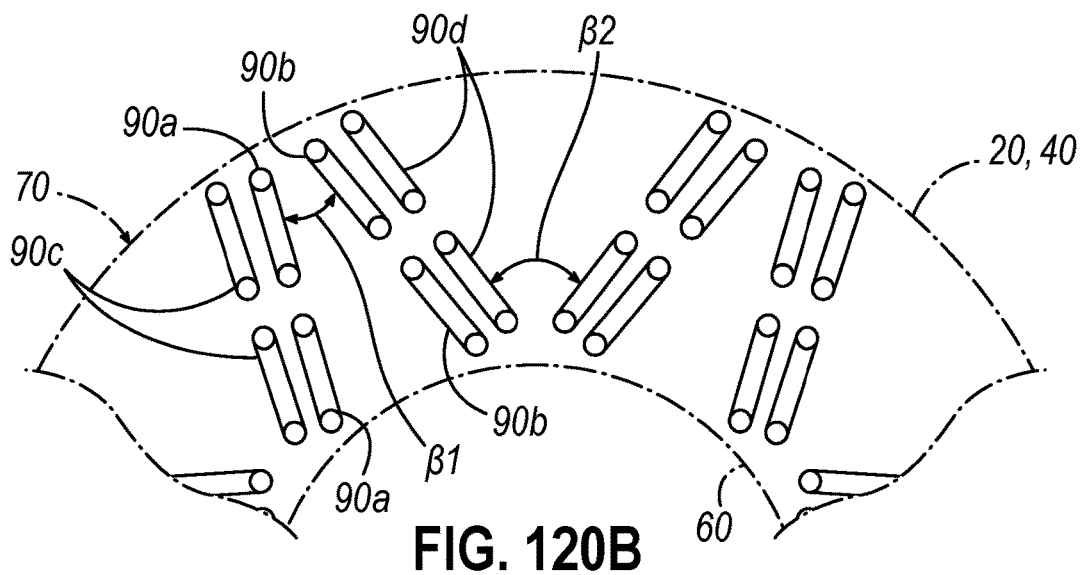
Figure 120C:
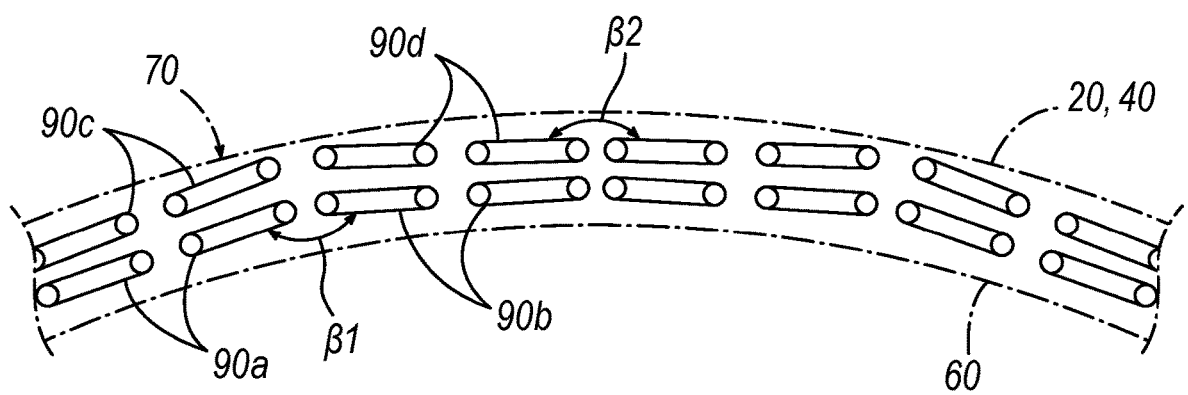
Figure 121:
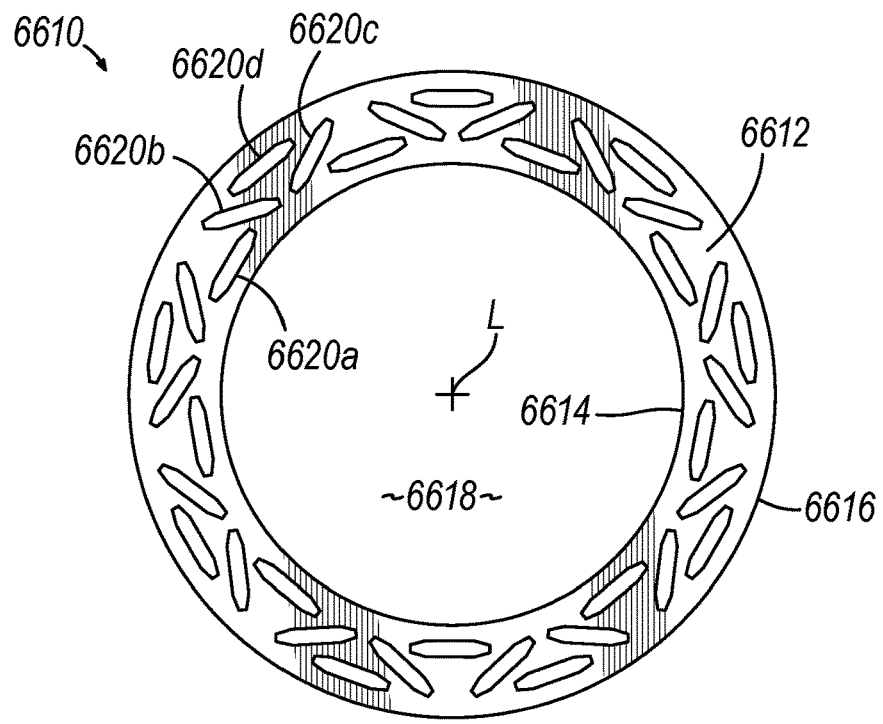
Figure 122:
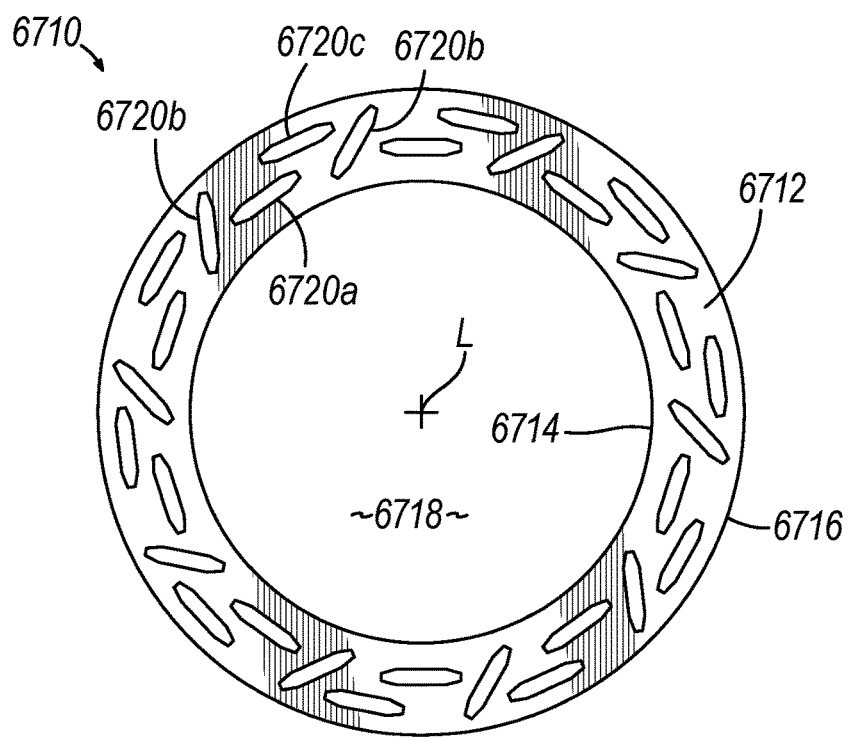
Figure 123:
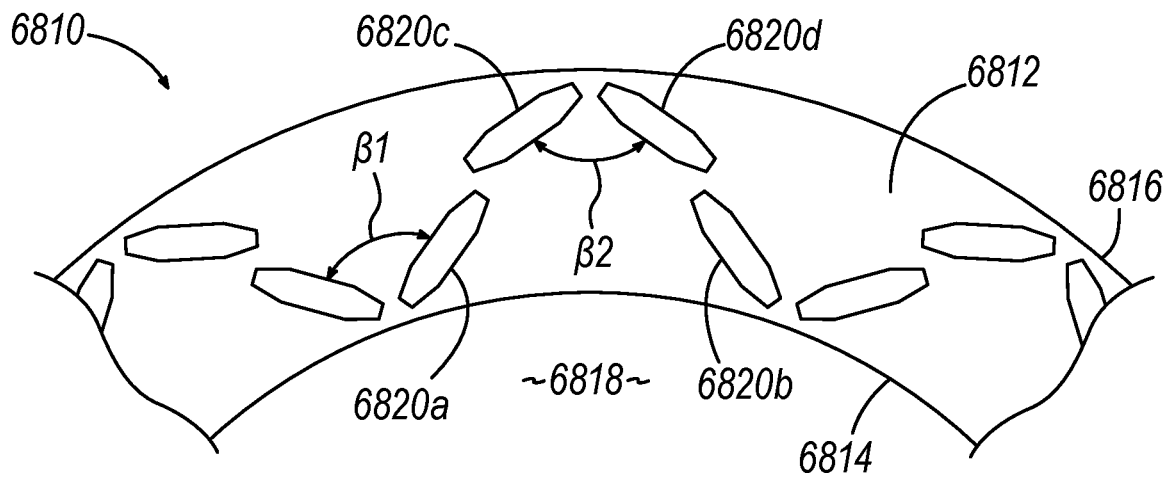
Figure 124:
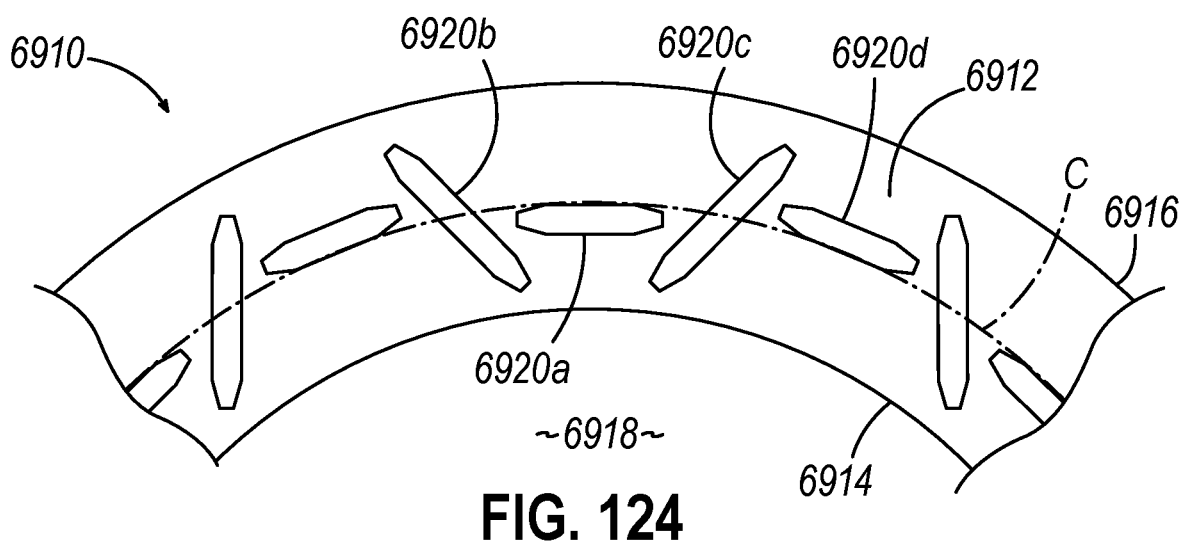
Figure 125A:
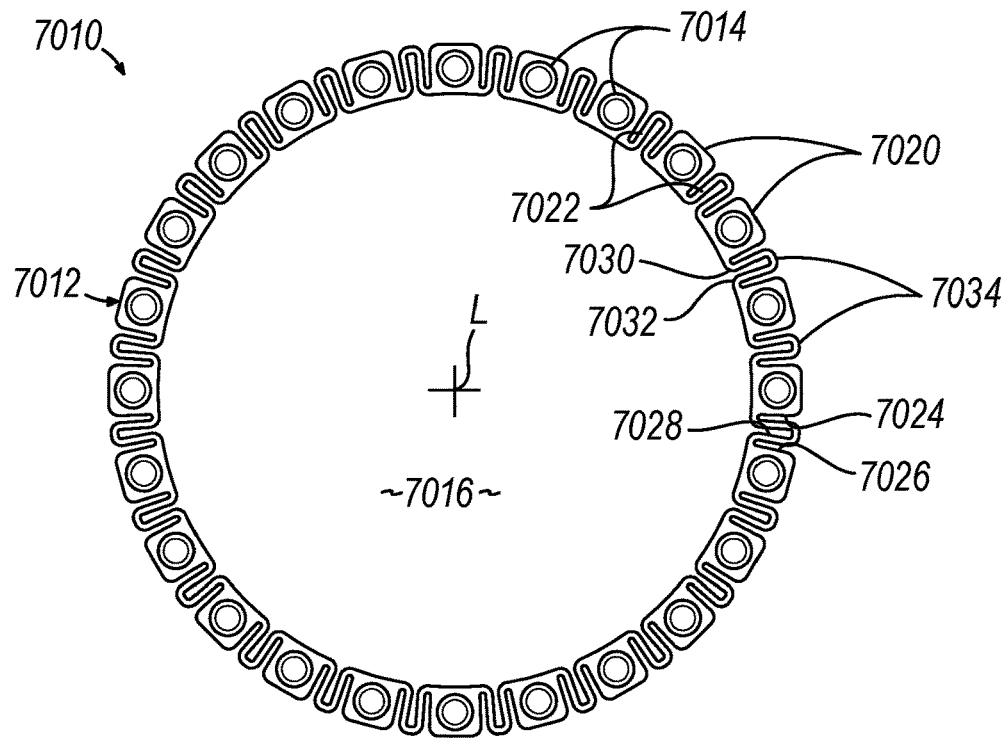
Figure 125B:
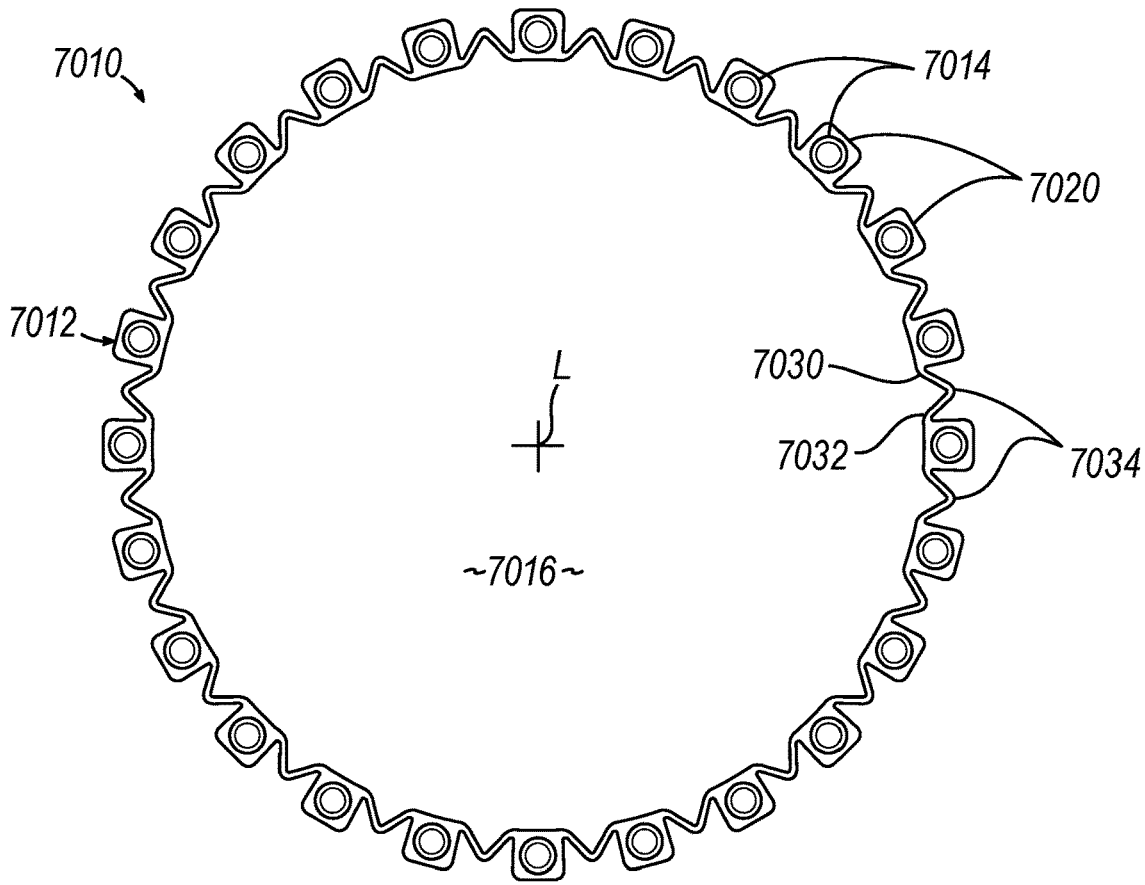
Figure 126:
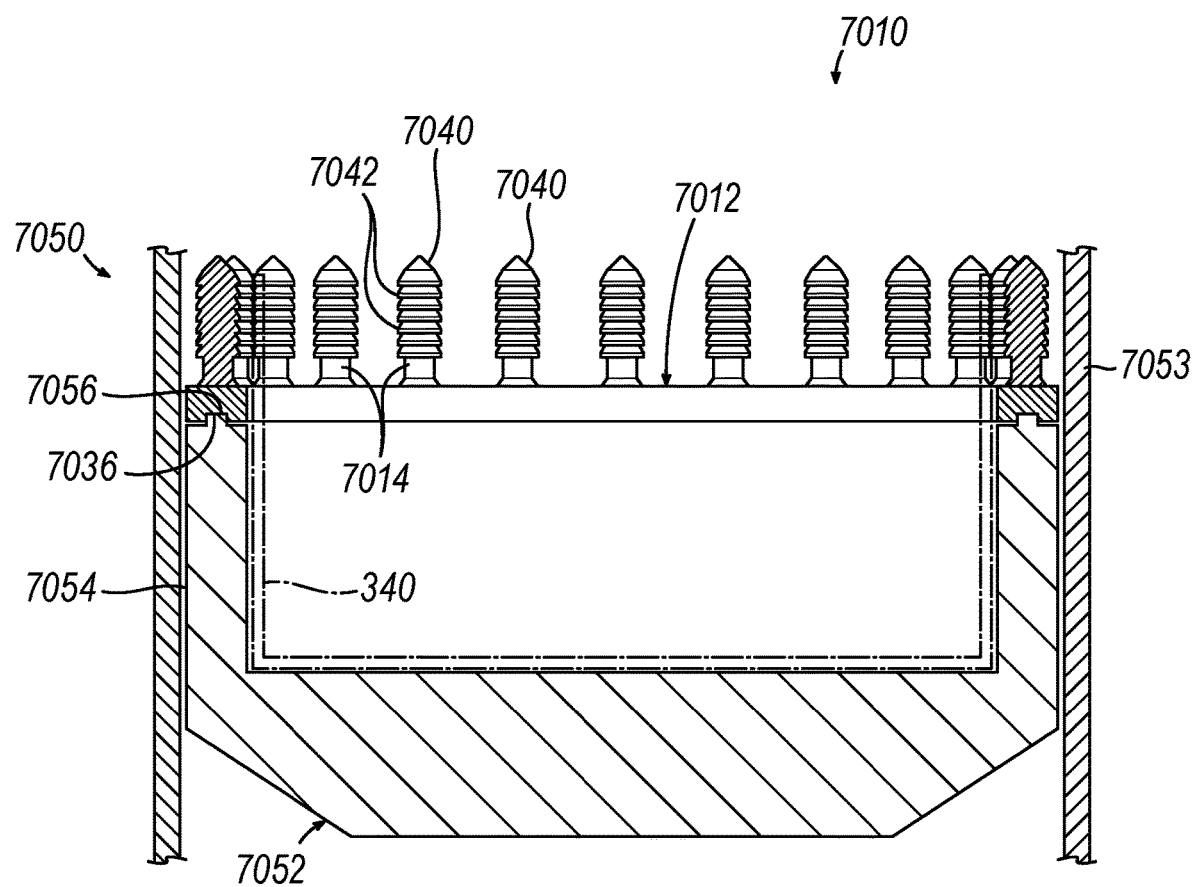
Figure 127:
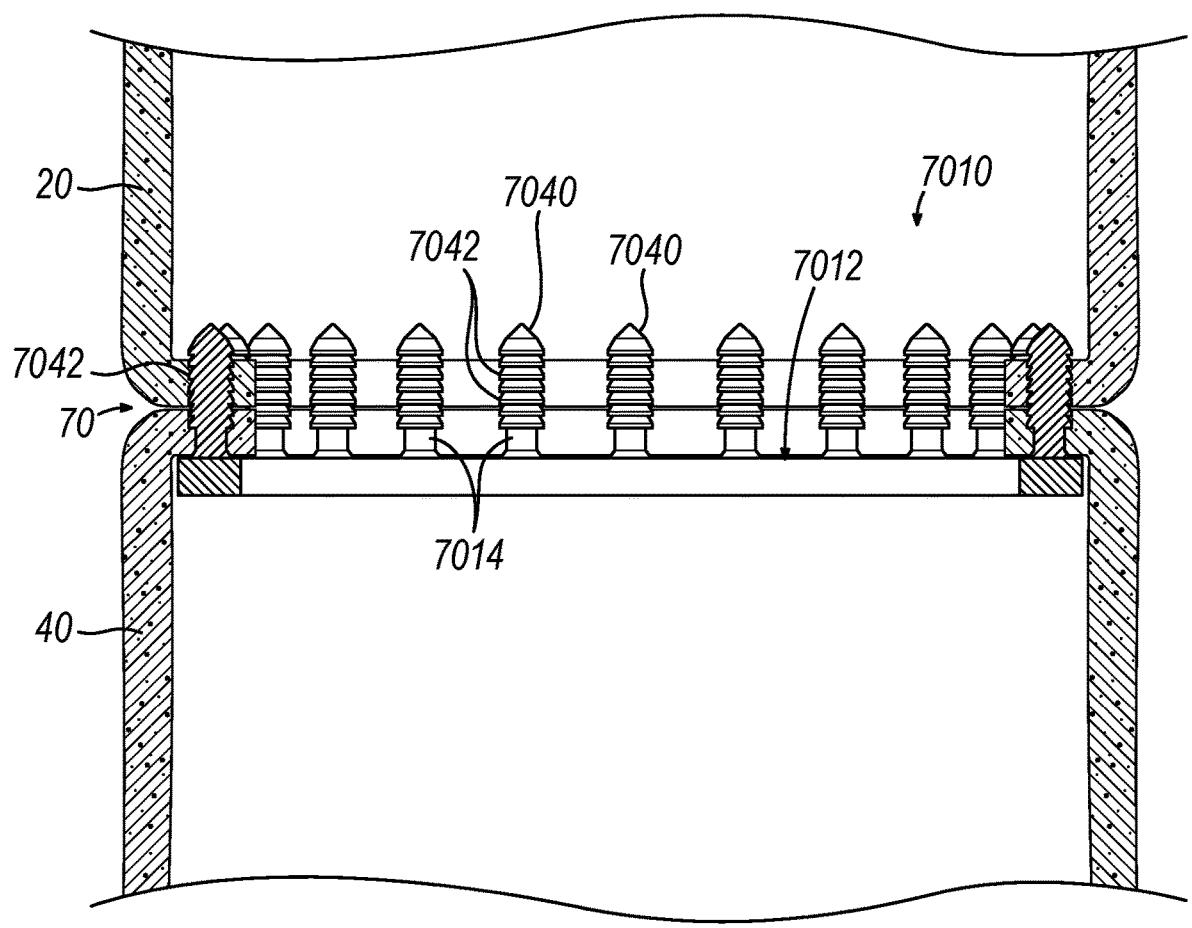
Figure 128A:
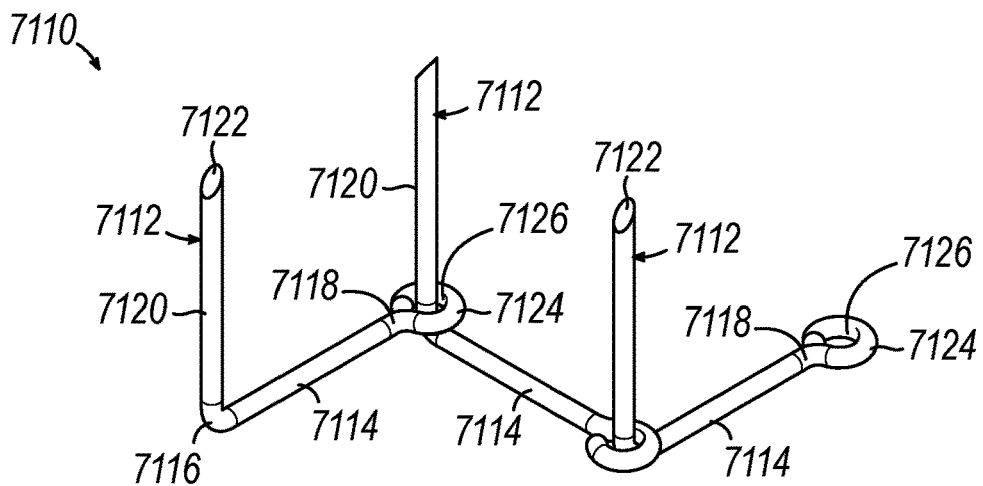
Figure 128B:
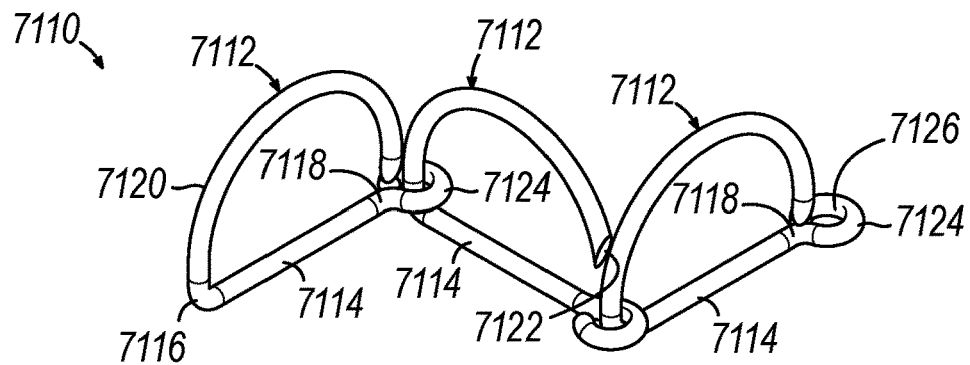
Figure 128C:
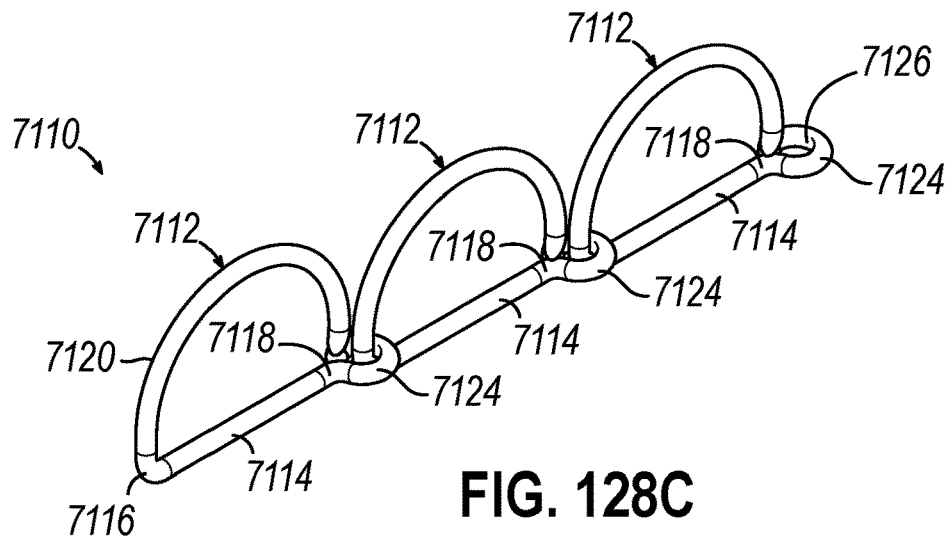
Figure 129:
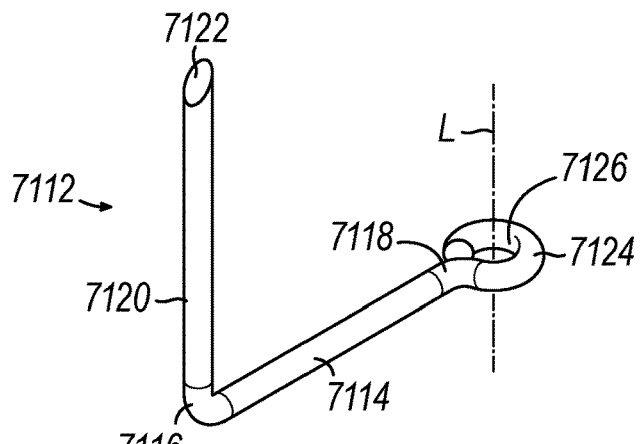
Figure 130:
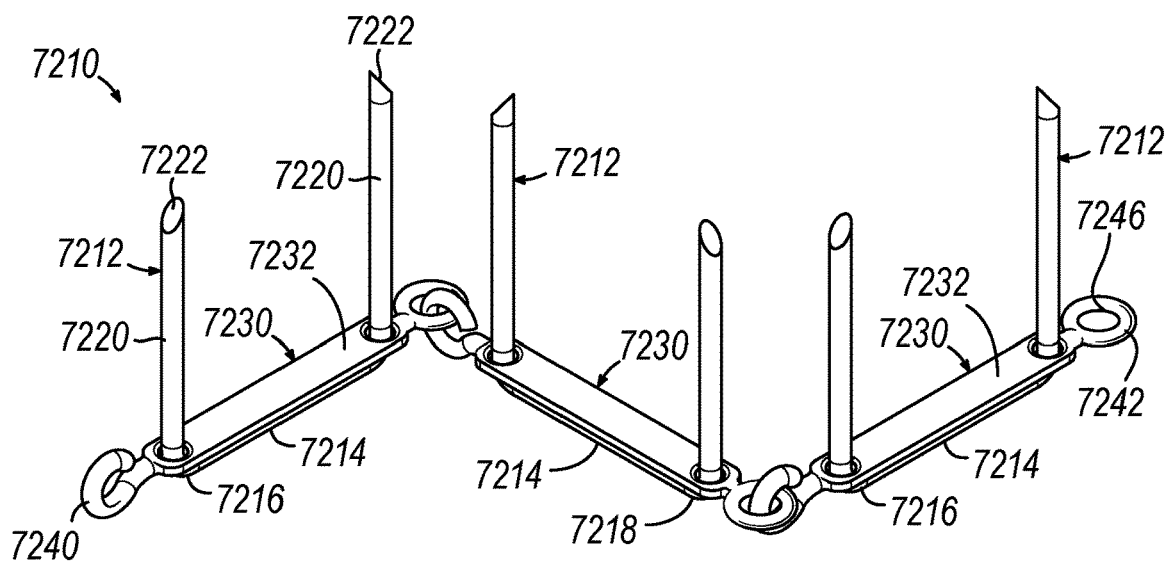
Figure 131:
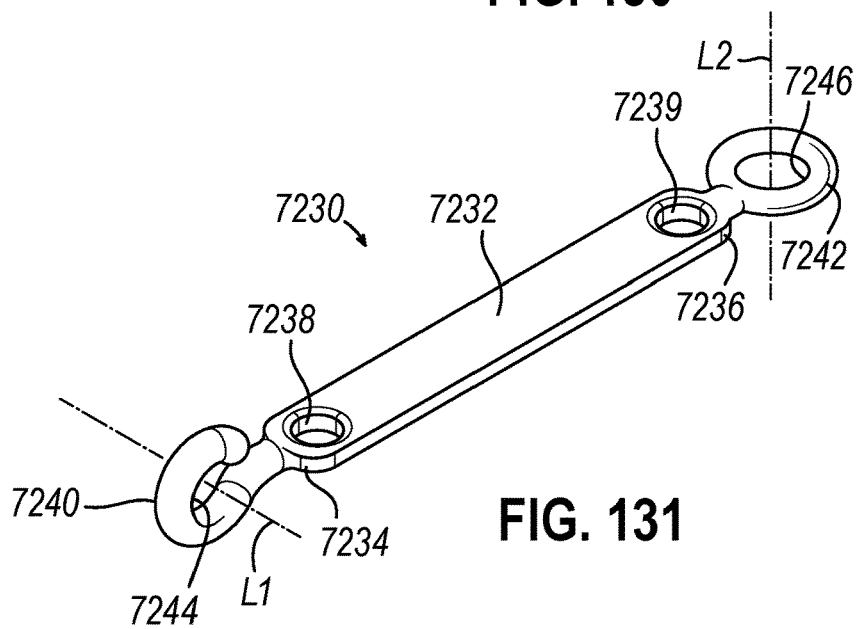
Figure 132:
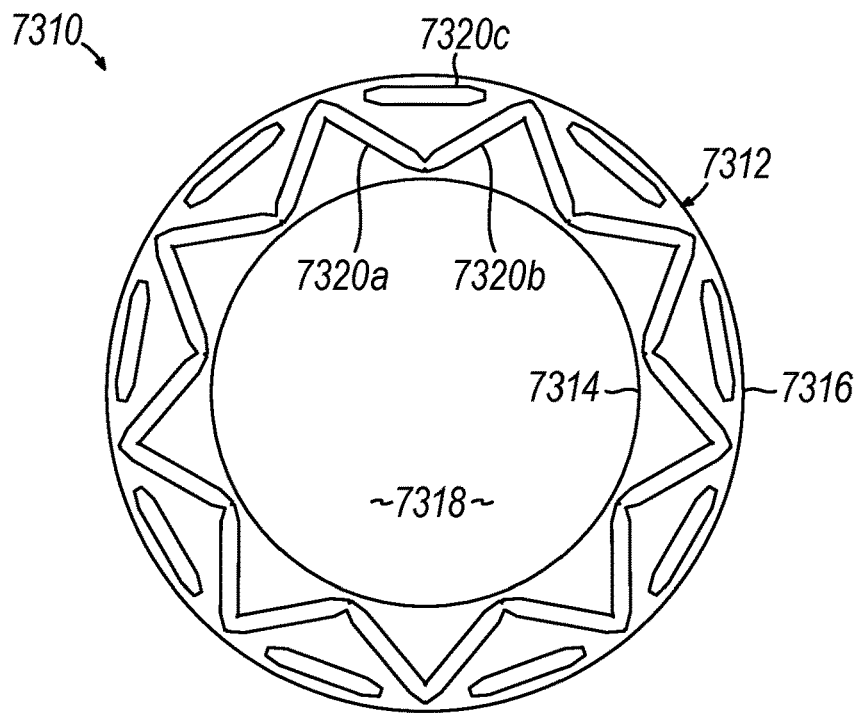
Figure 133:
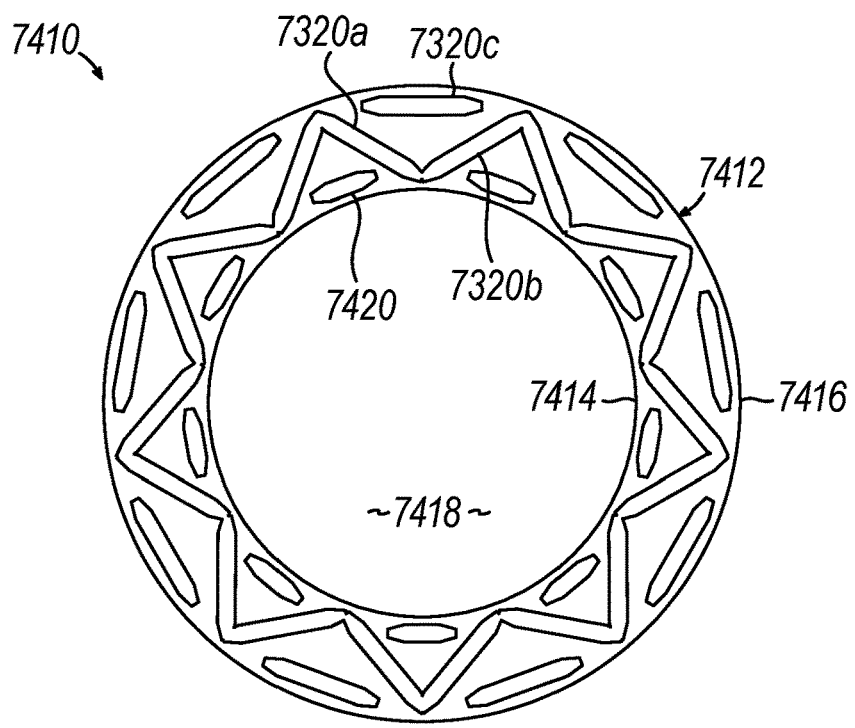
Figure 137:
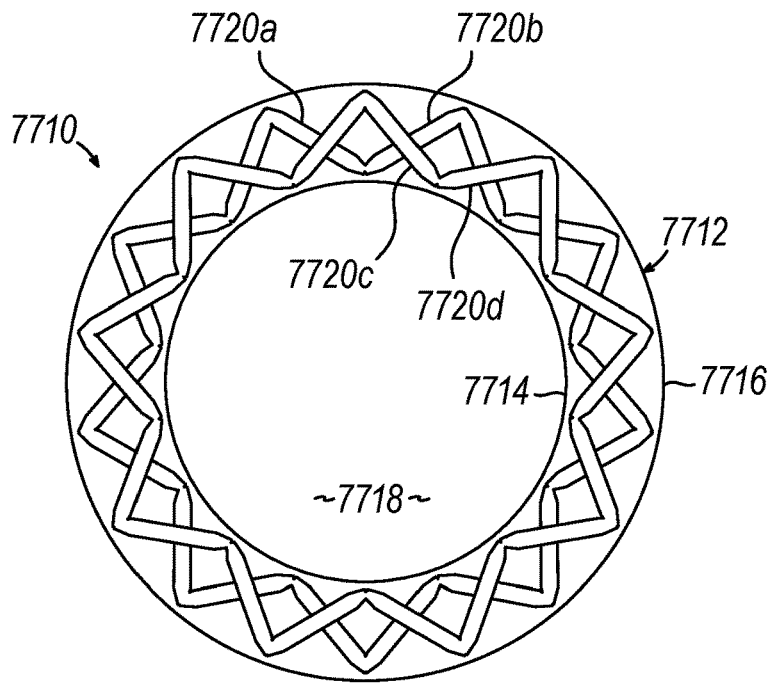
Figure 138:
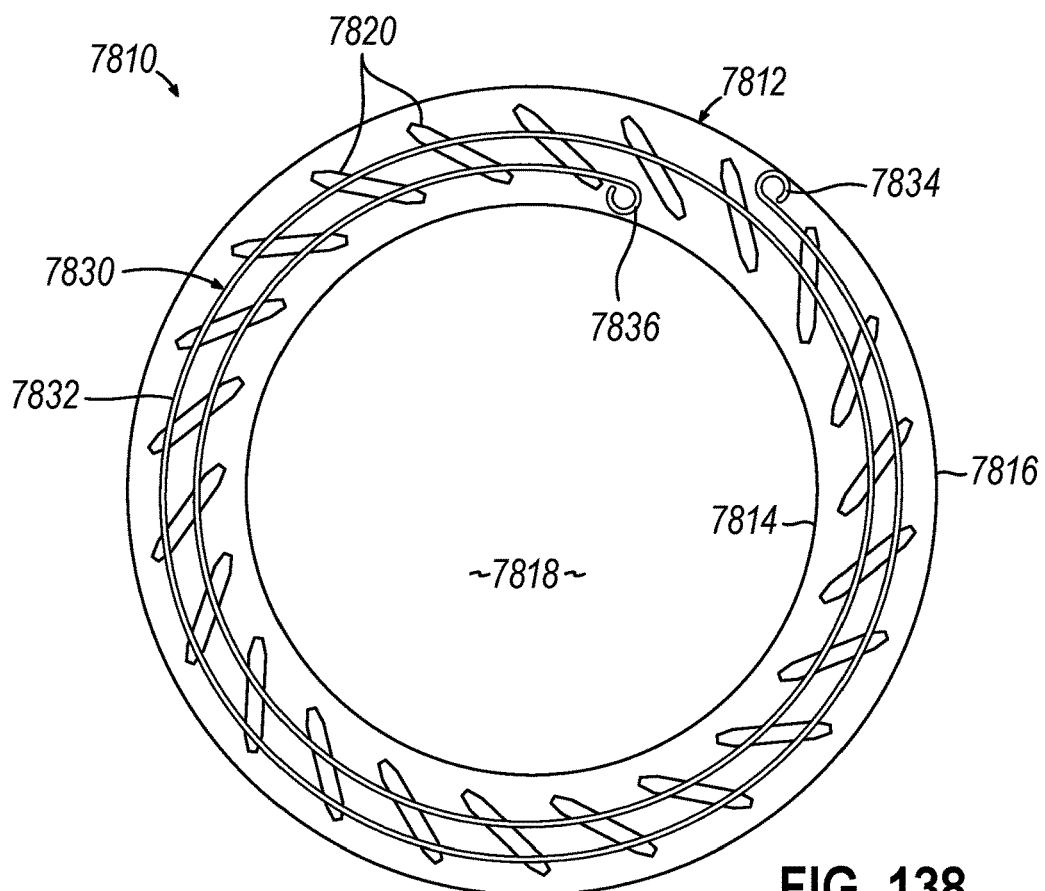
Figure 139:
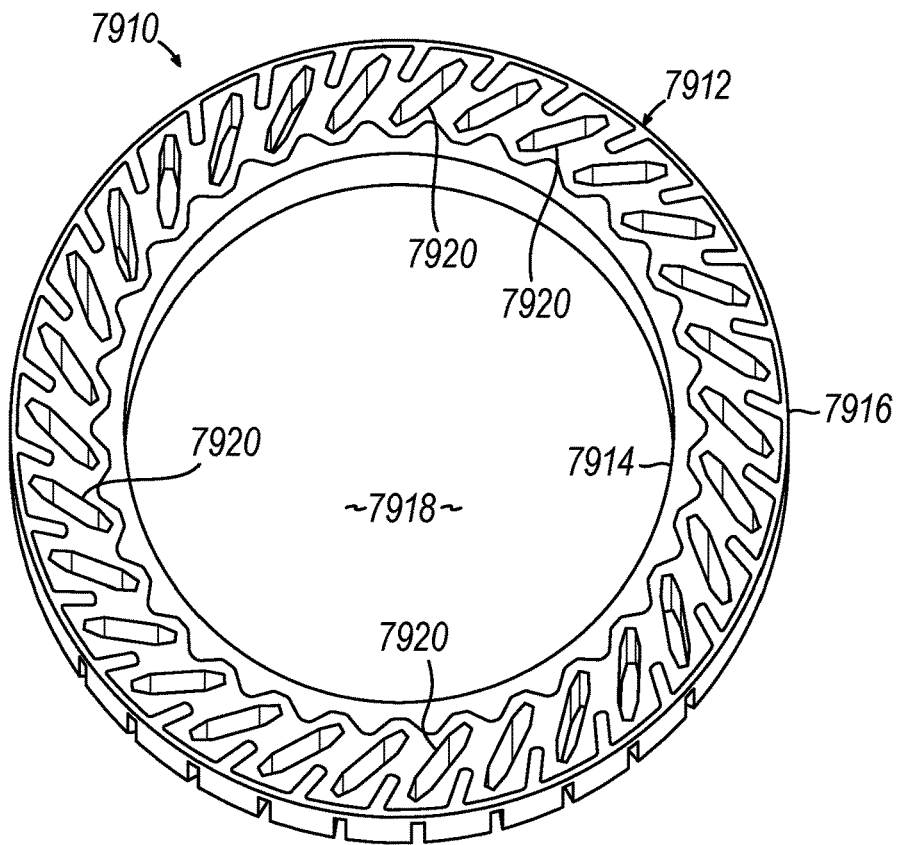
Figure 140A:
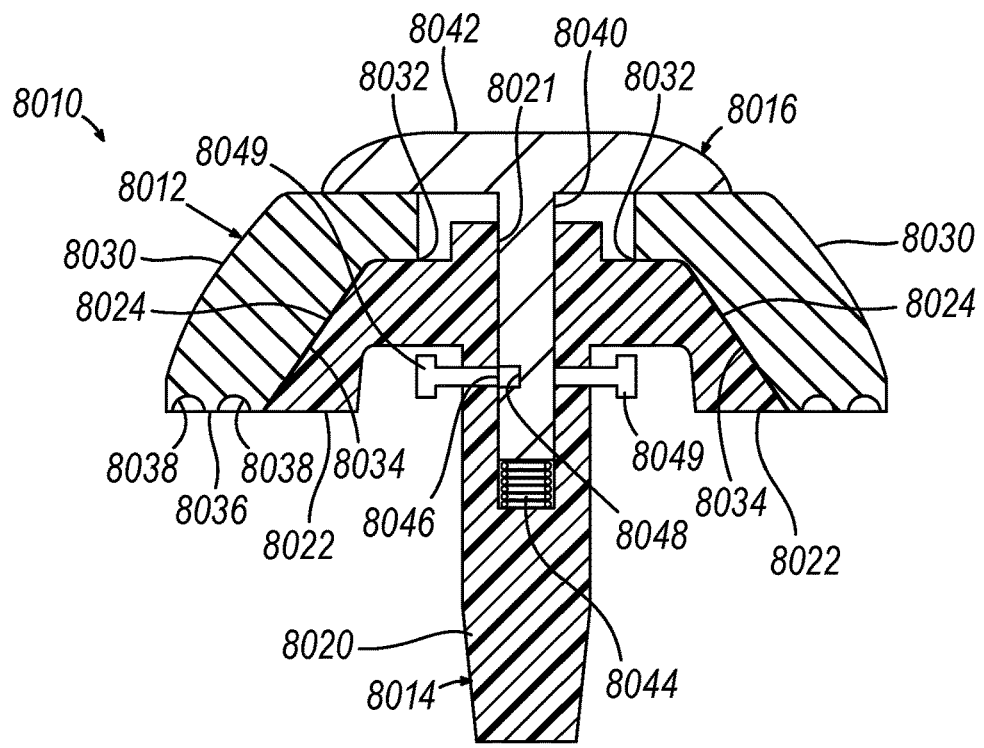
Figure 140B:
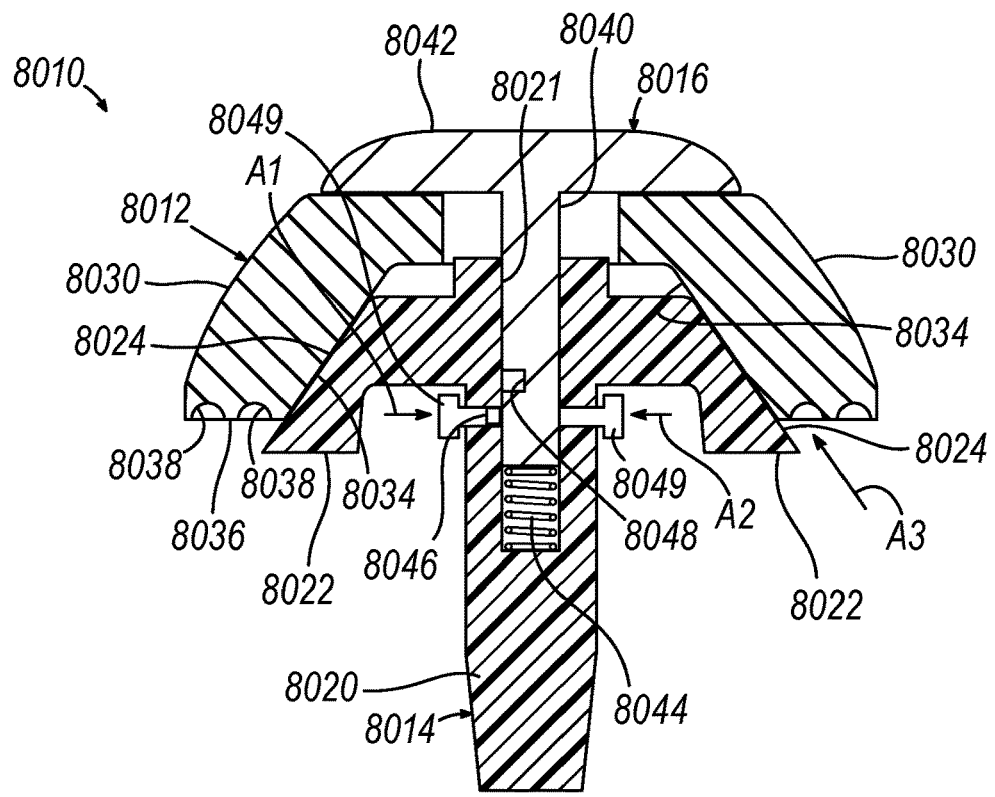
Figure 141:
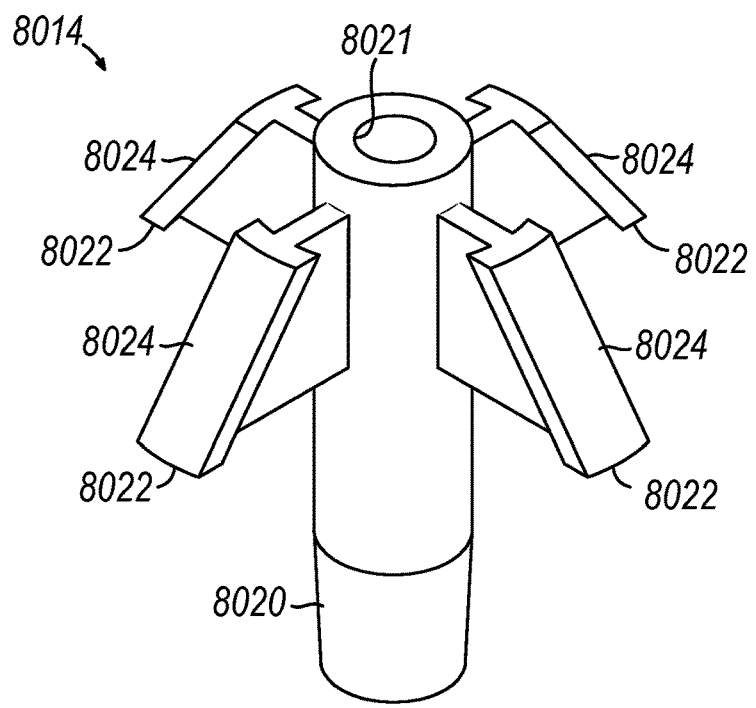
Figure 142A:
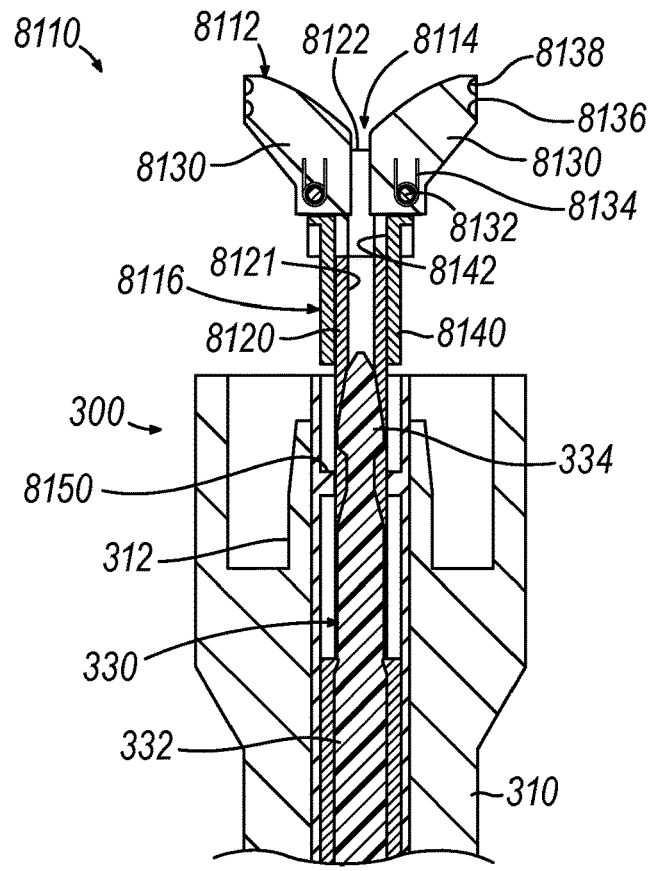
Figure 142B:
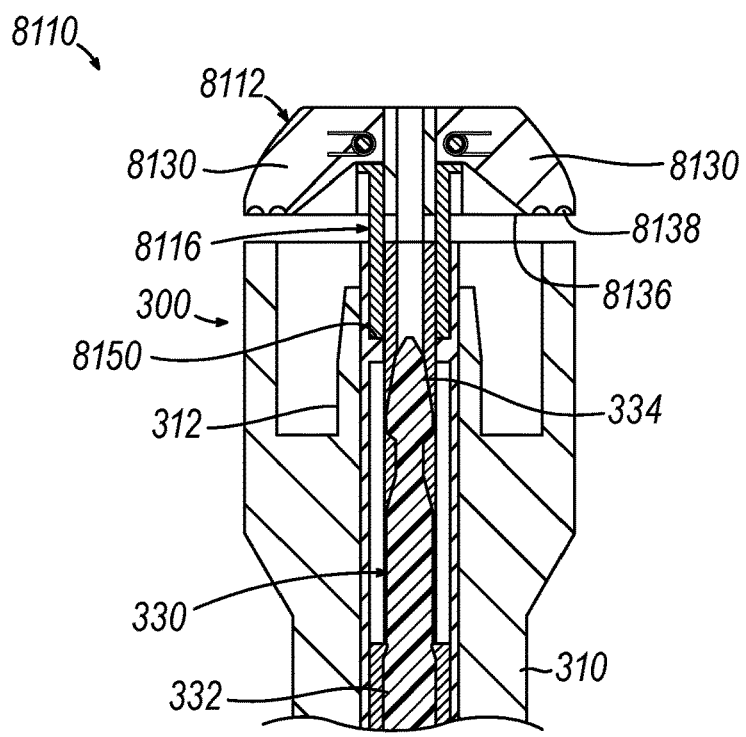
Figure 147:
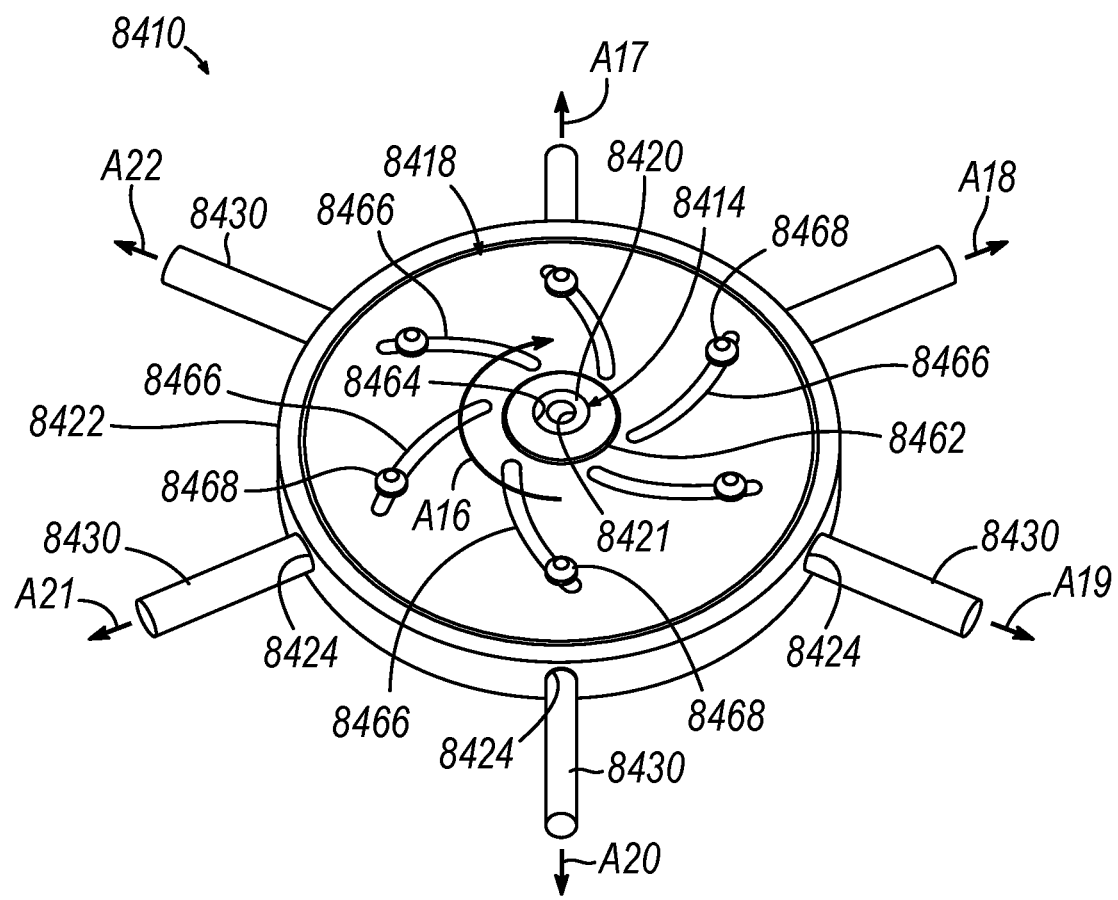
Figure 148:
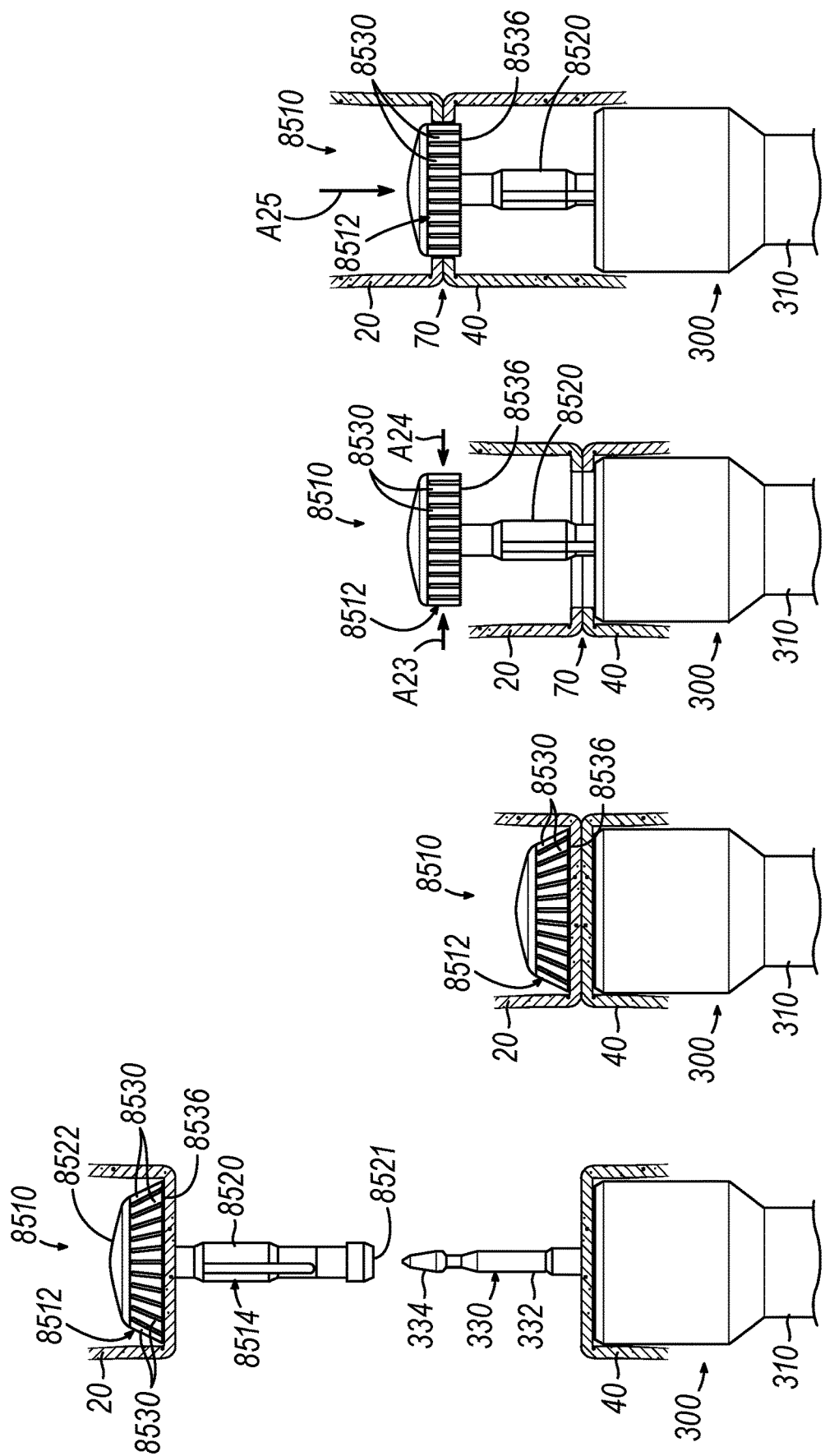
Figure 149:
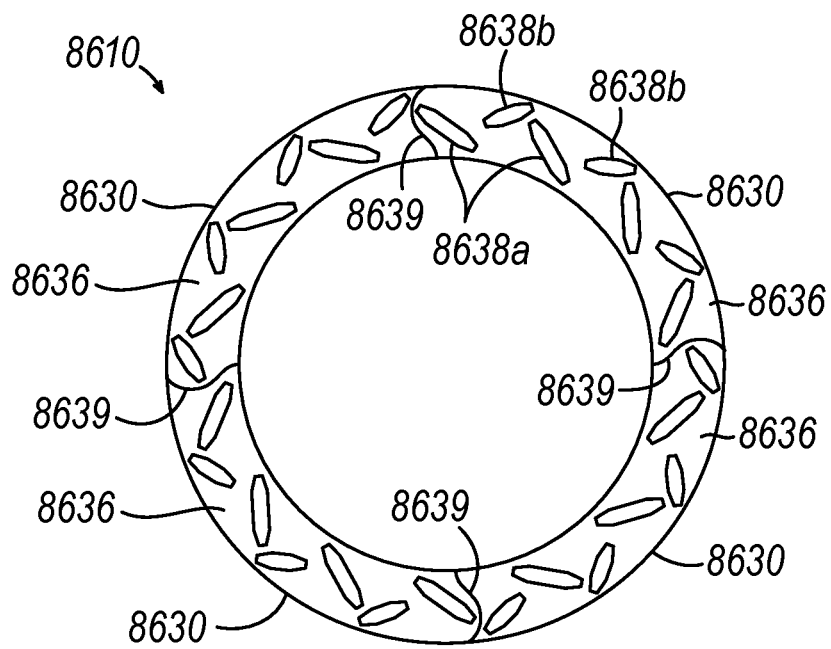
Figure 150:
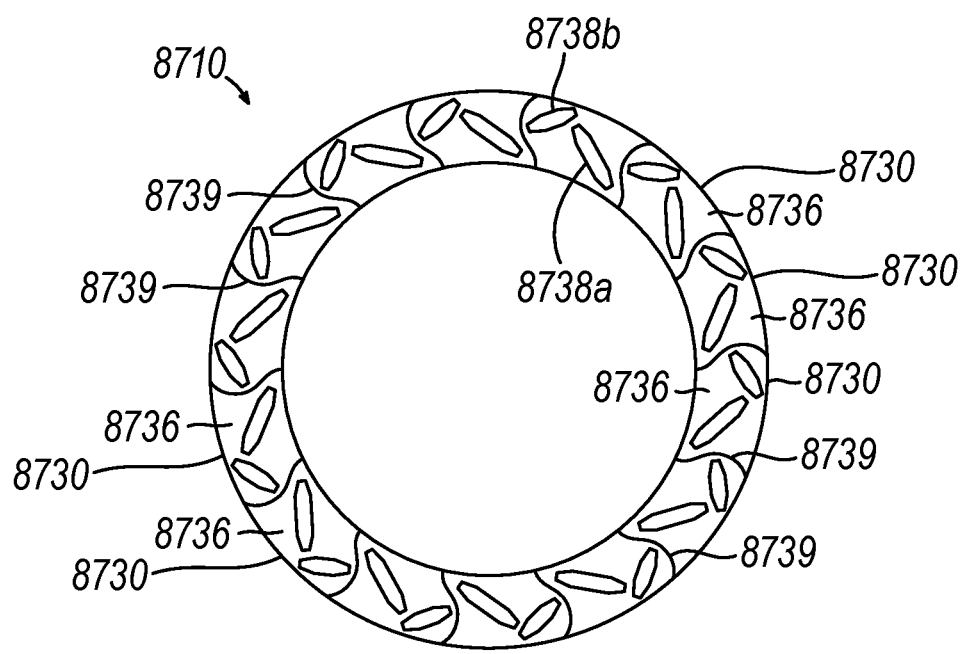

FIG. 101 depicts a top plan view of another exemplary deck member for use with the circular stapler of FIG. 1 and having two concentric annular arrays of linear staple openings arranged relative to each other in a plurality of X-shaped patterns;

FIG. 102A depicts a partial top plan view of two concentric annular arrays of staples driven from the deck member of FIG. 101, showing the annular arrays of staples in a radially unexpanded state;

FIG. 102B depicts a partial top plan view of the annular arrays of staples of FIG. 102A, showing the annular arrays of staples in a first radially expanded state;

FIG. 102C depicts a partial top plan view of the annular arrays of staples of FIG. 102A, showing the annular arrays of staples in a second radially expanded state;

FIG. 103 depicts a top perspective view of another exemplary deck member for use with the circular stapler of FIG. 1 and having a single annular array of X-shaped staple openings having uniform orientations;

FIG. 104 depicts a bottom perspective view of the deck member of FIG. 103;

FIG. 105 depicts a top plan view of the deck member of FIG. 103;

FIG. 106 depicts a top perspective view of an X-shaped staple assembly for use with the deck member of FIG. 103, showing the staple assembly in an initial state;

FIG. 107 depicts a side elevational view of a first staple of the staple assembly of FIG. 106;

FIG. 108A depicts a top perspective view of the staple assembly of FIG. 106 in a two-dimensional formed state;

FIG. 108B depicts a top perspective view of the staple assembly of FIG. 106 in a three-dimensional formed state;

FIG. 109A depicts a partial top plan view of an annular array of X-shaped staple assemblies driven from the deck member of FIG. 103, showing the annular array of staple assemblies in a radially unexpanded state;

FIG. 109B depicts a partial top plan view of the annular array of staple assemblies of FIG. 109A, showing the annular array of staple assemblies in a radially expanded state;

FIG. 110 depicts a top plan view of another exemplary deck member for use with the circular stapler of FIG. 1 and having a single annular array of X-shaped staple openings having alternating orientations;

FIG. 111 depicts a top perspective view of an exemplary X-shaped staple driver and another exemplary X-shaped staple assembly for use with the deck members of FIGS. 103 and 110;

FIG. 112 depicts a top plan view of another exemplary deck member for use with the circular stapler of FIG. 1 and having two concentric annular arrays of X-shaped staple openings;

FIG. 113 depicts a top plan view of another exemplary deck member for use with the circular stapler of FIG. 1 and having a single annular array of alternating linear and X-shaped staple openings;

FIG. 114 depicts a top plan view of another exemplary deck member for use with the circular stapler of FIG. 1 and having a single annular array of alternating deep and shallow X-shaped staple openings;

FIG. 115 depicts a top plan view of another exemplary deck member for use with the circular stapler of FIG. 1 and having a single annular array of overlapping deep X-shaped staple openings;

FIG. 116 depicts a partial top plan view of another exemplary deck member for use with the circular stapler of FIG. 1 and having three concentric annular arrays of staple openings;

FIG. 117A depicts a partial top plan view of three concentric annular arrays of staples driven from the deck member of FIG. 116, showing the annular arrays of staples in a radially unexpanded state;

FIG. 117B depicts a partial top plan view of the annular arrays of staples of FIG. 117A, showing the annular arrays of staples in a radially expanded state;

FIG. 118 depicts a partial top plan view of another exemplary deck member for use with the circular stapler of FIG. 1 and having four concentric annular arrays of staples;

FIG. 119 depicts a top plan view of another exemplary deck member for use with the circular stapler of FIG. 1 and having two concentric star-shaped arrays of linear staple openings;

FIG. 120A depicts a partial top plan view of two concentric star-shaped arrays of staples driven from the deck member of FIG. 119, showing the star-shaped arrays of staples in a radially unexpanded state;

FIG. 120B depicts a partial top plan view of the star-shaped arrays of staples of FIG. 120A, showing the star-shaped arrays of staples in a first radially expanded state;

FIG. 120C depicts a partial top plan view of the star-shaped arrays of staples of FIG. 120A, showing the star-shaped arrays of staples in a second radially expanded state;

FIG. 121 depicts a top plan view of another exemplary deck member for use with the circular stapler of FIG. 1 and having three concentric annular arrays of linear staple openings arranged relative to each other in a plurality of triangle-shaped patterns;

FIG. 122 depicts a top plan view of another exemplary deck member for use with the circular stapler of FIG. 1 and having three concentric annular arrays of linear staple openings arranged relative to each other in a plurality of parallelogram-shaped patterns;

FIG. 123 depicts a partial top plan view of another exemplary deck member for use with the circular stapler of FIG. 1 and having two concentric annular arrays of linear staple openings;

FIG. 124 depicts a partial top plan view of another exemplary deck member for use with the circular stapler of FIG. 1 and having three concentric annular arrays of linear staple openings;

FIG. 125A depicts a top plan view of an exemplary flexible barbed ring in a radially unexpanded state;

FIG. 125B depicts a top plan view of the flexible barbed ring of FIG. 125A, showing the flexible barbed ring a radially expanded state;

FIG. 126 depicts a cross-sectional side view of the flexible barbed ring of FIG. 125A, showing the flexible barbed ring loaded onto an exemplary fastening head assembly;

FIG. 127 depicts a cross-sectional side view of the flexible barbed ring of FIG. 125A, showing the flexible barbed ring securing first and second sections of the digestive tract of FIG. 7A together at an end-to-end anastomosis;

FIG. 128A depicts a partial perspective view of an exemplary staple chain for use with the circular stapler of FIG. 1, showing each staple of the staple chain in an initial state, and further showing the staple chain in a radially unexpanded state;

FIG. 128B depicts a partial perspective view of the staple chain of FIG. 128A, showing each staple of the staple chain in a formed state, and further showing the staple chain in the radially unexpanded state;

FIG. 128C depicts a partial perspective view of the staple chain of FIG. 128A, showing each staple of the staple chain in the formed state, and further showing the staple chain in a radially expanded state;

FIG. 129 depicts a perspective view of a staple of the staple chain of FIG. 128A, showing the staple in the initial state;

FIG. 130 depicts a partial perspective view of another exemplary staple chain for use with the circular stapler of FIG. 1, showing each staple of the staple chain in an initial state, and further showing the staple chain in a radially unexpanded state;

FIG. 131 depicts a perspective view of a backspan of the staple chain of FIG. 130;

FIG. 132 depicts a top plan view of another exemplary deck member for use with the circular stapler of FIG. 1 and having two concentric annular arrays of linear staple openings, with the linear staple openings of the radially inner array overlapping each other in an undulating pattern;

FIG. 133 depicts a top plan view of another exemplary deck member for use with the circular stapler of FIG. 1 and having three concentric annular arrays of linear staple openings, with the linear staple openings of the radially intermediate array overlapping each other in an undulating pattern;

FIG. 134 depicts a top plan view of another exemplary deck member for use with the circular stapler of FIG. 1 and having two concentric annular arrays of linear staple openings overlapping each other in an undulating pattern;

FIG. 135 depicts a magnified view of a select area as indicated in FIG. 134, showing the staple chain of FIG. 128A positioned within three adjacent staple openings of the deck member;

FIG. 136 depicts a top plan view of another exemplary deck member for use with the circular stapler of FIG. 1 and having three concentric annular arrays of linear staple openings, with the linear staple openings of the radially outer and radially intermediate arrays overlapping each other in an undulating pattern;

FIG. 137 depicts a top plan view of another exemplary deck member for use with the circular stapler of FIG. 1 and having a single annular array of linear staple openings overlapping each other in a double-undulating pattern;

FIG. 138 depicts a top plan view of another exemplary deck member for use with the circular stapler of FIG. 1 and having a single annular array of linear staple openings, showing an expandable ring positioned over the array of linear staple openings so as to be captured by staples deployed from the staple openings;

FIG. 139 depicts a top perspective view another exemplary deck member for use with the circular stapler of FIG. 1 and having a single annular array of linear staple openings in a radial spiral pattern;

FIG. 140A depicts a cross-sectional side view of another exemplary anvil for use with the circular stapler of FIG. 1, showing an anvil cap of the anvil in a proximal state, and further showing anvil head segments of the anvil in respective radially extended states;

FIG. 140B depicts a cross-sectional side view of the anvil of FIG. 140A, showing the anvil cap in a distal state, and further showing the anvil head segments in respective radially unextended states;

FIG. 141 depicts a perspective view of an anvil core of the anvil of FIG. 140A;

FIG. 142A depicts a cross-sectional side view of another exemplary anvil secured to the trocar of the stapling head assembly of FIG. 4 with the anvil spaced distally from the tubular body member of the stapling head assembly, showing a push member of the anvil in a proximal state, and further showing anvil head segments of the anvil in respective radially unextended states;

FIG. 142B depicts a cross-sectional side view of the anvil of FIG. 142A secured to the trocar of the stapling head assembly of FIG. 4 with the anvil retracted proximally toward the tubular body member of the stapling head assembly, showing the push member of the anvil in a distal state, and further showing the anvil head segments in respective radially extended states;

FIG. 143A depicts a cross-sectional side view of another exemplary anvil secured to the trocar of the stapling head assembly of FIG. 4 with the anvil spaced distally from the tubular body member of the stapling head assembly, showing a push member of the anvil in a proximal state, and further showing anvil head segments of the anvil in respective radially unextended states;

FIG. 143B depicts a cross-sectional side view of the anvil of FIG. 143A secured to the trocar of the stapling head assembly of FIG. 4 with the anvil retracted proximally toward the tubular body member of the stapling head assembly, showing the push member of the anvil in a distal state, and further showing the anvil head segments in respective radially extended states;

FIG. 144 depicts a perspective view of the anvil of FIG. 143A;

FIG. 145A depicts a cross-sectional side view of another exemplary anvil secured to the trocar of the stapling head assembly of FIG. 4 with the anvil spaced distally from the tubular body member of the stapling head assembly, showing a push member of the anvil in a proximal state, and further showing anvil head segments of the anvil in respective radially unextended states;

FIG. 145B depicts a cross-sectional side view of the anvil of FIG. 145A secured to the trocar of the stapling head assembly of FIG. 4 with the anvil retracted proximally toward the tubular body member of the stapling head assembly, showing the push member of the anvil in a distal state, and further showing the anvil head segments in respective radially extended states;

FIG. 146A depicts a top plan view of the anvil of FIG. 145A, showing the anvil head segments in the radially unextended states;

FIG. 146B depicts a top plan view of the anvil of FIG. 145A, showing the anvil head segments in the radially extended states;

FIG. 147 depicts a partial perspective view of another exemplary anvil for use with the circular stapler of FIG. 1, showing anvil head segment actuating rods of the anvil in respective radially extended states;

FIG. 148A depicts a side elevational view of another exemplary anvil positioned within a first section of a digestive tract and the stapling head assembly of FIG. 4 positioned within a separate second section of the digestive tract, with the anvil separated from the stapling head assembly, showing anvil head segments of the anvil in respective radially extended states;

FIG. 148B depicts a side elevational view of the anvil of FIG. 148A positioned within the first section of the digestive tract and the stapling head assembly of FIG. 4 positioned within the separate second section of the digestive tract, with the anvil secured to the stapling head assembly and retracted toward the stapling head assembly to thereby clamp tissue between the anvil and the stapling head assembly, showing the anvil head segments in the radially extended states;

FIG. 148C depicts a side elevational view of the anvil of FIG. 148A positioned within the first section of the digestive tract and the stapling head assembly of FIG. 4 positioned within the second section of the digestive tract, with the anvil spaced distally from the stapling head assembly after the stapling head assembly has been actuated to sever and staple the clamped tissue thereby joining the first and second sections of the digestive tract at an end-to-end anastomosis, showing the anvil head segments in respective radially unextended states;

FIG. 148D depicts a side elevational view of the anvil of FIG. 148A retracted through the anastomosis toward the second section of the digestive tract, showing the anvil head segments in the radially unextended states;

FIG. 149 depicts a bottom plan view of an exemplary segmented anvil head for use with the circular stapler of FIG. 1 and having four anvil head segments separated from each other by S-shaped slots; and FIG. 150 depicts a bottom plan view of another exemplary segmented anvil head for use with the circular stapler of FIG. 1 and having fourteen anvil head segments separated from each other by S-shaped slots.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," "clockwise," "counterclockwise," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
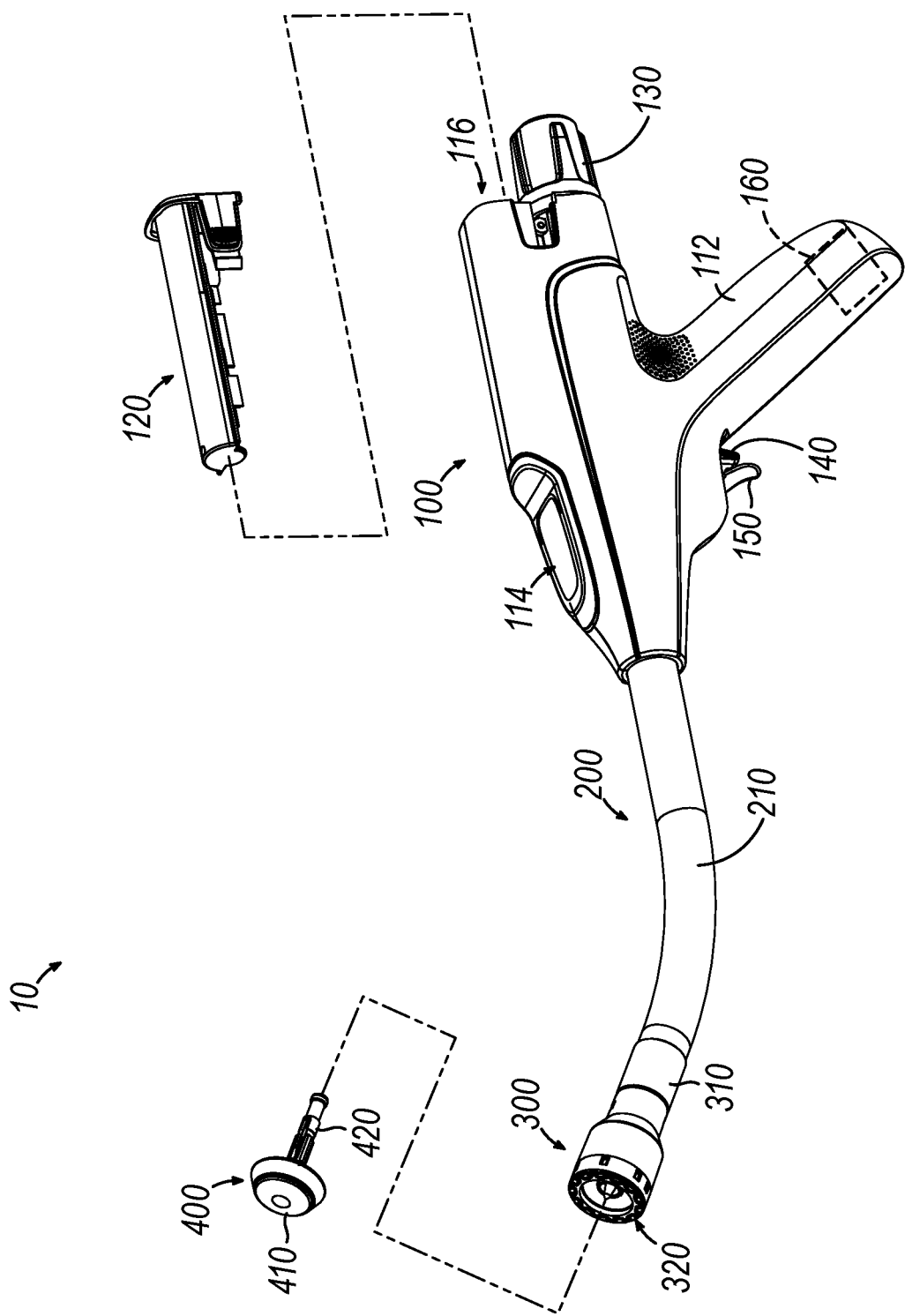
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
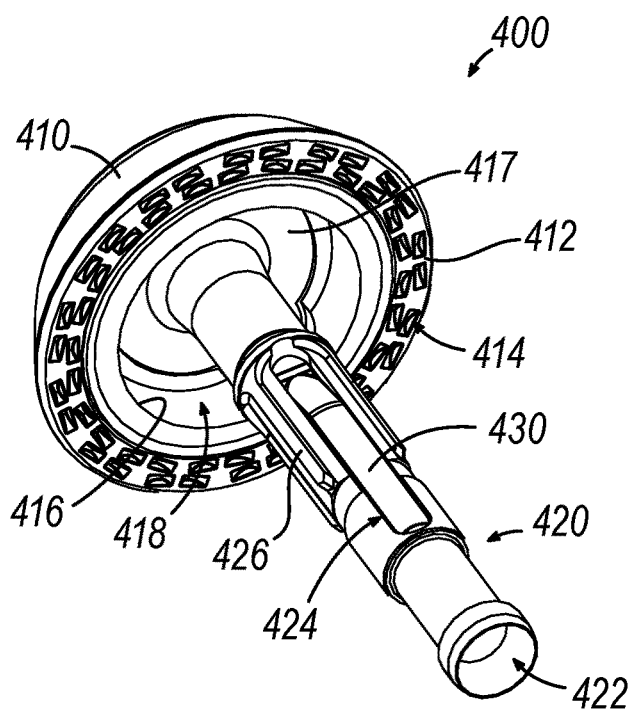
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members.

B. Exemplary Stapling Head Assembly

Figure 5:
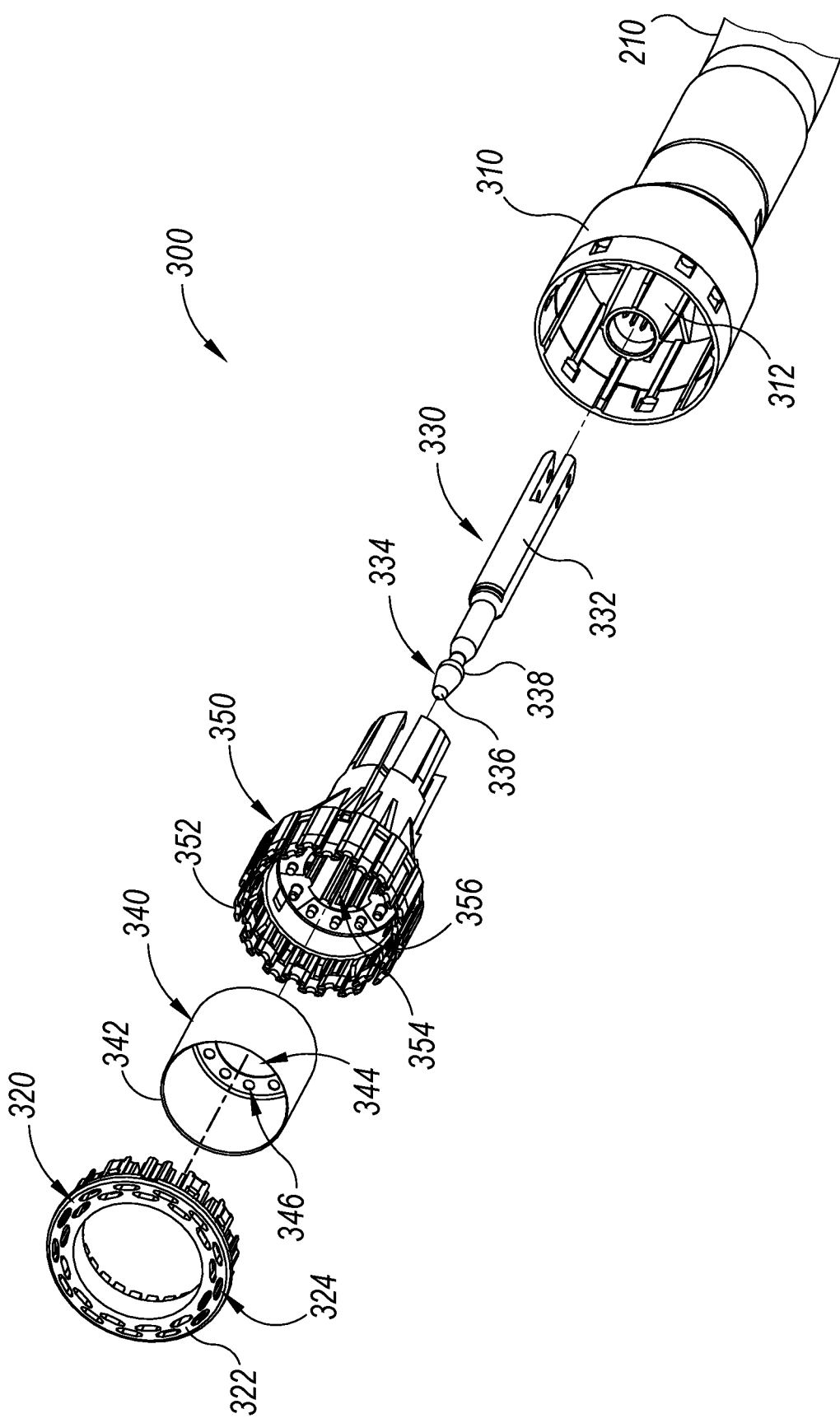
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 4, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
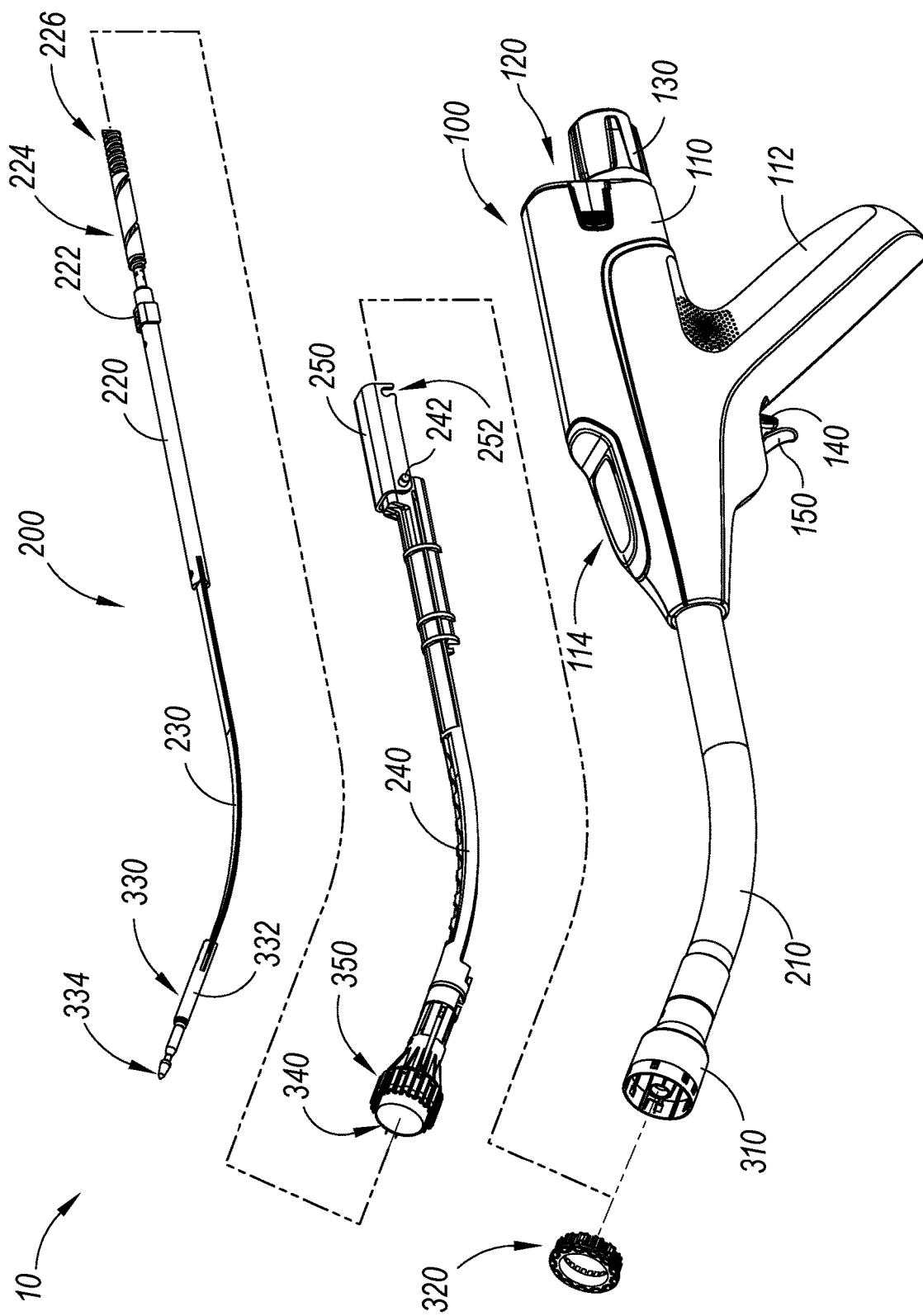
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
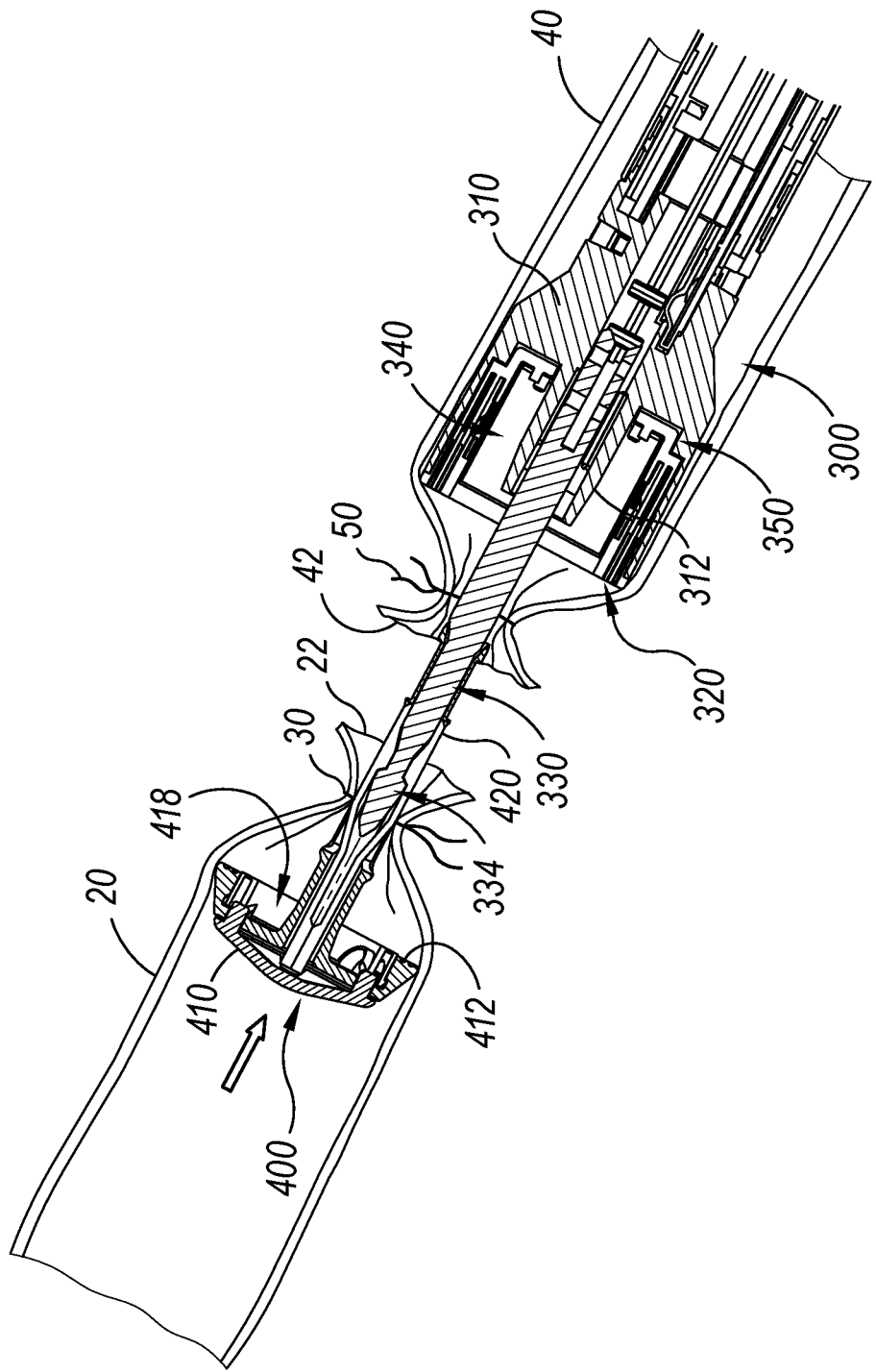
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
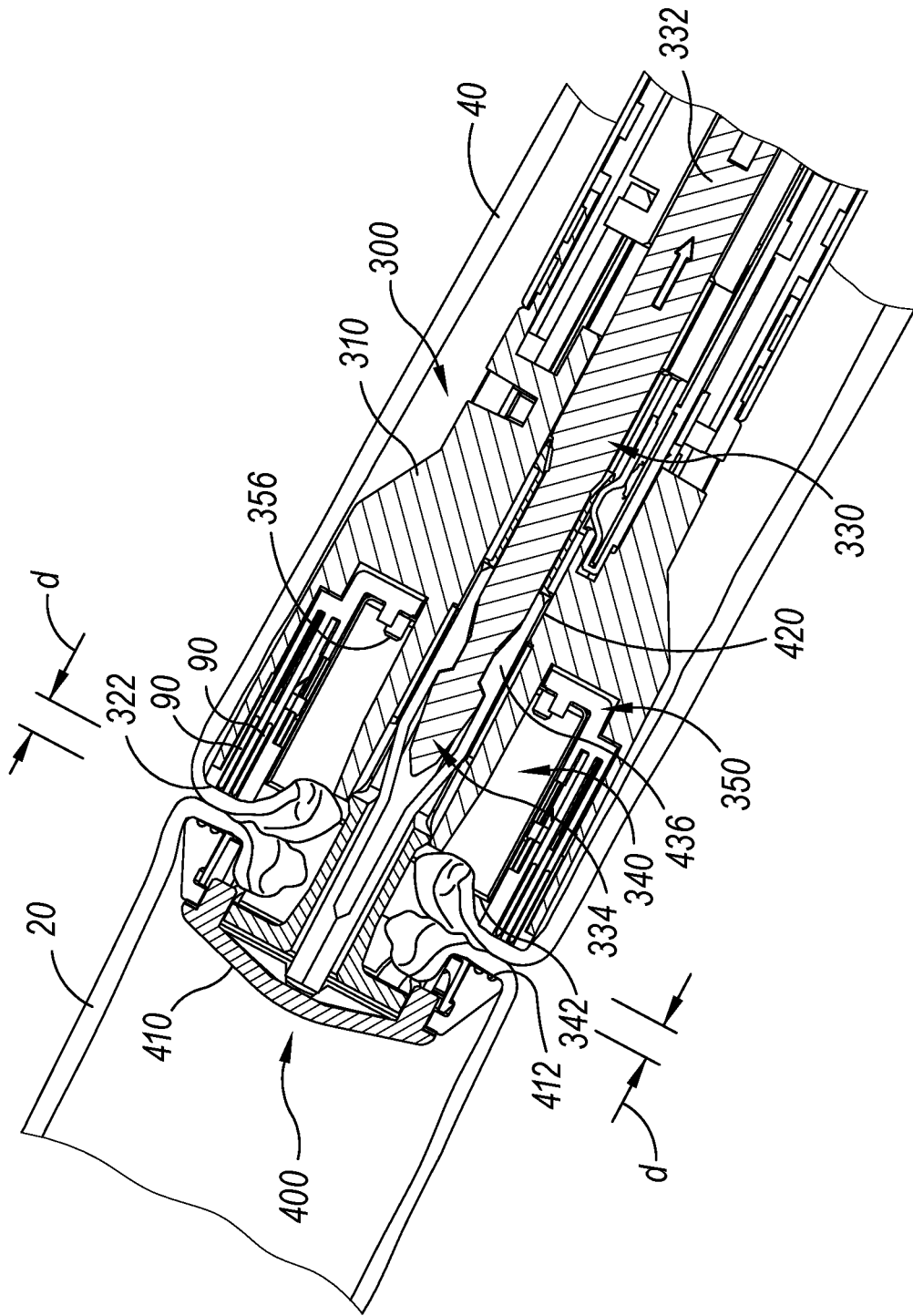
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
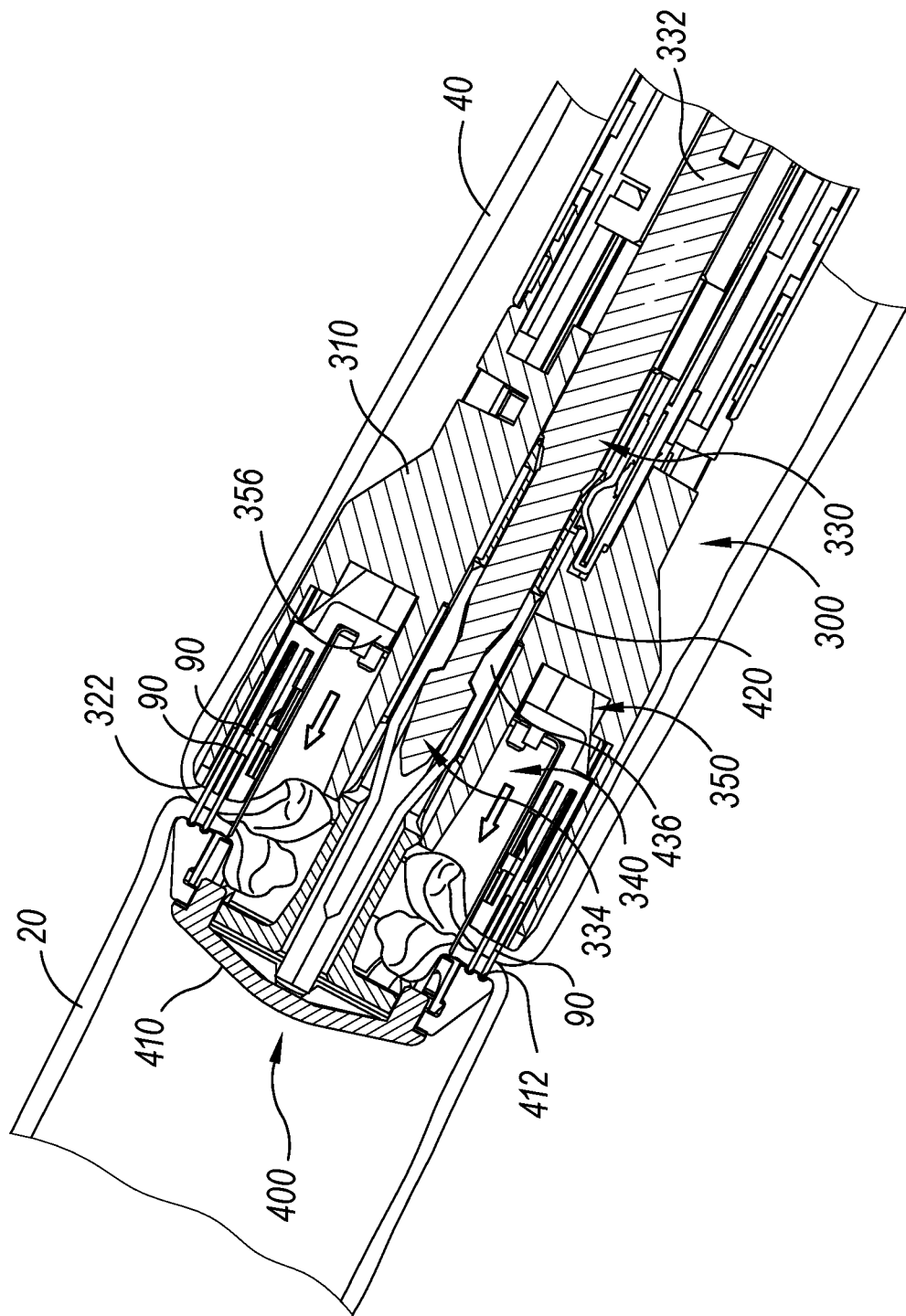
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
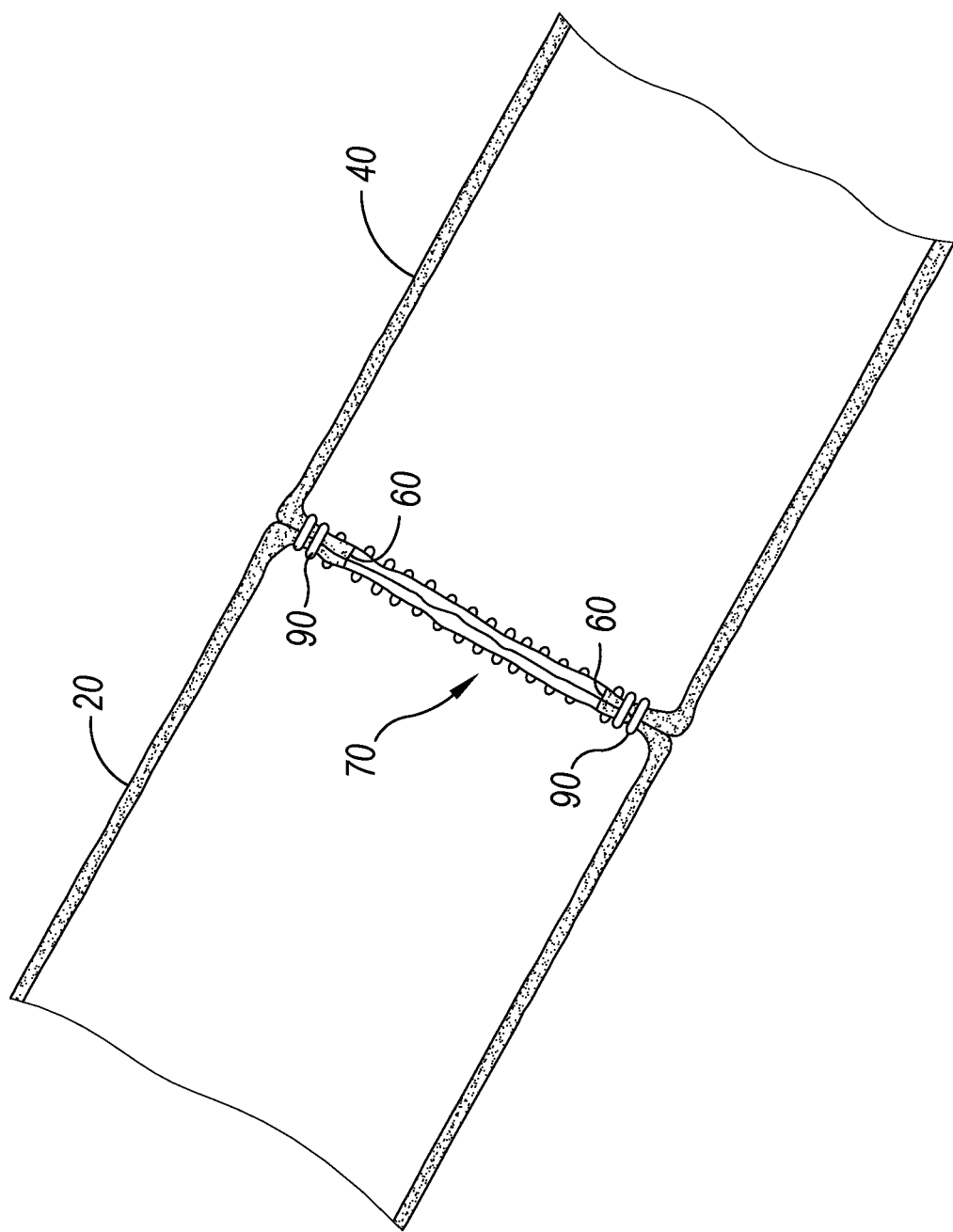
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary End Effector Having Staple Forming Features Arranged in Multiple Orientations As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable the annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and anvil (400) with features that enable formation of such an anastomosis and/or patterns of formed staples (90). Exemplary versions of such features are described in greater detail below.

A. Stapling Head Assembly with Alternating Arrays of Staple Forming Features

Figure 8:
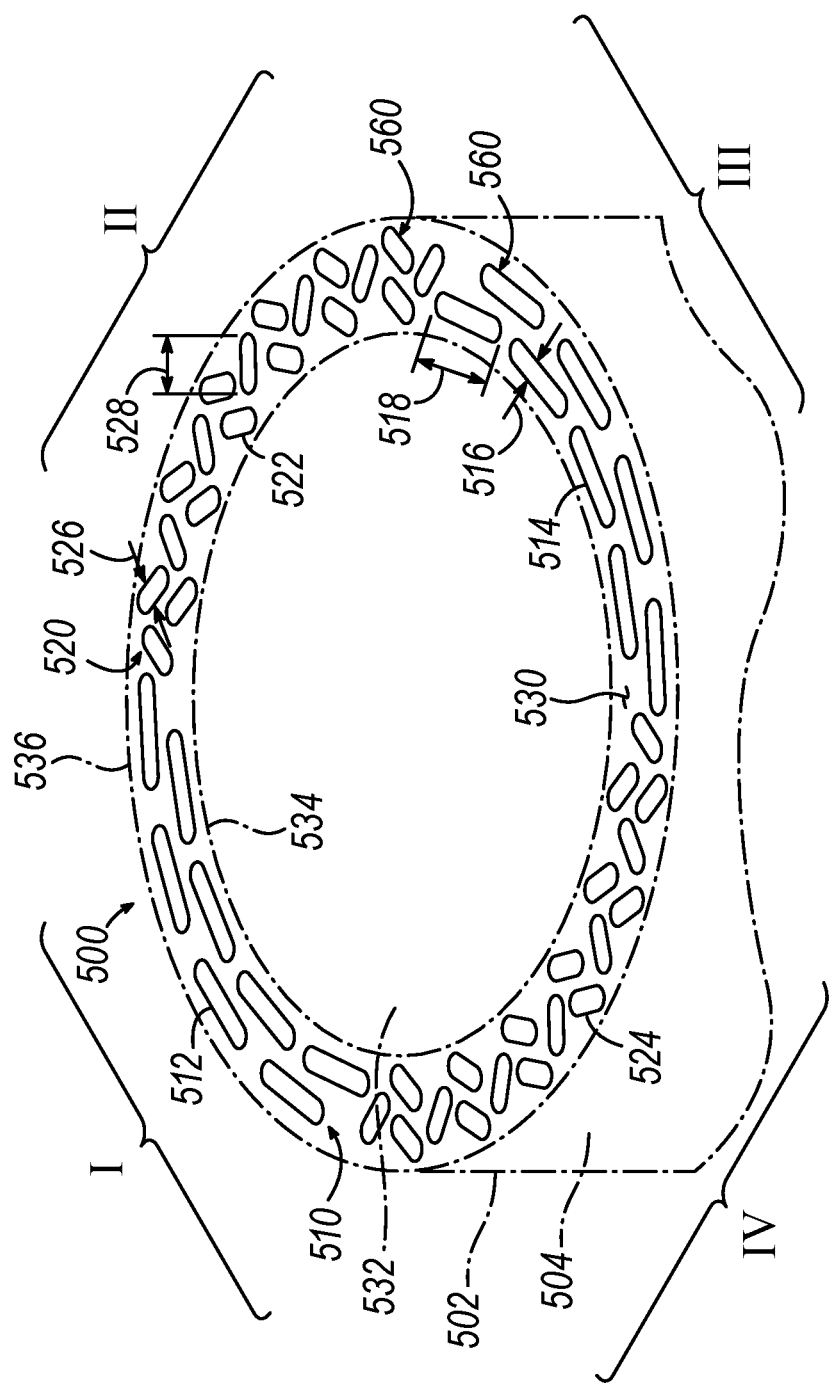
FIG. 8 depicts a schematic perspective view of a distal portion of an exemplary stapling head assembly configured for use with surgical stapler of FIG. 1.

FIG. 8 schematically shows another exemplary stapling head assembly (500) that is configured for use with surgical instrument (10) in place of stapling head assembly (300) described above. Stapling head assembly (500) is similar in structure and function to stapling head assembly (300) except as otherwise described below. In particular, stapling head assembly (500) includes a plurality of arrays (510, 520) of staple openings (560) oriented in different manners such that stapling head assembly (500) is configured to create an anastomosis between tubular anatomical structures (20, 40) of a patient with an annular array of formed staples that is capable of expanding radially outwardly with the stapled tissue. It will be appreciated that stapling head assembly (500) may be used in combination with an anvil (not shown) having similarly arranged arrays of staple forming pockets configured to align with the staple openings of stapling head assembly (500).

Stapling head assembly (500) includes a body member (502) and a deck member (504) disposed at a distal end of body member (502) and having a distally facing surface in the form of a deck surface (530) that surrounds a central longitudinal axis of stapling head assembly (500). Stapling head assembly (500) is shown with portions of the stapling head assembly (500) omitted to show details of the deck surface (530). Deck surface (530) includes an interior perimeter (534), an exterior perimeter (536), and a centerline (not shown) that is positioned equidistantly between interior perimeter (534) and exterior perimeter (536) and surrounds the central longitudinal axis. Both interior and exterior perimeters (534, 536) are circular in the present example. Interior perimeter (534) defines a lumen (532) that extends proximally through the deck member (504). Though not shown, stapling head assembly (500) may further include a longitudinal actuatable circular knife member and an anvil coupling member in the form of a trocar disposed within lumen (532).

As shown in FIGS. 8 and 9, deck surface (530) further includes a plurality of staple openings (560) that are arranged in a first array (510) and second array (520) about the deck surface (530) in an alternating pattern on circumferentially adjacent deck surface portions, each of which extends along a respective angular range of deck surface (530) about the central longitudinal axis. More specifically, first and second arrays (510, 520) of staple openings (560) are arranged in an alternating manner in quadrants (I, II, III, IV), where each quadrant (I, II, III, IV) extends successively along a respective 90 degree angular range of deck surface (530) about the central longitudinal axis. First and third quadrants (I, III) are diametrically opposed from one another about the central longitudinal axis, and second and fourth quadrants (II, IV) are diametrically opposed from one another about the central longitudinal axis. In the present example, first quadrant (I) includes a first iteration (512) (also referred to herein as a "section") of first array (510) of staple openings (560); second quadrant (II) includes a first iteration (522) of second array (520) of staple openings (560); third quadrant (III) includes a second iteration (514) of first array (510) of staple openings (560); and fourth quadrant (IV) includes a second iteration (524) of second array (520) of staple openings (560). In other words, each quadrant (I, II, III, IV) of deck surface (530) includes a respective array (512, 514, 522, 524) of staple openings (560), where arrays (512, 514) of the first and third quadrants (I, III) have the same first orientation relative to the centerline of deck surface (530), and where arrays (522, 524) of the second and the fourth quadrants (II, IV) have the same second orientation relative to the centerline of deck surface (530), where the first and second orientations are different.

FIG. 9 shows deck surface (530) with a first quadrant (I) at the 12 o'clock position, second quadrant (II) in the 3 o'clock position, a third quadrant (III) in the 6 o'clock position, and a fourth quadrant (IV) in the 9 o'clock position. As described above, first array (510) of staple openings (560) includes first and third sections (512, 514), where first section (512) is located in first quadrant (I) of deck surface (530) and third section (514) is located in third quadrant (III) diametrically opposed from first quadrant (I). Second array (520) of staple openings (560) includes second and fourth sections (522, 524), where second section (522) is located in second quadrant (II) of deck surface (530) and fourth section (524) is located in fourth quadrant (IV) of deck surface (530) diametrically opposed from second quadrant (II).

As shown in FIG. 8, in the present version each staple opening (560) of first array (510) has an elongate oval shape having a first width (516) that is generally equal to a second width (526) of staple openings (560) of second array (520). Staple openings (560) of first array (510) have a first length (518) that is longer than, and more specifically approximately twice as long as, a second length (528) of second staple openings (560) of second array (510).

As shown in FIG. 9, each section (512, 514) of first array (510) of staple openings (560) includes a first inner row (538) and a first outer row (540). First inner row (538) lies along an inner circle (IIC) and first outer row (540) lies along an outer circle (OIC) arranged concentrically about inner circle (IIC) and the central longitudinal axis of stapling head assembly (500). Each staple opening (560) of sections (512, 514) of first array (510) is arranged such that a length of the staple opening (560) is tangential to inner or outer circle (IIC, OIC), respectively, and thus tangential relative to the centerline of deck surface (530). Additionally, staple openings (560) in first inner row (538) are circumferentially offset from staple openings (560) in first outer row (540) so that staple openings (560) in first inner row (538) align with gaps (548) between adjacent staples openings (560) of the first outer row (540) to ensure effective sealing of the stapled tissue.

Each section (522, 524) of second array (520) of staple openings (560) includes a second inner row (542), a second middle row (544), and a second outer row (546). Second inner row (542) is positioned along inner circle (IIC). Second outer row (544) is positioned along outer circle (OIC). Second middle row (546) is positioned between inner circle (IIC) and outer circle (OIC), along the centerline of deck surface (530).

Each staple opening (560) of second inner row (542) is non-tangentially and angularly oriented relative to inner circle (IIC), and thus to the deck surface centerline, in a first angular orientation in which a first end (572) is spaced closer to the central longitudinal axis than an opposed second end (574). Similarly, each staple opening (560) of second outer row (546) of second array (520) is non-tangentially and angularly oriented relative to the outer circle (OIC), and thus to the deck surface centerline, in the same angular orientation. In the present version, each staple opening (560) in second inner and outer rows (542, 546) is oriented such that its length is angled at approximately 45 degrees relative to the respective inner and outer circles (IIC, OIC).

In contrast to staple openings (560) of second inner and outer rows (542, 546) of second array (520), each staple opening (560) of second middle row (546) of second array (520) is non-tangentially and angularly oriented relative to inner and outer circles (IIC, OIC), and thus to the deck surface centerline, in an opposite angular orientation in which first end (572) of each staple opening (560) is farther from the central longitudinal axis than its second ends (574). In the present version, each of staple opening (560) of the second middle row (574) is angled at approximately 40 degrees relative to the circles (IIC, OIC) and the deck surface centerline. Accordingly, in the present example, staple openings (560) of second array (520) are arranged in a herringbone pattern and thus are configured to apply a herringbone shaped staple pattern of staples to tissue. The non-tangential, angular orientation of staple openings (560), and thus the corresponding staples (90) deployed into tissue through openings (560), creates an anastomosis (70) in tissue structures (20, 40) about which the formed staples (90) in the stapled regions corresponding to second array (520) are configured to pivot relative to one another about the formed staple legs in the plane of the anastomosis (70). Consequently, the diametrically opposed circumferential portions of the applied staple pattern corresponding to second array (520) are configured to expand radially outwardly with stapled tissue structures (20, 40) during natural radial expansion of tissue structures (20, 40) at anastomosis (70), for example during peristalsis. In some instances, the circumferential portions of tissue structures (20,40) stapled by second array (520) of staple openings (560) may be capable of expanding radially outwardly approximately 125 percent to 200 percent more than the circumferential portions of tissue structures (20, 40) stapled by first array (510) of staple openings (560).

FIG. 10 shows an exemplary alternative deck surface (630) constructed and operable similar to deck surface (530) described above, except as otherwise described below. Deck surface (630) includes a first array (610) of staple openings (660), each of which is shorter in length than staple openings (560) of first array (510) and similar in length to staple openings (560) in second array (520). As a result, the first array (610) of staple openings (660) includes more staple openings (660) than first array (510) such that stapling head assembly (500) need be loaded with only one size of staples.

Figure 11:
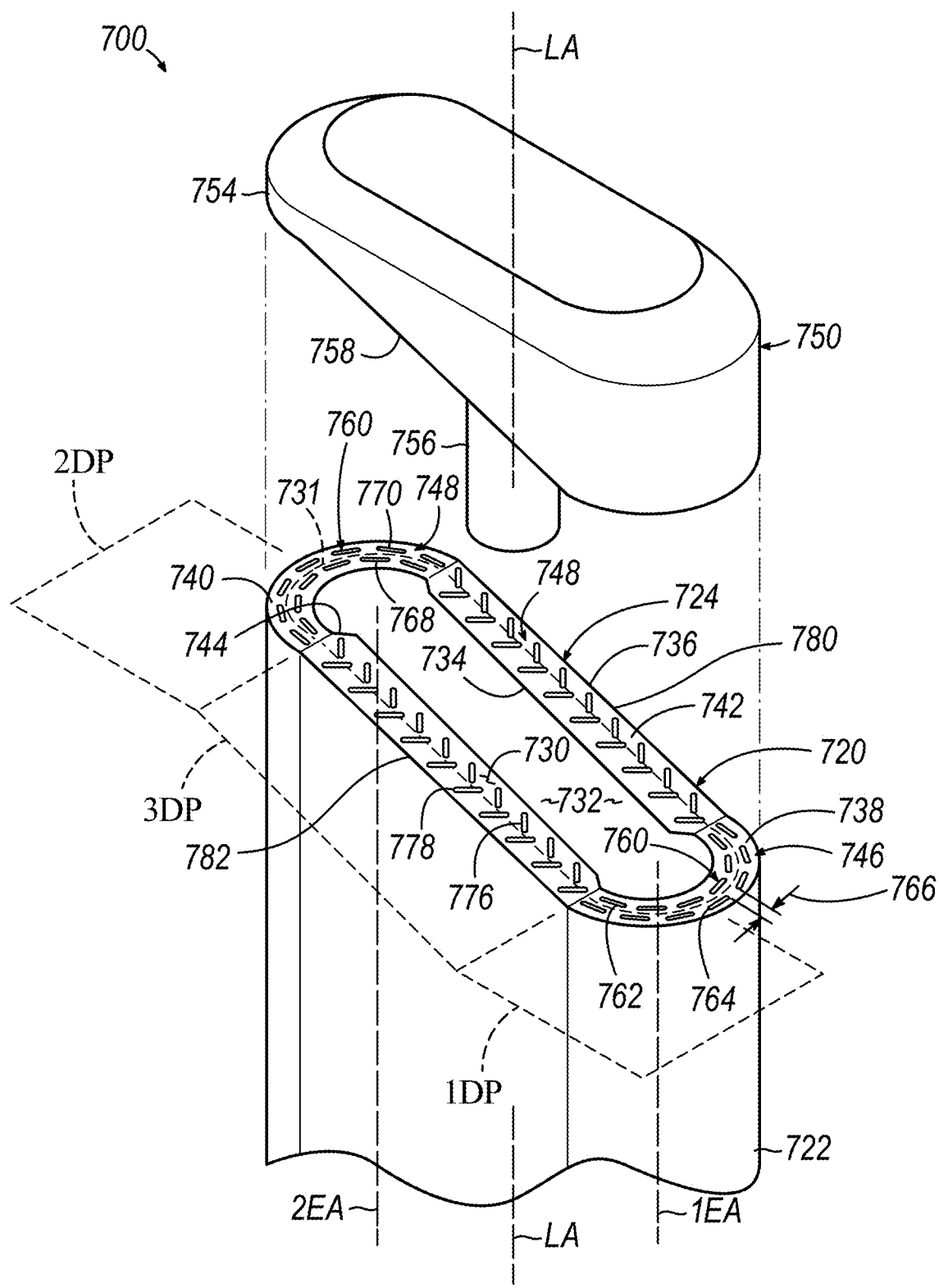
FIG. 11 depicts a schematic perspective view of another exemplary end effector including a stapling head assembly and an anvil configured for use with the surgical stapler of FIG. 1.

B. Second Exemplary End Effector with Alternating Arrays of Staple Forming Features and Stepped Deck Surface In some instances, it may be desirable to substitute a non-circular end effector for use with surgical instrument (10) to facilitate positioning of the end effector within the patient and to form an anastomosis (70) having an enlarged maximum diameter that more effectively facilitates peristalsis within the staple tissue structures (20, 40) at the site of the anastomosis (70). FIG. 11 shows an exemplary end effector (700) having such abilities. End effector (700) includes a stapling head assembly (720) and an anvil (750) configured to releasably couple with stapling head assembly (720) to compress, staple, and cut tissue. Stapling head assembly (720) is similar to stapling head assembly (500) described above except as otherwise described below. Stapling head assembly (720) includes a body member (722) and a deck member (724) having a stepped deck surface (730), and anvil (550) includes a shank (756) and a head (754) having a stepped proximal surface (758) configured to cooperate with stepped deck surface (730) to create an anastomosis (70) of enlarged diameter and having the ability to expand and contract radially with the stapled tissue structures.

FIG. 11 schematically shows non-circular end effector (700) with portions of non-circular stapling head assembly (720) and non-circular anvil (750) omitted to show details of stepped deck member (724) having various arrays of staple openings (760). Non-circular stapling head assembly (720) and non-circular anvil (750) are constructed and operable similar to stapling head assembly (300) and anvil (400) described above, except as otherwise described below.

Non-circular anvil (750) is similar to anvil (400) described above. Non-circular anvil (750) includes a head (754) and shank (756). Shank (756) extends proximally from head (754) and is configured to releasably couple with a coupling feature (not shown), such as an actuatable trocar, of stapling head assembly (720). Head (754) has a non-circular shape that matches the non-circular shape of an exterior profile of the stapling head assembly (720). Proximal surface (758) has a plurality of staple forming pockets (not shown) similar to staple forming pockets (414) described above and configured to align with staple openings (760) of deck member (724). Proximal surface (758) is configured to cooperate with deck surface (730) to clamp and staple tissue.

Figure 12:
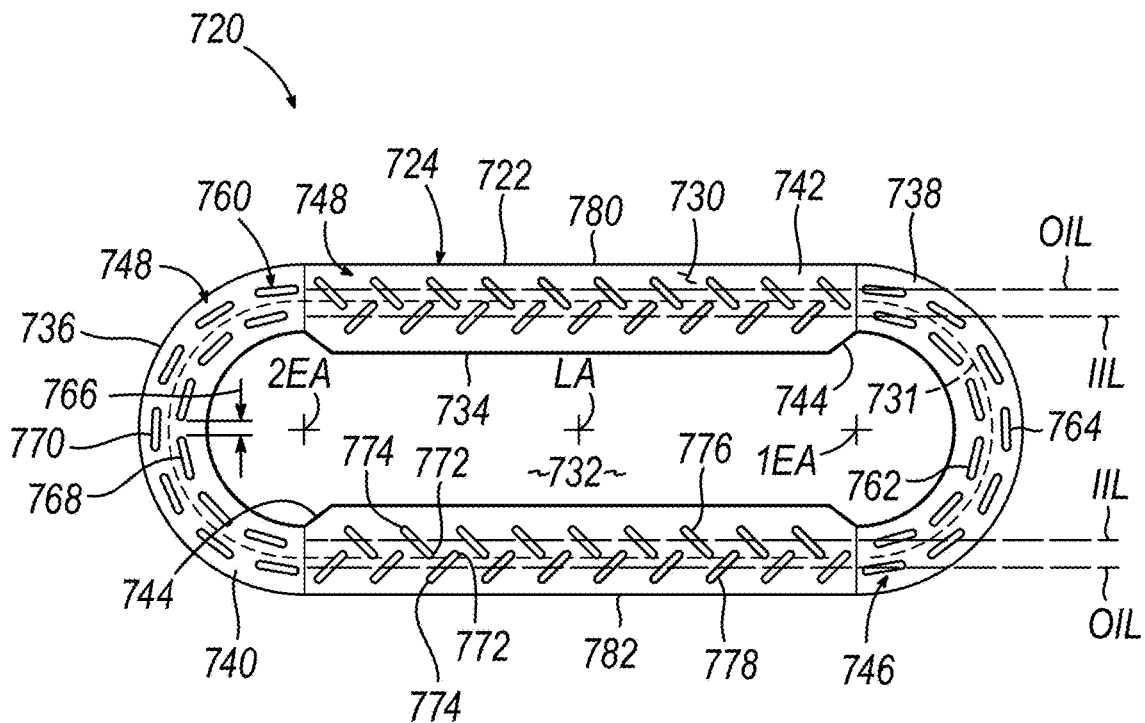
FIG. 12 depicts a top plan view of a deck surface of the stapling head assembly of FIG. 11.

As shown in FIGS. 11-12, body member (722) extends distally along a central longitudinal axis (LA) of stapling head assembly (720) from distal end of shaft assembly (200). Though not shown, stapling head assembly (720) may further include a knife member and a staple driver member slidably housed within body member (722) similar to knife (340) and staple driver member (350) of stapling head assembly (300).

Deck member (724) includes a distally presented stapling surface in the form of a deck surface (730). Deck surface (730) has a non-circular configuration with an exterior perimeter (736) defining a first non-circular shape and an interior perimeter (734) defining a second non-circular shape that is different than the first non-circular shape. In the present example, exterior perimeter (736) has an oval shape, and the interior perimeter has a "dogbone" shape that defines a lumen (732) within body member (722).

Figure 15:
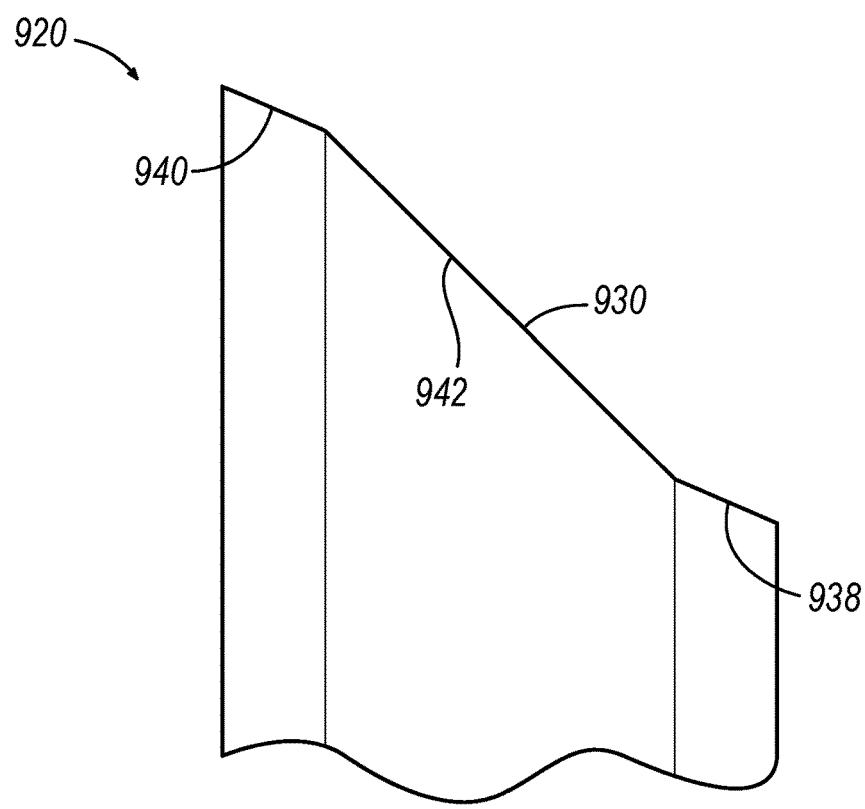
FIG. 15 depicts a side elevational view of another exemplary stapling head assembly including a stepped deck surface.

Deck surface (730) includes a first deck portion (738), a second deck portion (740), and a third deck portion (742), which collectively define a deck surface centerline (731) that surrounds central longitudinal axis (LA) and is spaced equidistantly between interior perimeter (734) and exterior perimeter (736). First deck portion (738) defines and wholly lies in a first deck plane (1DP) that is orthogonal to the central longitudinal axis (LA). Second deck portion (740) defines and wholly lies in a second deck plane (2DP) that is orthogonal to the central longitudinal axis (LA). Second deck plane (2DP) is distally positioned relative to the first deck plane (1DP) and is parallel to the first deck plane (1DP). In other versions, for example as shown in FIG. 15, first deck portion (738) and/or second deck portion (740) may define a corresponding deck plane that is obliquely angled relative to the central longitudinal axis (LA). Third deck portion (742) defines and wholly lies in a third deck plane (3DP) that is obliquely angled relative to the central longitudinal axis (LA) and the first and second deck planes (1DP, 2DP). Third deck portion (742) includes a chamfered interior corner (744) on both ends that transition into the first and second deck portions (738,740), thus providing deck surface (730) with a dog bone shape. In other versions, the interior corner may be rounded.

First deck portion (738) is positioned at a first longitudinal end of third deck portion (742) in a direction transverse to central longitudinal axis (LA). First deck portion (738) has an arcuate, semi-circular shape in first deck plane (1DP) and has a first array (746) of staple openings (760). Each staple opening (760) of first array (746) is tangent to a corresponding semi-circular arcuate portion of the deck surface centerline that extends about a first end axis (1EA), and first array (746) has a first inner row (762) and a first outer row (764). Each staple opening (760) of first outer row (764) is circumferentially indexed around the first end axis (1EA) by a distance that approximately equals half of the length of staple opening (760) in the first inner row (762) so that staple openings (760) of the first inner and outer rows (762,764) overlap in a staple opening gap (766) between adjacent staple openings (760), thus ensure proper sealing of the stapled tissue. It will be appreciated that staple openings (760) on each of deck portions (738, 740, 742) are suitable arranged in such a manner to ensure proper sealing of tissue.

Second deck portion (740) is positioned at an opposite second longitudinal end of the third deck portion (742) in a direction transverse to central longitudinal axis (LA). Similar to first deck portion (738), second deck portion (740) has an arcuate, semi-circular shape in second deck plane (2DP) and has a second array (748) of staple openings (760). Each staple opening (760) of second array (748) is tangent to a corresponding semi-circular arcuate portion of the deck surface centerline that extends about a second end axis (2EA), and second array (748) has a second inner row (768) and a second outer row (770).

Third deck portion (742) is positioned between the first and second deck portions (738, 740) along third deck plane (3DP) and has a linear shape. Third deck portion (742) has a first side (780) located on a first side of the central longitudinal axis (LA) and a second side (782) located on an opposed second side of central longitudinal axis (LA), such that each side (780, 782) is circumferentially adjacent to and interconnects first deck portion (738) and second deck portion (740) on a respective side of central longitudinal axis (LA). Accordingly, it will be appreciated that each of first deck portion (738), second deck portion (740), first side (780) of third deck portion (742), and second side (782) of third deck portion (742) extends along a respective, successive angular range of deck surface (730) about central longitudinal axis (LA). Each side (780, 782) of third deck portion (742) is formed with a greater transverse width, in a plane defined by deck surface (730) and in a direction perpendicular to the deck surface centerline (731), than either of first deck portion (738) and second deck portion (740) in order to effectively accommodate staple openings (760) that are orientated angularly relative to the deck surface centerline (731), as described in greater detail below.

Each side (780, 782) of third deck portion (742) includes a respective iteration of second array (748) of staple openings (760) having a third inner row (776) and a third outer row (778). Second array of staple openings are collectively arranged in a simplified herringbone pattern in which adjacent staple openings (760) define a V-shape. Third inner row (776) lies along an inner line (IIL) spaced a first distance from the longitudinal axis (LA) and third outer row (778)

lies along an outer line (OIL) spaced a second distance from the longitudinal axis (LA). Second distance is greater than first distance. Each staple opening (760) of third inner row (776) is oriented in a first angular, non-tangential orientation relative to inner line (IIC), and each staple opening (760) of third outer row (778) is oriented in an opposite second angular, non-tangential orientation relative to outer line (OIC). In the present example, staple openings (760) of third inner and outer rows (776, 778) are perpendicular to one another. A first end (772) of each staple opening (760) in third inner row (776) is closer to the longitudinal axis (LA) relative to a second end (774) of each staple opening (760) in third inner row (776). A first end (772) of each staple openings (760) in third outer row (778) is farther from the longitudinal axis (LA) relative to the second end (774) of each staple opening (760) in third outer row (778).

It will be appreciated that any of the exemplary stapling head assemblies described herein, such as stapling head assemblies (720, 820), may be further configured in accordance with any one or more of the teachings of U.S. patent application Ser. No. 17/401,430, entitled "Non-Circular End Effector Features for Circular Surgical Stapler," filed on Aug. 13, 2021, issued as U.S. Pat. No. 11,994,310 on Apr. 2, 2024, the disclosure of which is incorporated by reference herein.

C. Exemplary Stapling Head Assembly with Alternating Arrays of Staple Forming Features and Spacing for Anvil Coupling Feature In some instances, it may be desirable to modify stapling head assembly (720) to incorporate features that provide greater clearance for an actuatable trocar or other anvil coupling feature that is translatable along central longitudinal axis (LA).

Figure 13:
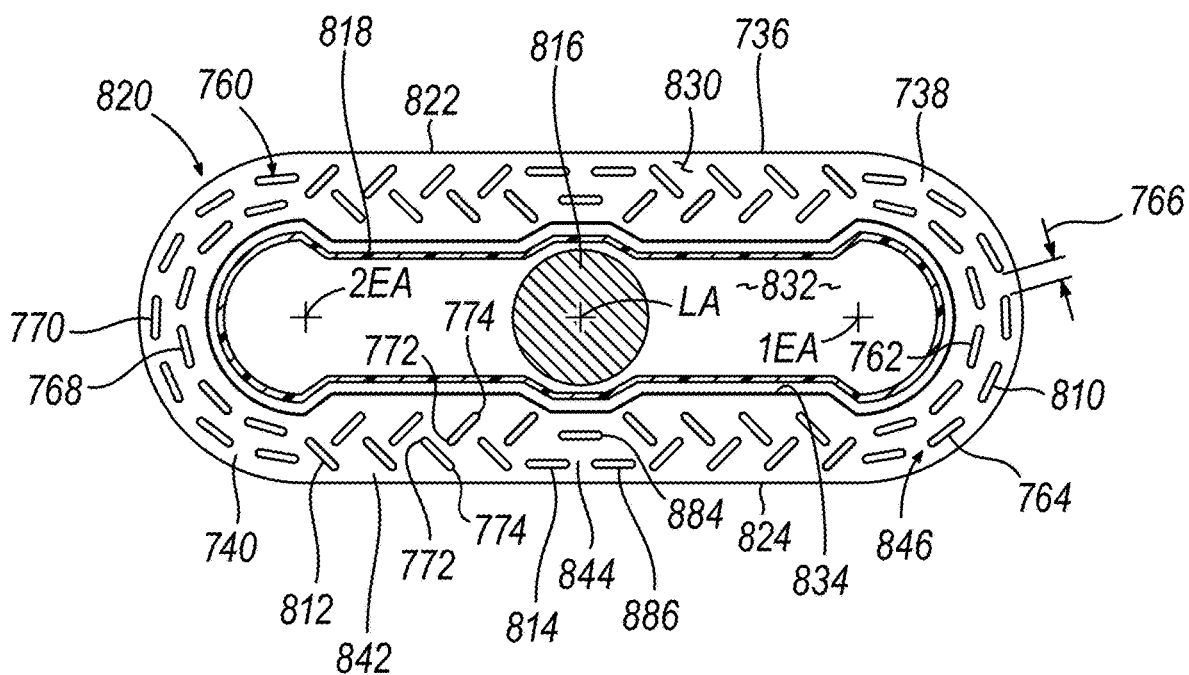
FIG. 13 depicts a top plan view of another exemplary stapling head assembly.

FIG. 13 shows an exemplary alternative stapling head assembly (820) that is constructed and operable similar to stapling head assembly (720) described above, except as otherwise described below. Stapling head assembly (820), like stapling head assembly (720), includes a body member (822) and a deck member (824) having a deck surface (830) with a first deck portion (738), a second portion (740), and a third deck portion (842) that interconnects first deck portion (738) and second deck portion (740). Though not shown, it will be understood that deck member (824) may be angularly stepped similar to deck member (724) described above. Specifically, first deck portion (738) may define a first deck plane that orthogonally intersects central longitudinal axis (LA); second deck portion (740) may define a second deck plane that also orthogonally intersects central longitudinal axis (LA) and thus is parallel with but distal to the first deck plane; and third deck portion (842) may define a third deck plane that is obliquely angled relative to central longitudinal axis (LA) and each of the first and second deck planes. In other versions, deck portions (738, 740, 842) may be coplanar such that deck surface (830) defines a single deck plane that either orthogonally or obliquely intersects central longitudinal axis (LA).

Third deck portion (842) of deck member (824) differs from third deck portion (742) of deck member (724) in that third deck portion (842) includes a pair of central portions (844) diametrically opposed about the central longitudinal axis (LA) and each having a radially outwardly extending recess feature positioned along inner perimeter (834) of deck member (824). As a result, inner perimeter (834) of deck surface (830) steps away from the central longitudinal axis (LA) at each central portion (844) resulting in central portion (844) having a narrower transverse width than other portions of third deck portion (842). In the present version, each central portion (844) deviates from third deck portion (842) with a linear portion of inner perimeter (834) that extends transverse and away from longitudinal axis (LA) and returns to third deck portion (842) with another linear portion that extends at an opposite angle transversely and toward the longitudinal axis (LA). This configuration of central portions (844) provides additional clearance for proximal and distal translation of trocar (816) within lumen (832). In some versions, inner perimeter (834) at central portions (844) may have a round, oval, square, triangular shape, or any additional shape known in the art to provide additional clearance between moving and non-moving members. As shown, knife member (818) is formed with a similar dog bone shape that complements the dog bone shape of interior perimeter (834), for example as disclosed in greater detail in U.S. patent application Ser. No. 17/401,430, entitled "Non-Circular End Effector Features for Circular Surgical Stapler," filed on Aug. 13, 2021, issued as U.S. Pat. No. 11,994,310 on Apr. 2, 2024, incorporated by reference above.

Each of first deck portion (738) and second deck portion (740) of deck member (824) includes a respective iteration of a first array (810) of staple openings (760) that is similar to first array (746), described above. Each side of third deck portion (842) includes three distinct zones, where staple openings (760) are arranged differently in each zone. A first zone extends between first deck portion (738) and the corresponding central portion (844); a second zone extends between second deck portion (740) and central portion (844); and a third zone extends through central portion (844). Staple openings (760) of the first zone are oriented angularly and non-tangentially relative to the deck surface centerline in a first simplified herringbone pattern, similar to staple openings (760) in third deck portion (742) of stapling head assembly (720). Staple openings (760) of the second zone are oriented angularly and non-tangentially relative to the deck surface centerline in a second simplified herringbone pattern (812) that mirrors the first simplified herringbone pattern about a line that extends through the central longitudinal axis (LA) and bisects each of the central portions (844). Staple openings (760) of the third zone are oriented in a third pattern (814) in which each staple opening (760) extends parallel to the deck surface centerline.

In each central portion (844) of third deck portion (842), third array (814) of staple openings (760) includes an inner row (884) and an outer row (886). In the present version, Inner row (884) includes a single staple opening (760) that is aligned with central longitudinal axis (LA). In other versions, inner row (884) may include multiple staple openings (760) that span across the linear distance of the central portion (844). Outer row (886) includes two staple openings (760) that define a staple gap (766) between them that is aligned with the single staple opening (760) of inner row (884). It will be appreciated that the staple pattern portions applied to tissue structures (20, 40) by the first and second zones of third deck portion (842) as described above exhibit a greater ability to radially expand and contract than the staple pattern portions applied by the third zone and by first and second deck portions (738, 740).

Figure 14:
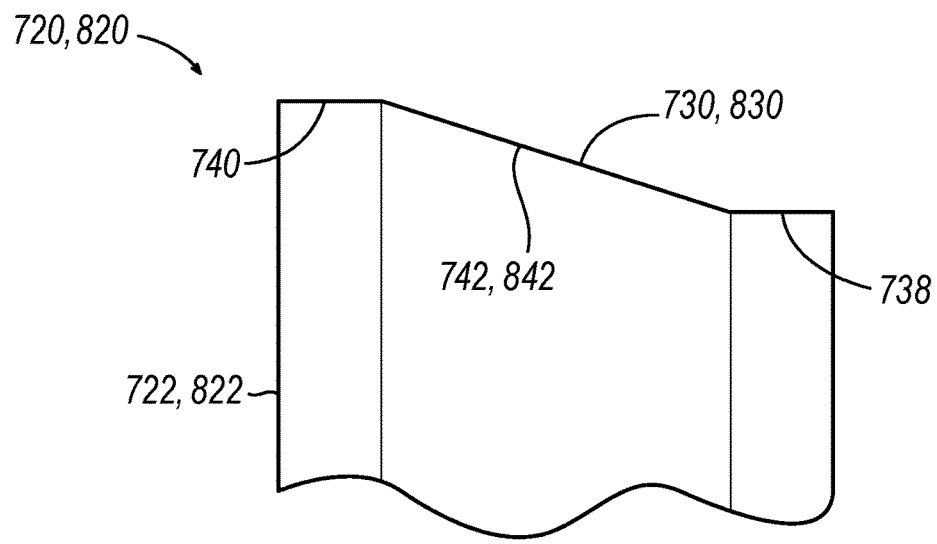
FIG. 14 depicts a side elevational view of the stapling head assemblies of FIGS. 11 and 13, including a stepped deck surface.

FIG. 14 schematically shows stapling head assemblies (720, 820) having a deck surface (730, 830) that is stepped. As described above, deck surface (730, 830) includes first deck portion (738) orthogonal to the central longitudinal axis (LA), second deck portion (740) orthogonal to the central longitudinal axis (LA) and parallel to the first deck portion (738), and third deck portion (742, 842) that is obliquely angled relative to the central longitudinal axis (LA) and each of the first and second deck portions (738, 740).

D. Exemplary Stapling Head Assembly with Obliquely Angled Deck Surface Portions

FIG. 15 schematically shows another exemplary stapling head assembly (920) that is constructed and operable similar to stapling head assemblies (720, 820) described above, except as otherwise described below. Stapling head assembly (920) includes a deck surface (930) having a first deck portion (938) obliquely angled relative to the central longitudinal axis (LA), a second deck portion (940) obliquely angled relative to the longitudinal axis (LA), and a third deck portion (942) obliquely angled relative to the central longitudinal axis (LA). In the present version, third deck portion (942) is more steeply angled relative to central longitudinal axis (LA) than each of first and second deck portions (938, 940), which themselves be oriented at the same oblique angle or different oblique angles relative to central longitudinal axis (LA). It will be appreciated that any suitable angular arrangement of deck portions (938, 940, 942) may be provided in other versions.

E. Exemplary Stapling Head Assembly with Elliptical Deck Member

Figure 16:
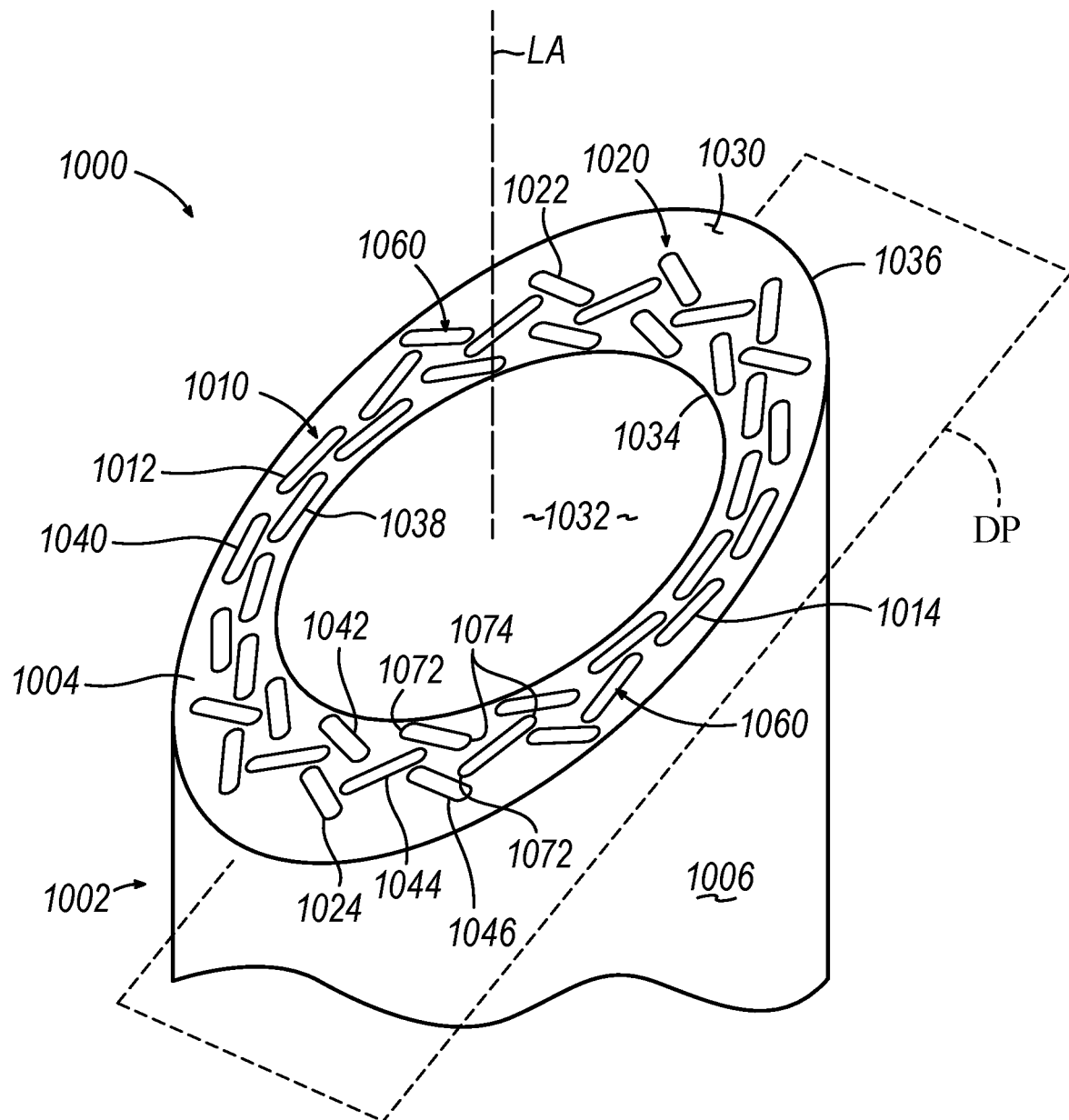
FIG. 16 depicts a schematic perspective view of another exemplary stapling head assembly including an angled elliptical deck surface.
Figure 17:
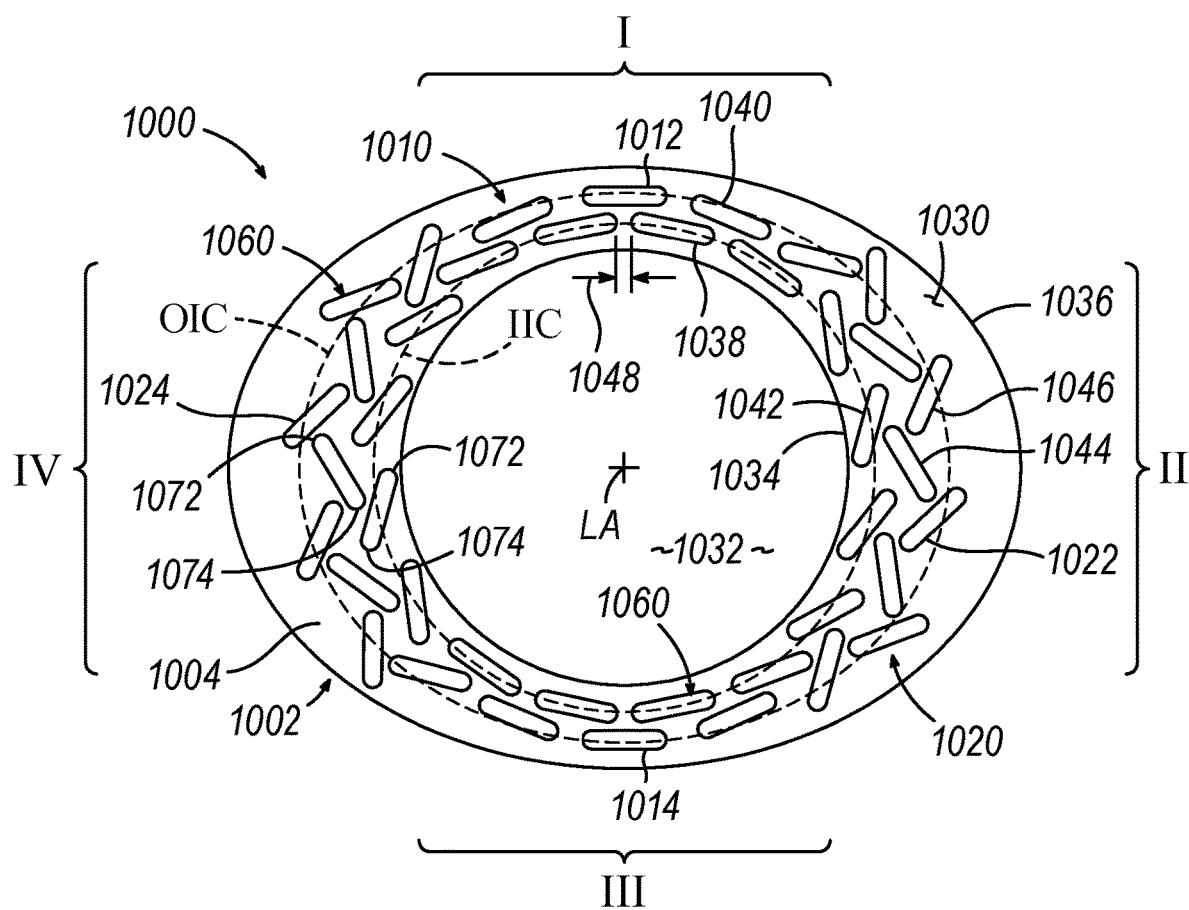
FIG. 17 depicts a top plan view of the elliptical deck surface of the stapling head assembly of FIG. 16.

In some instances, it may be desirable to maintain a circular shaped interior perimeter and a corresponding inner diameter of deck member (320), and a circular shaped exterior perimeter and a corresponding outer diameter of stapling head assembly (300). In some such instances, it may also be desirable to incorporate one or more arrays of staple openings that are obliquely angled relative to an deck surface centerline of deck member (320) to thereby enable the resulting staple pattern applied to tissue structures (20, 40) to expand and contract radially with the tissue structures (20, 40) at anastomosis (70), for example during peristalsis. FIGS. 16-17 show an exemplary stapling head assembly (1000) having such features and configured for use surgical instrument (10) in place of stapling head assembly (300). It will be appreciated that stapling head assembly (1000) is similar to stapling head assembly (300) except as otherwise described.

Stapling head assembly (1000) includes a body member (1002) operatively attached to the distal end of shaft assembly (200) (see FIG. 1) and having a circular exterior surface (1006). In other versions, body member (1002) may have an oval exterior surface (not shown). Stapling head assembly (1000) further includes an elliptical deck member (1004) having a distally facing surface in the form of an elliptical deck surface (1030).

Elliptical deck surface (1030) defines a deck plane (DP) that is obliquely angled relative to the central longitudinal axis (LA), and includes an interior perimeter (1034) and an exterior perimeter (1036). Interior perimeter (1034) is circular and defines a circular lumen (1032) that extends proximally within the deck member (1004). Exterior perimeter (1036) has an oval shape within deck plane (DP). Elliptical deck surface (1030) includes a first (1010) of staple openings (1060) and a second array (1020) of staple openings (1060) extending through deck surface (1030).

First array (1010) of staple openings (1060) has a first section (1012) and a third section (1014). First section (1012) is located in a first quadrant (I) of the deck surface (1030) and third section (1014) is located in a third quadrant (III) of deck surface (1030) that is diametrically opposed relative to first quadrant (I). Second array (1020) of staple openings (1060) has a second section (1022) and a fourth section (1024). Second section (1022) is located in a second quadrant (II) of the deck surface (1030) and fourth section (1024) is located in a fourth quadrant (IV) of deck surface (1030) that is diametrically opposed relative to second quadrant (II). Second and fourth quadrant (II, IV) are located in a wider portion of deck surface (1030) configured to accommodate the second array (1020) of staple openings (1060) that have a herringbone pattern configured to enable radial expansion and contraction of the corresponding portions of stapled tissue. As described in greater detail below, each staple opening (1060) of first array (1010) located in first and third sections (1012, 1014) extends tangentially to a deck surface centerline. In contrast, each staple opening (1060) of second array (1020) located in second and fourth sections (1022, 1024) extends obliquely angularly and non-tangentially relative to the deck surface centerline, defining a herringbone pattern. Accordingly, the staple pattern portions applied to tissue structures (20, 40) by second and fourth sections (1022, 1024) are configured to have a greater degree of radial expandability and contractibility than the staple pattern portions applied to tissue structures (20, 40) by first and third sections (1012, 1014).

Staple openings (1060) of first and second arrays (1010, 1020) are sized and configured similarly to staple openings (558) or (560) of stapling head assembly (500) (see FIGS. 8-9). Staple openings (1060) in the first array (1010) may be longer than staple openings (1060) of second array (1020) or may be sized the same as staple openings (660) (see FIG. 10). In the present version, staple openings (1060) of both arrays (1010, 1020) are similarly sized.

First array (1010) of staple openings (1060) includes a first inner row (1038) and a first outer row (1040). Both first and second sections (1012, 1014) have first inner and first outer rows (1038, 1040). First inner row (1038) lies along an inner circle (IIC). Inner circle (IIC) is centered around the longitudinal axis (LA). First inner row (1038) is positioned within the first outer row (1040) that lies along an outer ellipse (OIE). Staple openings (1060) in first inner row (1038) are circumferentially indexed relative to staple openings (1060) in first outer row (1040) and vise-versa so that staple openings (1060) in first outer row (1038) overlap a gap (1048) between staples openings (558) of the first inner row (540).

Second array (1020) of staple openings (1060) includes a second inner row (1042), a second middle row (1044), and a second outer row (1046). Second inner row (1042) is positioned along inner circle (IIC) and is angularly oriented relative to inner circle (IIC). Second outer row (1044) is positioned along outer ellipse (OIE) and is angularly orientated relative to outer ellipse (OIE). Second middle row (1046) is positioned along inner ellipse (IIE). Inner ellipse (IIE) is positioned within outer ellipse (IIE) and inner circle (IIC) is concentrically positioned within inner ellipse (IIE).

Staple openings (560) of second inner row (1042) are non-tangentially angularly oriented relative to inner circle (IIC) with a first end (1072) that is spaced closer longitudinal axis than the second end (1074). Staple openings (1060) of second outer row (1046) are angularly oriented relative to the outer ellipse (OIE) oriented at the same angle relative to staple openings (1060) in second inner row (542). In the present version, staple openings (560) in second inner and second outer rows (542, 546) are angled with an offset angle of 45 degrees relative to the respective inner circle (IIC) and outer ellipse (IIC, OIE).

Staple openings (1060) of second middle row (1044) are angularly oriented in an opposite direction relative to staple openings (1060) in second inner and outer rows (1042, 1046) resulting in the first ends (1072) of each of staple openings (1060) in second middle row (1044) being farther from longitudinal axis (LA) than second ends (1074). Staple openings (560) of the second middle row (574) are offset at an angle of 40 degrees relative to the inner ellipse (IIE).

III. Exemplary End Effectors Having Non-Circular Features

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure a stapling head assembly (1120) and an anvil (1150) with a knife member (1110) having a shape that enables formation of such an anastomosis and/or patterns of formed staples (90). Exemplary versions of such features are described in greater detail below.

Figure 18:
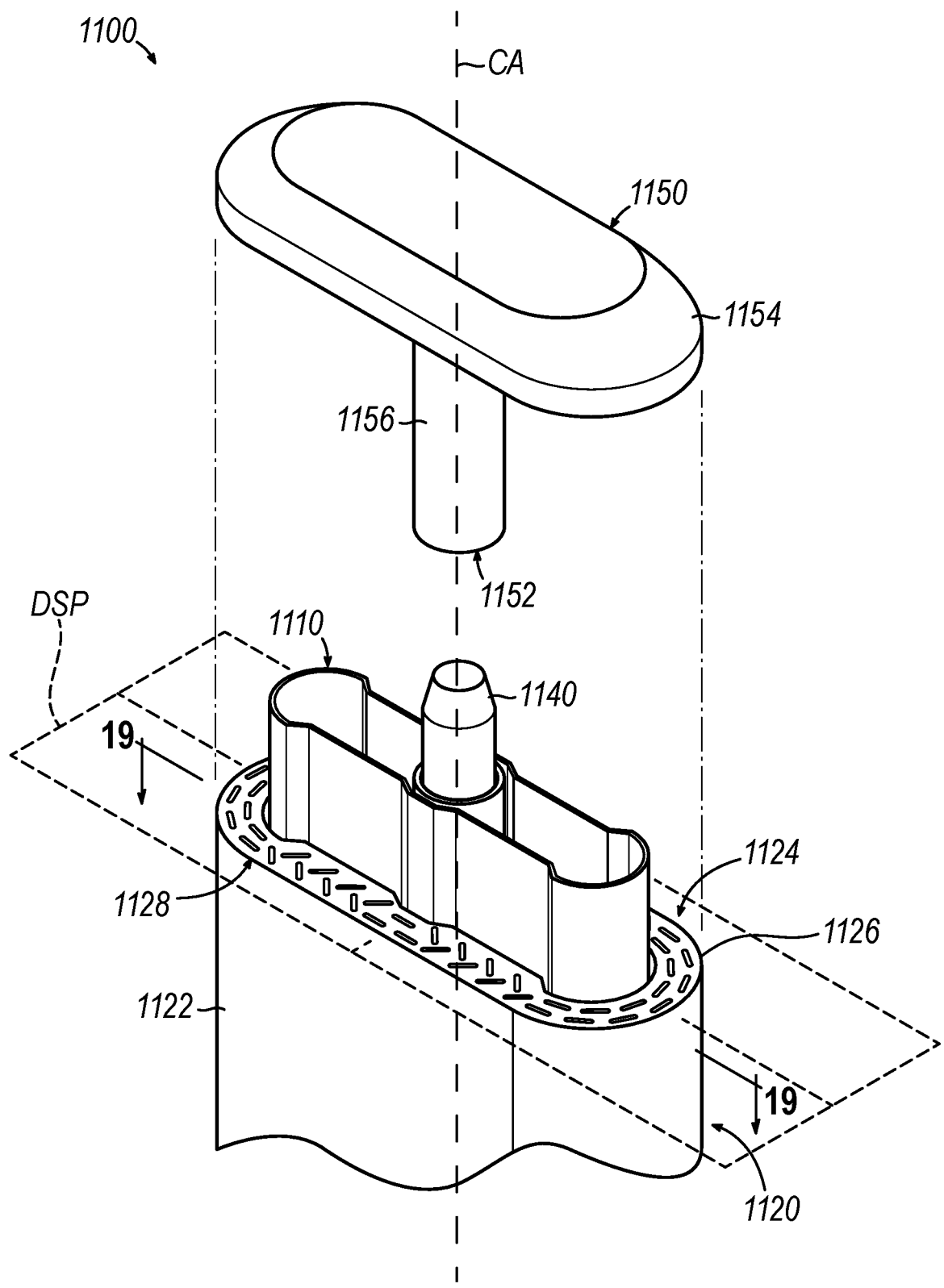
FIG. 18 depicts a perspective view of another exemplary end effector including a stapling head assembly and anvil for use with the circular stapler of FIG. 1.

A. Exemplary Non-Circular End Effector Having Oval Knife Member with Arcuate End Portions FIG. 18 shows an exemplary non-circular end effector (1100) having a stapling head assembly (1120) and an anvil (1150) configured to releasably couple with stapling head assembly (1120). It will be appreciated that stapling head assembly (1120) and anvil (1150) are similar in structure and function to stapling head assembly (300) and anvil (400) described above except as otherwise described. In particular, and as described in greater detail below, stapling head assembly (1120) of the present example includes an oval knife member (1110) with arcuate end portions (1138) configured to create an anastomosis between tubular anatomical structures (20, 40) of a patient having an elongated transverse cross-sectional shape.

Stapling head assembly (1120) of end effector (1100) includes a housing in the form of a body member (1122). Body member (1122) includes a deck member (1124) having a distally facing deck surface (1126), and a knife member (1110) at least partially disposed within body member (1122). Body member (1122) extends distally along a longitudinal axis defined as a central axis (CA) from a distal end of shaft assembly (200) and further includes a staple driver member (not shown) slidably housed therein similar to stapler driver member (350) of stapling head assembly (300). Body member (1122) is fixedly secured to an outer sheath (210) of shaft assembly (200), and body member (1122) and outer sheath (210) thus serve together as a mechanical ground for stapling head assembly (1120).

A coupling feature in the form of a trocar (1140) is positioned coaxially within an inner core member (not shown) of stapling head assembly (1120). Like trocar (330), trocar (1140) is operable to translate distally and proximally relative to body member (1122) in response to rotation of knob (130) relative to casing (110) of handle assembly (100). Trocar (1140) is configured for insertion into anvil (1150) through bore (1152) and latches to anvil (1150) like trocar (330).

Similar to anvil (400) described above, anvil (1150) includes a head (1154) and shank (1156) extending proximally from head (1154) and is configured to releasably couple with trocar (1140) of stapling head assembly (1120). Head (1154) has an elongate shape similar to an exterior profile of body member (1122) of stapling head assembly (1120) and a low-profile shape that defines a proximal surface (1158) having a plurality of staple forming pockets (not shown) similar to staple forming pockets (414) described above. Proximal surface (1158) is configured to cooperate with deck surface (1126) to clamp and staple tissue. In the present version, anvil (1150) further includes a washer (not shown) recessed within anvil (1150) of suitable shape that functions in a manner similar to washer (417) described above.

Figure 19:
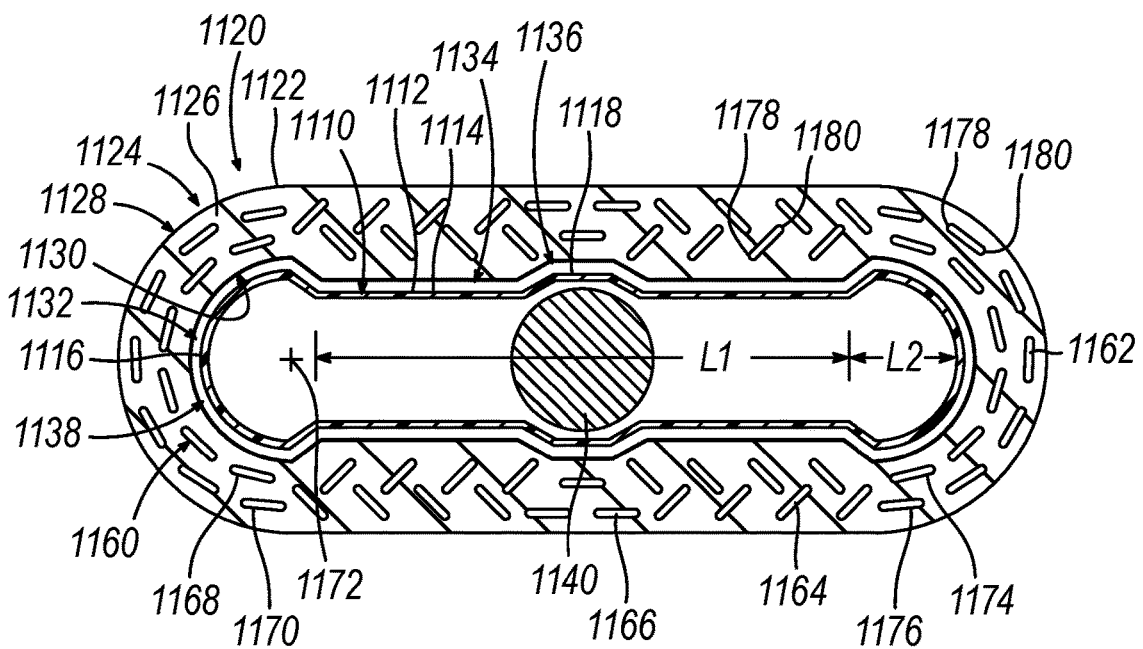
FIG. 19 depicts a top plan view of the stapling head assembly of FIG. 18.

As shown in FIG. 19, deck member (1124) includes a distally presented stapling surface in the form of a deck surface (1126). Deck surface (1126) has a non-circular configuration with an exterior perimeter (1128) defining a first non-circular shape and an interior perimeter (1130) defining a second non-circular shape that is different than the first non-circular shape. Exterior perimeter (1128) and interior perimeter (1130) lie within a deck surface plane (DSP) that orthogonally intersects central axis (CA) of stapling head assembly (1120), as shown in FIG. 18. Exterior perimeter (1128) has an oval, elongate first non-circular shape. Interior perimeter (1130) defines a lumen (1132) within deck member (1124) and has a second non-circular shape.

As shown in FIG. 19, interior perimeter (1130) of deck surface (1126) includes four linear medial portions (1134), two outwardly extending central portions (1136) each interconnecting an adjacent pair of linear medial portions (1134), and two arcuate end portions (1138) each interconnecting an opposed pair of linear medial portions (1134). Central portions (1136) are diametrically opposed from one another about central axis (CA) and are in the form of radially outwardly extending angled step features configured to provide clearance for proximal and distal translation of trocar (1140) therebetween. In other versions, interior perimeter (1130) may include two linear medial portions (1134) and two arcuate end portions (1138), with no intervening outwardly extending central portions (1136) of the type shown herein.

Deck surface (1126) of the present version has a narrower transverse width, measured between interior and exterior perimeters (1130, 1128), at arcuate end portions (1138) and at central portions (1136), and a thicker transverse width along linear portions (1134). Accordingly, interior perimeter (1130) has the shape of a dog bone, with an elongate central shaft feature defined by linear medial portions (1134) and outwardly extending central portions (1136) in combination, and a pair of bulbous end features defined by arcuate end portions (1138). More specifically, the dog bone shape has a first arcuate end portion (1138) on a first side of central axis (CA), and a second arcuate end portion (1138) on an opposed second side of central axis (CA). In other versions, interior perimeter (1130) of deck surface (1126) may define various other suitable shapes, such as a flower pedal shape where interior perimeter (1130) further includes a linear angled portion (not shown) that further transitions between linear medial portions (1134) and arcuate end portions (1138).

Deck surface (1126) further includes a plurality of staple openings (1160) configured to receive and house staples (not shown), similar to staples (90) described above. In the present example, staple openings (1160) are arranged on deck surface (1126) in a first array (1162) of staple openings (1160), a second array (1164) of staple openings (1160), and a third array (1166) of staple openings (1160). First array (1162) of staple openings (1160) is positioned along each of arcuate end portions (1138); second array (1164) of staple openings (1160) is positioned along each of linear medial portions (1134); and third array (1166) of staple openings (1160) is positioned along each of outwardly extending central portions (1136). First array (1162) of staple openings (1160) is arranged with a different configuration than second array (1164) of staple openings (1160). Third array (1166) of staple openings (1160) is arranged with a similar configuration as first array (1162) of staple openings (1160).

First array (1162) of staple openings (1160) includes a first inner row (1168) and a first outer row (1170). Each of staple openings (1160) in first array (1162) extends tangentially to the respective arcuate end portion (1138) about a respective end axis (1172), which is central to the respective arcuate end portion (1138). Each of staple openings (1160) of first inner row (1168) is staggered relative to each of staple openings (1160) of first outer row (1170), such that each staple opening (1160) of inner row (1168) is circumferentially offset from each staple opening (1160) of outer row (1170).

Second array (1164) of staple openings (1160) includes a second inner row (1174) and a second outer row (1176) angled perpendicularly to each other in a herringbone configuration. Each staple opening (1160) includes a first end (1178) and an opposed second end (1180). Each staple opening (1160) of second inner row (1174) is oriented angularly relative to the corresponding linear portion (1134) and an imaginary circumferential midline of deck surface (1126) such that first end (1178) of each staple opening (1160) in second inner row (1174) is closer to interior perimeter (1130) that second end (1180). Each staple opening (1160) in second outer row (1176) has an angular orientation that is opposite that of staple openings (1160) of first inner row (1168), where first end (1178) of each staple opening (1160) in second outer row (1176) is closer to exterior perimeter (1128) than the corresponding second end (1180). This angular configuration of staple openings (1160) in second arrays (1164) may allow for outward radial expansion of the formed staple array deployed by deck member (1124) at portions arranged along linear medial portions (1134) of interior perimeter (1130). This radial expandability of the formed staple array in combination with the overall elongate shape of the formed staple array may provide for an improved anastomosis that exhibits the benefits described above.

Knife member (1110) of the present example has a distal knife edge (1112) that defines an edge plane (not shown) that is parallel to deck surface plane (DSP) seen in FIG. 18 and orthogonally intersects central axis (CA) of stapling head assembly (1120). Knife edge (1112) has a non-circular, dog bone-like shape in the edge plane that complements the dog bone-like shape of interior perimeter (1130) of deck surface (1126) described above. More specifically, knife edge (1112), similar to interior perimeter (1130), includes four linear medial edge portions (1114), a pair of arcuate end edge portions (1116) diametrically opposed from one another about central axis (CA), and a pair of radially outwardly extending central edge portions (1118) diametrically opposed from one another about central axis (CA) and interconnecting adjacent pairs of linear medial edge portions (1114). In other versions, knife member (1110) may be suitably sized and shaped to omit outwardly protruding central edge portions (1118) such that arcuate end edge portions (1116) are interconnected by an opposed pair of elongate linear edge portions.

As seen in FIG. 19, knife member (1110) is suitably shaped and sized smaller than interior perimeter (1130) of deck member (1124) to provide for a uniform gap between the exterior perimeter of knife member (1110) and interior perimeter (1130) of deck member (1124). In other words, the exterior perimeter of knife member (1110), at least at knife edge (1112), closely conforms to but is spaced inwardly from interior perimeter (1130) of deck member such that the exterior surface of knife member (1110) closely confronts but does not contact the interior surface of deck member (1124). Accordingly, knife member (1110) is operable to freely translate proximally and distally relative to deck member (1124) during a distal firing stroke and a subsequent proximal retraction stroke.

As shown in FIG. 19, knife member (1110) of the present version is shaped such that linear medial edge portions (1114) and central edge portions (1118) have a combined first length (L1) in a direction transverse to and extending through central axis (CA), and each end edge portion (1116) has a second length (L2) in the same direction. First length (L1) is greater than second length (L2). In some versions, first length (L1) is greater than second length (L2) by a ratio of 3:1. Additionally, each arcuate end edge portion (1116) may be formed with a semi-circular shape having a diameter that is equal to a transverse distance between radially outermost portions of opposed central edge portions (1118), which distance may be greater than a transverse distance between each opposed pair of linear medial edge portions (1114), thus providing the dog bone shape seen in FIGS. 18 and 19.

As described above, in other versions interior perimeter (1130) of deck member (1124) may be formed with various non-circular shapes, other than the dog bone shape shown and described herein, that are suitable to create an anastomosis (70) of enlarged diameter. It will be appreciated that in such alternative versions, knife member (1110) may also be alternatively shaped such that knife edge (1112) defines a shape that complements the shape of interior perimeter (1130) of deck member (1124). In some such versions, interior perimeter (1130) of deck member (1124) and knife edge (1112) may each be formed with various types of elongate oval shapes. In other such versions, interior perimeter (1130) of deck member (1124) and knife edge (1112) may each be formed with a flower pedal shape having a plurality of pointed or rounded lobes arranged circumferentially about central axis (CA), symmetrically or non-symmetrically.

Figure 20:
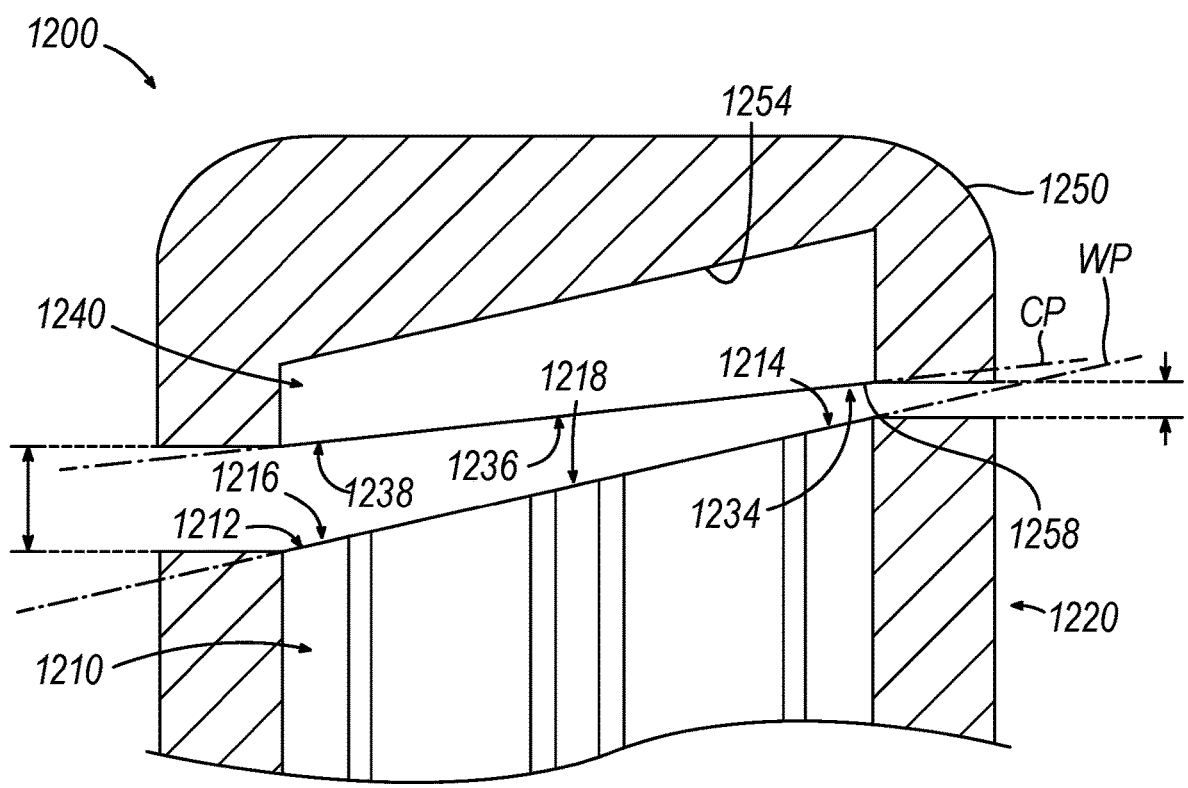
FIG. 20 depicts a cross-sectional side view of yet another exemplary end effector including a stapling head assembly and an anvil for use with the circular stapler of FIG. 1, with the anvil spaced apart from the stapling head assembly.

B. Second Exemplary Non-Circular End Effector Having Angled Knife Edge and Angled Washer In some instances, it may be desirable to substitute an angled knife member (1210) and an angled washer (1240) to promote a progressive slicing-type cutting action, rather than an abrupt guillotine-type cutting action, to minimize the force required to cut through tissue and angled washer (1240). FIGS. 20-21C schematically show a portion of another example of a non-circular end effector (1200) that operates in such a manner, where end effector (1200) includes a stapling head assembly (1220) having an angled knife member (1210), and an anvil (1250) having an angled washer (1240). Non-circular end effector (1200) is constructed and operable similar to end effector (1100) described above, except as otherwise described below.

As shown in FIG. 20, knife member (1210) includes a knife edge (1212) defining a single cutting edge plane (CP) that intersects and is obliquely angled relative to central axis (CA). Knife edge (1212) includes a first edge portion (1214), a second edge portion (1216), and a third edge portion (1218), where edge portions (1214, 1216, 1218) are coplanar within cutting edge plane (CP). First edge portion (1214) is located on a first side of central axis (CA) and second edge portion (1216) is located on a second side of central axis (CA) along cutting edge plane (CP), such that first and second edge portions (1214, 1216) are diametrically opposed from one another about central axis (CA). Third edge portion (1218) is located between first and second edge portions (1214, 1216) along cutting edge plane (CP). First edge portion (1214) extends distally farther than second edge portion (1216). Third edge portion (1218) is disposed between first edge portion (1214) and second edge portion (1216).

Anvil (1250) differs from anvil (1150) in that anvil (1250) includes angled washer (1240) having an angled proximal surface (1258) with a distal first washer portion (1234) on a first side of central axis (CA), a proximal second washer portion (1236) on a second side of central axis (CA), and a third washer portion (1238) therebetween through which central axis (CA) extends. Proximal surface (1258) defines a washer plane (WP) that intersects central axis (CA) at an oblique angle such that washer plane (WP) is non-parallel relative to central axis (CA). In some versions, washer (1240) may be non-angled such that proximal surface (1258) is perpendicular relative to central axis (CA). In the present version, washer plane (WP) and cutting edge plane (CP) intersect central (CA) at different oblique angles, such that washer plane (WP) is angled relative to cutting edge plane (CP). In the present version, washer plane (WP) is less steeply angled than cutting plane (CP) relative to central axis (CA). However, both washer plane (WP) and cutting edge plane (CP) slope in the same direction such that the distal-most first edge portion (1214) of knife member (1210) is aligned with the distal-most first washer portion (1234) of washer proximal surface (1258), as shown in FIG. 20. In yet other versions, washer plane (WP) and cutting edge plane (CP) may be sloped in different directions, for example such that the distal-most first edge portion (1214) of knife member (1210) is aligned with the proximal-most second washer portion (1238) of washer proximal surface (1258).

Figure 21A:
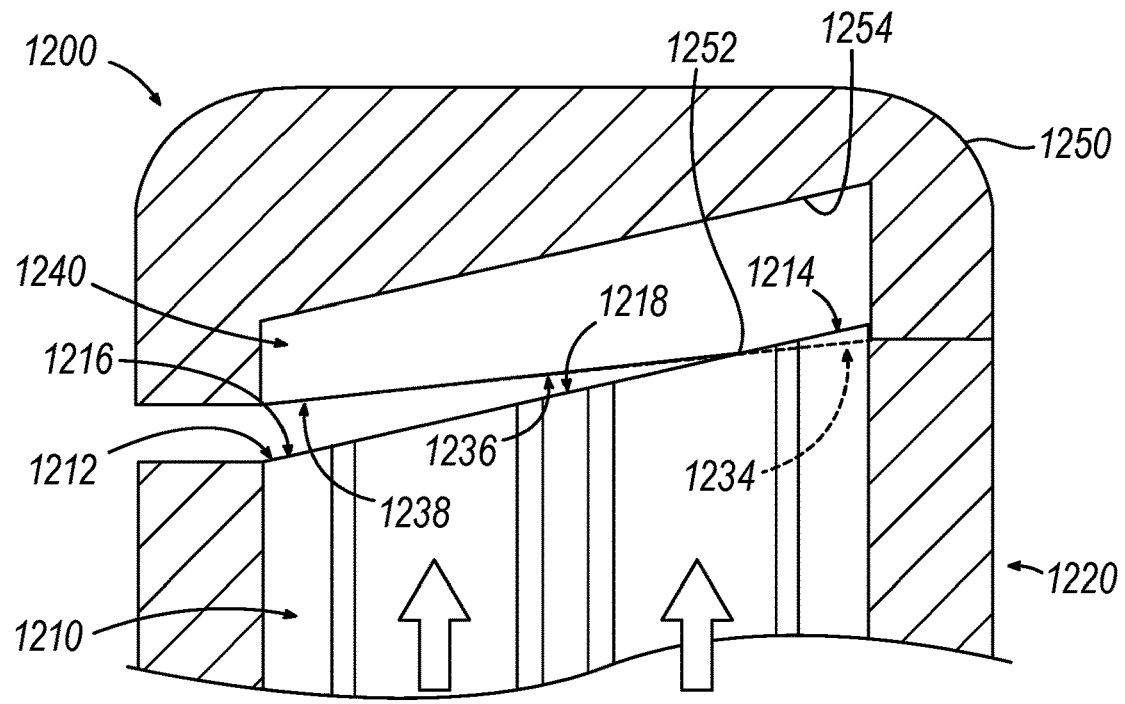
FIG. 21A depicts a cross-sectional side view of the stapling head assembly and the anvil of FIG. 20, with the knife member engaging a first side portion of a washer of the anvil on a first side of the central axis.

FIG. 21A schematically shows knife edge (1212) being transitioned distally towards anvil (1250). First edge portion (1214) engages and cuts through first washer portion (1234) at a distal advancing point of contact (1252). Point of contact (1252) is located where cutting edge plane (CP) distally intersects washer plane (WP) and a portion of knife edge (1212) engages a portion of proximal surface (1258). Knife edge (1212) engages and cuts at point of contact (1252) in a distal slicing manner through the tubular anatomical structures (20, 40) of a patient before cutting washer (1240). While only one point of contact (1252) is shown, it will be appreciated that the circumferentially closed configuration of knife edge (1212) about central axis (CA) may yield two opposed points of contact (1252) throughout the distal cutting stroke of knife member (1210).

Figure 21B:
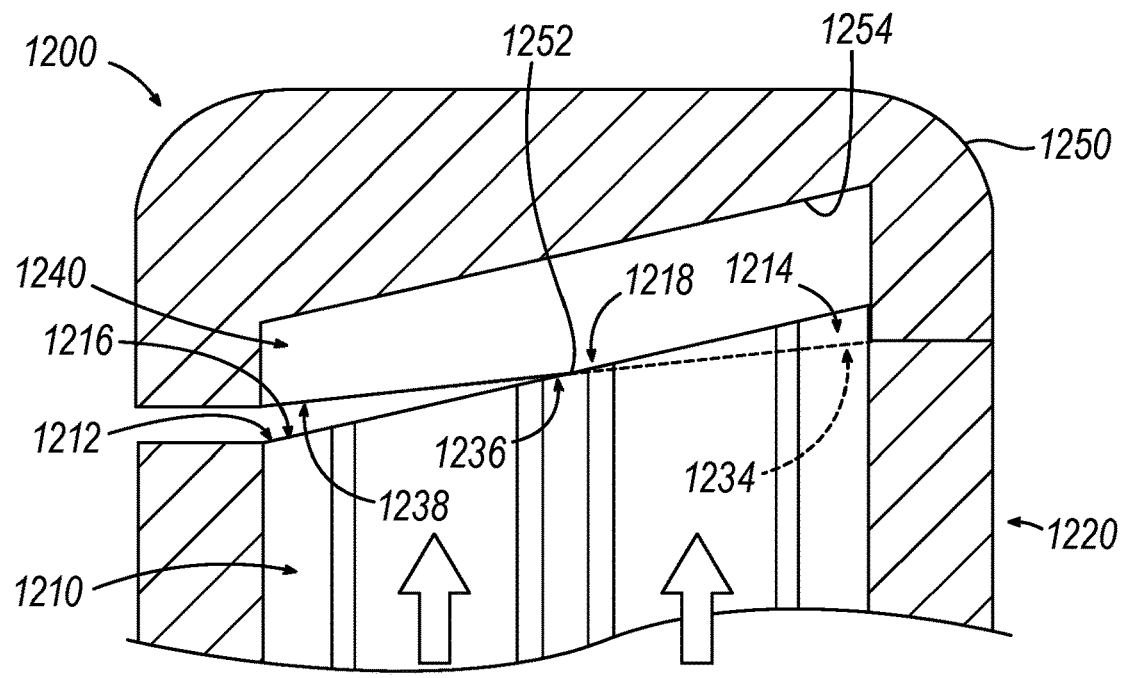
FIG. 21B depicts a cross-sectional side view of the stapling head assembly and the anvil of FIG. 20, with the knife member engaging a middle portion of the washer through which the central axis extends.
Figure 21C:
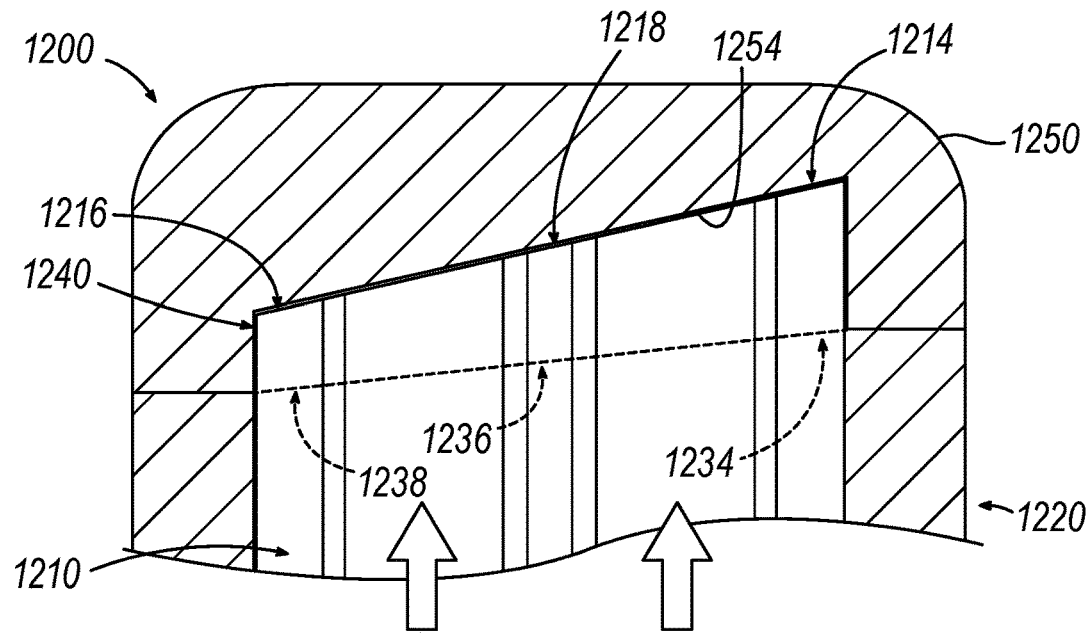
FIG. 21C depicts a cross-sectional side view of the stapling head assembly and anvil of FIG. 20, with the knife member engaging a second side portion of the washer on a second side of the central axis.

FIG. 21B schematically shows knife edge (1212) being transitioned further distally through third washer portion (1238) after cutting through the tubular anatomical structures (20, 40) at point of contact (1252) between third edge portion (1218) and third washer portion (1238). As knife edge (1212) translates distally, point of contact (1252) moves along washer plane (WP) from first washer portion (1234) through third washer portion (1238), as shown.

FIG. 21C schematically shows knife edge (1212) fully transition distally through angled washer (1240) and transect angled washer (1240). Cutting edge plane (CP) has fully passed distally through washer plane (WP), and knife edge (1212) may confront a washer seat (1254). The completion of this slicing stroke may produce audible and/or tactile feedback to the user to indicate completion of tissue cutting and stapling.

Figure 22:
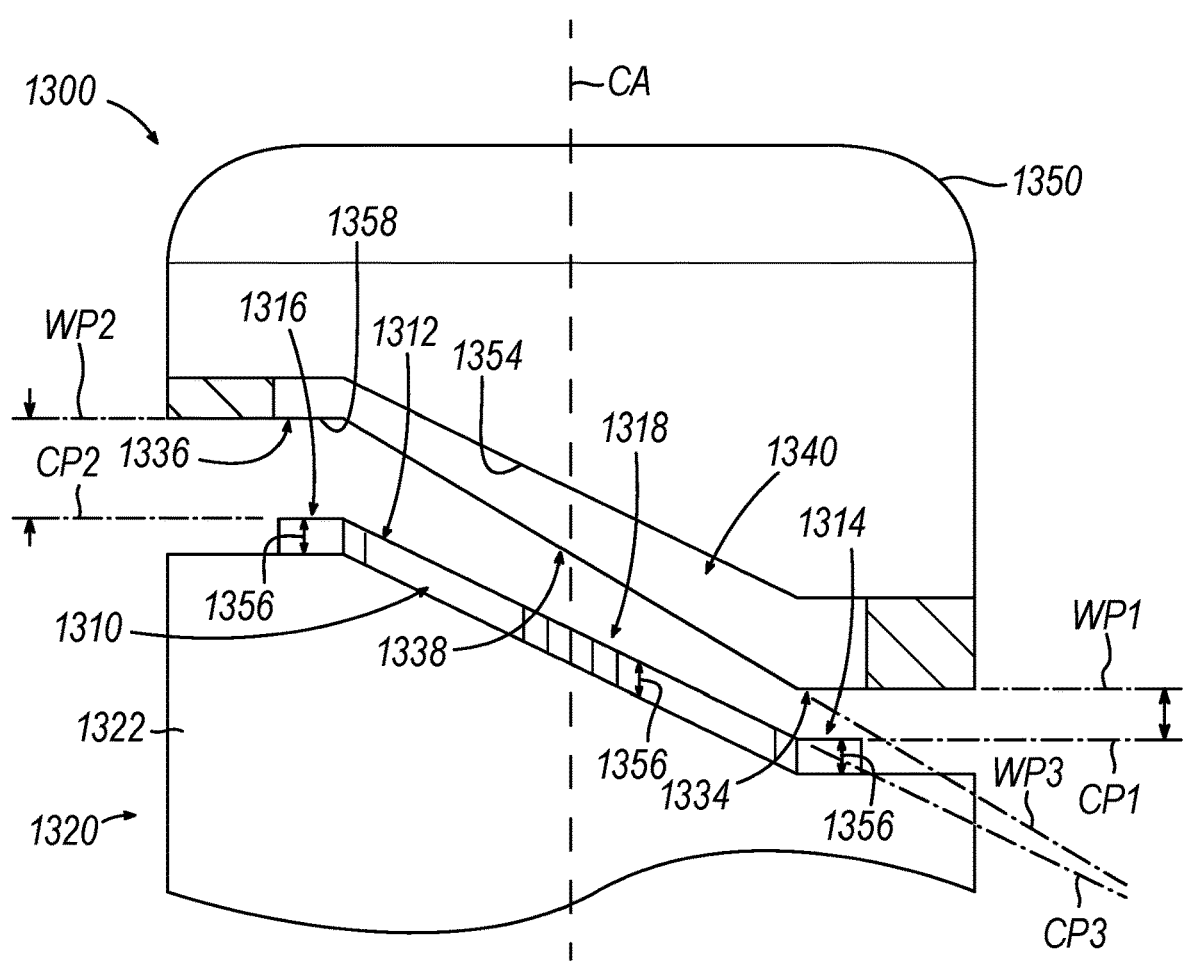
FIG. 22 depicts a cross-sectional side view of yet another exemplary stapling head assembly and anvil, with the anvil spaced apart from the stapling head assembly.

C. Third Exemplary Non-Circular End Effector Having Angled Knife Member with an Angularly Stepped Knife Edge and Angularly Stepped Washer In some instances, it may be desirable to substitute a knife member (1310) including a stepped knife edge (1312) and an anvil (1350) including a stepped washer (1340) to promote a slicing-type cutting action to minimize the force required to cut through tissue and stepped washer (1340). FIGS. 22-23C schematically show a third example of a non-circular end effector (1300) that operates in such a manner, where end effector (1300) includes a stapling head assembly (1320) having a knife member (1310) with an angularly stepped knife edge (1312), and an anvil (1350) having an angularly stepped washer (1340). Non-circular end effector (1300) is constructed and operable similar to non-circular end effector (1200) described above, except as otherwise described below.

As shown in FIG. 22, stepped knife edge (1312) has a first edge portion (1314) defining a first cutting edge plane (CP1) that intersects and is perpendicular relative to central axis (CA); a second edge portion (1316) defining second cutting edge plane (CP2) that is also perpendicular relative to central axis (CA) and thus parallel to first cutting edge plane (CP1); and a third edge portion (1319) defining a third cutting edge plane (CP3) that is obliquely angled relative to central axis (CA) and each of first cutting edge plane (CP1) and second cutting edge plane (CP2). First edge portion (1314) is located on a first side of central axis (CA) and second edge portion (1316) is located on a second side of central axis (CA) such that first and second edge portions (1314, 1316) are diametrically opposed from one another. Third edge portion (1318) extends obliquely between first and second edge portions (1314, 1316) across central axis (CA). In other versions, first and second cutting planes (CP1, CP2) may be non-perpendicular to central axis (CA).

Anvil (1350) differs from anvil (1250) in that anvil (1350) includes stepped washer (1340) having a proximal surface (1358) that defines more than one washer plane relative to central axis (CA). In particular, proximal surface (1358) includes a first washer portion (1334) defining a first washer plane (WP1) perpendicular to central axis (CA); a second washer portion (1336) diametrically opposed from first washer portion (1334) and defining a second washer plane (WP2) perpendicular to central axis (CA) and parallel to first washer plane (WP1); and a third washer portion (1338) defining a third washer plane (WP3) obliquely angled relative to central axis (CA) and each of first washer plane (WP1) and second washer plane (WP2). Third washer plane (WP3) is angled more steeply than third cutting edge plane (CP3) angle relative to central axis (CA). Third washer plane (WP3) slopes in the same direction as third cutting edge plane (CP3) such that the distal-most second edge portion (1316) of knife member (1310) is aligned with the distal-most second washer portion (1336) of washer (1340). First washer portion (1334) is more proximally located relative to second washer portion (1336) and has a greater axial thickness than second washer portion (1336). Accordingly, at any given longitudinal position of anvil (1350) relative to stapling head assembly (1320) prior to engagement between knife member (1310) and washer (1340), the axial gap between second edge portion (1316) and second washer portion (1336) is larger than the axial gap between first edge portion (1314) and first washer portion (1334). Third washer portion (1338) has an axial thickness that varies in a radial direction between first washer portion (1334) and second washer portion (1336).

Figure 23A:
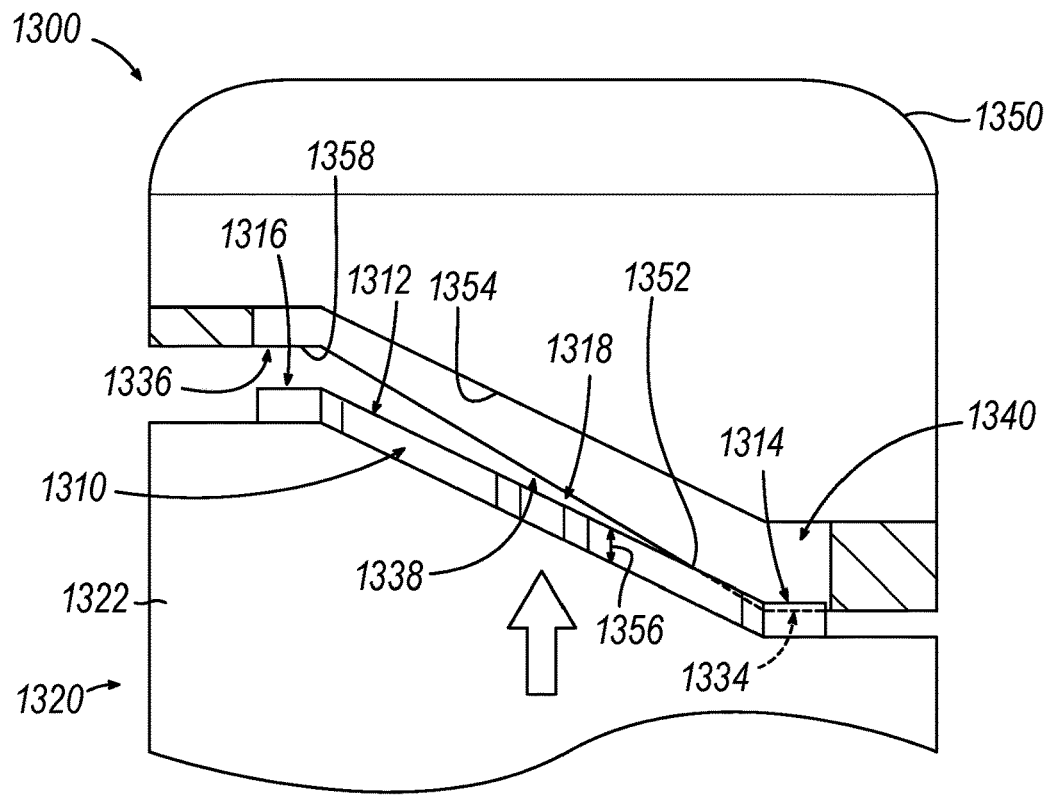
FIG. 23A depicts a cross-sectional side view of the stapling head assembly and anvil of FIG. 22, with the knife member engaging the washer on a first side portion on a first side of the central axis.

FIG. 23A schematically shows stepped knife edge (1312) being transitioned distally towards stepped washer (1340). First edge portion (1314) has engaged and cut through first washer portion (1334) after cutting through a corresponding portion of tubular anatomical structures (20, 40) disposed between first edge portion (1314) and first washer portion (1334), with a guillotine-type cutting action. The portions of tubular anatomical structures (20, 40) disposed between third edge portion (1318) and third washer portion (1338) are then progressively cut at a distally advancing point of contact (1352) located at the intersection between third cutting edge plane (CP3) and third washer plane (WP3) with a slicing-type cutting action. This progressive slicing of third washer portion (1338) and corresponding tissue by third edge portion (1318) may require less force at any given position of point of contact (1352) as compared to the force required to cut first washer portion (1334) and corresponding tissue with first edge portion (1314) and the force required to cut second washer portion (1336) with second edge portion (1316). In FIG. 23A, point of contact (1352) is at an intersection of third cutting edge plane (CP3) and third washer plane (WP3). First edge portion (1314) is distally passing first washer portion (1334) and a portion of third edge portion (1318) is partially passing a portion of third washer portion (1338). In some versions, third edge portion (1318) may begin to engage third washer portion (1338) while first edge portion (1314) engages first washer portion (1334) or after first edge portion (1314) has engaged entirety of first washer portion (1334).

Figure 23B:
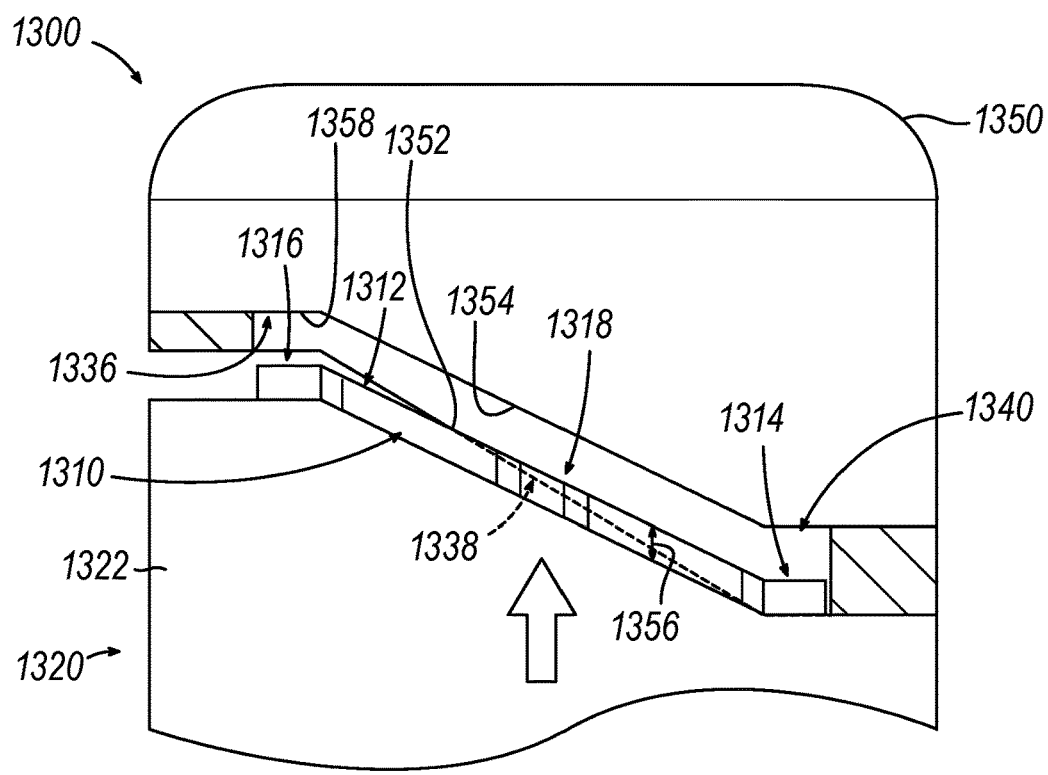
FIG. 23B depicts a cross-sectional side view of the stapling head assembly and anvil of FIG. 22, with the knife member engaging a middle portion of the washer through which the central axis extends.
Figure 23C:
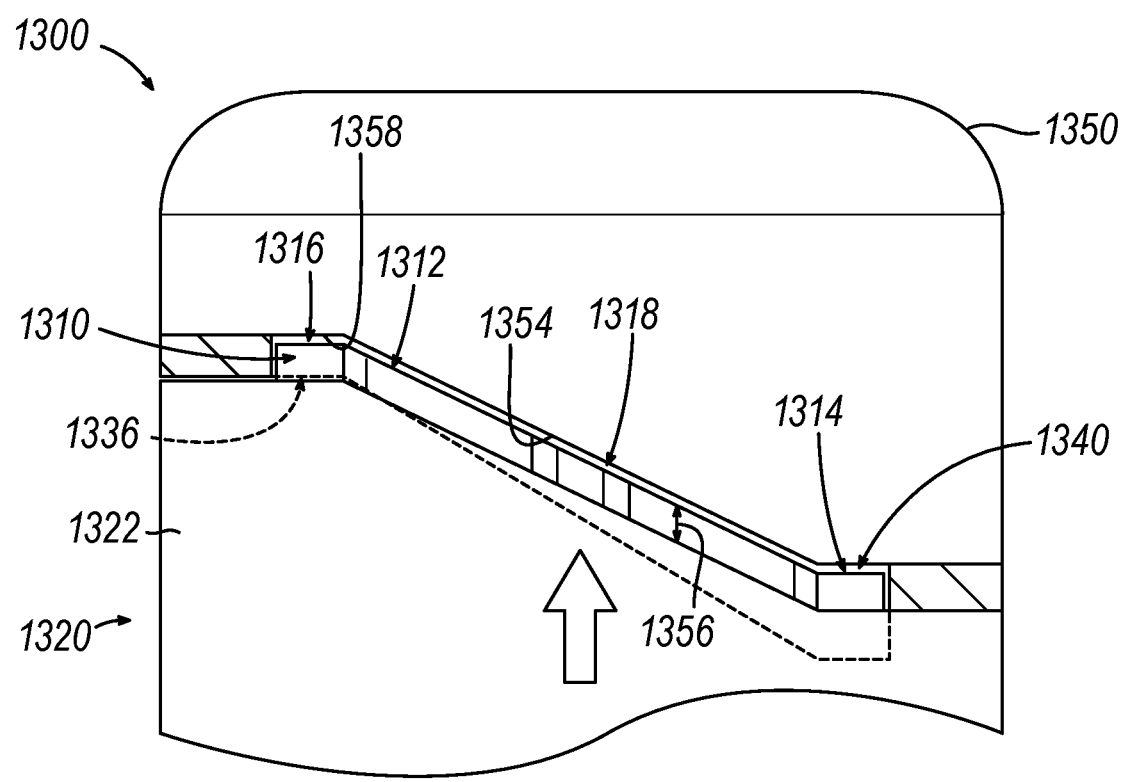
FIG. 23C depicts a cross-sectional side view of the stapling head assembly and anvil of FIG. 22, with the knife member engaging a second side portion of the washer on a second side of the central axis.

FIG. 23B schematically shows stepped knife edge (1312) being transitioned further distally through third washer portion (1338) and corresponding portions of tubular anatomical structures (20, 40) at point of contact (1352) between third edge portion (1318) and third washer portion (1338) in a slicing manner. As stepped knife edge (1312) translates distally, point of contact (1352) moves distally along third washer plane (WP3) until third cutting edge plane (CP3) fully passes distally through all of third washer plane (WP3) at an intersection of third washer plane (WP3) and second washer plane (WP2).

FIG. 23C schematically shows stepped knife edge (1312) fully transitioned distally and fully transecting stepped washer (1340). Second edge portion (1316) has cut through the second washer portion (1336) and corresponding portions of tubular anatomical structures (20.40) in a guillotine manner all at once. Cutting edge planes (CP1, CP2, CP3) have fully passed distally through washer planes (WP1, WP2, WP3), and stepped knife edge (1312) may confront a washer seat (1354). The completion of this slicing stroke may produce audible and/or tactile feedback to the user to indicate completion of tissue cutting and stapling.

Figure 24:
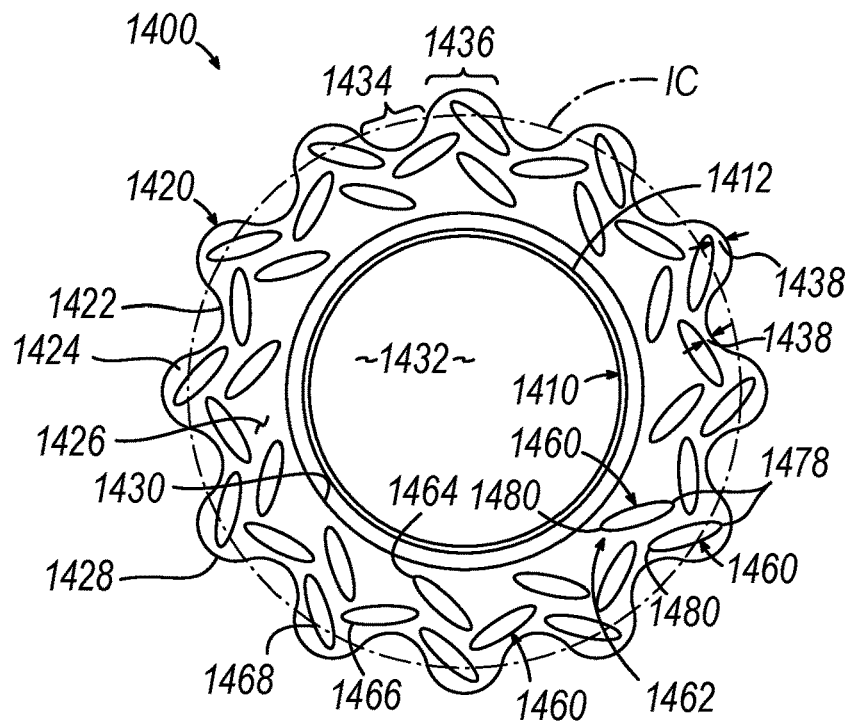
FIG. 24 depicts a top plan view of an exemplary stapling head assembly including a deck member with an undulating exterior perimeter and a circular interior perimeter, and a circular knife member.

D. Exemplary Stapling Head Assembly with an Undulating Exterior Perimeter and Circular Knife Member FIG. 24 shows a portion of another example of a stapling head assembly (1420) for use with an instrument (10) configured to create an anastomosis defining a larger lumen between tubular anatomical structures (20,40) of a patient while minimizing the cross-sectional area of stapling head assembly (1420). Stapling head assembly (1420) may be constructed and operable similar to stapling head assembly (300), except as otherwise described below.

In this example, stapling head assembly (1420) includes a body member (1422) extending distally from shaft assembly (200) and a knife member (1410) located within body member (1422). Stapling head assembly (1420) further includes a deck member (1424) located within a distal end of body member (1422). Deck member (1424) has a distally presented stapling surface in the form of a deck surface (1426). Deck surface (1426) includes a non-circular, undulating (also referred to as sinuous) exterior perimeter (1428) and a circular interior perimeter (1430), and staple openings (1460). Undulating exterior perimeter (1428) includes concave portions (1434) and convex portions (1436). Concave and convex portions (1434, 1436) define an circumference (IC) farther spaced from central axis (CA) relative to spacing between circular interior perimeter (1430) and central axis (CA). Circumference (IC) is a midline defined by alternating concave and convex portions (1434, 1436) of undulating exterior perimeter (1428). Concave and convex portions (1434, 1436) are configured allow for a minimum distance (1438) from staple openings (1460) to undulating exterior perimeter (1428). Minimum distance (1438) allows adequate spacing for effective stapling while allowing the tubular anatomical structure (20,40) to conform to the undulating exterior perimeter (1428) during insertion of end effector (1400) within the body without over expanding the tubular anatomical structure (20,40). Circular interior perimeter (1430) defines a circular lumen (1432). Circular Knife member (1410) includes a circular knife edge (1412) concentrically located within circular lumen (1432). Circular knife edge (1412) is complements and conforms to circular interior perimeter (1430).

Staple openings (1460) are arranged in an array of staple openings (1462) including a first row (1464), a second row (1466), and third row (1468) of staple openings (1460) concentrically arranged on deck surface (1426) between undulating exterior and circular interior perimeters (1428, 1430). First row (1464) is concentrically arranged within second row (1466), and second row (1466) is concentrically arranged within third row (1468).

Staple openings (1460) are oval shaped and include a first end (1478) and a second end (1480) and are angularly oriented relative to circular interior perimeter (1430). First end (1478) of first and third row (1464, 1468) are spaced a shorter radial distance from circular interior perimeter (1430) relative to second end (1480). Second end (1480) of first and third row (1464, 1468) is spaced a father radial distance relative to circular interior perimeter (1430).

Staple openings (1460) of second row (1466) are angularly arranged at an oppose angle relative to circular interior perimeter (1430). First end (1478) of staple opening (1460) of second row (1466) is spaced a farther radial distance from circular interior perimeter (1430) relative to second end (1480) of staple opening (1460). Staple openings (1460) located in second and third row (1466, 1468) further define undulating exterior perimeter (1428). Staple openings (1460) in third row (1468) further defines convex portion (1436) and staple openings (1460) in second row (1466) further defines concave portion (1434) so that staple openings (1460) are a minimum distance (1438) from undulating exterior perimeter (1428).

In summary, and as shown in FIG. 24, each staple opening (1460) of deck member (1424) extends angularly and non-tangentially relative to circumference (IC). Accordingly, staples deployed distally through staple openings (1460) and into tissue are configured to define an array of formed staples that is expandable radially outwardly to accommodate radial expansion and similar movements of the stapled tissue at the anastomosis. The undulating shape of exterior perimeter (1428) of deck member (1424) provides deck surface (1426) with sufficient surface area to accommodate three annular rows of angled staple openings (1460) such that any given radial line drawn outwardly from a central axis of deck member (1424) extends through at least one staple opening (1460), thus ensuring proper sealing of the tissue with staples. Furthermore, the undulating shape of exterior perimeter (1428) of deck member (1424) minimizes the resultant outer diameter of stapling head assembly (1420), thus enabling the corresponding surgical instrument to be manipulated and positioned more easily via minimal contact with the inner walls of tubular anatomical structures (20, 40). Finally, though not shown, it will be appreciated that an exterior perimeter of the corresponding anvil may be formed with a similar undulating shape.

Figure 25:
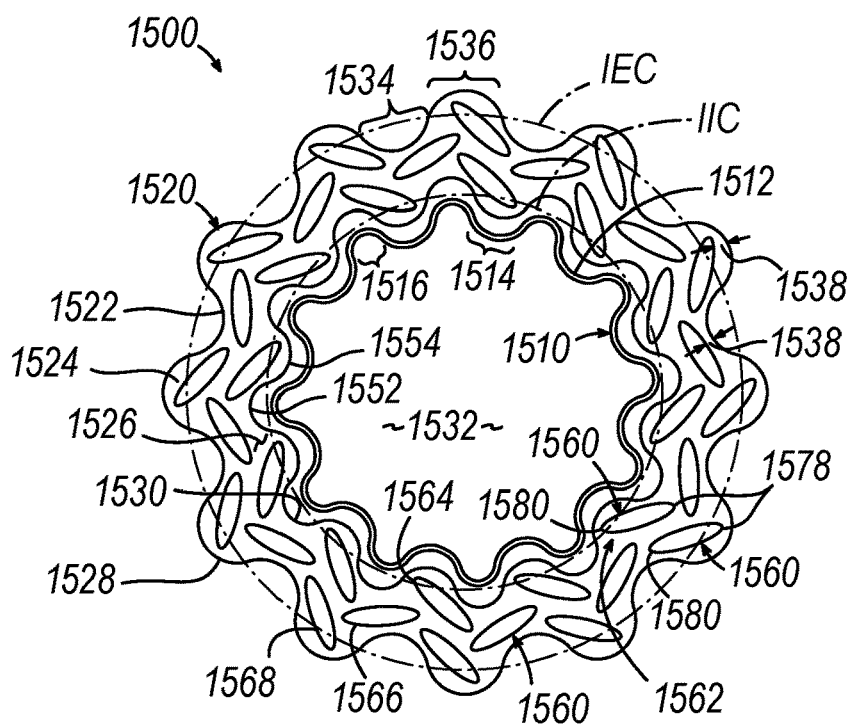
FIG. 25 depicts a top plan view of an exemplary stapling head assembly including a deck member with an undulating exterior perimeter and an undulating interior perimeter, and an undulating knife member.

E. Exemplary Non-Circular Stapling Head Assembly with Undulating Perimeters and Undulating Knife Member FIG. 25 shows a portion of another example of a non-circular stapling head assembly (1520) for use with instrument (10). Non-circular stapling head assembly (1520) is configured to create an anastomosis defining a larger lumen between tubular anatomical structures (20, 40) of a patient while minimizing the cross-sectional area of the non-circular stapling head assembly (1520). Non-circular stapling head assembly (1520) is constructed and operable similar to stapling head assembly (1420), except as otherwise described below.

In this example, non-circular stapling head assembly (1520) includes a body member (1522) extending distally from shaft assembly (200) and an undulating knife member (1510) located within body member (1522). Stapling head assembly (1520) further includes a deck member (1524) located within a distal end of body member (1522). Deck member (1524) includes a distally presented stapling surface in the form of a deck surface (1526). Deck surface (1526) includes a non-circular, undulating exterior perimeter (1528); a non-circular, undulating interior perimeter (1530); and staple openings (1560). Exterior and interior undulating perimeters (1528, 1530) define exterior and interior circumferences (IEC, INC) spaced from central axis (CA). Exterior circumference (IEC) is spaced a further distance than imaginary interior circumference (INC). Exterior and interior circumferences (IEC, INC) are midlines for respective exterior concave and convex portions (1534, 1536) and interior concave and convex portions (1552, 1554). Exterior concave and convex portions (1534, 1536) and interior concave and convex portions (1552, 1554) are configured allow for a minimum distance (1538) from staple openings (1560) to undulating exterior perimeter (1528). Minimum distance (1538) allows adequate spacing for effective stapling while allowing the tubular anatomical structure (20, 40) to conform to undulating exterior perimeter (1528) during insertion without overly expanding the tubular anatomical structure (20, 40).

Interior concave and convex portions (1552, 1554) are circumferentially clocked a few degrees from exterior convex and concave portions (1536, 1534), respectively. In some versions, interior concave and convex portions (1552, 1554) are circumferentially aligned with exterior convex and concave portions (1536, 1534), respectively. Interior concave and convex portions (1552, 1554) are spaced a minimum distance (1538) from staple openings (1560). Minimum distance (1538) allows for effective stapling, while providing creation of a larger lumen within the tubular anatomical structure (20, 40). Undulating interior perimeter (1530) defines an undulating lumen (1532). Undulating knife member (1510) includes an undulating knife edge (1512) concentrically located within undulating lumen (1532). Undulating knife edge (1512) complements the shape of interior concave and convex portions (1552, 1554) of undulating interior perimeter (1530). Undulating knife edge (1512) includes concave and convex edge portions (1514, 1516) that complement respective interior convex and concave portions (1554, 1552).

Staple openings (1560) are arranged in an array (1562) including first, second, and third rows (1564, 1566, 1568) concentrically arranged on deck surface (1526) between undulating exterior and interior perimeters (1528, 1530). First row (1564) is concentrically arranged within second row (1566), and second row (1566) is concentrically arranged within third row (1568). Staple openings (1560) are oval shaped and include a first end (1578) and a second end (1580). Each of staple openings are angularly oriented relative to central axis (CA). First ends (1578) of staple openings (1560) of first and third row (1564, 1568) are spaced a shorter radial distance from central axis (CA) relative to second end (1580). Staple openings (1560) of second row (1566) are arranged with an opposite angle relative to angle of staple openings (1560) of first and third row (1564, 1566). First ends (1578) of second row (1566) are spaced a farther radial distance from central axis (CA) relative to second end (1580).

The undulating shape of exterior perimeter (1528) of deck member (1524) maximizes the resultant outer diameter of deck member (1524) and stapling head assembly (1520), thus enabling the corresponding surgical instrument to be manipulated and positioned more easily via minimal contact with the inner walls of tubular anatomical structures (20, 40). Additionally, the undulating shape of interior perimeter (1530) of deck member (1524) maximizes the resultant inner diameter of deck member (1524) and thus the resultant outer diameter of the undulating shaped knife member (1510), which allows for cutting tissue to create an anastomosis of an enlarged resultant diameter having the benefits described above.

Figure 26:
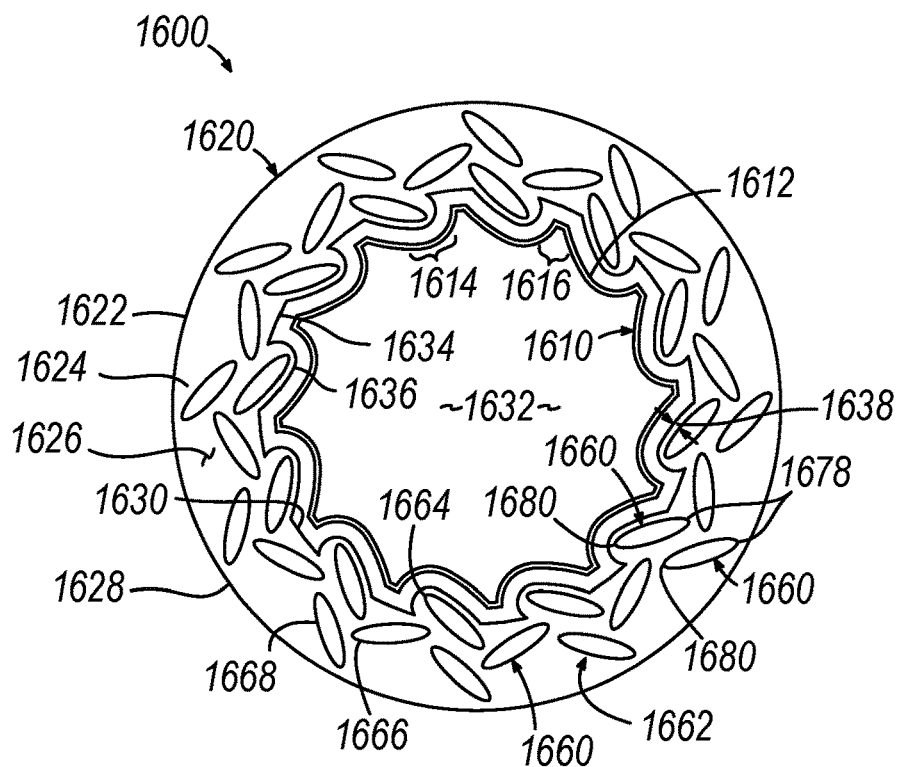
FIG. 26 depicts a top plan view of an exemplary stapling head assembly including a deck member with a circular exterior perimeter and a sawblade shaped interior perimeter, and a sawblade shaped knife member.

F. Exemplary Stapling Head Assembly with Circular Exterior Perimeter and Sawblade Knife Member FIG. 26 shows a portion of another example of a stapling head assembly (1620) suitable for use with instrument (10) and configured to create an anastomosis defining a larger lumen between tubular anatomical structures (20, 40) of a patient. Stapling head assembly (1620) is constructed and operable similar to stapling head assemblies (1420, 1520), except as otherwise described below.

In this example, stapling head assembly (1620) includes a circular body member (1622) extending distally from shaft assembly (200) and an undulating knife member (1610) positioned within circular body member (1622). Stapling head assembly (1620) further includes a deck member (1624) located within a distal end of circular body member (1622). Deck member (1624) includes a distally presented stapling surface in the form of a deck surface (1626). Deck surface (1626) includes a circular exterior perimeter (1628); a non-circular, sawblade shaped, interior perimeter (1630); and staple openings (1660) arranged in an array similar to the array of staple openings (1462) of stapling head assembly (1420).

Interior perimeter (1630) of deck member (1624) includes outwardly recessed tangent portions (1634) and inwardly protruding convex portions (1636). Tangent portions (1634) lie along a circumference (not shown). Tangent portions (1634) are connected to adjacent convex portions (1636) that curve inwards towards a central axis (not shown) and back to the circumference to next adjacent tangent portion (1634) along the circumference. Convex portions (1636) curve around staple openings (1660) with a minimum distance (1638) between convex portion (1636) and staple openings (1660). Minimum distance (1638) allows adequate spacing for effective stapling and allows sawblade-shaped knife member (1610) to have a larger resultant radius. Sawblade interior perimeter (1630) defines a sawblade shaped lumen (1632). Knife member (1610) is disposed within sawblade shaped lumen (1632) and includes a knife edge (1612) having tangent and convex portions (1634, 1636) giving knife edge (1612) a sawblade shape. Knife edge (1612) includes tangent and concave edge portions (1614, 1616) that complement tangent and convex portions (1634, 1636) of interior perimeter (1630) of deck member (1624).

Figure 27:
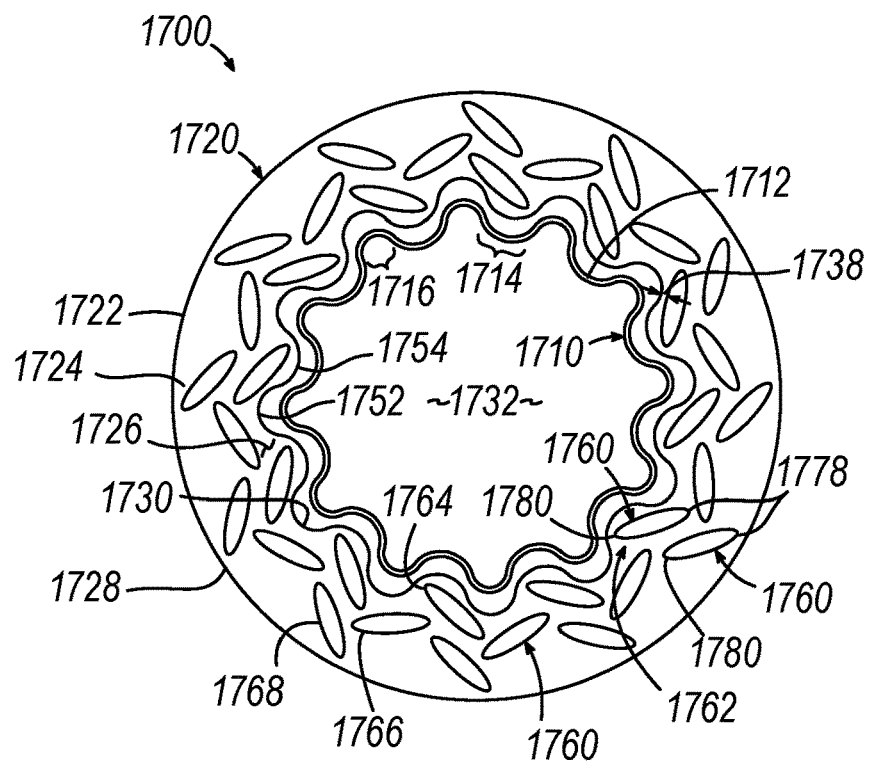
FIG. 27 depicts a top plan view of a stapling head assembly including a deck member with a circular exterior perimeter and an undulating interior perimeter, and an undulating knife member.

G. Exemplary Stapling Head Assembly with Circular Exterior Perimeter and Undulating Knife Member FIG. 27 shows a portion of another example of a stapling head assembly (1720) for use with instrument (10) configured to create an anastomosis defining a larger lumen between tubular anatomical structures (20, 40) of a patient. Stapling head assembly (1720) is constructed and operable similar to stapling head assemblies (1420, 1520, 1620), except as otherwise described below.

In this example, stapling head assembly (1720) includes a circular body member (1722) extending distally from shaft assembly (200) and an undulating knife member (1710). Stapling head assembly (1720) further includes a deck member (1724) disposed within body member (1722). Deck member (1724) includes a distally presented stapling surface in the form of a deck surface (1726). Deck surface (1726) includes a circular exterior perimeter (1728), a non-circular, undulating interior perimeter (1730), and an array of staple openings (1762) similar to the array of staple openings (1762) of stapling head assembly (1620). Undulating interior perimeter (1730) includes alternating concave and convex portions (1752, 1754). Undulating interior perimeter (1730) defines a circumference (not shown) that is a midline between concave and convex portions (1752, 1754). Concave and convex portions (1752, 1754) are configured to allow for a minimum distance (1738) between staple openings (1760) and undulating interior perimeter (1730). Minimum distance (1738) allows adequate spacing for effective stapling and allowing undulating knife member (1610) to have a larger resultant radius. Undulating knife member (1710) includes an undulating knife edge (1712) having alternating concave and convex edge portions (1714, 1716) that complement convex and concave portions (1754, 1752), respectively, of deck member (1724).

IV. Exemplary End Effector with Staple Line Alignment Feature

In some procedures where an anastomosis is created, one or more structures with a lumen may be transected where a linear sealing and transection staple line is formed in the tissue structure. By way of example only, and not limitation, in procedures such as sigmoid colectomy or lower anterior resection, two linear sealing and transection staple lines are formed as a step. One transection staple line is in the descending upper colon and one in the lower colon.

When creating the anastomosis in these exemplary procedures, at least one of these transection staple lines will interact with the circular staple pattern because it is necessary to cut through and staple over portions of at least one of the transection staple lines. For instance, in some versions of these procedures the transection staple line in the descending upper colon can be avoided when creating the anastomosis by creating a "J" pouch and putting the anvil of the stapler into the side of the colon above this upper transection staple line. However, in this example the lower transection staple line will be stapled into the anastomosis since it is practical to place the staple cartridge directly at the end of the sealed lower colon during an anastomosis procedure.

To create the anastomosis with acceptable sealing and integrity, it can be desirable to try to minimize the interaction between the linear transection staples and the staples deployed in the annular pattern. In exemplary versions that will be described further below, alignment features can be incorporated into the end effector to help minimize these staple-to-staple interactions. In doing so, a better balance between stapled and unstapled compressed tissue may be achieved. Also, these alignment features may aid in preventing the transection linear staple line from interfering with the stretch of the anastomotic staple line. Furthermore, these alignment features may allow operators using the stapler to better plan and control the twist and local tissue tension around the so-called "dog ears" that represent tissue mass adjacent to the stapled intersection of the transection staple and anastomotic staples. Still other benefits to using the alignment features described herein will be apparent to those of ordinary skill in the art in view of the teachings herein.

A. Exemplary Stapling Head Assembly and Anvils

Figure 28:
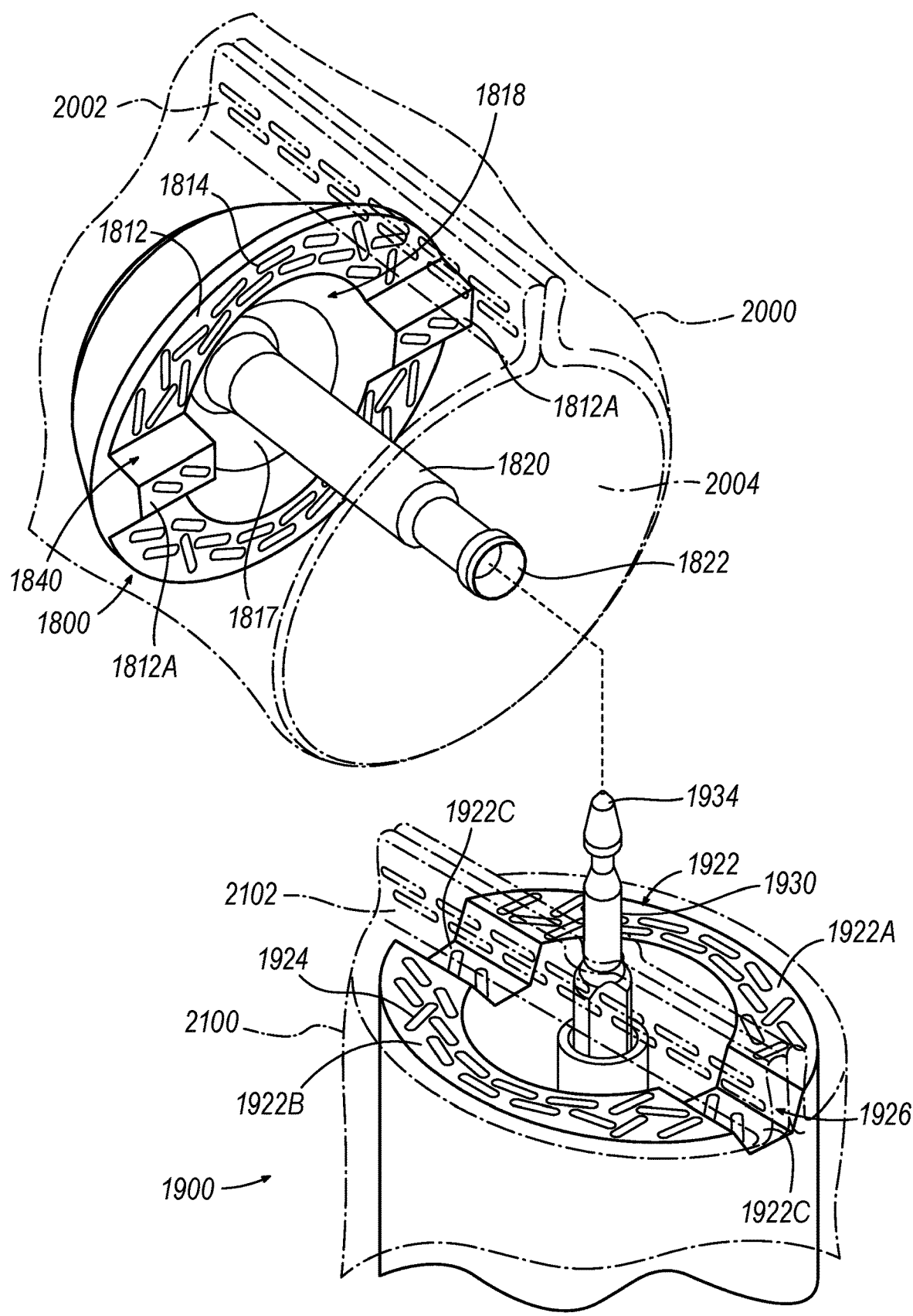
FIG. 28 depicts a perspective view of an alternate anvil and stapling head assembly, including staple line alignment features, for use with the circular stapler of FIG. 1.

Referring to FIG. 28, an exemplary anvil (1800) is shown separate from an exemplary portion of a stapling head assembly (1900). Anvil (1800) and stapling head assembly (1900) are usable with instrument (10). For instance, in some versions, instrument (10) is fit with stapling head assembly (1900) in place of stapling head assembly (300) described above. Furthermore, instrument (10) can be fit with anvil (1800) in place of anvil (400) described above.

In the present example, anvil (1800) is shown positioned within a tubular anatomical structure or lumen (2000), shown in phantom. Tubular anatomical structure (2000) is sealed with a transecting staple line (2002). In the present example, transecting staple line (2002) initially represented a distal end of tubular anatomical structure (2000). However, to avoid a proximal stapling surface (1812) of anvil (1800) interacting with transecting staple line (2002) when forming an anastomosis, tubular anatomical structure (2000) is oriented in a "J" shape with staple line (2002) moved proximally and laterally so that proximal stapling surface (1812) of anvil (1800) contacts a sidewall (2004) within tubular anatomical structure (2000) when forming an anastomosis.

In the present example, stapling head assembly (1900) is shown positioned with a tubular anatomical structure or lumen (2100), shown in phantom. Tubular anatomical structure (2100) is sealed with a transecting staple line (2102). As shown, stapling head assembly (1900) includes coupling member (1930) that extends through transecting staple line (2102). Coupling member (1930) is configured to couple with a coupling member (1820) of anvil (1800) in a similar fashion to that described above with respect to stapling head assembly (300) and anvil (400). Once anvil (1800) and stapling head assembly (1900) are coupled together, the anastomosis procedure continues as will be described further below.

Figure 29:
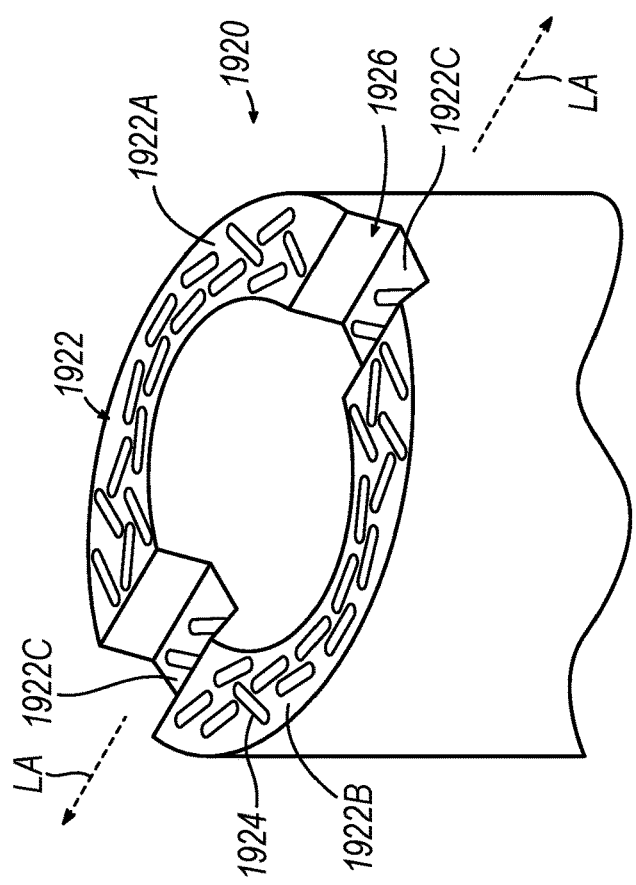
FIG. 29 depicts a perspective view of the annular deck member of the stapling head assembly of FIG. 28.

FIG. 29 depicts annular deck member (1920) of stapling head assembly (1900). Annular deck member (1920) comprises deck surface (1922) that in the present example includes a first planar portion (1922A), a second planar portion (1922B), and a third portion (1922C) between first and second planar portions (1922A, 1922B). In some versions, the first planar portion (1922A) and the second planar portion (1922B) are coplanar. In the present example, third portion (1922C) is configured as an alignment feature (1926) for aligning deck member (1920) with transecting staple lines (2102). Alignment feature (1926) defines a groove with deck surface (1922) where groove is configured to align with and receive tissue having transecting staple line (2102). In the illustrated version, alignment feature (1926) is non-coplanar with first planar portion (1922A) and second planar portion (1922B). When compressing the tissue of tubular anatomical structures (2000, 2100) when forming an anastomosis (as will be described further below), tissue with transecting staple line (2102) rests below deck surface portions (1922A, 1922B) such that staple-to-staple interactions between transected staple line (2102) and the anastomotic staples are minimized.

Figure 31:
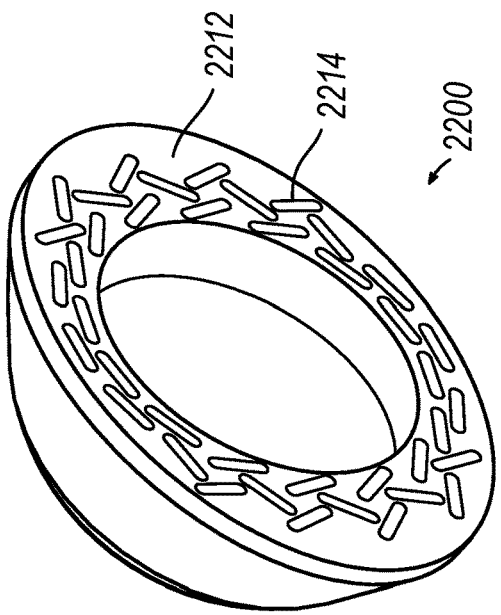
FIG. 31 depicts a perspective view of a portion of an alternate anvil similar to that shown in FIG. 30, but without an alignment feature component.
Figure 30:
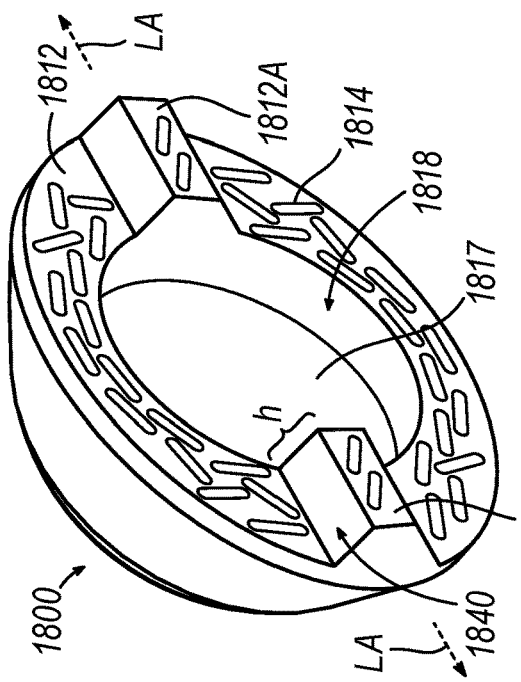
FIG. 30 depicts a perspective view of a portion of the anvil of FIG. 28.

FIGS. 30 and 31 depicts portions of respective anvils (1800, 2200). As shown, both anvils (1800, 2200) are shown without the coupling member that connects with coupling member (1930) of stapling head assembly (1900) so that proximal stapling surfaces (1812, 2212) are more readily visible. Both anvils (1800, 2200) have an oval shape as shown, and this oval shape matches the oval shape of annular deck member (1920). Accordingly, the staple openings (1924) of stapling head assembly (1900) align with the staple forming pockets (1814, 2214) of respective anvils (1800, 2200) when stapling head assembly (1900) is coupled with either anvil (1800, 2200).

With anvil (1800), a step feature (1840) is included, whereas such a step feature is omitted from anvil (2200). Step feature (1840) in the present example is configured as a raised portion that is sized and shaped to complement the groove configuration of alignment feature (1926) of deck member (1920). In some other versions, step feature (1840) may be omitted as illustrated with anvil (2200), or step feature (1840) could be configured as a recess rather than a raised portion. Furthermore, step feature (1840) could have different heights (h) representing the degree to which step feature (1840) is raised or protrudes away from proximal stapling surface (1812) toward deck member (1920), or the degree to which step feature is recessed in the case of a negative height (h). For example, in one version step feature (1840) may be raised as shown, but sized such that, when aligned with deck member (1920), step feature (1840) assists in alignment by minimally engaging the groove of alignment feature (1926) such that alignment feature (1926) maintains its ability to receive and accommodate tissue with transecting staple line (2102). In such a version, step feature (1840) is meant to merely aid in aligning anvil (1800) to the overall oval shape of deck member (1920) of stapling head assembly (1900). In such an example, the height (h) of stepped featured (1840) is less than the depth of the groove defining alignment feature (1926).

With deck member (1920) and anvil (1800), each have an oval shape, and accordingly each define a respective longitudinal axis (LA) that extends along the long dimension of the respective oval shapes. In the illustrated examples shown in FIGS. 28-30, alignment feature (1926) of deck member (1920) and stepped feature (1840) of anvil (1800) are oriented along respective longitudinal axes (LA). In other versions however, alignment feature (1926) and stepped feature (1840) may have other orientations relative to respective longitudinal axes (LA) of deck member (1920) and anvil (1800).

In some procedures, stapling head assemblies described herein, including e.g., stapling head assembly (1900) and anvils described herein, including e.g., anvils (400, 600) can be arranged relative to other components of instrument (10) for ease of use of instrument (10). For example, in lower anterior resection, the transection linear staple line is often generally parallel to the plan of the patient's back. In this case, the orientation of alignment feature (1926) and/or stepped feature (1840) should line up to this such that their orientation is generally perpendicular to body assembly or handle assembly (100) of instrument (10). This orientation improves the ease of use of instrument (10) between the patient's legs. In view of the teachings herein, other procedure-specific orientations and configurations for instrument (10) having an end effector with one or more alignment features as described herein will be apparent to those of ordinary skill in the art.

B. Exemplary Anastomosis Procedure

FIGS. 32A-32D depict a series of partial section views showing portions of instrument (10) being used to form anastomosis (70) between two tubular anatomical structures (2000, 2100). By way of example only, tubular anatomical structures (2000, 2100) may comprise sections of a patient's esophagus, colon, or other portions of the patient's digestive tract, or any other tubular anatomical structures.

Figure 32A:
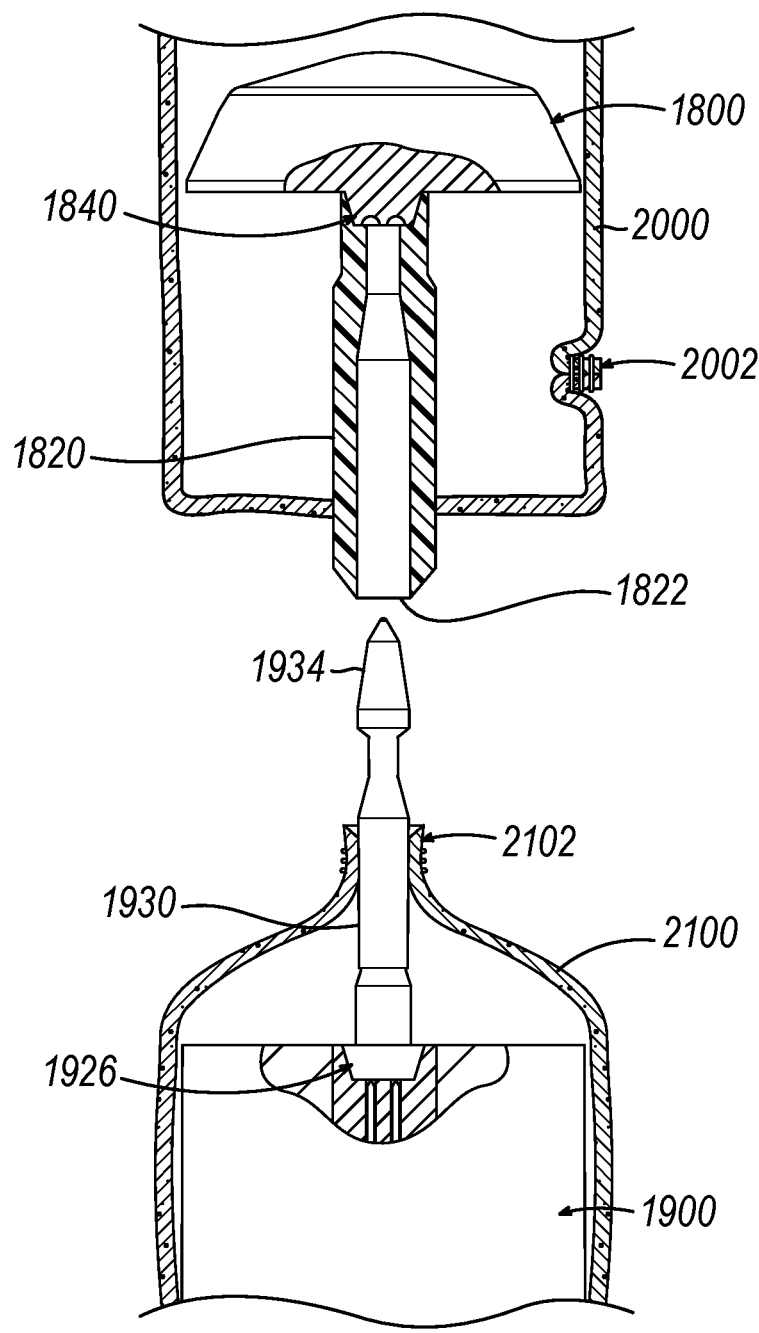
FIGS. 32A-32D depict a series view in partial cross section of the stapling head assembly of FIG. 28 used with the anvil of FIG. 31 to create an anastomosis.

As shown in FIG. 32A, anvil (1800) is positioned in one tubular anatomical structure (2000) and stapling head assembly (1900) is positioned in another tubular anatomical structure (2100). Anvil (1800) is positioned in tubular anatomical structure (2000) such that coupling member (1820) punctures and protrudes from sidewall (2004) of tubular anatomical structure (2000). In some other versions, coupling member (1820) does not puncture sidewall (2004). Instead, it merely contacts the interior of sidewall (2004) and subsequently connects with coupling member (1930) of stapling head assembly (1900), which punctures sidewall (2004) from the exterior. In the present example, and as mentioned above, transection staple line (2002) is shown to the side using the "J" pouch technique described above to eliminate staple-to-staple interactions between the staples of transection staple line (2002) and the staples to be deployed in forming the anastomosis.

Stapling head assembly (1900) is positioned in tubular anatomical structure (2100) such that coupling member (1930) punctures and protrudes from the stapled end of tubular anatomical structure (2100) shown by transection staple line (2102). Stapling head assembly (1900) is then urged distally to ensure that stapling head assembly (1900) is fully seated near the distal end of tubular anatomical structure (2100) with coupling member (1930) visible on the exterior of tubular anatomical structure (2100).

Figure 32B:
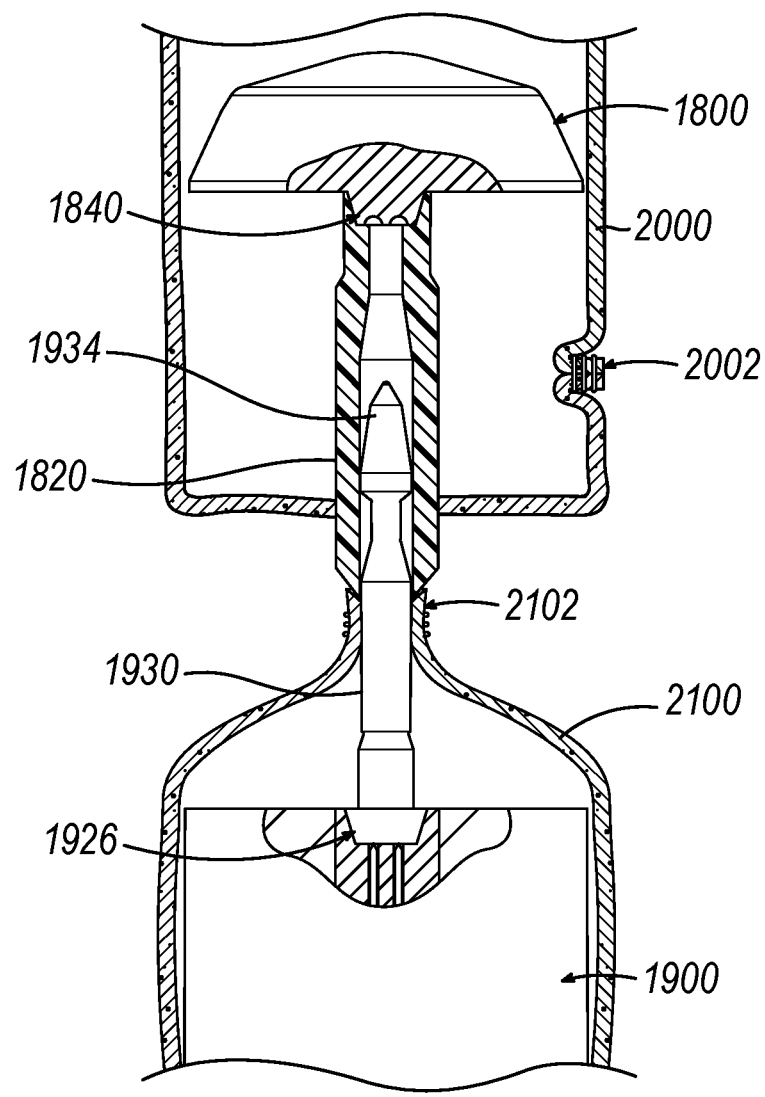
Figure 32C:
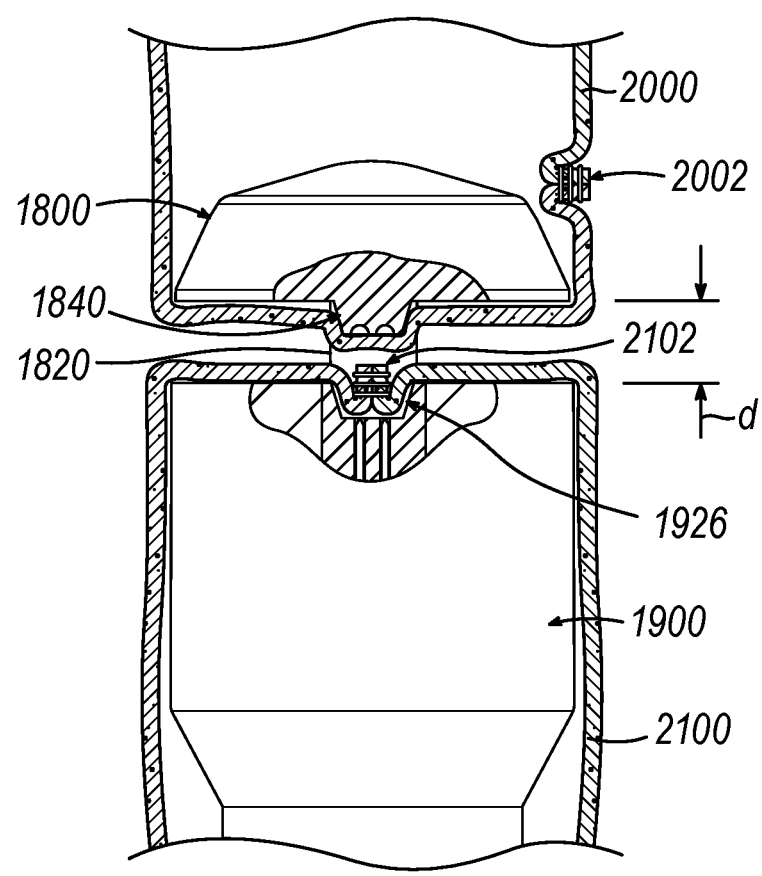

Next, anvil (1800) is secured to coupling member (1930) by inserting coupling member (1930) into a bore (1822) of coupling member (1820) as shown in FIG. 32B. Latch members (not shown, but similar to latch members (430) described above) of anvil (1800) engage a head (1934) of coupling member (1930), thereby providing a secure fit between anvil (1800) and coupling member (1930). The operator then rotates knob (130) of instrument (10) while holding casing (110) stationary via pistol grip (112). This rotation of knob (130) causes coupling member (1930) and anvil (1800) to retract proximally toward deck member (1920) as shown in FIG. 32C. With stapling head assembly (1900) at the distal end of tubular anatomical structure (2100), alignment feature (1926) aligns with transection staple line (2102) and receives transection staple line (2102) within the groove or recess defined by alignment feature (1926) as shown in FIG. 32C.

Figure 32D:
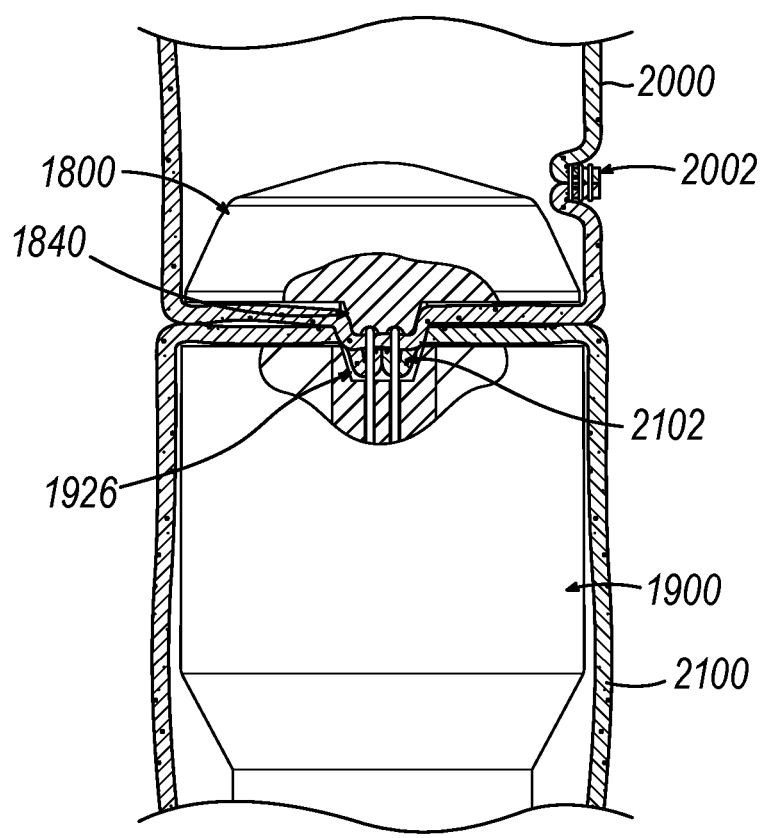

As shown in FIG. 32D, further proximal retraction of coupling member (1930) and anvil (1800) compresses the tissue of tubular anatomical structures (2000, 2100) between surfaces (1812, 1922) of anvil (1800) and stapling head assembly (1900). As this occurs, the operator may observe the tactile resistance or feedback via knob (130) while turning knob (130), with such tactile resistance or feedback indicating that the tissue is being compressed. Additionally, the operator may observe the tactile feedback of step feature (1840) aligning with alignment feature (1926) such that the oval shapes of anvil (1800) and stapling head assembly (1900) align for complete overlapping coverage where stapling openings (1924) align with respective corresponding staple forming pockets (1814). As the tissue is being compressed, the operator may visually observe the position of an indicator needle (not shown) within user interface feature (114) of handle assembly (100) to determine whether the gap distance (d) between opposing surfaces (1812, 1922) of anvil (1800) and stapling head assembly (1900) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (1900) by actuating drive bracket (250) distally to thereby drive knife member (not shown) and staple driver member (not shown) distally together. As knife member translates distally, excess tissue that is positioned within annular recess (1818) of anvil (1800) and the interior of knife member is cut. Additionally, washer (1817) positioned within annular recess (1818) of anvil (1800) is broken by knife member when the knife member completes a full distal range of motion. It should be understood that washer (1817) may also serve as a cutting board for knife member to assist in cutting of tissue.

As staple driver member (not shown) translates distally, staple driver member drives staples (90) through the tissue of tubular anatomical structures (2000, 2100) and into staple forming pockets (1814) of anvil (1800). Staple forming pockets (1814) deform the driven staples (90) into a "B" shape or a three-dimensional shape, for example, such that the formed staples (90) secure the ends of tissue together, thereby coupling tubular anatomical structure (2000) with tubular anatomical structure (2100).

After the operator has actuated (or "fired") stapling head assembly (1900) as shown, the operator rotates knob (130) to drive anvil (1800) distally away from stapling head assembly (1900), thereby increasing the gap distance (d) to facilitate release of the tissue between surfaces (1812, 1922). The operator then removes instrument (10) from the patient, with anvil (1800) still secured to coupling member (1930). With instrument (10) removed, the tubular anatomical structures (2000, 2100) are left secured together by two annular arrays of staples (90) at an anastomosis (70). The inner diameter of the anastomosis (70) is defined by the severed edge (60) left by the knife member.

C. Exemplary Alternate Shaped Stapling Head Assemblies and Anvils

Figure 33:
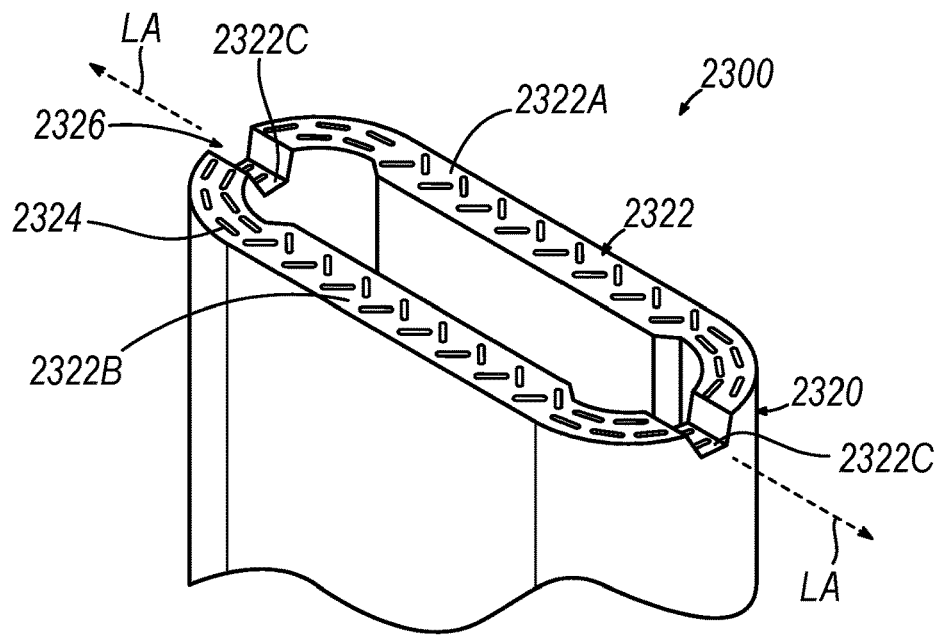
FIG. 33 depicts a perspective view of an alternate exemplary annular deck member of a stapling head assembly with the annular deck member having a dog-bone shape and an alignment feature.
Figure 34:
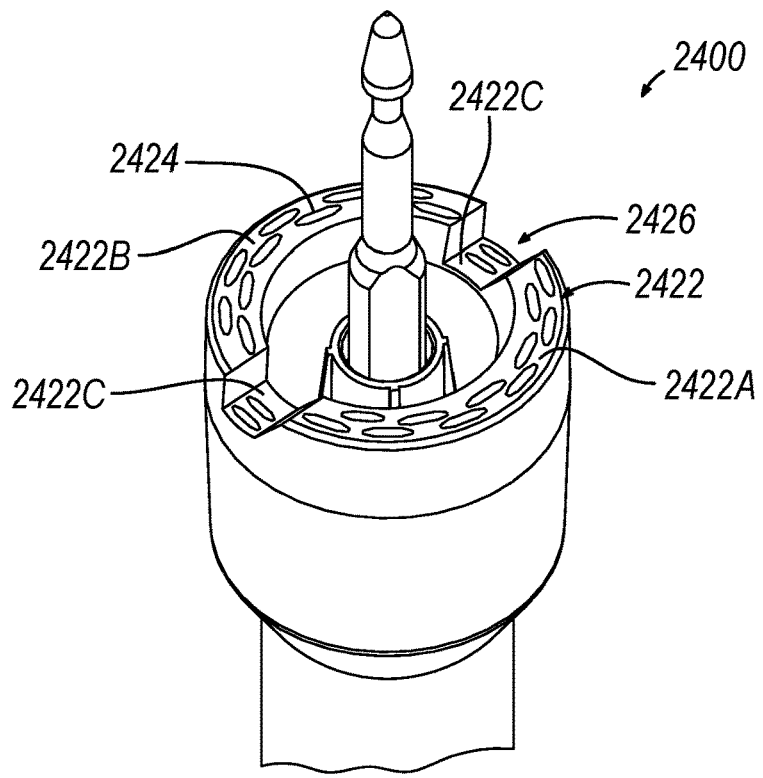
FIG. 34 depicts a perspective view of an alternate exemplary stapling sigmoid colectomy head assembly having a circular shape with an alignment feature.

FIGS. 33 and 34 depict portions of stapling head assemblies (2300, 2400), which have respective deck members (2320, 2420) that incorporate respective alignment features (2326, 2426) similar to alignment feature (1926) described above. As shown with respective to stapling head assembly (2300) of FIG. 33, deck member (2320) of stapling head assembly (2300) is dog-bone shaped with an elongated curved shape. In this manner deck member (2320) defines a longitudinal axis (LA) along its long dimension. In the present example, alignment feature (2326) is oriented along this longitudinal axis (LA). Stapling head assembly (2300) is shown without coupling member (1930) to clearly illustrate the shape of deck member (2320). It is understood that stapling head assembly (2300) includes all the corresponding components described with respect to stapling head assembly (300) above, those components being adapted to accommodate the dog-bone shape of deck member (2320). Furthermore, stapling head assembly (2300) is usable with instrument (10) by replacing stapling head assembly (300) with stapling head assembly (2300). In doing so a matching anvil (not shown) that has a corresponding dog-bone shape to deck member (2320) would be used with instrument (10) in place of anvil (400). Accordingly, the staple openings (2324) of stapling head assembly (2300) would align with the staple forming pockets of the respective anvil when stapling head assembly (2300) is coupled with the corresponding anvil.

Similar to alignment feature (1926), alignment feature (2326) defines a groove within deck surface (2322). Deck surface (2322) includes a first planar portion (2322A), a second planar portion (2322B), and a third portion (2322C) between first and second planar portions (2322A, 2322B). In the present example, third portion (2322C) is configured as alignment feature (2326) for aligning deck member (2320) with transecting staple lines (2102). For example, the groove defined by alignment feature (2326) is configured to align with and receive tissue having transecting staple line (2102). In this manner, when compressing the tissue of tubular anatomical structures (2000, 2100) when forming an anastomosis (as described above), tissue with transecting staple line (2102) rests below deck surface portions (2322A, 2322B) such that staple-to-staple interactions between transected staple line (2102) and the anastomotic staples are minimized.

As shown with respective to stapling head assembly (2400) of FIG. 34, deck member (2420) of stapling head assembly (2400) is circular shaped. In this manner deck member (2320) defines a diameter. In the present example, alignment feature (2326) is oriented along the diameter of the circular shaped deck member (2420). Stapling head assembly (2400) is shown with coupling member (1930), which would couple to an anvil's coupling member such as anvil (400) and its coupling member or shank (420). It is understood that stapling head assembly (2400) includes all the corresponding components described with respect to stapling head assembly (300) above, those components being adapted to accommodate the alignment feature (2426) of deck member (2420). Furthermore, stapling head assembly (2400) is usable with instrument (10) by replacing stapling head assembly (300) with stapling head assembly (2400). In doing so a matching circular anvil with a stepped feature like stepped feature (1840) described above (not shown) would be used with instrument (10) in place of anvil (400). In another version though, circular shaped anvil (400) without a stepped feature, as described above, can also be used with stapling head assembly (2400) with instrument (10). In either case, the staple openings (2424) of stapling head assembly (2400) would align with the staple forming pockets of the respective anvil when stapling head assembly (2400) is coupled with the anvil.

Similar to alignment feature (1926), alignment feature (2426) defines a groove within deck surface (2422). Deck surface (2422) includes a first planar portion (2422A), a second planar portion (2422B), and a third portion (2422C)

between first and second planar portions (2422A, 2422B). In the present example, third portion (2422C) is configured as alignment feature (2426) for aligning deck member (2420) with transecting staple lines (2102). For example, the groove defined by alignment feature (2426) is configured to align with and receive tissue having transecting staple line (2102). In this manner, when compressing the tissue of tubular anatomical structures (2000, 2100) when forming an anastomosis (as described above), tissue with transecting staple line (2102) rests below deck surface portions (2422A, 2422B) such that staple-to-staple interactions between transected staple line (2102) and the anastomotic staples are minimized. While dog-bone, oval, and circular shaped stapling head assemblies and anvils having alignment features are described herein, other shaped structures for these may be used and will be apparent to those of ordinary skill in the art. Additionally, further exemplary oval and dog-bone shaped stapler end effectors are shown and described in U.S. patent application Ser. No. 17/401,428, entitled "Staple Forming Features for Circular Surgical Stapler," filed on Aug. 13, 2021, issued as U.S. Pat. No. 11,998,209 on Jun. 4, 2024; and U.S. patent application Ser. No. 17/401,430, entitled "Non-Circular End Effector Features for Circular Surgical Stapler," filed on Aug. 13, 2021, issued as U.S. Pat. No. 11,944,310 on Apr. 2, 2024. The disclosures of each are incorporated by reference herein.

D. Exemplary Tissue Gaps and Staple Configurations

As described above, deck surface (1922) of deck member (1920) has first and second planar portions (1922A, 1922B) and third portion (1922C). In one version, third portion (1922C) is not coplanar with first and second portions (1922A, 1922B). As also mentioned above, the tissue gap or gap distance (d) represents the distance between deck surface (1922) and proximal stapling surface (412, 1812) of anvil (400, 1800). In versions of instrument (10) using stapling head assembly (1900) with anvil (400), gap distance (d) is non-uniform across the end effector as there is a greater distance between the surfaces of anvil (400) and deck member (1920) at third portion (1922C) defining alignment feature (1926) compared to the distance at first and second planar portions (1922A, 1922B). This is the case, because alignment feature (1926) defines a groove that is recessed relative to first and second planar portions (1922A, 1922B).

Other versions of instrument (10) can incorporate alignment feature (1926) or a similar alignment feature and also be paired with an anvil having a complementary stepped feature (1840) or a similar complementary stepped feature. This could be the case, for instance, when instrument (10) includes stapling head assembly (1900) and anvil (1800). In these versions, the height (h) of stepped feature (1840) relative to the depth of the recess or groove of alignment feature (1926) will define gap distance (d) at third portion (1922C). In some instances, gap distance (d) at third portion (1922C) is the same as gap distance (d) at first and second planar portions (1922A, 1922B). In other versions, gap distance (d) at third portion (1922C) is smaller or larger than gap distance (d) at first and second planar portions (1922A, 1922B). In view of the teachings herein, various other configurations of instrument (10) to achieve various gap distances (d) across the anvil and deck member surfaces will be apparent to those of ordinary skill in the art.

In some versions with a non-uniform tissue gap or gap distance (d), staple geometry differs across deck surface (1922) of deck member (1920). For example, FIGS. 35A and 35B depict staples (2590, 2690) with each having a different unformed staple leg length. Staple (2590) has an unformed staple leg length (L1) that is shorter than unformed staple leg length (L2) of staple (2690). In one version, staples (2690) with their longer unformed staple leg length (L2) are used with stapling head assembly (1900) at third portion (1922C) where alignment feature (1926) is located. At the other first and second planar portions (1922A, 1922B), staples (2590) with their shorter unformed staple leg length (L1) are used. In such an example, the staples with the longer unformed staple leg length provide improved stapling performance at the areas there the transection line staples interact with the anastomotic staples. For example, the longer unformed staple leg length staples can provide more secure integration of the staple lines and minimize leaks around the dog ears. In some other instances, staples (2590) may be used at third portion (1922C) instead, and staples (2690) used at first and second planar portions (1922A, 1922B). For instance, this could be helpful in minimizing staple-to-staple interactions at the overlap of transection line staples and anastomotic staples. The nature of the tissue being stapled as well as the configuration of the transection line staples may inform the operator as to which stapling configuration is desired when using staples of differing unformed staple leg lengths.

FIGS. 36A and 36B depict staples (2790, 2890) with each having a different staple wire size or diameter. Staple (2790) has a staple wire size that is larger than the staple wire size of staple (2890). In one version, staples (2790) with their larger wire size are used with stapling head assembly (1900) at third portion (1922C) where alignment feature (1926) is located. At the other first and second planar portions (1922A, 1922B), staples (2890) with their smaller wire size are used. In such an example, the staples with the larger wire size provide improved stapling performance at the areas there the transection line staples interact with the anastomotic staples. For example, the staples with the larger wire size or diameter can provide more secure integration of the staple lines and minimize leaks around the dog ears. In some other instances, staples (2890) may be used at third portion (1922C) instead, and staples (2790) used at first and second planar portions (1922A, 1922B). For instance, this could be helpful in minimizing staple-to-staple interactions at the overlap of transection line staples and anastomotic staples. The nature of the tissue being stapled as well as the configuration of the transection line staples may inform the operator as to which stapling configuration is desired when using staples of differing wire size.

FIGS. 37A and 37B depict staples (2990, 3090) with each having a different formed staple height. Staple (2990) has an unformed staple height (H1) that is shorter than formed staple height (H2) of staple (3090). In one version, staples (3090) with their longer formed staple height (H2) are used with stapling head assembly (1900) at third portion (1922C) where alignment feature (1926) is located. At the other first and second planar portions (1922A, 1922B), staples (2990) with their shorter formed staple height (H1) are used. In such an example, staples (3090) with their greater formed staple height provide improved stapling performance at the areas there the transection line staples interact with the anastomotic staples. For example, the staples with the larger formed staple height can provide more secure integration of the staple lines and minimize leaks around the dog ears. In some other instances, staples (2990) may be used at third portion (1922C) instead, and staples (3090) used at first and second planar portions (1922A, 1922B). For instance, this could be helpful in minimizing staple-to-staple interactions at the overlap of transection line staples and anastomotic staples. The nature of the tissue being stapled as well as the configuration of the transection line staples may inform the operator as to which stapling configuration is desired when using staples of differing formed staple heights.

V. Exemplary Stapler Features for Forming Non-Tangential Staple Patterns

In some scenarios, the tissue forming the tubular anatomical structures (20, 40) may need to expand and contract in the radial direction after being stapled together as described above. For instance, when structures (20, 40) are organ portions of a patient's digestive tract, those organ portions may need to expand and contract during peristalsis to accommodate passage of digestive matter (e.g., chyme, waste products of the digestive process, stool, etc.). Therefore, the portion of the tubular anatomical structures (20, 40) that are stapled together may need to withstand such expansion and contraction while also maintaining the structural integrity of the staples (90) and the tissue at the staples (90), to continue suitably securing the ends of anatomical structures (20, 40) together.

The configuration and/or arrangement of formed staples (90) may restrict the ability of anastomosis (70) to expand radially in some cases. Therefore, it may be desirable to incorporate a staple pattern or staples that in turn enhance the structural integrity of the stapled ends of the anatomical structures (20, 40), thereby better accommodating for such expansion and contraction during peristalsis or other normal anatomical functioning.

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) may be generally smaller than that of each tubular anatomical structure (20, 40). In other words, anastomosis (70) and severed edges (60) extend radially inwardly within the interior of the tubular anatomical structure (20, 40). With severed edges (60) extending radially inwardly, such severed edges (60) may act as an obstruction for the passage of digestive matter. If such an obstruction becomes too great, it may negatively impact the patient's ability to digest food, or even damage the integrity of stapled tissue (20, 40). Therefore, in order to minimize such obstructions, it may be desirable to a minimize the length to which severed edge (60) extends radially inwardly within the interior of tubular anatomic structure (20, 40).

Since staples (90) are fired in a longitudinal direction that is substantially parallel with the length of the adjacent anatomical structures (20, 40), and since knife member (340) is located radially inward from deck surface (322), the width of deck surface (322) (i.e., the distance between the inner diameter and outer diameter of deck surface (322)) may be a factor in the length to which severed edges (60) extend radially inwardly from structures (20, 40). Therefore, to the extent it may be desirable to alter the staple pattern formed by staple openings (324) defined by deck surface (322), it may also be desirable to minimize the width of deck surface (322) in order to accommodate such a change in staple pattern. Additionally, it may be desirable to minimize the width of deck surface (322) in the direction substantially perpendicular to the length of adjacent anatomical structures (20, 40) in order to reduce the length of severed edges (60) and the chance severed edges (60) become an undesirable obstruction.

In some procedures, it may be desirable to form an anastomosis (70) of enlarged diameter and/or to enable the annular arrays of formed staples (90) to expand radially outwardly, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and anvil (400) with features that enable formation of such an anastomosis and/or patterns of formed staples (90). Exemplary versions of such features are described in greater detail below. The below described features may be readily incorporated into instrument (10), such that a modified version of instrument (10) may include any one or more of the various features described below.

A. Exemplary Alternative Staple Patterns and Staples

As shown in FIG. 4, staple openings (324) each have a length that extends along an axis that is parallel to the closest tangent line of the inner diameter or outer diameter of annular deck member (320). In order to better accommodate for radial expansion and contraction, as described above, it may be desirable to have a staple deck with at least some staple openings that have a length extending along an axis that forms a non-parallel relationship with the closest tangent line of either the inner diameter or outer diameter of deck member (320). It should be understood that a staple opening that extends long a length that forms a non-parallel relationship with the closest tangent line of either the inner or outer diameter of a deck member is considered a non-tangential staple opening housing a non-tangentially oriented staple. The length of a staple opening may be considered the portion of the staple opening in which the crown of a staple extends to connect to the legs of a staple.

Figure 38:
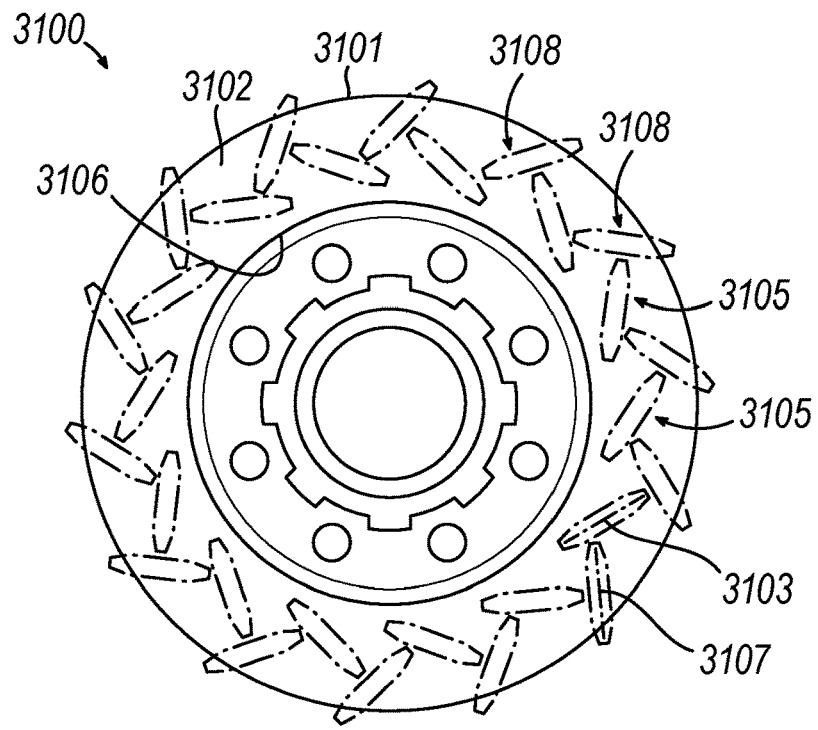
FIG. 38 depicts a top plan view of an alternative deck member that may be incorporated into the stapling head assembly of FIG. 4, the deck member defining an inner array of staple openings and an outer array of staple openings of uniform size, where the outer annular array is sized and arranged to not fit within the parameters of the deck member.

FIG. 38 shows an exemplary staple deck member (3100) having a deck surface (3102) defined by an outer diameter (3104) and an inner diameter (3106). Deck surface (3102) attempts to define an outer array of stale openings (3108) and an inner array of staple openings (3105) forming a traditional herringbone pattern. Array of staple openings (3105, 3108) both having individual openings extending in a non-tangential relationship without modifying (A) the width of deck surface (3102) or (B) the size of staple openings (3105, 3108) as compared to staple openings (324) described above. However, as best shown in how a portion of staple openings (3108) extend past the outer diameter (3104) of deck surface (3102), staple openings (3108, 3105) are difficult to orient in a non-tangential relationship without undesirably increasing the width of deck surface (3102).

Figure 44:
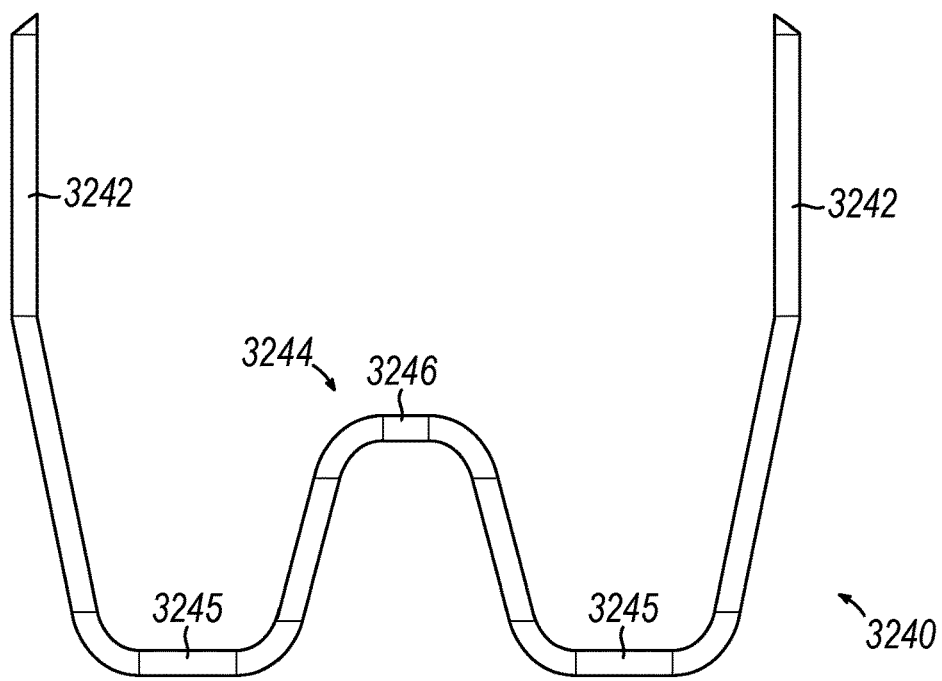
FIG. 44 depicts an elevational front view of an alternative staple that may be applied via the circular stapler of FIG. 1.
Figure 45:
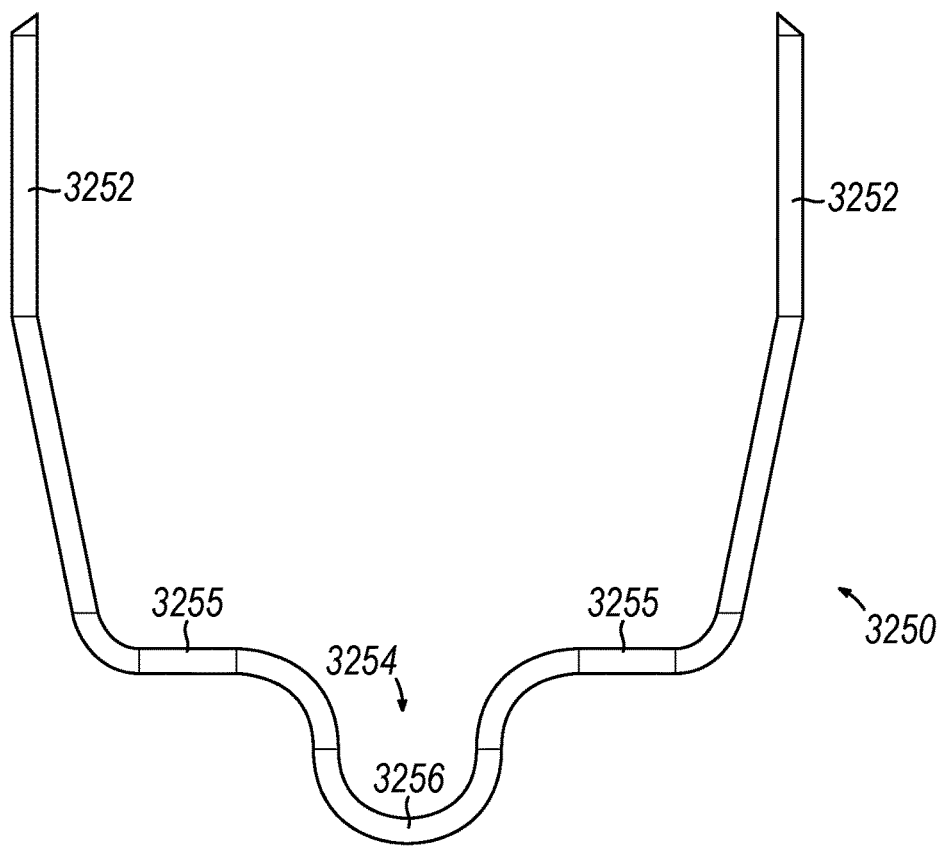
FIG. 45 depicts an elevational front view of an alternative staple that may be applied via the circular stapler of FIG. 1.
Figure 46:
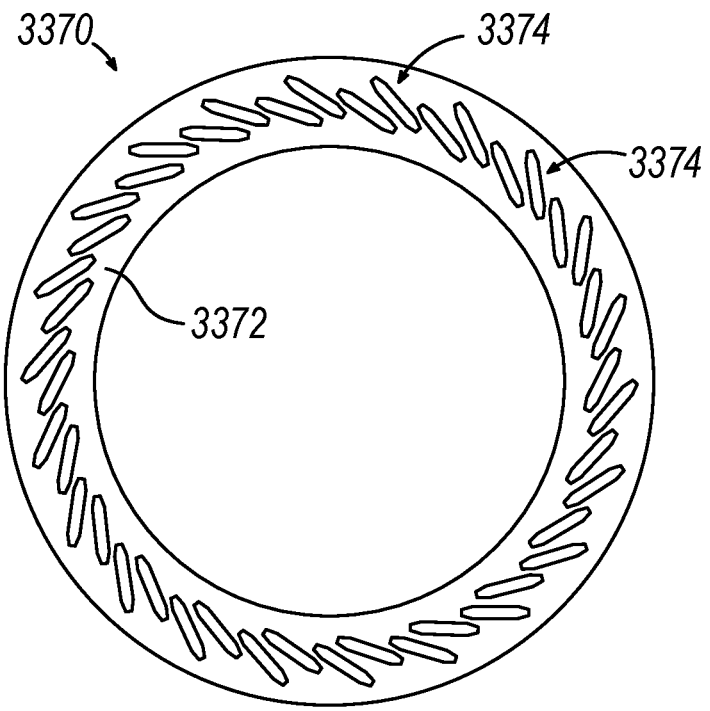
FIG. 46 depicts a top plan view of another alternative deck member that may be incorporated into the stapling head assembly of FIG. 4.
Figure 47:
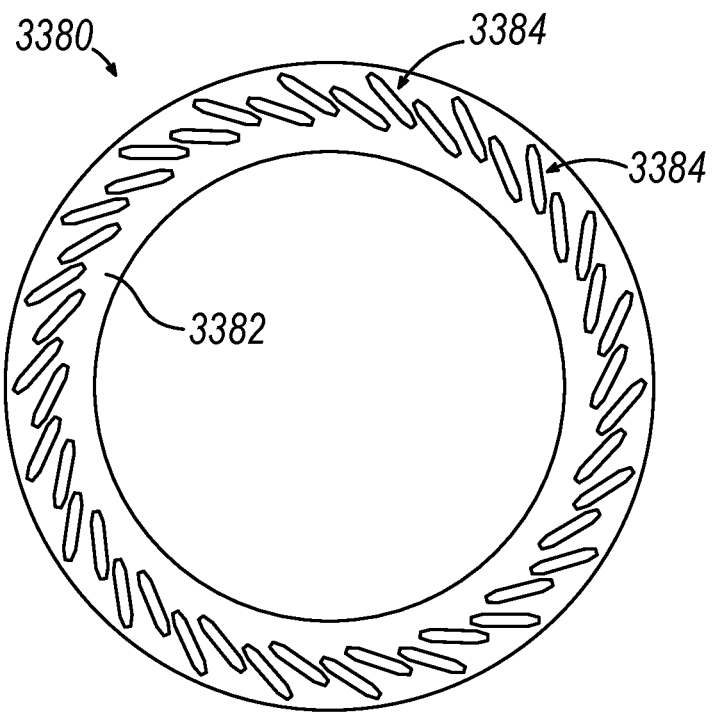
FIG. 47 depicts a top plan view of another alternative deck member that may be incorporated into the stapling head assembly of FIG. 4.
Figure 48:
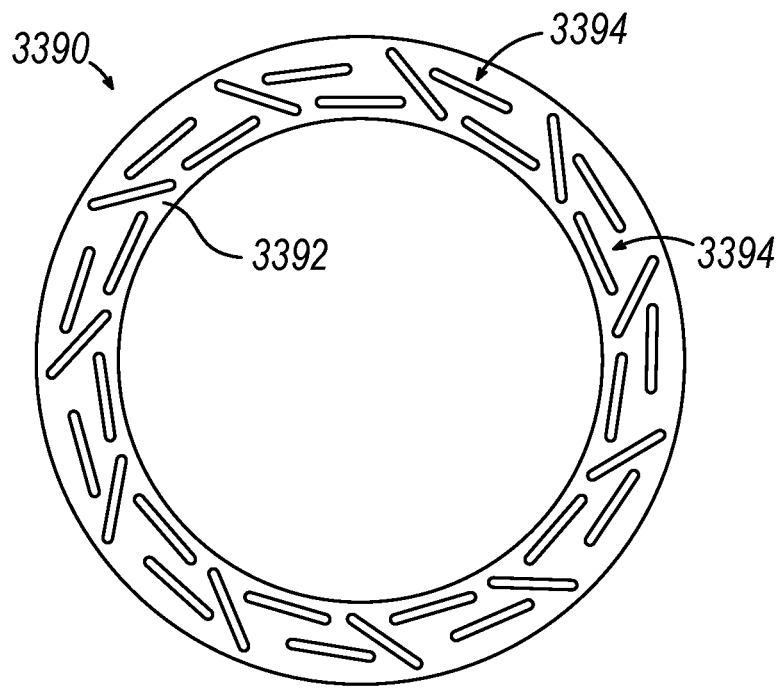
FIG. 48 depicts a top plan view of another alternative deck member that may be incorporated into the stapling head assembly of FIG. 4.
Figure 49:
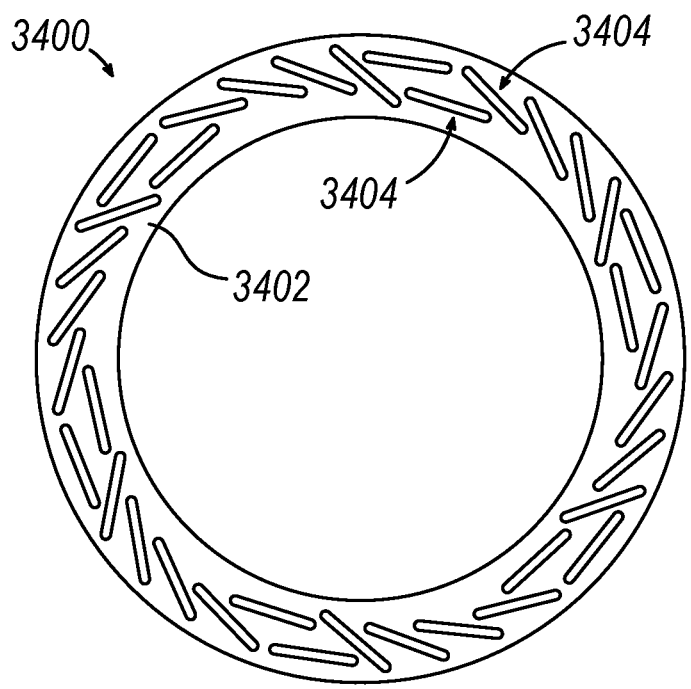
FIG. 49 depicts a top plan view of another alternative deck member that may be incorporated into the stapling head assembly of FIG. 4.
Figure 50:
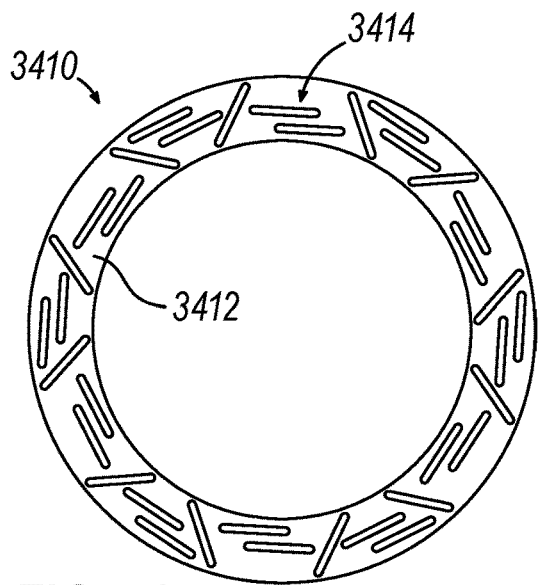
FIG. 50 depicts a top plan view of another alternative deck member that may be incorporated into the stapling head assembly of FIG. 4.
Figure 51:
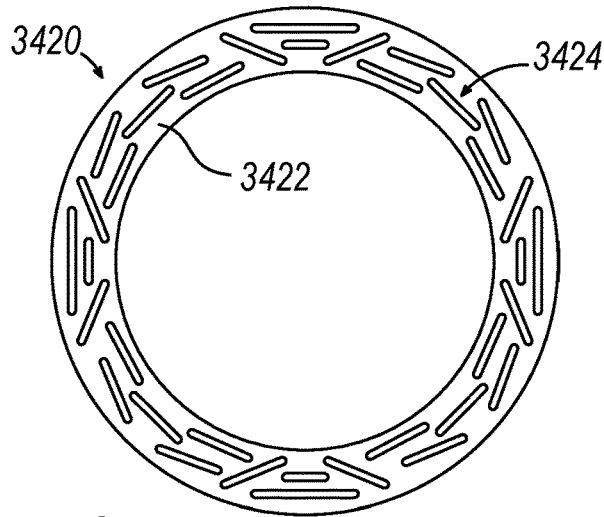
FIG. 51 depicts a top plan view of another alternative deck member that may be incorporated into the stapling head assembly of FIG. 4.
Figure 52:
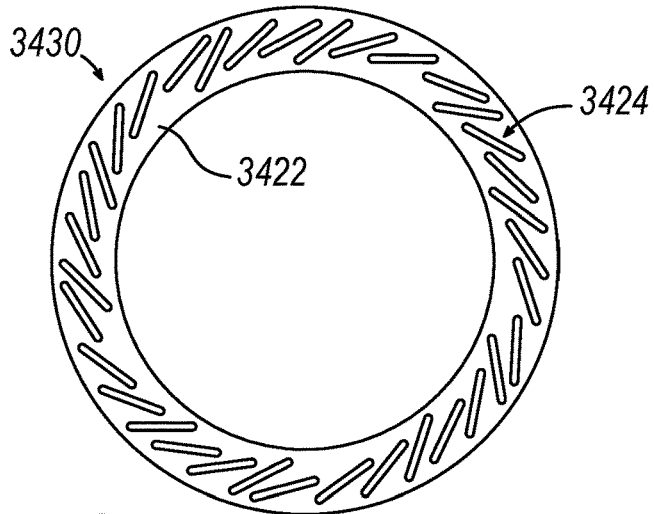
FIG. 52 depicts a top plan view of another alternative deck member that may be incorporated into the stapling head assembly of FIG. 4.

FIGS. 39-43 and 46-52 show a variety of staple decks defining non-tangential staple patterns that do not require increasing the width of their corresponding deck surface. Such staple patterns may in turn enhance the structural integrity of the stapled ends of the anatomical structures (20, 40) to better accommodate expansion and contraction of tubular structures (20, 40). FIGS. 44-45 show a variety of staples (3240, 3250) that may be incorporated to enhance the structural integrity of staples anatomical structures (20, 40) to better accommodate expansion and contraction of tubular structures (20, 40).

Figure 39:
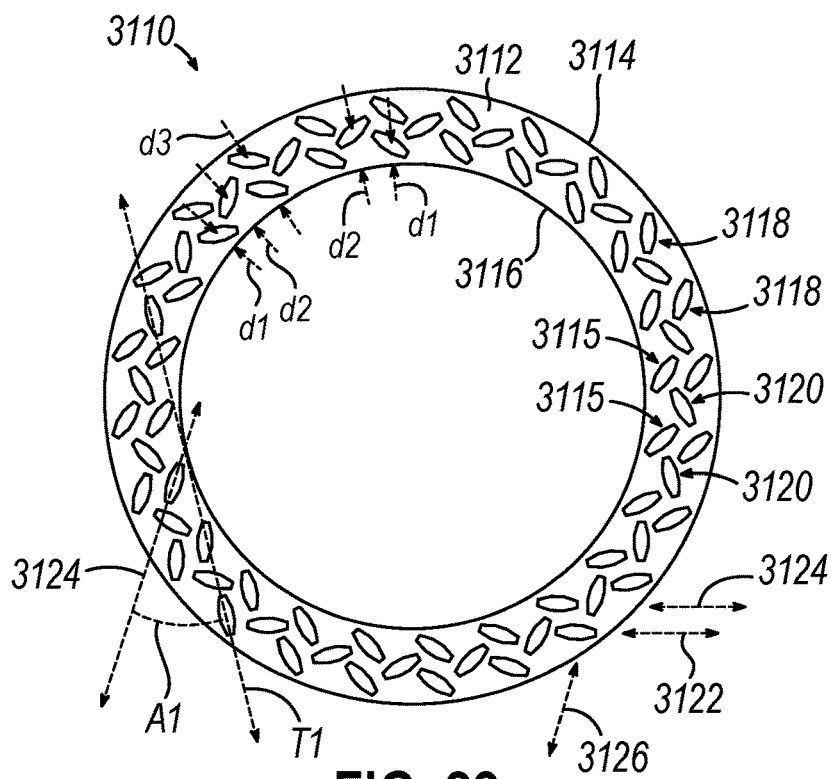
FIG. 39 depicts a top plan view of an alternative deck member that may be incorporated into the stapling head assembly of FIG. 4.

FIG. 39 shows an exemplary staple deck member (3110) having a deck surface (3112) defined by an outer arched perimeter (e.g., an outer diameter (3114)) and an inner arched perimeter (e.g., an inner diameter (3116)). Deck surface (3112) defines an inner array of staple openings (3115), an outer array of staple openings (3118), and an intermediate array of staple openings (3120) located between the outer and inner arrays of staple openings (3115, 3118). Staple openings in annular array of staple openings (3115, 3118, 3120) may have any suitable size as would be apparent to one skilled in the art in view of the teachings herein. As an example, staple openings may be uniform in size and be around 0.03 inches by 0.08 inches in size.

The center of individual staple openings in the inner array of staple openings (3115) are position a first distance (d1) away from inner diameter (3116). The center of individual staple openings in the intermediate array of staple openings (3120) are positioned a second distance (d2) away from inner diameter (3116). The center of individual staple openings in the outer array of staple openings (3118) are positions a third distance (d3) away from inner diameter (3116). As also shown, inner and outer array of staples openings (3115, 3118) extend along respective axis (3122, 3124) that are substantially parallel with each other, while intermediate array of staple openings (3120) extends along an axis that intersections with axis (3122, 3124) of inner and outer array of staple openings (3115, 3118).

Each individual staple extends along a respective axis (3122, 3124, 3126) that is non-tangential with the closest tangent line of the inner and outer diameter (3116, 3114) of deck surface (3112). This is exemplified in FIG. 39 with an individual staple opening of the inner array of staple openings (3115) that extends along axis (3124) that forms an angle (A1) with its closest tangent line (T1). The closest tangent line for each staple opening (3115, 3118, 3120) may be measured from the center of the respective staple opening (3115, 3118, 3120) as exemplified with distances (d1, d2, d3). With staple openings (3115, 3118, 3120) extending along a non-tangential axis (3122, 3124, 3126) staples fired out of opening may be able to better expand radially after coupling structures (20, 40), thereby enhancing the quality of the anastomosis (70).

In the current example, staple openings in the inner array and outer array of staple openings (3115, 3118) extend along axis (3124, 3122) that form a 45-degree angle with the closest tangent line, while staple openings in the intermediate array of staple openings (3120) extend along an axis (3126) that form a 40-degree angle with the closest tangent line. It should be understood that individual staple openings may extend along an axis that forms angles different than other staple openings, even if located in the same array (3115, 3118).

It should be understood that staple deck member (3110) couple with a staple driver member configured to acuate staples housed within openings (3115, 3118, 3120); while an anvil is may have corresponding staple forming pockets dimensioned to deform a corresponding staple driven out of openings (3115, 3118, 3120) in accordance with the description herein. In other words, it should be understood a stapler driver member and an anvil may have complementary features suitably oriented to interact with staples housed within openings (3115, 3118, 3120).

Figure 40:
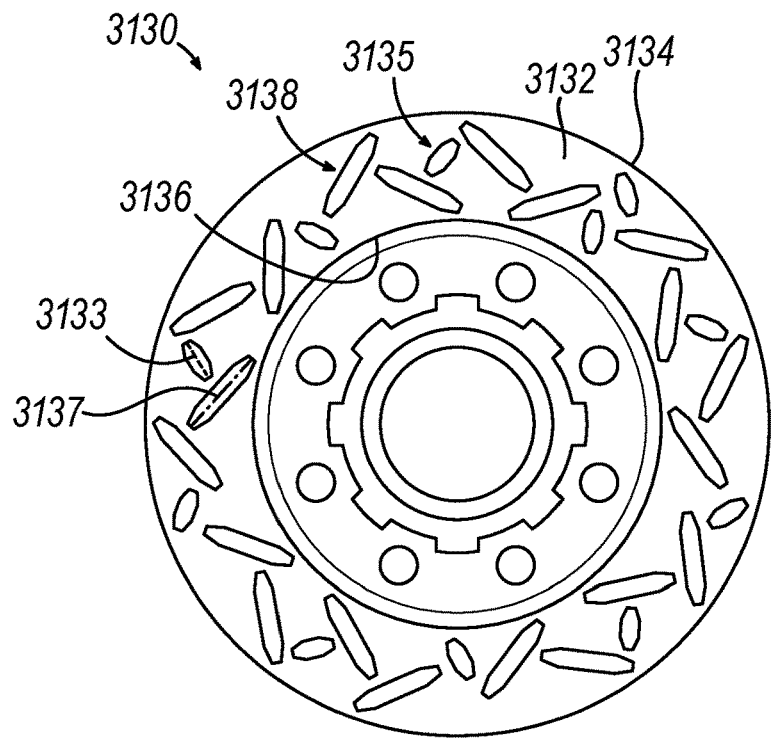
FIG. 40 depicts a top plan view of another alternative deck member that may be incorporated into the stapling head assembly of FIG. 4.

FIG. 40 shows an exemplary staple deck member (3130) having a deck surface (3132) defined by an outer diameter (3134) and an inner diameter (3136). In the current example, deck surface (3132) defines a plurality of smaller stapler openings (3135) and a plurality of larger staples opening (3138), all extending non-tangentially on the circumference of deck surface (3132). Each large staple opening (3138) extends along a respective axis (3137) while each small staple opening (3135) also extends along a respective axis (3133). Similar to axis (3122, 3124, 3126) described above, axis (3133, 3137) extends to form an angle with the closest tangent line for the individual staple openings (3135, 3138). With staple openings (3135, 3138) extending along a non-tangential axis (3133, 3137), staples fired out of opening may be able to better expand radially after coupling structures (20, 40), thereby enhancing the quality of the anastomosis (70).

Larger staple openings (3138) may house larger staples (90), while smaller staple openings (3135) may house smaller staples (90). This difference in staple hole sizes may allow for a herringbone pattern to fit within deck surface (3132) sized similarly to deck surface (322) describe above. Smaller staples openings (3135) may be spread out from each other by having two larger staple openings interposed between adjacent smaller staple openings (3135). This may spread the additional stress on stapled tissue caused by using a shorter staple crown in the smaller staples (90).

Figure 41:
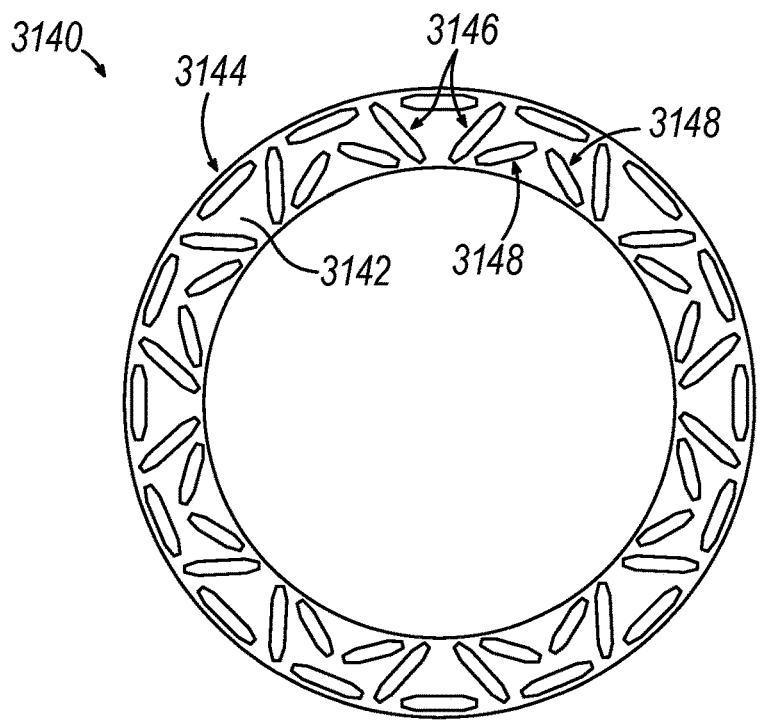
FIG. 41 depicts a top plan view of another alternative deck member that may be incorporated into the stapling head assembly of FIG. 4.

FIG. 41 shows an exemplary staple deck member (3140) having a deck surface (3142) defined by an outer diameter and an inner diameter. In the current example, deck surface (3142) defines an outer array of larger staple openings (3144), a plurality of larger oblique staple openings (3146), and a plurality of smaller oblique staple openings (3146). Outer array of larger staple openings (3144) may be tangential, similar to staple openings (324) described above. Oblique staple openings (3146, 3148) may be non-tangential, similar to stapler openings (3135) described above, thereby extending on an axis forming an angle with the closest tangent line for the individual staple openings (3146, 3148). With staple openings (3146, 3148) extending along a non-tangential axis, staples fired out of opening may be able to better expand radially after coupling structures (20, 40), thereby enhancing the quality of the anastomosis (70).

This particular pattern of allows for smaller staples in the smaller staple openings (3148) to grow in capture length while the longer staples in longer staple openings (3144, 3146) are able to get closer together allowing for expansion to occur.

Figure 42:
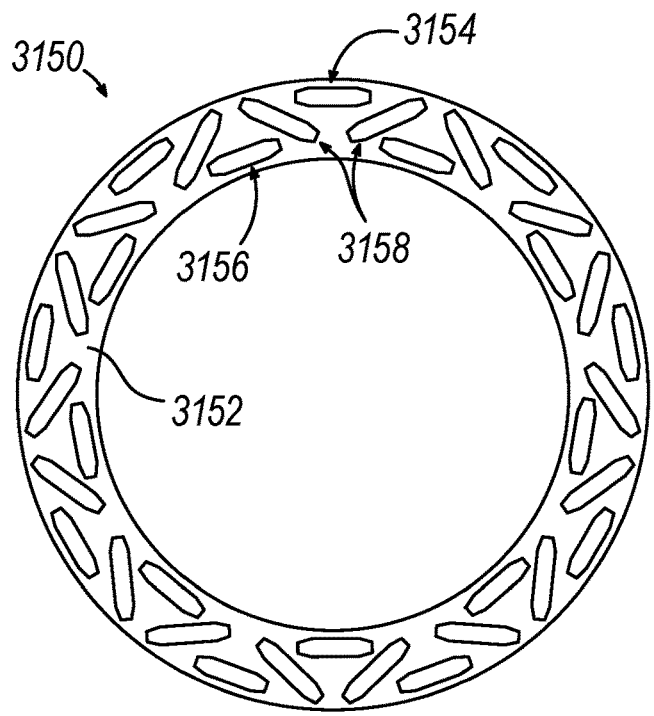
FIG. 42 depicts a top plan view of another alternative deck member that may be incorporated into the stapling head assembly of FIG. 4.

FIG. 42 shows an exemplary staple deck member (3150) having a deck surface (3152) defined by an outer diameter and an inner diameter. In the current example, deck surface (3152) defines an outer array of staple openings (3144), an inner array of staple openings (3156) and a plurality of oblique staple openings (3158). All openings (3154, 3156, 3158) may be substantially the same size. Outer array of staple openings (3154) and inner array of staple openings (3156) may be tangential, similar to staple openings (324) described above. Oblique staple openings (3158) may be non-tangential, similar to staple openings (3135) thereby extending on an axis forming an angle with the closest tangent line for the individual staple openings (3158). With staple openings (3158) extending along a non-tangential axis, staples fired out of opening may be able to better expand radially after coupling structures (20, 40), thereby enhancing the quality of the anastomosis (70). This particular pattern uses on size staple, which may simplify manufacturing.

Figure 43:
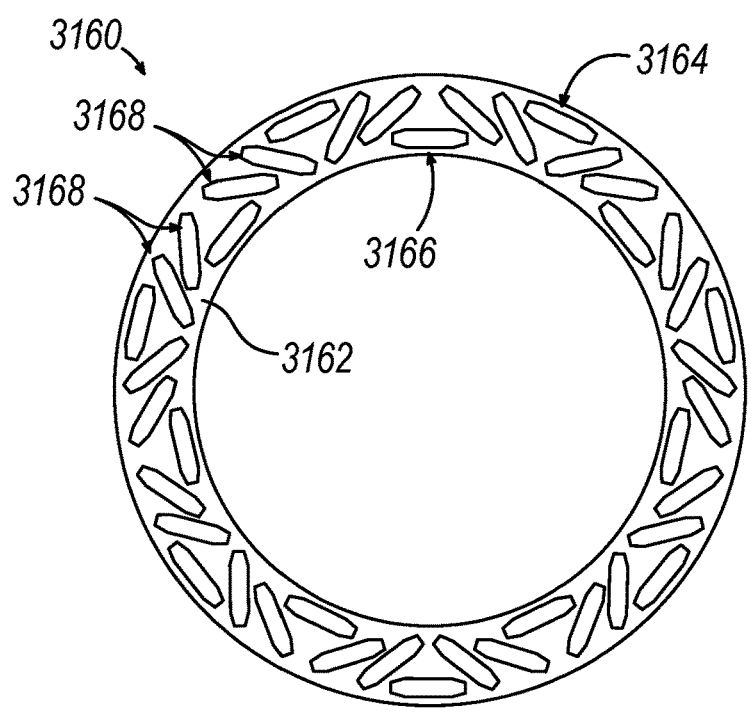
FIG. 43 depicts a top plan view of another alternative deck member that may be incorporated into the stapling head assembly of FIG. 4.

FIG. 43 shows an exemplary staple deck member (3160) having a deck surface (3162) defining an outer array of staple openings (3164), an inner array of staple openings (3166) and a plurality of oblique staple openings (3168). Staple opening (3164, 3166, 3168) are substantially similar to stapler openings (3154, 3156, 3158) described above, expective that outer and inner array of staple openings (3164, 3166) are dispersed further apart such that there are fewer outer and inner array of stapling openings (3164, 3166) and more oblique staple openings (3168). This particular pattern may predisposition the fired oblique staples to "lie down" against the fired tangential staples.

FIGS. 46-52 show various other staple deck members (3370, 3380, 3390, 3400, 3410, 3420, 3430) having deck surfaces (3372, 3382, 3392, 3402, 3412, 3422, 3432) that define various staple opening (3374, 3384, 3394, 3404, 3414, 3424, 3434) forming various staple patterns, either entirely formed of non-tangential staple openings, or some type of combination of non-tangential and tangential staple openings in order to provide the various benefits discussed above.

It should be understood that all staple deck members (3110, 3130, 3140, 3150, 3160, 3370, 3380, 3390, 3400, 3410, 3420, 3430) may couple with a staple driver member configured to actuate staples housed within openings (3115, 3118, 3120, 3135, 3138, 3144, 3146, 3148, 3154, 3156, 3158, 3164, 3166, 3168, 3374, 3384, 3394, 3404, 3414, 3424, 3434); while an anvil may have corresponding staple forming pockets dimensioned to deform a corresponding staple driven out of openings (3115, 3118, 3120, 3135, 3138, 3144, 3146, 3148, 3154, 3156, 3158, 3164, 3166, 3168, 3374, 3384, 3394, 3404, 3414, 3424, 3434) in accordance with the description herein. In other words, it should be understood a stapler driver member and an anvil may have complementary features suitably oriented to interact with staples housed within openings (3115, 3118, 3120, 3135, 3138, 3144, 3146, 3148, 3154, 3156, 3158, 3164, 3166, 3168, 3374, 3384, 3394, 3404, 3414, 3424, 3434).

As mentioned above, FIGS. 44-45 show different staples (3240, 3250) that may be readily incorporated into any staple deck member (320, 3110, 3130, 3140, 3150, 3160, 3370, 3380, 3390, 3400, 3410, 3420, 3430) described above in order to enhance the structural integrity of stapled anatomical structures (20, 40) by promoting expansion of staples (3240, 3250) in response to being under tension, such as when tubular structures (20, 40) expand during peristalsis.

First staple (3240) includes a pair of legs (3242) connected together by a crown (3244). Legs (3242) may be substantially similar to legs of staples (90) described above. Therefore legs (3242) may bend in response to contact with staple forming pockets (414) of anvil in order to staple anatomical structure (20, 40) together. Crown (3244) includes a pair a lateral connecting members (3245) extending from an end of a respective leg (3242) toward each other. Both lateral connecting members (3245) extend into an upward bend (3246).

Upward bend (3246) may allow for a fired stapled (3240) to provide a higher compression of stapled tissue, which may enhance the quality of an anastomosis (70). Additionally, upward bend (3246) may provide additional material for crown (3244) to expand under tension, thereby acting a spring. In other words, that additional material provided by upward ben (3246) may allow crown (3244) to expand when staple (3240) is under a tension that pulls lateral connecting members (3245) away from each other. Therefore, when staple (3240) is fired in a non-tangential relationship, radial expansion of anatomical structures (20, 40) may pull crown (3244), at least partially in a direction that promotes such expansion of crown (3244).

Second staple (3250) includes a pair of legs (3252) connected together by a crown (3254). Legs (3252) may be substantially similar to legs of staples (90) described above. Therefore legs (3252) may bend in response to contact with staple forming pockets (414) of anvil in order to staple anatomical structure (20, 40) together. Crown (3254) includes a pair a lateral connecting members (3255) extending from an end of a respective leg (3252) toward each other. Both lateral connecting members (3255) extend into a downward bend (3256).

Downward bend (3256) may provide similar spring like characteristics as to upward bend (3246) described above. Additionally, downward bend (3256) extends away from legs (3252), thereby proving room such that tips of legs (3252) may not contact crown (3254) as legs (3252) bend toward crown (3254). This may inhibit crown (3254) from developing any surface irregularities after the firing of staple (3250) due to contact with sharp portions of legs (3252), which may in turn prevent crown (3254) from developing any sharp surfaces caused by such contact.

B. Exemplary Firing Member Increasing the Diameter of Knife Member

Figure 53:
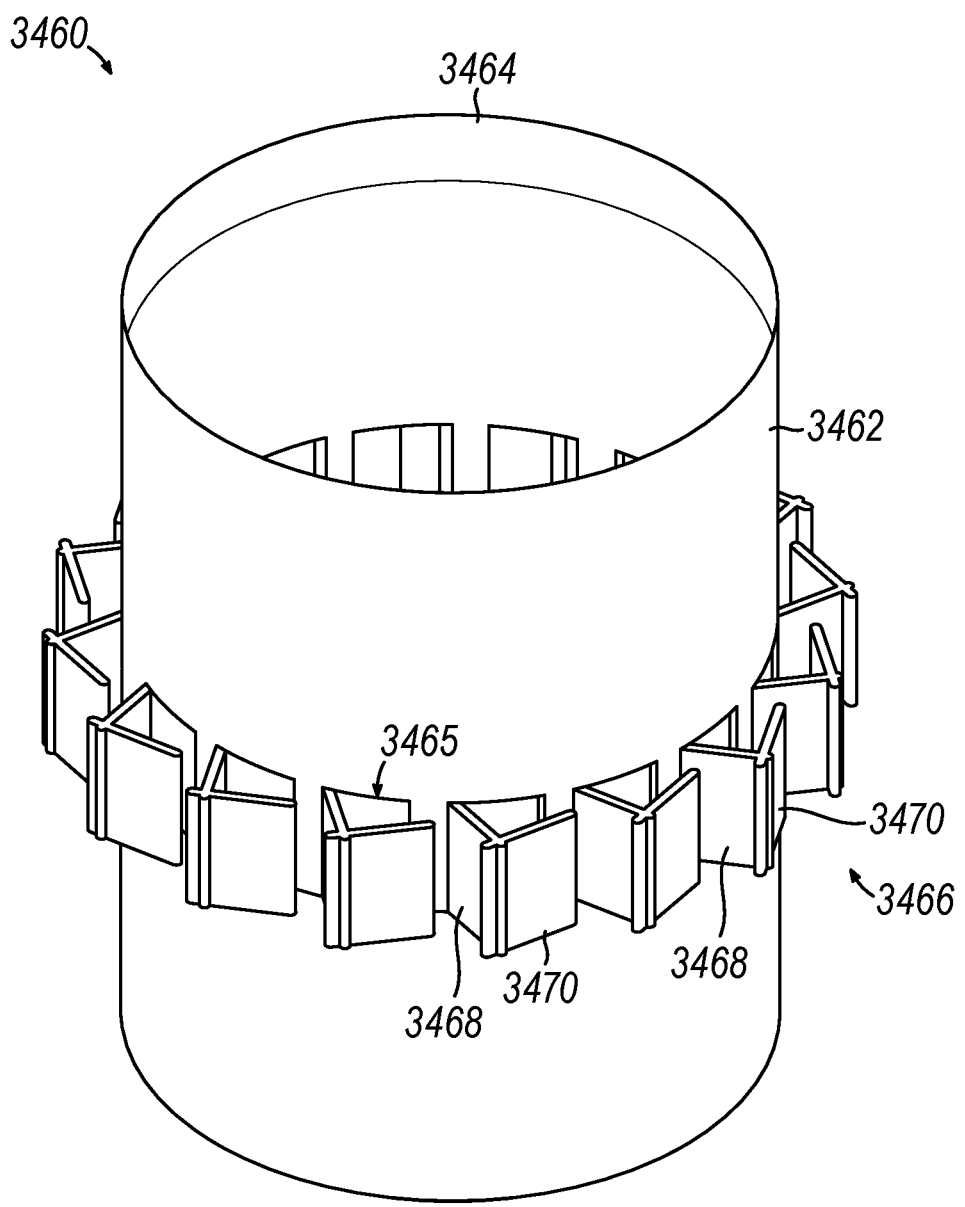
FIG. 53 depicts a perspective view of an exemplary firing member that may be readily incorporated into the stapling head assembly of FIG. 4.

In some instances, it may be desirable to increase the diameter of knife number (340) in order to reduce the length at which anastomosis (70) and severed edges (60) extend radially inward from the interior of the tubular anatomical structure (20, 40). FIG. 53 shows an example firing number (3460) that may readily incorporated into stapling head assembly (300) describe above. In particular, firing member (3460) includes a cylindraceous body (3462) terminating distally into a cutting edge (3464). Cutting edge (3464) may act similar to cutting edge (342) described above. Cylindraceous body (3462) may be actuated in similar fashion to that of staple driver member (350) and knife member (340) described above.

Additionally, firing member (3460) includes a plurality of staple drives (3466) fixed to and extending radially outward from cylindraceous body (3462). In the current example, staple drivers (3466) extend away from a portion of cylindraceous body (3462) defining an opening (3465). Staple drivers (3466) each include a first firing body (3468) directly fixed to cylindraceous body (3462) and a second firing body (3470) extending from first firing body (3468). Each firing body (3468, 3470) may be configured to drive an individual staple (90, 3240, 3250) such that one staple driver (3466) may fire two or more staples (90, 3240, 3250) aligned in a non-tangential relationship similar to the non-tangential relationship described above.

Figure 54:
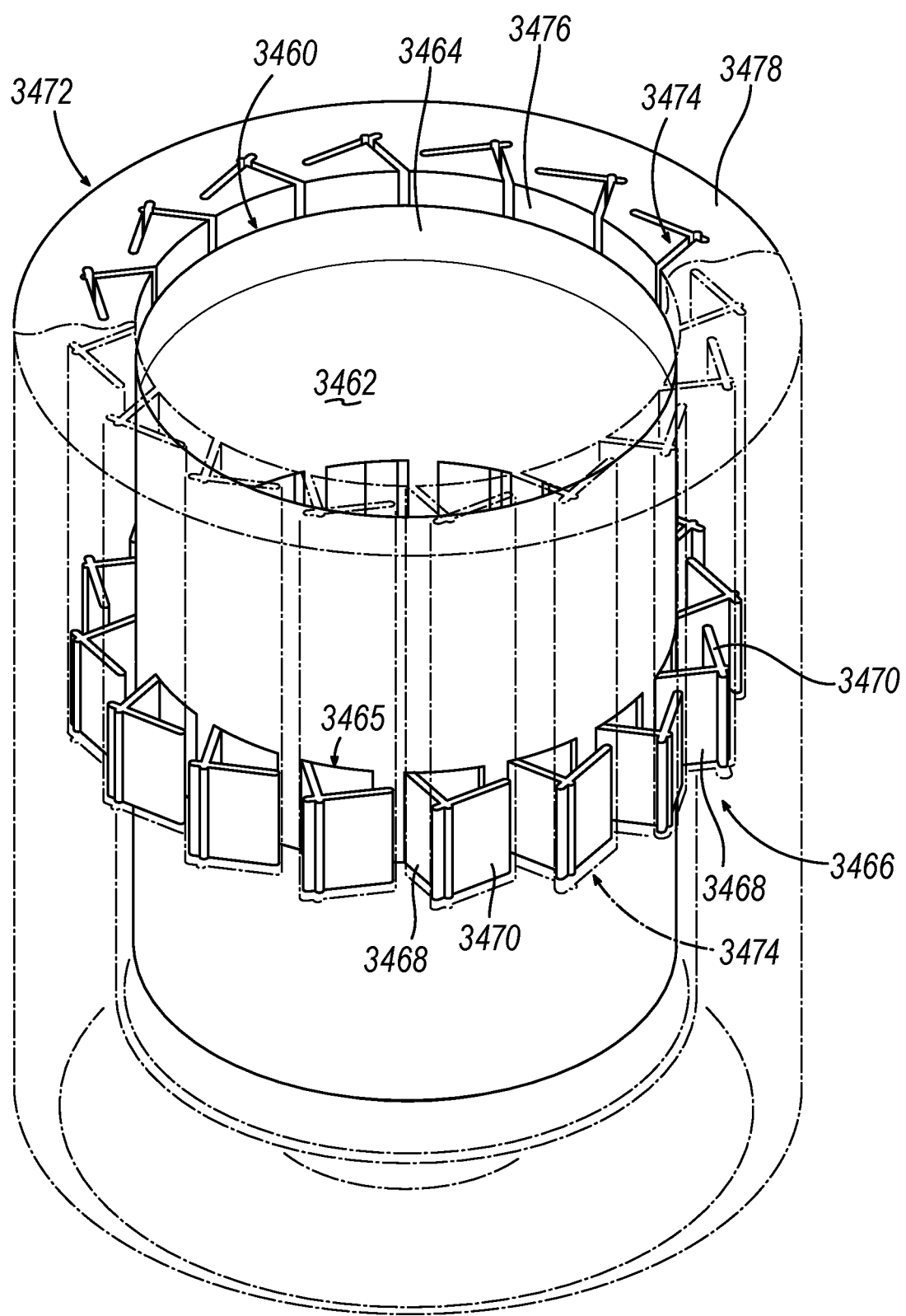
FIG. 54 depicts a perspective view of the firing member of FIG. 53 slidably contained in an exemplary tubular body member and staple deck that may be readily incorporated into the stapling head assembly of FIG. 4.
Figure 55:
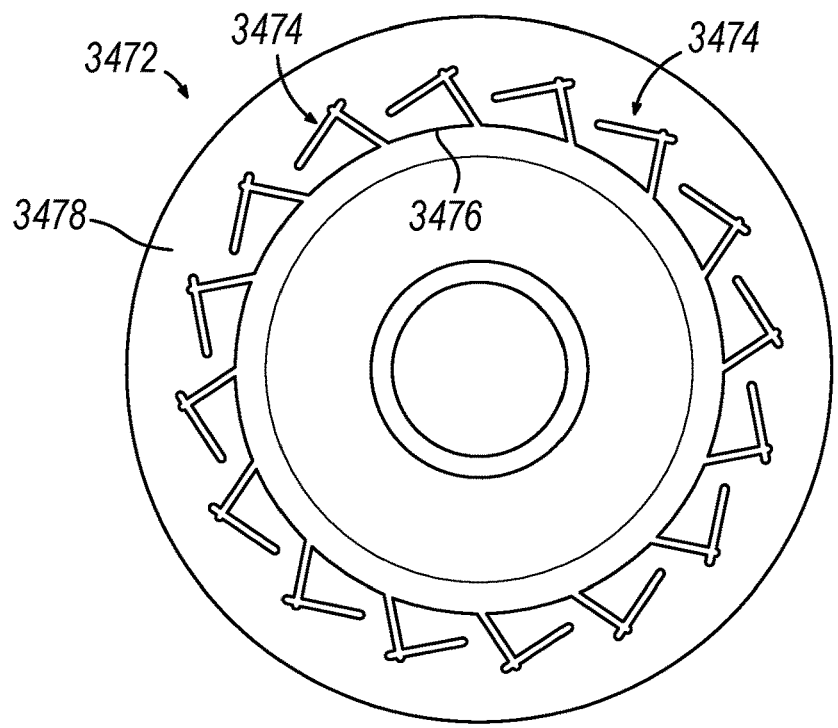
FIG. 55 depicts a top plan view of the firing member of FIG. 53 and the staple deck of FIG. 24.

As will be described in greater detail below, since staple drives (3466) and cutting edge (3464) are incorporated into a single firing member (3460), cutting edge (3464) may have a larger diameter (3464) compared to cutting edge (342) described above. FIG. 54 shows firing member (3460) slidably housed within a tubular body member (3472), while FIG. 55 shows tubular body member (3472). Tubular body number (3472) may be readily incorporated into stapling head assembly (300) described above in replacement of tubular body member (310) described above. It should be understood that tubular body member (3472) may include a core member similar to core member (312) described above.

Tubular body member (3472) includes an interior surface (3476) defining a recessed cavity which slidably houses cylindraceous body (3462). Cylindraceous body (3462) may slidingly abut against interior surface (3476), which in turn may allow for cutting edge (3464) to be larger in diameter compared to cutting edge (342) described above. Tubular body number (3472) also includes a top surface (3478). Top surface (3478) may act as a deck surface, similar to deck surface (342) described above. Alternatively, top surface (3478) may be configured to attach to a suitable deck surface. Top surface (3478) and interior surface (3476) together define a plurality of complementary driver recesses (3474) dimensioned to slidably house a corresponding staple driver (3466). Driver recesses (3474) may also contain staples (90, 3240, 3250), which may rest above a respective driving body (3468, 3470) such that actuation of driving body (3468, 3470) toward top surface (3478) drives staples (90, 3240, 3250) distally past top surface (3478).

Due to this configuration of tubular body member (3472) and firing member (3460), fired staples (90, 3240, 3250) may be radially closer to cutting edge (3464) as compared to stapling head assembly (300) described above. Therefore, utilizing tubular body member (3472) and firing member (3460) may allow an operator to fire staples (90, 3240, 3250) in a non-tangential relationship while also reducing the size at which severed edges (60) extend from the interior of lumens (20, 40).

Figure 56:
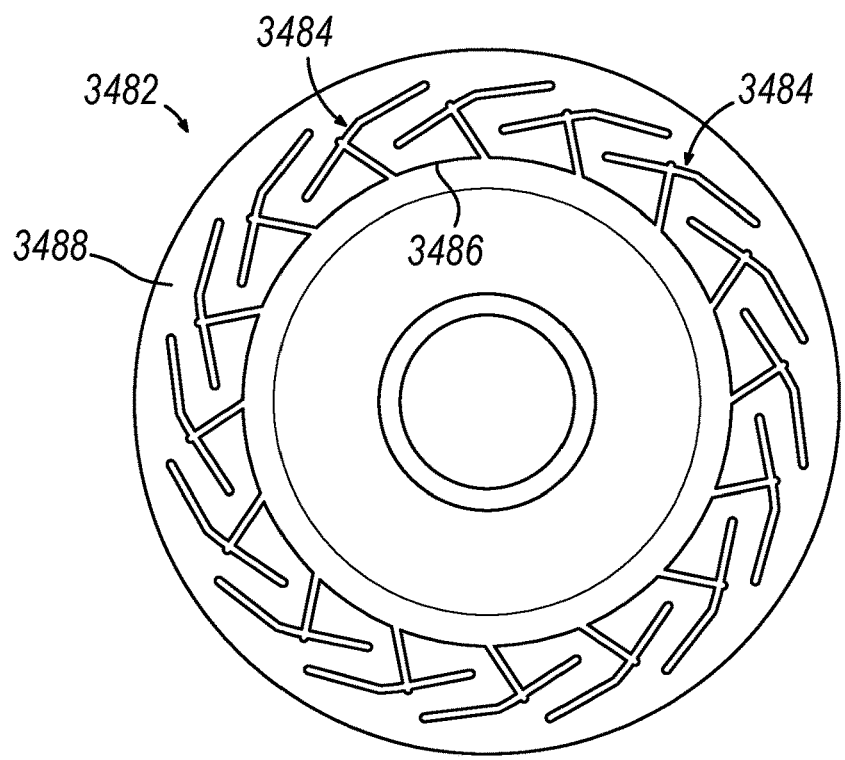
FIG. 56 depicts a top plan view an alternative firing member and staple deck that may be readily incorporated into the stapling head assembly of FIG. 4.
Figure 59:
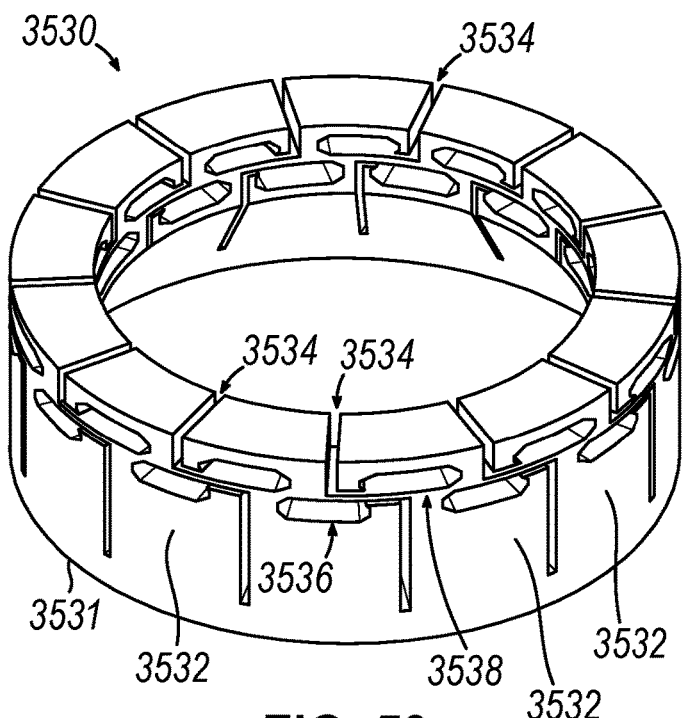
FIG. 59 depicts a perspective view of an alternative deck assembly that may be incorporated into the stapling head assembly of FIG. 4, the deck assembly being configured to capture tissue for stapling in a radial direction.

While staples drivers (3466) currently include a first driving body (3468) and a second driving body (3470) configured to each fire a staple (90, 3240, 3250), staple drivers (3466) may be configured with more driving bodies such that staple drivers (3466) may fire more staples. FIG. 56 shows an alternative tubular body member (3482) that is substantially similar to tubular body member (3472) described above, with differences elaborated below.

Therefore, tubular body member (3482) includes an interior surface (3486), a top surface (3488), and a plurality of complementary driver recesses (3484). Tubular body member (3482) is configured to receive a staple driver that may fire three staples (90, 3240, 3250) rather than two. Tubular body member (3482) is substantially similar to tubular body member (3472) described above, except complementary driver recess (3484) is modified to receive a staple driver with three driver bodies, thereby allowing tubular body member (3482) to house staples (90, 3240, 3250) oriented in a different staple pattern. Therefore, it should be understood, firing member (3460) and tubular body member (3472) may be modified to fire any suitable staple pattern as would be apparent to one skilled in the art in view of the teachings herein.

C. Exemplary Stapling Head Assemblies Reducing the Width of Staple Deck

In some instances, it may be desirable to fire staples in a radial direction (either partially or entirely) of stapling head assembly (300) rather than in the longitudinal direction of stapling head assembly (300). This may allow for staples to covers a greater surface area of stapled tissue (20, 40), thereby enhancing the staple quality, without having to increase the amount of space severed ends (60) takes up within the anatomical structures (20, 40).

FIGS. 57-58B show an anvil (3500) and a stapling assembly (3506) that may be used to fire staples (90) in a direction that has a radial axis (R) and a longitudinal axis (LA) component rather than strictly just a longitudinal axis (LA) component. Anvil (3500) is substantially similar to anvil (400) described above, but with difference elaborated below. In particular, anvil (3500) includes an obliquely oriented proximal stapling surface (3502) defining a plurality of staple forming pockets (3504). Compared to proximal stapling surface (412) of anvil (400) described above, obliquely oriented proximal stapling surface (3502) faces a normal direction that has at least a component in the radial direction defined by radial axis (R). As will be described in greater detail below, this radial direction component may allow anvil (3500) to capture and staple a greater surface area of tissue (20, 40) without producing severed ends (60) that extend further within lumens (20, 40) in the radial direction.

Stapling head assembly (3506) may be substantially similar to stapling head assembly (300) described above, but with differences described below. In particular, stapling head assembly (3506) includes an obliquely oriented deck surface (3508) defining staple opening (3510), a longitudinal driver (3512), and a plurality of oblique staple drivers (3514) slidably housed within a respective staple opening (3510). Obliquely oriented deck surface (3508) faces in a normal direction that extends in a complementary fashion with deck surface (3508) such that as anvil (3500) is proximally driven in order to grasp tissue (20, 40), tissue (20, 40) located between surfaces (3502, 3508) may be suitably stapled in accordance with the description herein. Therefore, as best seen between FIGS. 58A-58B, anvil (3500) may be proximally actuated toward stapling head assembly (3506) such that tissue (20, 40) may be grasped between surfaces (3502, 3508) while surfaces (3502, 3508) define a suitable gap distance.

Staple openings (3510) may together form any suitable staple pattern as would be apparent to one skilled in the art in view of the teachings herein. Staple openings (3510) are dimensioned to slidably house an oblique driver (3515) and a corresponding staple (90) such that oblique driver (3515) may actuate along a path that is substantially parallel with the normal direction of deck surface (3508). Longitudinal driver (3512) is configured to actuate along a path parallel with longitudinal axis (LA). However, as also exemplified between FIGS. 58A-58B, longitudinal driver (3512) is configured to abut against oblique driver (3514) such that actuation of longitudinal driver (3512) driver movement of oblique driver (3514) toward deck surfaced (3508) to thereby drive staple (90) against staple forming pocket (3504) to suitable staple tissue (20, 40) in accordance with the description herein.

Figure 74:
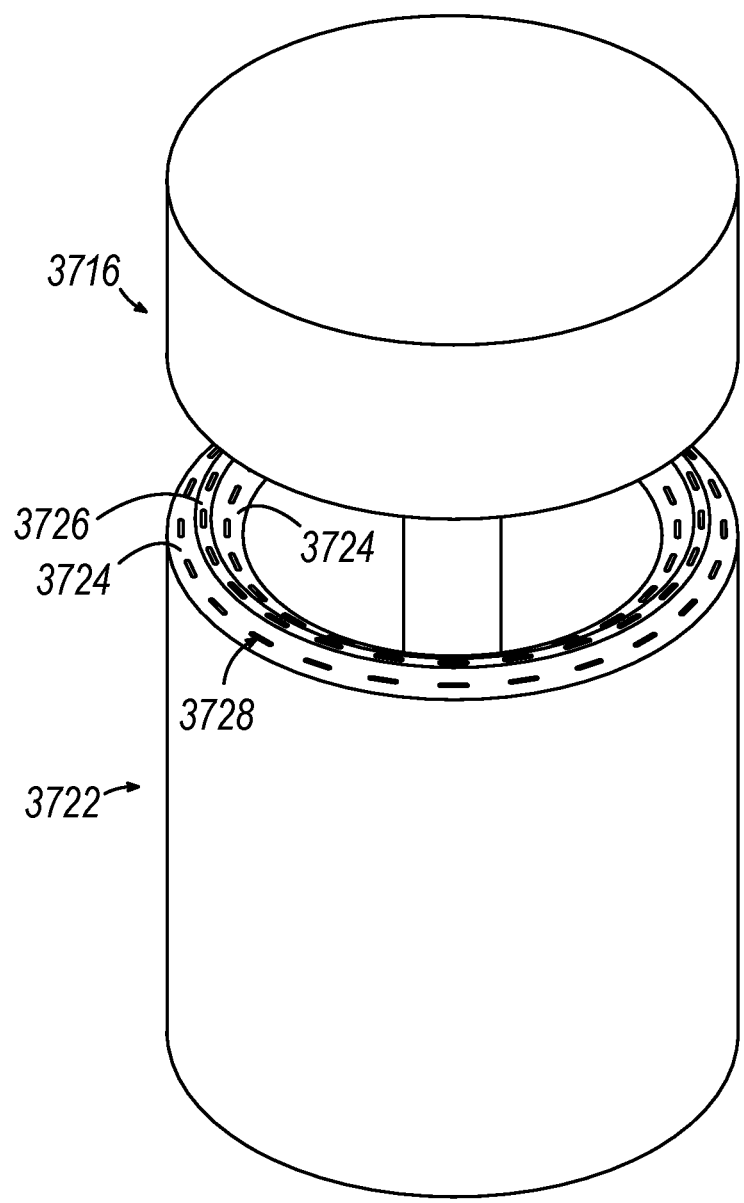
FIG. 74 depicts a perspective view of an alternative anvil and stapling head assembly that may be incorporated into the circular stapler of FIG. 1.
Figure 75:
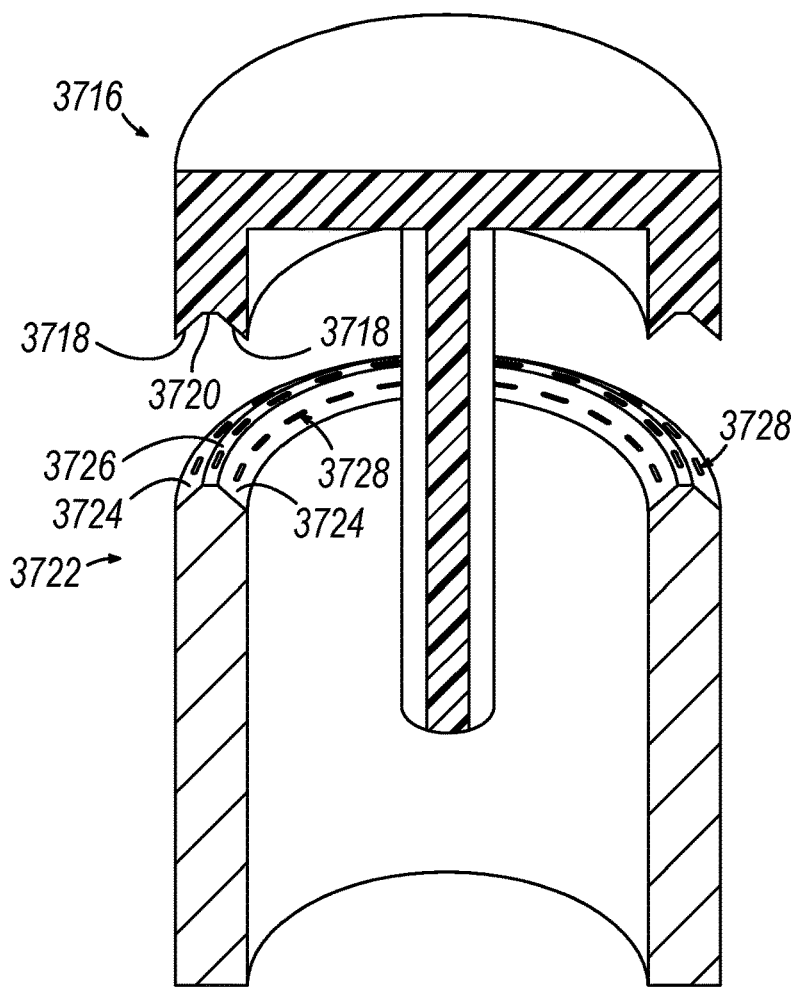
FIG. 75 depicts a cross-sectional view of the anvil and stapling head assembly of FIG. 74.
Figure 76:
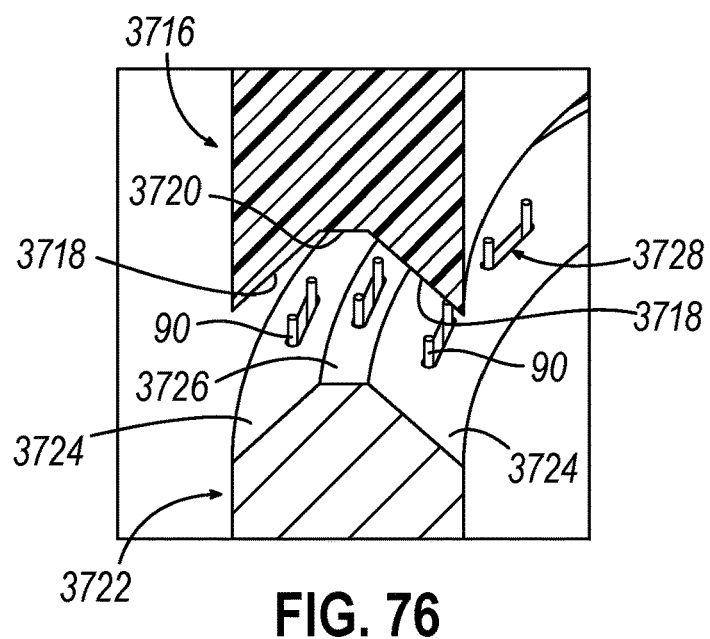
FIG. 76 depicts an enlarged perspective view of the anvil and stapling head assembly of FIG. 74.

In some instances, it may be desirable to utilize oblique surfaces (3502, 3508) to grasp tissue (20, 40), but still fire staples (90) in a longitudinal direction. Grasping tissue (20, 40) with oblique surface (3502, 3508) may increase the surface area interaction with tissue (20, 40) and also may reduce tissue strain on stapled tissue. FIGS. 74-76 show an exemplary anvil (3716) and stapling head assembly (3722) that may be substantially similar to anvil (400) and stapling head assembly (300) described above, but with differences elaborate below. In particular, anvil (3716) includes a pair of obliquely oriented proximal surfaces (3718) connected by a flat proximal surface (3720), while stapling head assembly (3722) includes a pair of obliquely oriented deck surfaces (3724) connected by a flat deck surface (3726). Each surface (3724, 3726) defining an annular row of staple openings (3728) while each surface (3718, 3720) includes complementary staple forming pockets.

Surfaces (3718, 3720) on anvil (3716) are complementary to surfaces (3724, 3726) on stapling head assembly (3722) such that when tissue (20, 40) is captured, a suitable gap distance may be defined. Grasping tissue (20, 40) with oblique surfaces (3718, 3724) and flat surfaces (3720, 3726) may increase the surface area interaction with tissue (20, 40) and also may reduce tissue strain on stapled tissue. As shown in FIG. 76, staples (90) may be fired longitudinally out of openings (3728).

In instances where staples (90) are fired in the radial direction, tissue (20, 40) may also need to be compressed in the radial direction to form a suitable gap distance (d). Proximal retraction of anvil (400) to form gap distance (d), as discussed above, may not provide the necessary compression required to form gap distance (d) for firing staples (90) in the radial direction. FIGS. 59-60A and FIGS. 61-63B show two different examples of a staple deck assembly (3530, 3545) that may be used to form a gap distance (d) in the radial direction.

As shown in FIGS. 53-60A, staple deck assembly (3530) includes an annular base (3531) acting as a connecting point for an annular array of resilient bodies (3532). Annular array of resilient bodies (3532) each define a lower staple opening (3536) and an upper staple opening (3538) such that resilient bodies (3532) as a whole together define an upper array of staple openings and a lower array of staple openings. Resilient bodies (3532) are separated from adjacent resilient bodies (3532) via a respective cut-out (3534), thereby allowing resilient bodies (3532) to radially flex relative to annular base (3531). Resilient bodies (3532) may radially flex relative to annular base (3531) in order to compress tissue (20, 40) between radially facing surface (3544) of an anvil (3542) in order to define a suitable gap distance (d).

Figure 60A:
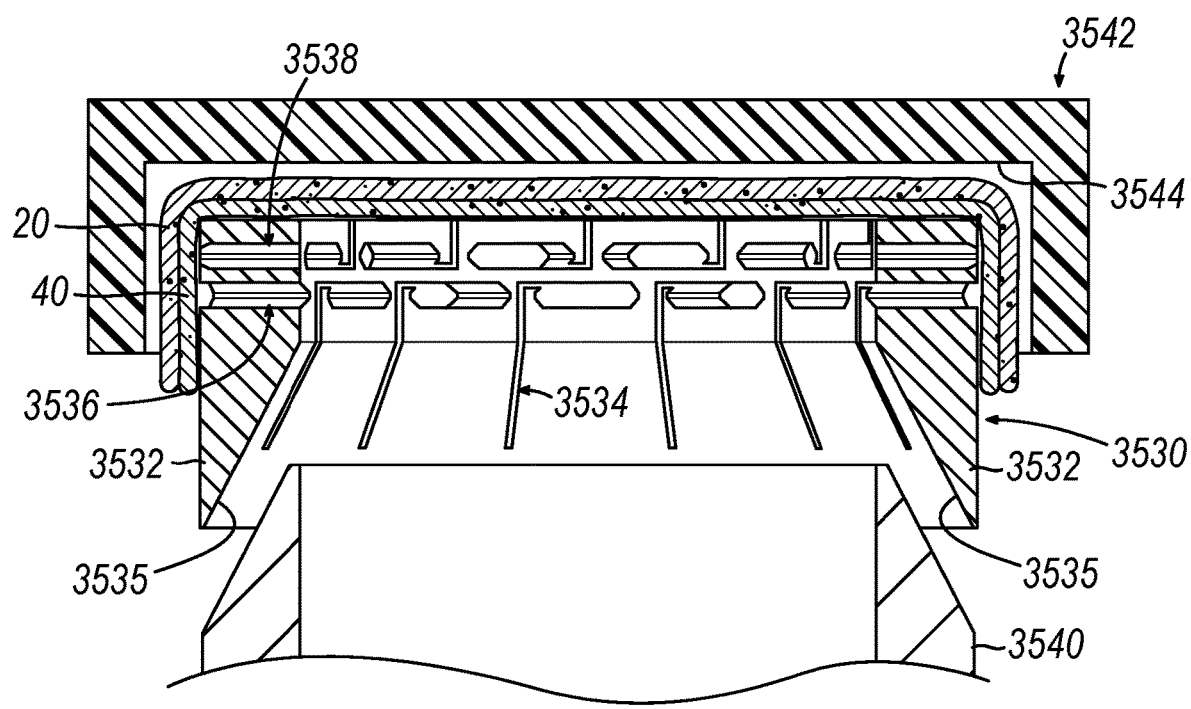
FIG. 60A depicts a cross-sectional view of the deck assembly of FIG. 59 capturing tissue with an anvil.
Figure 60B:
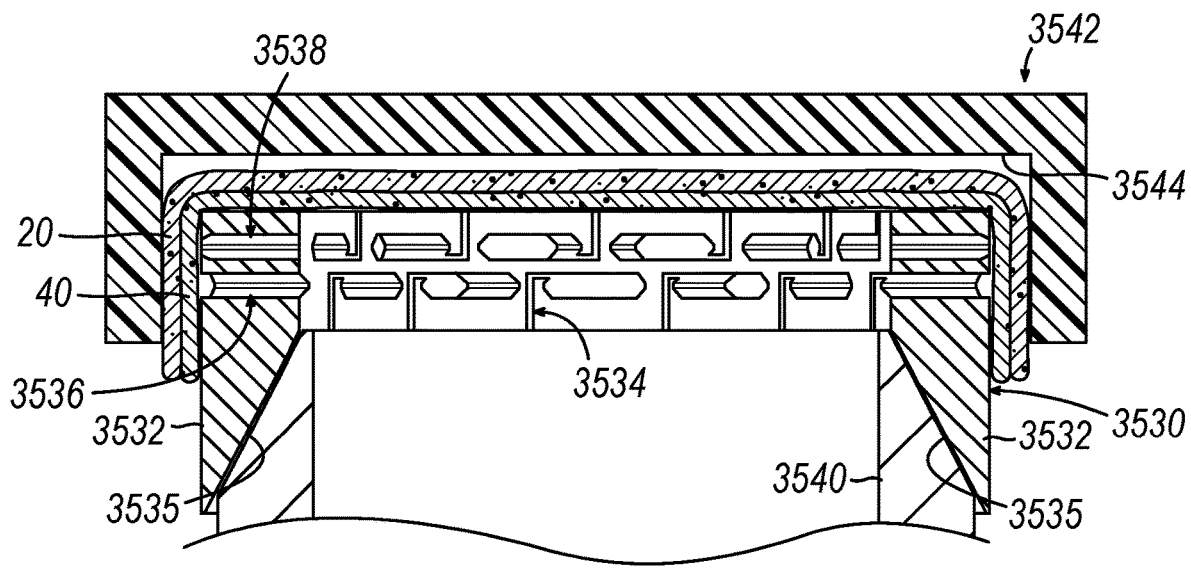
FIG. 60B depicts a cross-sectional view of the deck assembly of FIG. 59 further capturing tissue with an anvil.
Figure 61:
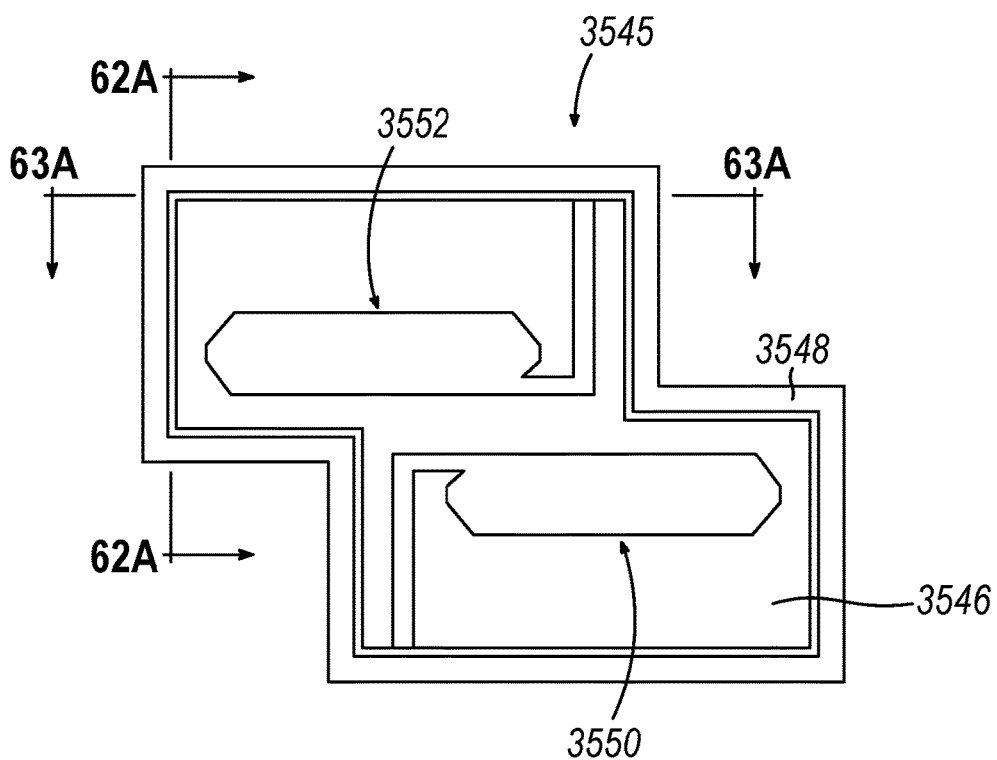
FIG. 61 depicts a front elevational view of another alternative deck assembly that may be incorporated into the stapling head assembly of FIG. 4, the deck assembly being configured to capture tissue for stapling in a radial direction.
Figure 62A:
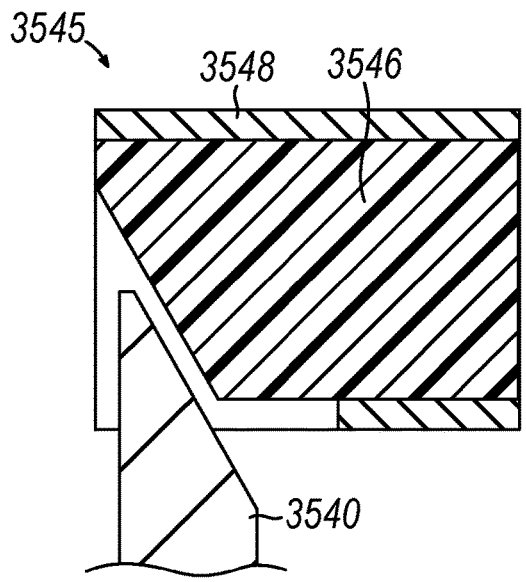
FIG. 62A depicts a cross-sectional view of the deck assembly of FIG. 61, taken along line 62A-62A of FIG. 61, where the deck assembly is in a first position.
Figure 62B:
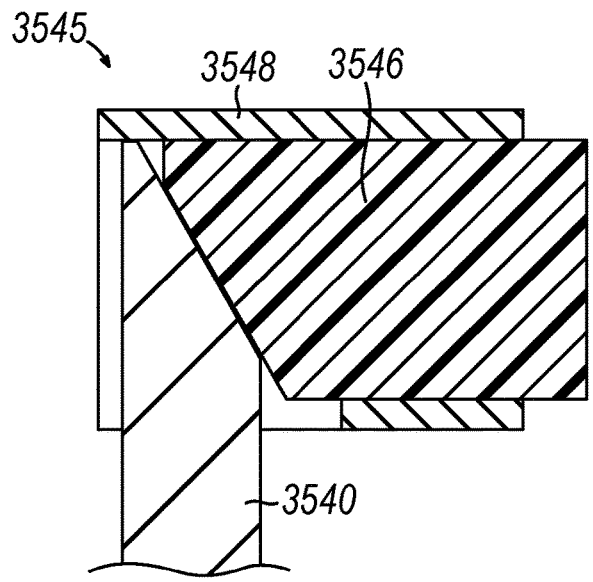
FIG. 62B depicts a cross-sectional view of the deck assembly of FIG. 61, taken along line 62A-62A of FIG. 61, where the deck assembly is in a second position.
Figure 63A:
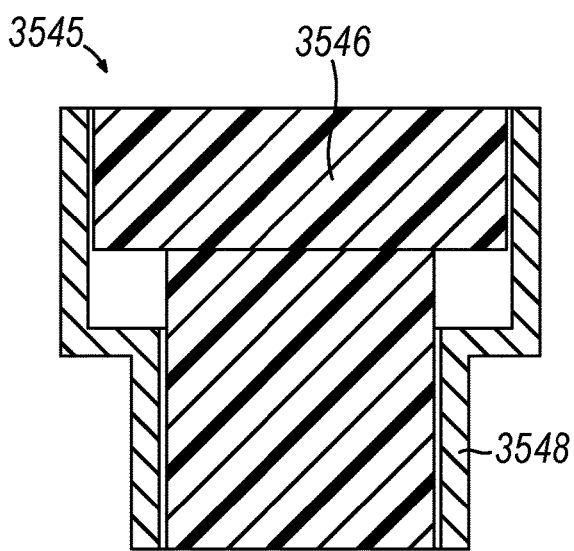
FIG. 63A depicts a cross-sectional view of the deck assembly of FIG. 61, taken along line 63A-63A of FIG. 61, where the deck assembly is in the first position.
Figure 63B:
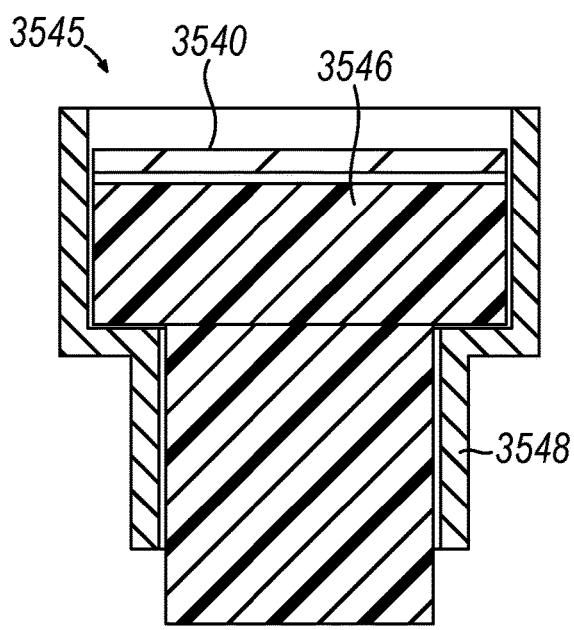
FIG. 63B depicts a cross-sectional view of the deck assembly of FIG. 61, taken along line 63A-63A of FIG. 61, where the deck assembly is in the second position.
Figure 64:
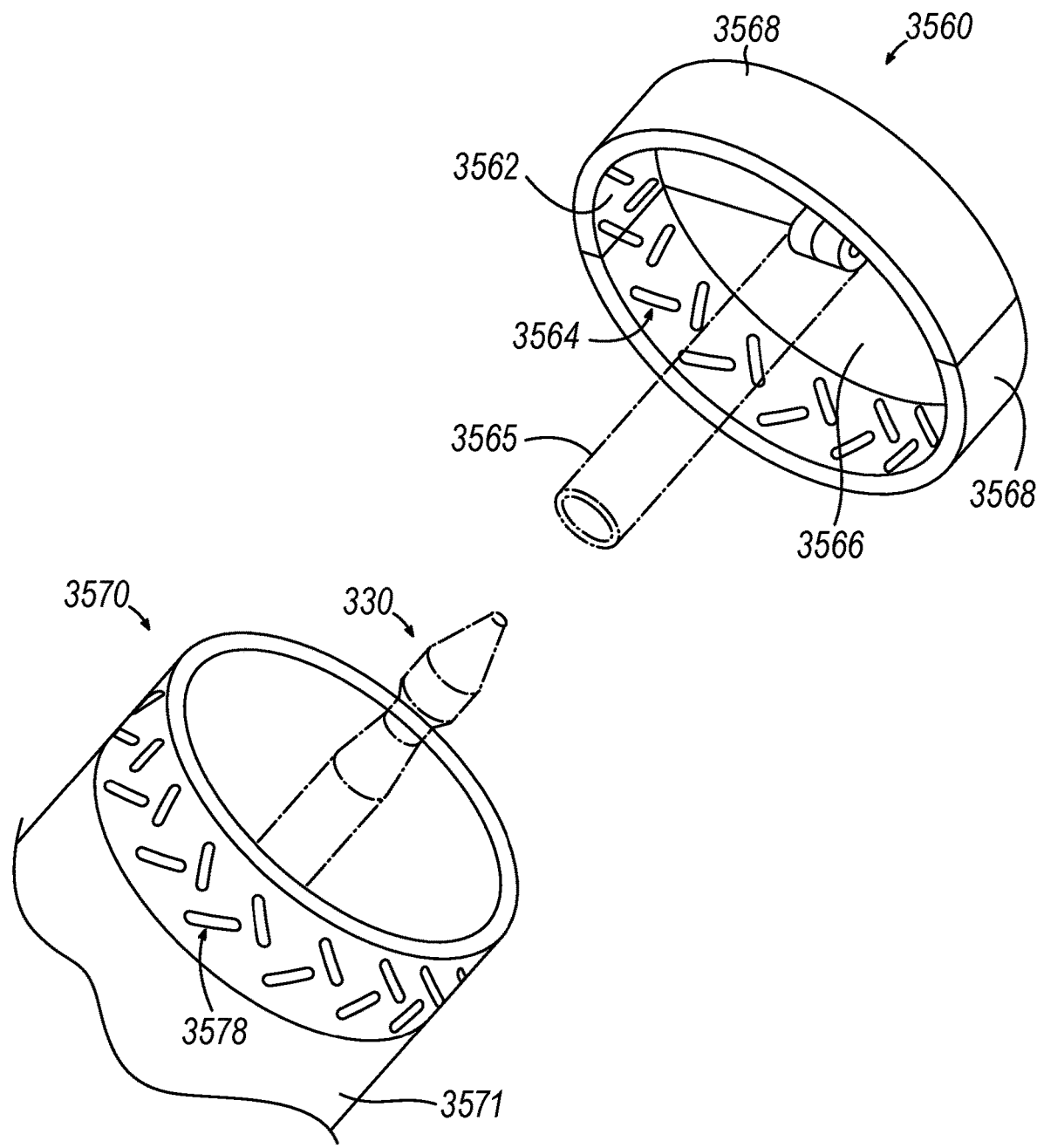
FIG. 64 depicts a perspective view of an alternative anvil and stapling head assembly that may be incorporated into the circular stapler of FIG. 1.

As best shown in FIGS. 60A-60B, each resilient body (3532) includes a tapered cam surface (3535). Tapered cam surface (3535) may engage a longitudinally actuating cam body (3540). In particular, as longitudinally actuating cam body (3540) actuates distally in the longitudinal direction, contact between cam body (3540) and cam surface (3535) drives resilient bodies (3532) toward radially facing surface (3544) of anvil (3542). Resilient bodies (3532) are sufficiently resilient such that if cam body (3540) is driven proximally, resilient bodies (3532) may then flex radially inward. Therefore, it should be understood that an operator may control the gap distance (d) between resilient bodies (3532) and radially facing surface (3544) of anvil (3542) by actuating longitudinally translating cam body (3540) distally and proximally.

Anvil (3542) may be substantially similar to anvil (400) described above, with differences elaborated below. Radially facing surface (3544) may have suitable staple forming pockets aligned with staples openings (3536, 3538). Staple openings (3536, 3538) may house an individual staple (90) such that staples may be fired radially outward from staple opening (3536, 3538) against staple forming pockets of radially facing surface (3544) in order to staple tissue (20, 40) captured between resilient bodies (3532) and radially facing surface (3544).

In some instances, rather than flex resilient bodies (3532) toward and away an annular base (3531), it may be desirable to translate bodies defining staple openings (3536, 3538) within a housing in order to define gap distance (d) in the radial direction in accordance with the description herein. FIGS. 61-63B show a segment of an exemplary deck assembly (3545). Deck assembly (3545) includes a plurality of radially translating bodies (3546) which may be slidably contained in a housing (3548). Housing (3548) may extend in an annular shape while slidable containing individual bodies (3546). Bodies (3546) may define staple openings (3550, 3552), such that when bodies (3546) are assembled as a whole within housing (3548), staple openings (3550, 3552) form an upper and lower array of stapler openings in a similar shape formed by staple openings (3536, 3538) described above.

As shown in FIGS. 62A-63B, in order to control the gap distance (d) in this example, translating cam body (3540) may engage a portion of translating bodies (3546) to thereby push translating bodies (3546) along a radial path defined by housing (3548), thereby allowing an operator to determine and set a desired gap distance (d) in accordance with the description herein. Translating bodies (3546) may be sufficiently resilient such that if translating cam body (3540) disengages bodies (3546), bodies (3546) may return to the position shown in FIGS. 62A and 63A.

FIGS. 64-66C show an exemplary anvil (3560) and stapling head assembly (3570) that may be used to fire a plurality of staples (90) in the radial direction while also severing tissue (20, 40) captured between anvil (3560) and stapling head assembly (3570). Anvil (3560) includes a pair of coupling halves (3568) pivotally attached to each other via a pin (3569), and a shank (3565) extending away from coupling halves (3568). Shank (3565) may be substantially similar to shank (420) described above. Therefore, shank (3565) may be configured to couple to trocar (330) in order to actuate anvil (3560) proximally toward stapling head assembly (3570) in accordance with the description herein.

Figure 65A:
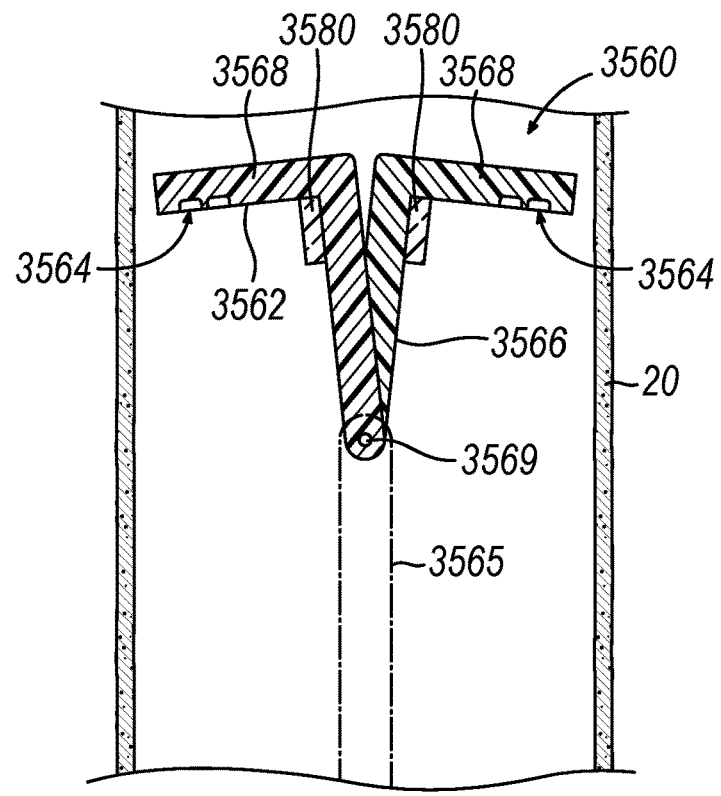
FIG. 65A depicts a cross-sectional view of the anvil of FIG. 64 in a folded position being inserted within a lumen of a patient.
Figure 65B:
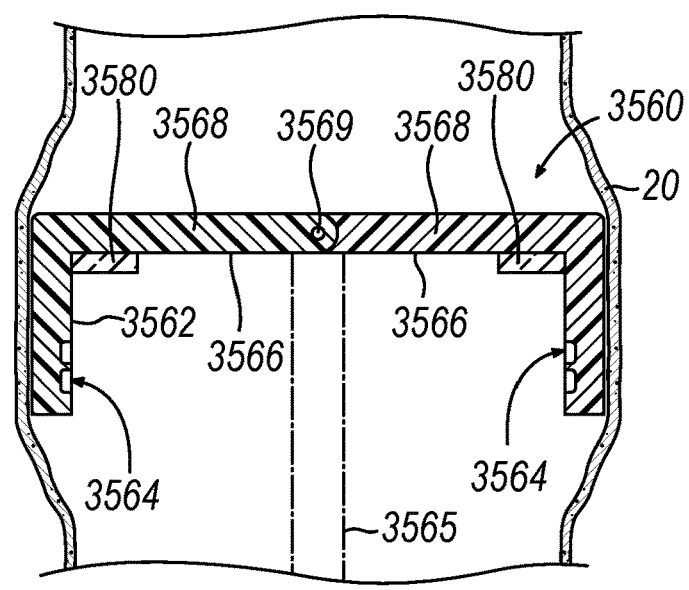
FIG. 65B depicts a cross-sectional view of the anvil of FIG. 64 in an unfolded position within the lumen of a patient.

Coupling halves (3568) fold about pin (3569) between a folded position (see FIG. 65A) and an unfolded position (see FIG. 65B). In the folded position, anvil (3560) may more easily be inserted through an anatomical structure (20) for purposes of placing anvil (3560) near stapling head assembly (3570). In the unfolded position, coupling halves (3568) together form a radially facing surface (3562) defining staple forming pockets (3564) and a flat surface (3566). Staple forming pockets (3564) may align with staples (90) during firing of staples (90) in accordance with the description herein, while flat surface (3566) may be configured to cooperate with a cutting edge (3576) of stapling head assembly (3570) in order to sever tissue (20, 40).

Stapling head assembly (3570) includes a cylindraceous body (3571) defining a plurality of radially facing staple openings (3578), a cylindrical firing member (3572) slidably disposed within cylindraceous body (3571), and a plurality of radially actuating staple drivers (3575) each suitably attached to a staple (90) aligned with a respective staple opening (3578). Firing member (3572) includes a camming surface (3574) and a distally presented cutting edge (3576). Camming surface (3574) is configured to actuate distally in order to drive stapler drivers (3575) radially out toward staple openings (3578) such that staples (90) are driven into staple forming pockets (3564) of anvil (3560) in order to staple tissue (20, 40) and form an anastomosis (70). Cutting edge (3576) is configured to cooperate with flat surface and a breakable washer (3580) such that distal actuation of firing member (3572) leads to the severing of tissue (20, 40) captured between cutting edge (3576) and washer (3580). Washer (3580) may be any suitable shape and may be divided into any suitable number of pieces in order to accommodate the folding of coupling halves (3568) in accordance with the description herein.

FIGS. 65A-66C show an exemplary use of anvil (3560) and stapling head assembly (3570) in order to capture tissue (20, 40) together and then cooperatively staple and sever tissue (20, 40) to form an anastomosis (70). First as shown in FIG. 65A, anvil (3560) may have halves (3568) in the folded position in order to insert anvil (3560) more easily through lumen (20). Once near the desired position, anvil (3560) may be unfolded such that folding halves (3568) pivot about pin (3569) in order to suitably form flat surface (3566) and radially facing surface (3562). Shank (3565) may be coupled with trocar (330) in accordance with the description herein and actuated to the position shown in FIG. 66A.

Figure 66A:
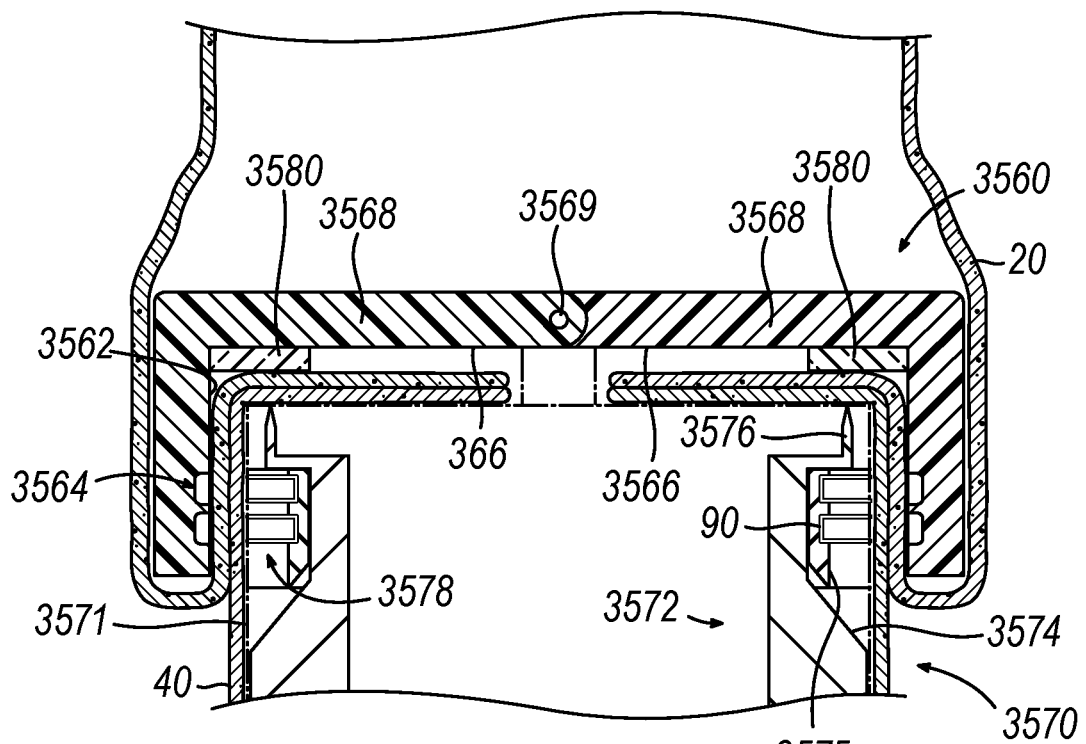
FIG. 66A depicts a cross-sectional view of the anvil of FIG. 64 coupled to the stapling head assembly of FIG. 64 in a pre-fired position.
Figure 66B:
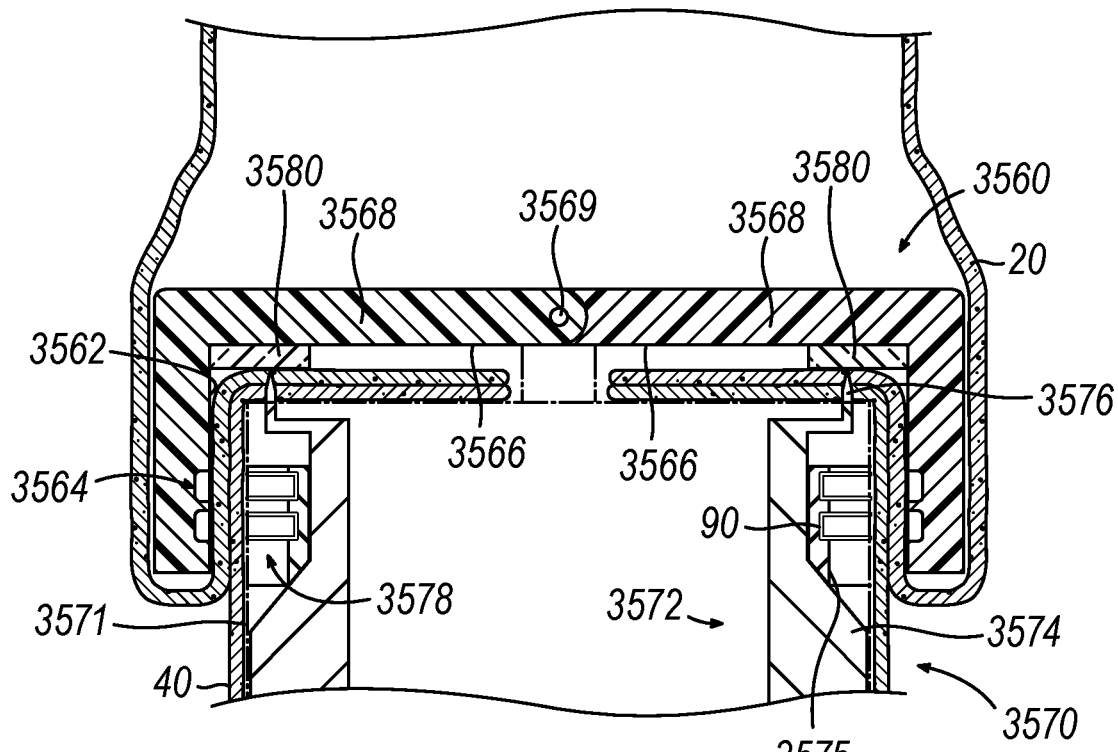
FIG. 66B depicts a cross-sectional view of the anvil of FIG. 64 coupled to the stapling head assembly of FIG. 64 in the middle of the firing processes.
Figure 66C:
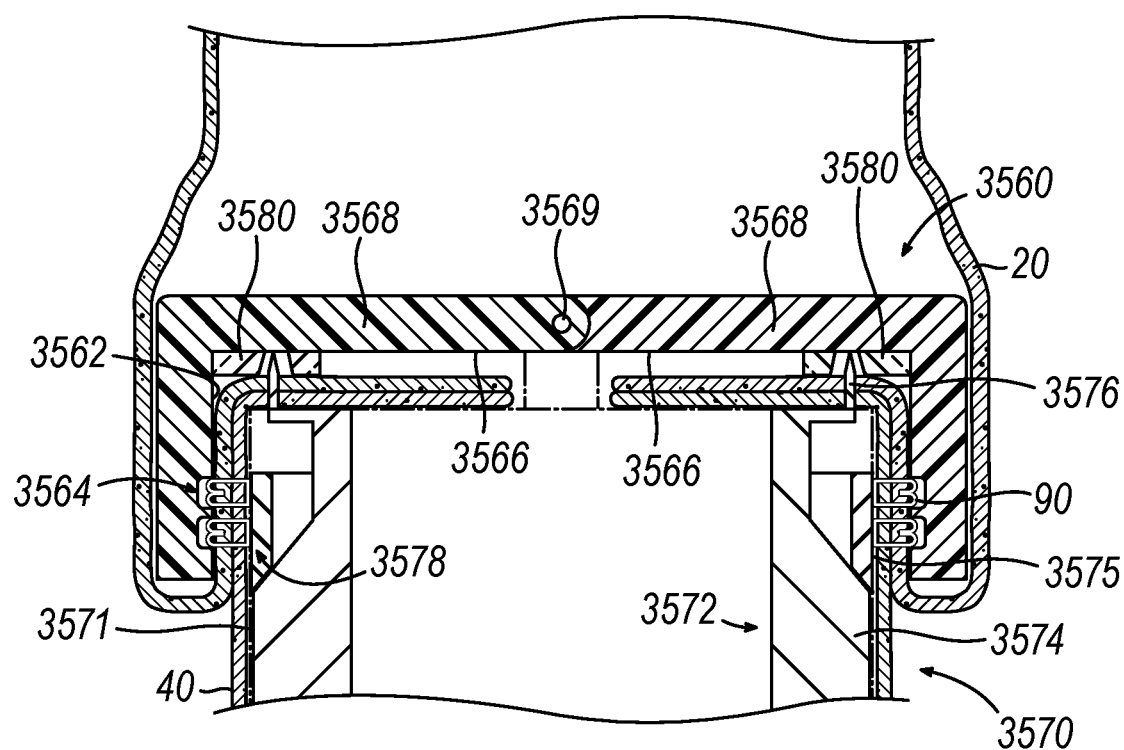
FIG. 66C depicts a cross-sectional view of the anvil of FIG. 64 coupled to the stapling head assembly of FIG. 64 completing the firing processes.
Figure 67A:
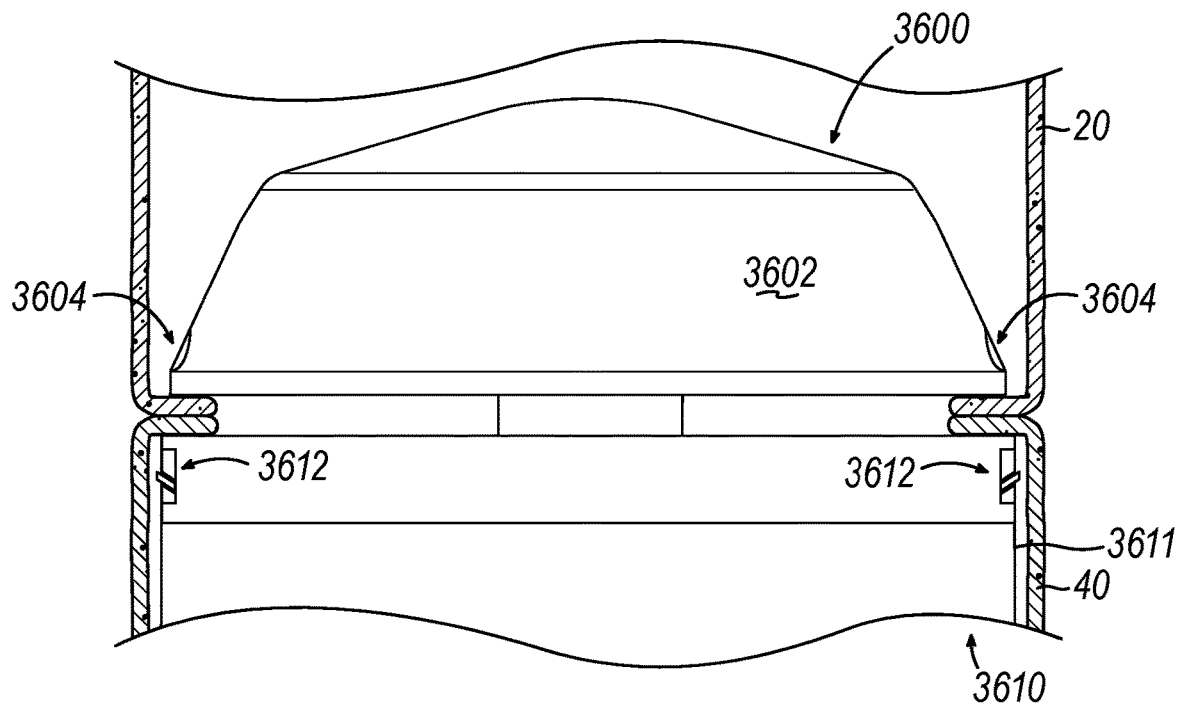
FIG. 67A depicts an elevational side view of an exemplary anvil and stapling head assembly that may be incorporated into the circular stapler of FIG. 1, the anvil and stapling head assembly grasping tissue lumens, in a pre-fired position.
Figure 67B:
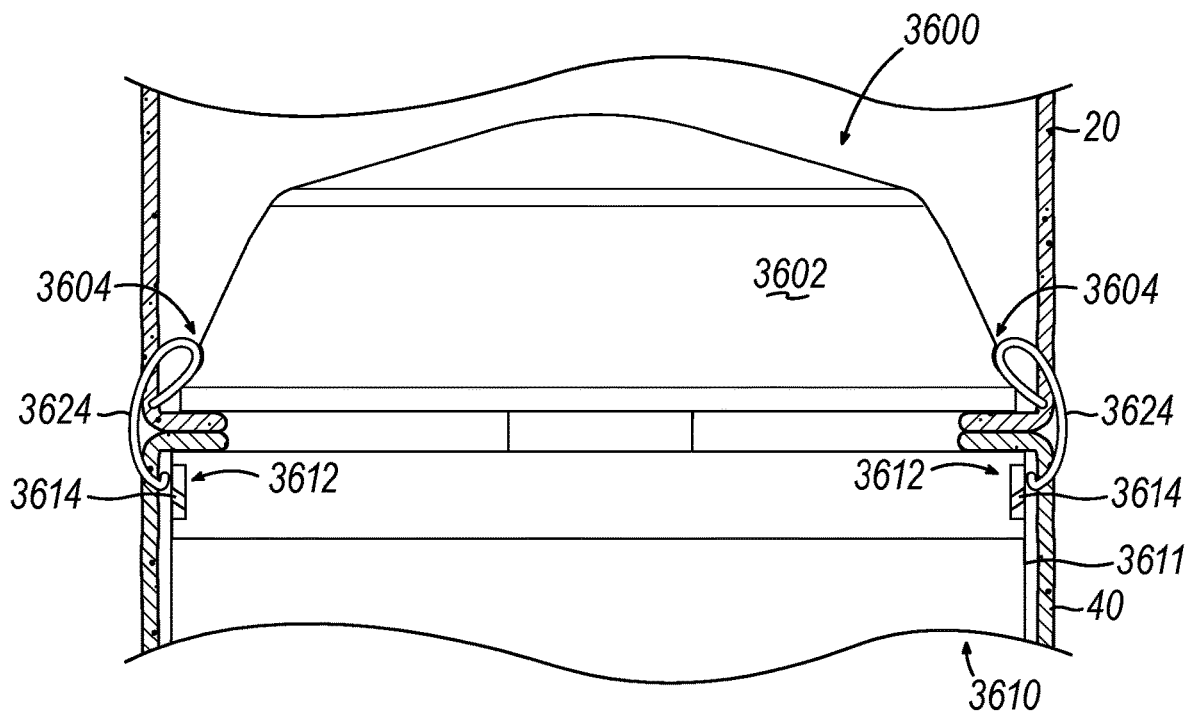
FIG. 67B depicts an elevational side view of the anvil and stapling head assembly of FIG. 67A in a post-fired position.

Once in the position shown in FIG. 66A, an operator may actuate firing member (3572) in accordance with the description herein. As best shown in FIG. 66B, distal actuation of firing member (3572) may allow cutting edge (3576) to sever tissue (20, 40) that is between breakable washer (3580) and a distal end of stapling head assembly (3570). Next, as shown in FIG. 66C, further distal actuation of firing member (3572) allows cam surface (3574) of firing member (3572) to abut against a complementary surface of staple drivers (3575), thereby forcing staple drivers (3575) radially outward toward tissue (20, 40) interposed between staple forming pockets (3564) and the portion of cylindrical body (3571) defining staple openings (3578). In response, staples (90) are driven through tissue (20, 40), against staple forming pockets (3564) and then back into tissue (20, 40) in order to staple tissue (20, 40) together, thereby leaving a newly formed anastomosis. The breaking of breakable washer (3580) may signal to an operator that tissue has been severed and stapled in accordance with the description herein.

In some instances, it may be desirable to fire staples in the radial direction and deform such a staple on the outer surface of an anvil, rather than an inner surface of anvil. This may allow the size of anvil to be smaller than if staples were fired radially outward against an interior surface of anvil.

FIGS. 67A-68B show an anvil (3600) and a stapling head assembly (3610) configured to deform legs (3624) of a staple (3620) on an exterior surface (3602) of anvil (3600). Anvil (3600) includes outer surface (3602) defining a plurality of staple forming pockets (3604). Staple forming pockets (3604) are formed on the outer surface (3602) of anvil (3600) such that staple forming pockets (3604) do not face toward a portion of stapling head assembly (3610). As will be described in greater detail below, stapling head assembly (3610) is configured to drive staples (3620) along an arched path (3618) such that even though staple openings (3612) of stapling head assembly (3610) do not face directly toward staple forming pockets (3604), legs (3624) of staples (3620) deform against staple forming pockets (3604).

Figure 68A:
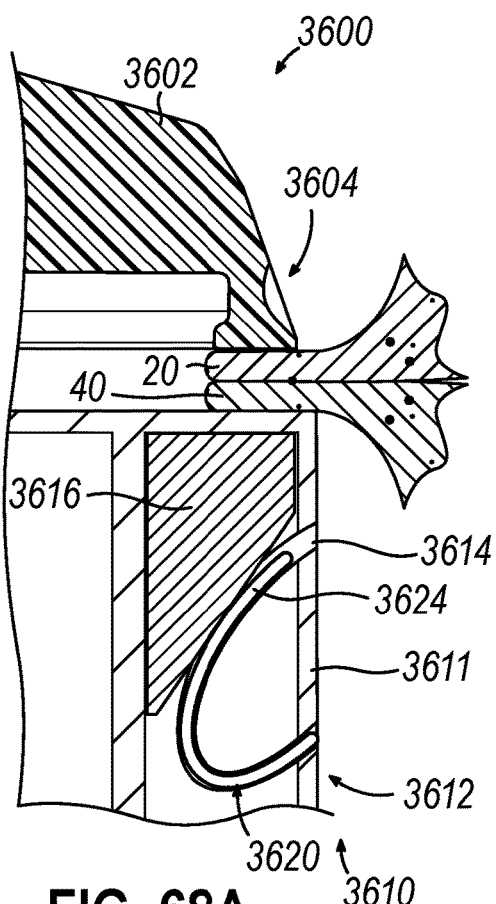
FIG. 68A depicts an enlarged cross-sectional view of the anvil and stapling head assembly of FIG. 67A in the pre-fired position.
Figure 68B:
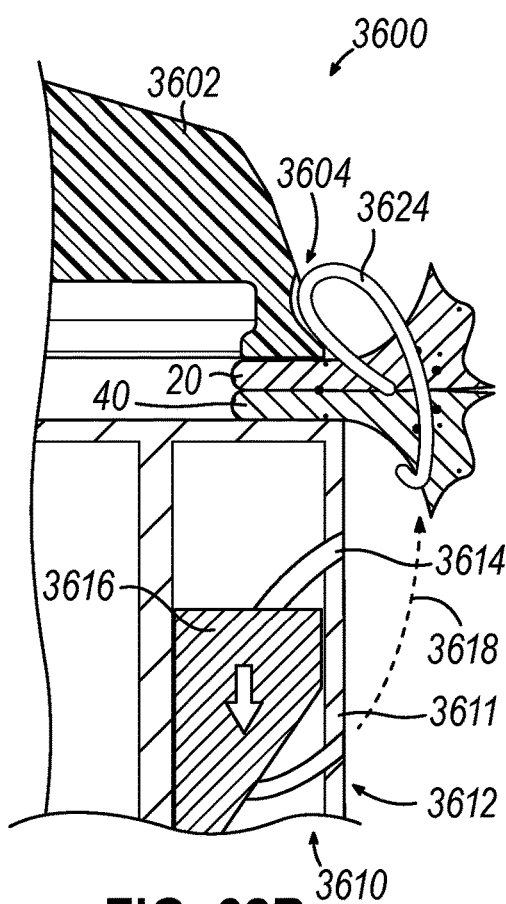
FIG. 68B depicts an enlarged cross-sectional view of the anvil and stapling head assembly of FIG. 67A in the post-fired position.
Figure 69:
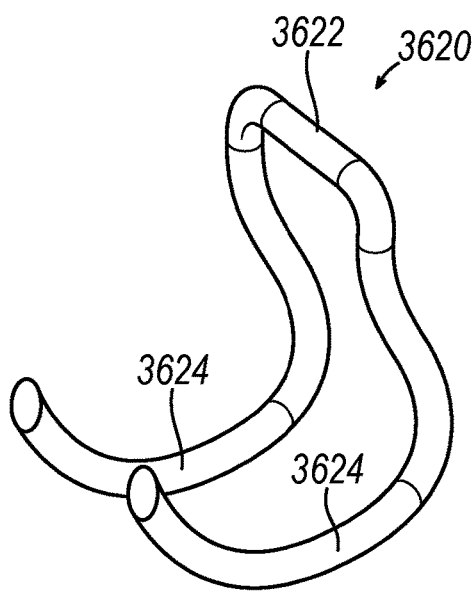
FIG. 69 depicts a perspective view of an exemplary staple configured to be used with the anvil and stapling head assembly of FIG. 67A.
Figure 70:
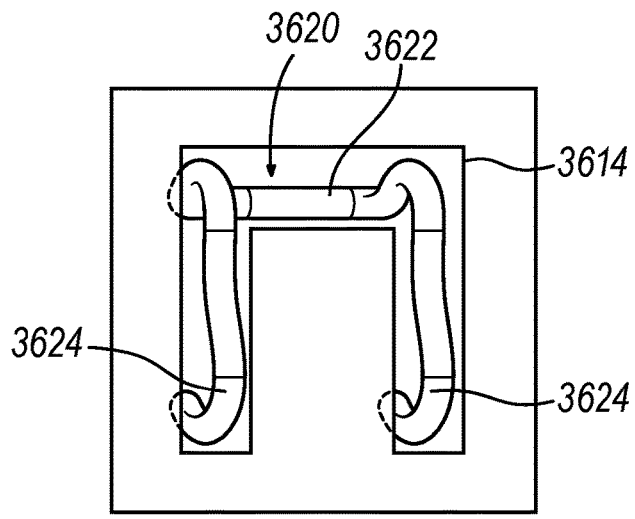
FIG. 70 depicts a perspective view of the staple of FIG. 69 housed within a staple guiding surface of the stapling head assembly of FIG. 67A.

As shown in FIGS. 68A-68B, stapling head assembly (3610) includes a tubular body member (3611) defining an annular array of radially presented staple openings (3612). Tubular body member (3611) also defines a staple guiding surface (3614) extending from an interior of tubular body member (3611) into each staple opening (3612). Staple guiding surface (3614) slidably houses staples (3620) within staple openings (3612). Staple guiding surface (3614) is sufficiently arched to complement the arched profile of hooked legs (3624) of staple (3620) such that when staples (3620) are driven out of staple openings (3612) in accordance with the description herein, staples (3620) travel along an arched path (3618) to engage staple forming pockets (3604) located on the outer surface (3602) of anvil (3600), thereby stapling tissue (20, 40) and shown in FIGS. 67B and 68B.

Stapling head assembly (3610) also includes a staple driver (3616). Staple driver (3616) is configured to actuate relative to tubular body member (3611) in order to cam against crown (3622) of staple (3620) to thereby drive staples (3620) along the path provided by staple guiding surface (3614). In the current example, staple driver (3616) has a slanted camming surface such that as staple (3620) travels along the arched path provided by staple guiding surface (3614), staple driver (3616) may maintain suitable contact with crown (3622). Any suitable mechanism may actuate staple driver (3616) as would be apparent to one skilled in the art in view of the teachings herein.

As mentioned above, staple (3620) includes a crown (3622) and two C-style hooked legs (3624) extending from respective ends of crown (3622). C-style hooked legs (3624) cooperatively engage staple guiding surface (3614) in order to travel arched path (3618) to thereby engage staple forming pockets (3604) that face away from respective staple openings (3612), rather than conventionally facing toward staple openings (3612). This feature may allow anvil (400) to suitably deform staples (3620) fired in a radial direction without having to increase the radial size of anvil (400).

In some instances, it may be desirable to sever tissue along a path that extends radially from a stapling head assembly rather than along a conventional path that extends parallel with the longitudinal axis of the stapling head assembly (e.g., as done by stapling head assemblies (300, 700)). This may increase the diameter at which knife cuts tissue (20, 40), which may in turn reduce the size which severed edges (60) extends radially within lumens (20, 40).

Figure 71:
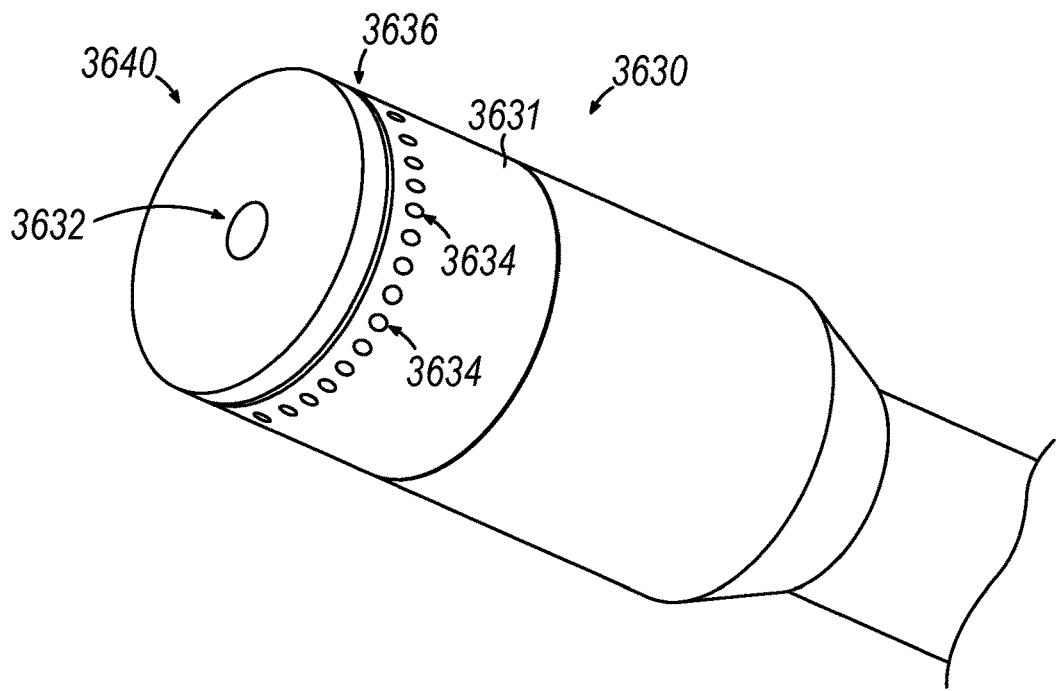
FIG. 71 depicts a perspective view of a stapling head assembly that may be incorporated into the circular stapler of FIG. 1, the stapling head assembly being configured to sever tissue with a radially retractable blade.
Figure 72:
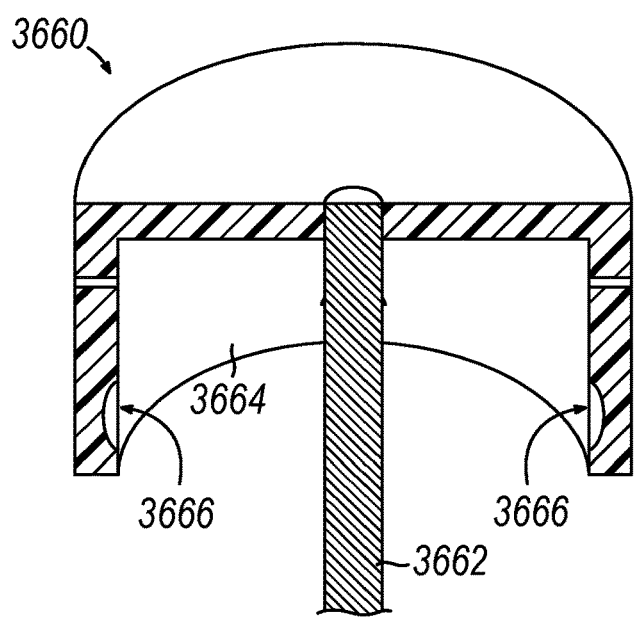
FIG. 72 depicts a cross-sectional view of an anvil configured to couple with the stapling head assembly of FIG. 71.

FIG. 71 shows a stapling head assembly (3630) that includes a radial cutting assembly (3640) configured to sever tissue captured against a tubular body (3631) of stapling head assembly (3630) above staple openings (3634). Stapling head assembly (3630) is configured to drive staples out of staple opening (3634) in the radial direction away from tubular body (3631) against staple forming pocket (3666) (see FIG. 72) of an anvil (3660). Stapling head assembly (3630) includes an opening (3632) dimensioned to couple with a shank (3662) of anvil (3660). Anvil (3660) includes a radially facing surface (3664 configured to face toward the exterior surface of tubular body (3631) when coupled with stapling head assembly (3630). In particular, radially facing surface (3664) of anvil (3660) is configured to face tubular body (3631) such that staple openings (3634) align with stapling forming pockets (3666). Therefore, when staples are driven radially out of staple opening (3634), staples with be driven through tissue and against a respective staple forming pocket (3666) to thereby staple tissue.

Stapling head assembly (3630) also defines a radially presented severing slot (3636) dimensioned to allow a retractable blade (3642) of radial cutting assembly (3640) to extend through. Retractable blade (3642) may extend out of radially presented severing slot (3636) in order to circumferentially cut tissue captured between tubular body (3631) and a portion of surface (3664) located distally above staple forming pockets (3666). As will be described in greater detail below, retractable blade (3642) may selectively extend out of slot (3636) and back within slot (3636) in order to sever tissue in accordance with the tissue herein.

Figure 73A:
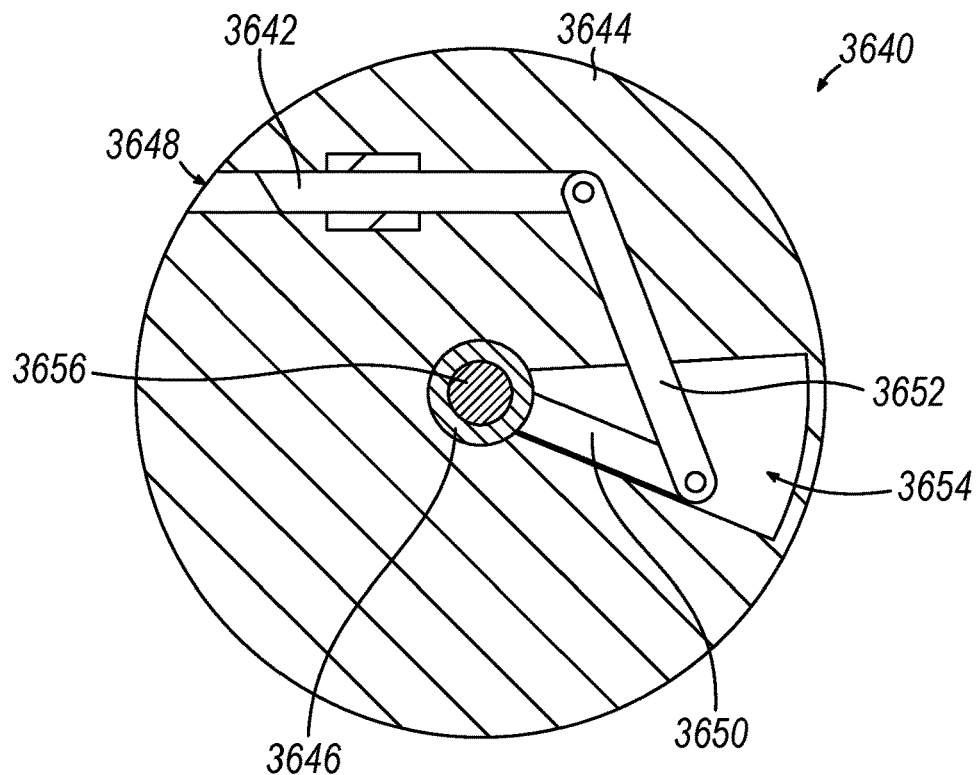
FIG. 73A depicts a cross-sectional view of a cutting assembly of the stapling head assembly of FIG. 71, with a radially retractable blade in a retracted position.
Figure 73B:
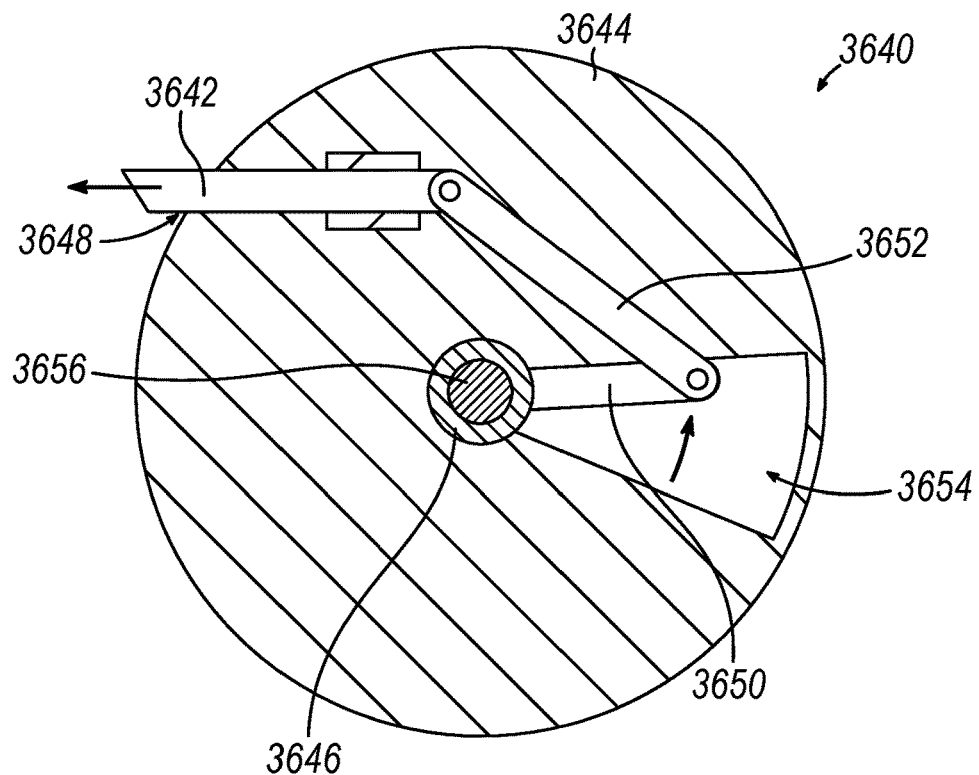
FIG. 73B depicts a cross-sectional view of the cutting assembly of FIG. 73A with the radially retractable blade in an extended position.
Figure 73C:
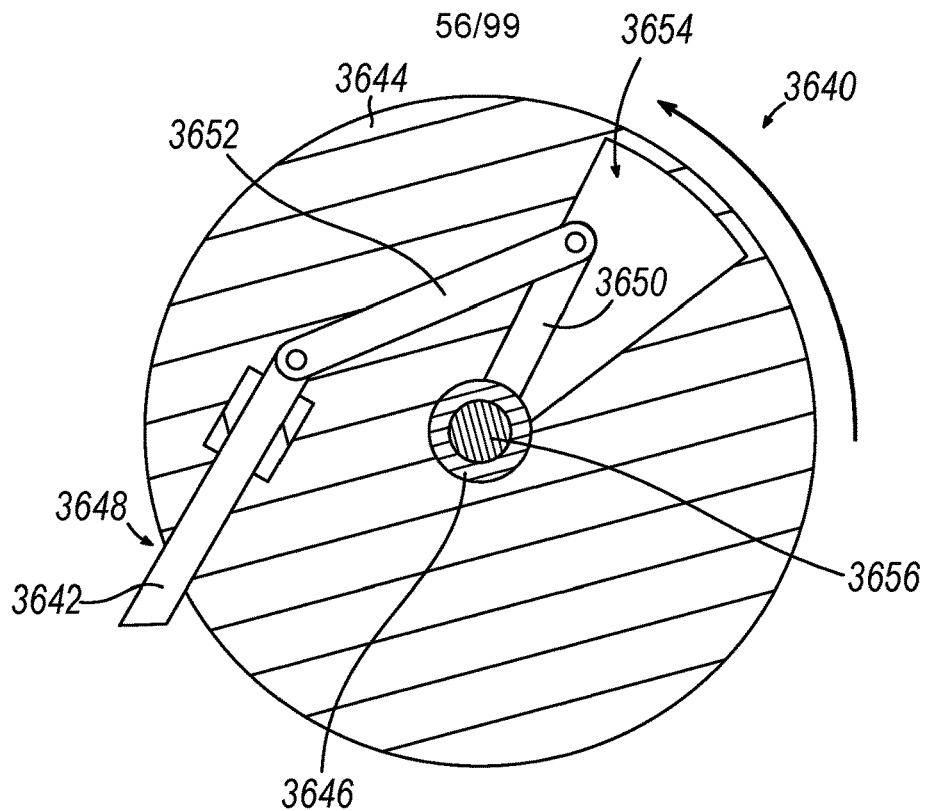
FIG. 73C depicts a cross-sectional view of the cutting assembly of FIG. 73A with the radially retractable blade in the extended position and rotated.
Figure 73D:
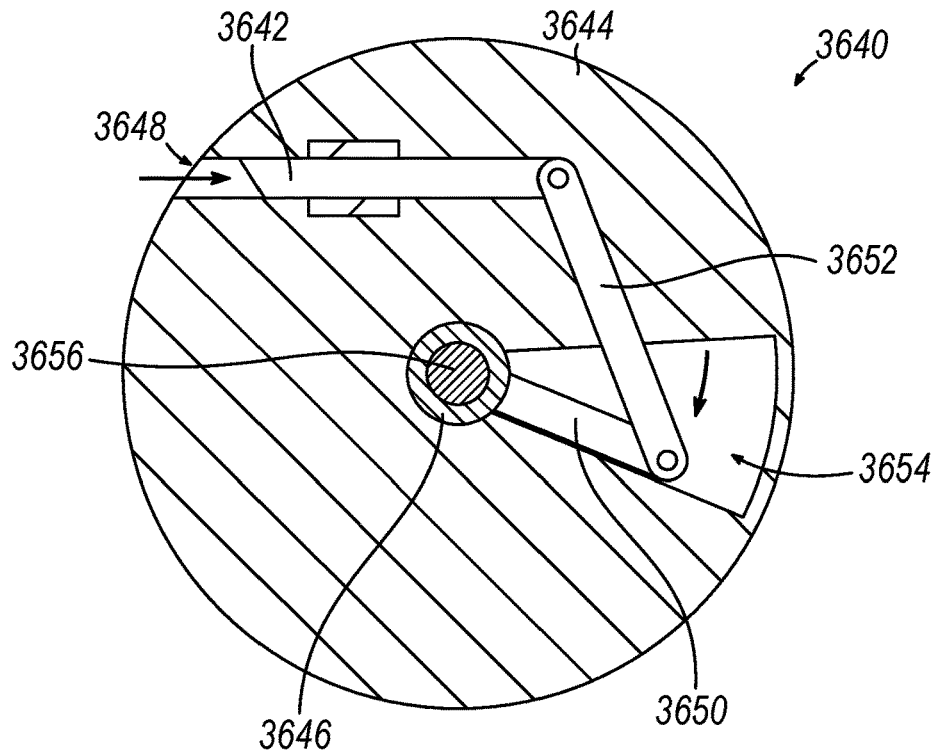
FIG. 73D depicts a cross-sectional view of the cutting assembly of FIG. 73A with the radially retractable blade in the retracted extended position after being rotated.

FIGS. 73A-73 show the various components of radial cutting assembly (3640) and how radial cutting assembly (3640) drives retractable blade (3642) between the retracted position (see FIGS. 73A and 73D) and the extended position (see FIGS. 73B and 73C). It should be understood that while blade (3642) is in the extended position, blade (3642) may extend radially out of severing slot (3636) in order to engage and sever tissue. It should also be understood that when blade is in the retracted position, blade (3642) is prevented from engagement with tissue, thereby preventing inadvertent damage to tissue.

Radial cutting assembly (3640) includes retractable blade (3642), a rotatable blade housing (3644), a rotating shaft (3646), a first link (3650) attached to rotating shaft (3646), a second link (3652) pivotally attached to first link (3650) and retractable blade (3642), and a drive shaft (3656). Drive shaft (3656) may rotate about its own longitudinal axis in order to rotate the entirety of radial cutting assembly (3640) relative to the rest of stapling head assembly (3630). Rotatable blade housing (3644) defines a blade guide slot (3648) and a link recess (3654). Blade guide slot (3648) slidably receives retractable blade (3642) in order to guide blade (3642) along the path between the retracted position and the extended position. link recess (3654) provides adequate room for links (3650, 3652) to move in order to drive blade (3642) along the path defined by blade guide slot (3648).

Rotating shaft (3646) is configured to be rotated about its own longitudinal axis in order to pivot first link (3650) and second link (3652) to thereby drive translation of retractable blade (3642) between the retracted position and the extended position. Therefore, rotating shaft (3646) may rotate in a first rotational direction to drive blade (3642) into the extended position; while rotating shaft (3646) may also rotate in a second rotational direction to drive blade (3642) into the retracted position. First link (3650) has one end directly attached to rotating shaft (3646) such that rotation of rotating shaft (3646) drives rotation of first link (3650) about the longitudinal axis of rotating shaft (3646). Second link (3652) is pivotally coupled to ends of both first link (3650) and blade (3642). Therefore, when first link (3650) rotates, second link (3652) translate and rotates in order to drive translation of blade ((3650).

As best shown between FIGS. 73A-73B, when it is suitable for blade (3642) to actuate from the retracted position to the extended position, rotating shaft (3646) may rotate in the first rotational direction. Therefore, first link (3650) rotates within link recess (3654), while second link (3652) rotates and translates within link recess (3654), thereby driving translation of blade within blade guide slot (3648) into the extended position. With blade (3642) in the extended position, as shown between FIGS. 73B-73C, drive shaft (3656) may be rotated about its own longitudinal axis, thereby rotating the entirely of cutting assembly (3640), including blade (3642). Since blade (3642) is exposed in the extended position, blade (3642) may sever tissue captured between radially facing surface (3664) of anvil (3660) and tubular body (3631) of stapling head assembly (3630).

Once blade (3642) has been suitable rotate to completely sever tissue, blade (3642) may then be retracted by rotating shaft (3646) in the second rotational direction in accordance with the description above, thereby actuating blade (3642) into the retracted position.

VI. Exemplary Stapling Head Assembly with Staples Having Expandable Crowns

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable the annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and anvil (400) with features that enable formation of such an anastomosis and/or patterns of formed staples (90). Exemplary versions of such features are described in greater detail below.

A. Exemplary Stapling Head Assembly with "V" Shaped Expandable Staples

FIGS. 77-81 illustrate portions of an exemplary stapling head assembly (4300) that is similar to exemplary stapling head assembly (300) described above. In some versions, stapling instrument (10) can be fitted with stapling head assembly (4300) instead of stapling head assembly (300) and be operable as described above. Stapling head assembly (4300) is configured the same as stapling head assembly (300) except stapling head assembly (4300) includes deck member (4320) with deck surface (4322) and staple openings (4324). Also, staple driver member (350), when used with stapling head assembly (4300) is configured with staple drivers (4352) that have a differing shape from staple drivers (352) as will be discussed further below. Furthermore, stapling head assembly (4300) is configured for use with expandable staples generally having a "V" shape as will be described further below.

1. Exemplary Expandable Staples with "V" Shaped Crown

Figure 77:
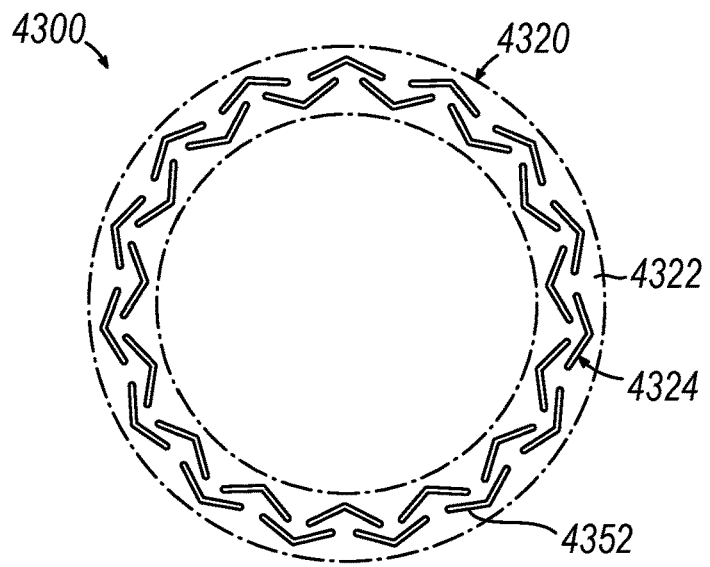
FIG. 77 depicts a top view of portions of an exemplary alternate stapling head assembly for use with the instrument of FIG. 1.

Referring to FIGS. 77-81, stapling head assembly (4300) is configured for use with expandable staples (3890). In the present example, staples (3890) are configured with a "V" shape that allows each staple (3890) to expand after being deployed as will be discussed in greater detail below. Referring to FIG. 77, deck member (4320) is shown with deck surface (4322) having "V" shaped openings (4324). With staples (3890) not shown in FIG. 77, staples drivers (4352) are visible through openings (4324). As shown, staple drivers (4352) have a corresponding "V" shape to openings (4324) such that staple drivers (4352) are configured to deploy staples (3890), with their "V" shape, through openings (4324).

Figure 78:
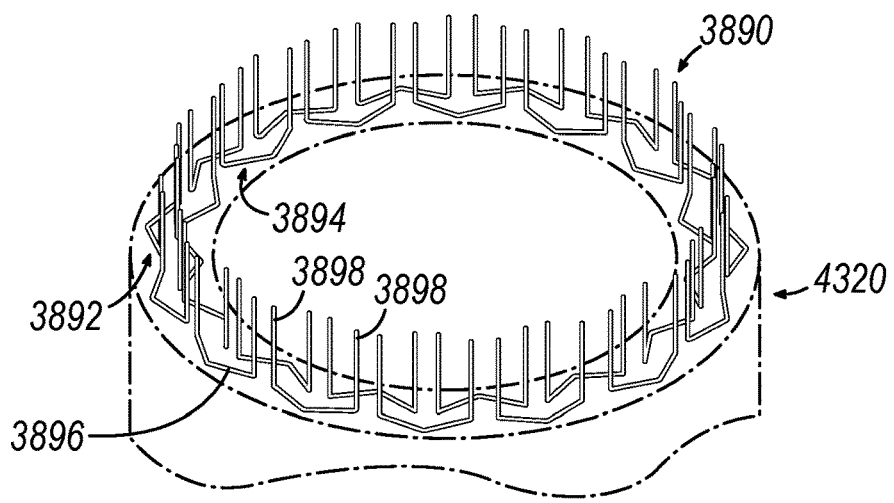
FIG. 78 depicts a perspective view of portions the stapling head assembly of FIG. 8, showing an array of expandable staples in an unformed state.

Referring to FIG. 78, a portion of deck member (4320) is shown in phantom to reveal a plurality of undeployed staples (3890) loaded within deck member (4320). As shown in the present example, staples (3890) are arranged in two annular or ring-shaped rows where there is an outer row (3892) and an inner row (3894). Staples (3890) are further arranged such that each row is staggered or offset from the other, and such that staples (3890) in one row oppose staples (3890) in the other row. With this opposing arrangement, staples (3890) in one row are effectively rotated 180 degrees from staples (3890) in the other row. In some versions, the size and/or shape of staples (3890) in inner row (3894) can differ from that of outer row (3892) to assist in establishing the circular staple pattern shown.

Figure 79:
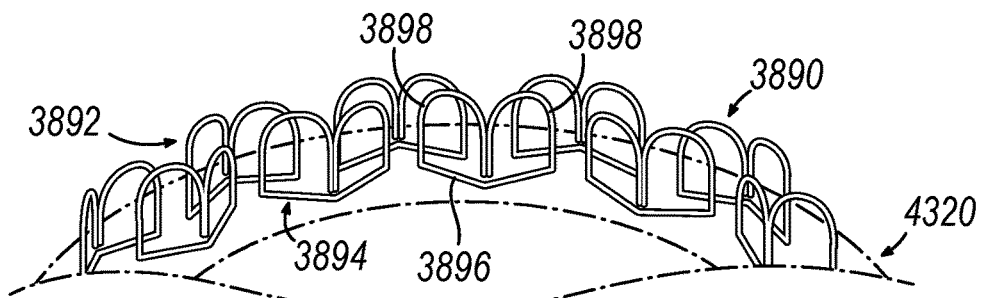
FIG. 79 depicts a partial perspective view of the staples of FIG. 78, shown in a formed state.

Staples (3890) each comprise a crown (3896) and a pair of legs (3898). Furthermore, staples (3890) have a "V" shape where a top view looking down onto crown (3896) presents a "V" shape. The "V" shape can further be described as having two straight portions or lines with a vertex between them. In this fashion, staples (3890) define an angle between the pair of legs (3898). As understood from comparing FIGS. 78 and 79, staples (3890) have this "V" shape in both the undeployed state as shown in FIG. 78 and in the deployed state as shown in FIG. 79. As shown in FIG. 79, when staples (3890) are deployed or fired from instrument (10), as described above, the interaction of staples (3890) with anvil (400) deforms the pair of legs (3898) to bend them in a curved manner forming a "B" shape.

Figure 80:
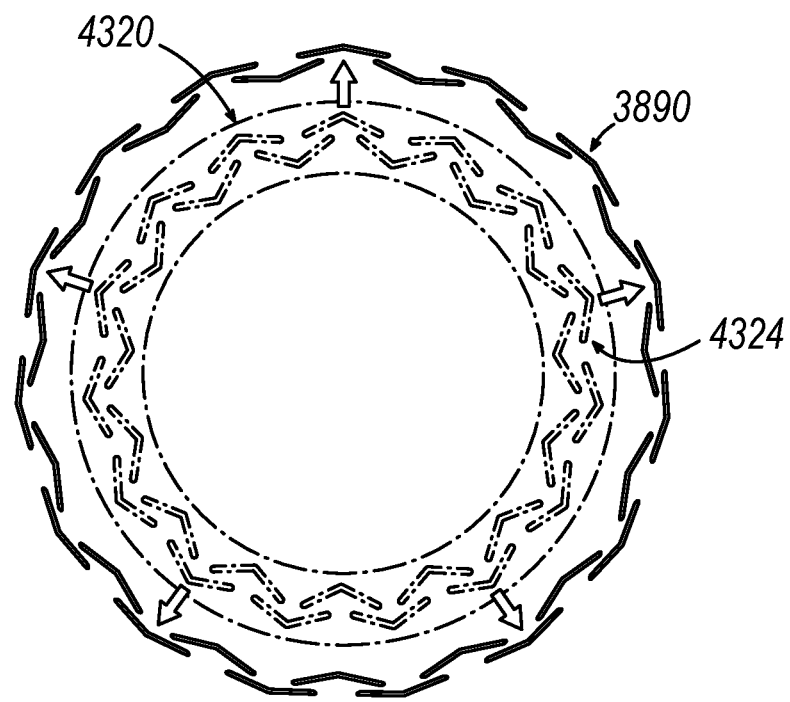
FIG. 80 depicts a top view of portions of the stapling head assembly of FIG. 77, showing the movement of the staple line based on staple expansion.
Figure 81:
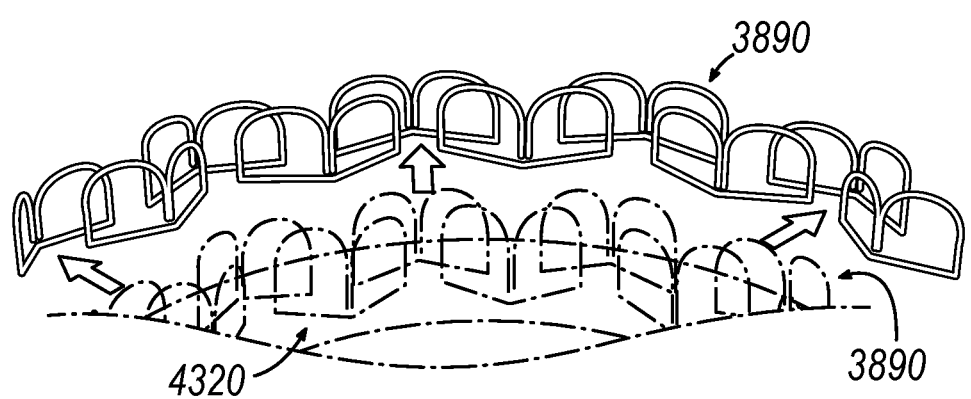
FIG. 81 depicts a partial perspective view of the formed staples of FIG. 79, showing the movement of the staple line based on staple expansion.

Referring now to FIGS. 80 and 81, staples (3890) are configured as expandable staples. For instance, FIG. 80 illustrates the staple deck (4320) showing openings (4324) from which staples (3890) would have initially been deployed. As shown in FIG. 80 and further in FIG. 81, after staples (3890) have been deployed they may undergo an expansion allowing them to move radially. This expansion allows for the plurality of staples (3890) forming the ring shape or pattern to define a first or initial diameter, and then subsequently allowing the same plurality of staples (3890) to define a second or subsequent diameter that is larger than the initial diameter. In this manner, the diameter of the lumen at the anastomosis is increased.

In the present example, the "V" shape configuration of staples (3890) contributes to the ability of staples (3890) to expand or be expandable. In some versions, staples (3890) are formed with the "V" shape and after deployment, staples (3890) can experience tension based on radial tissue forces, e.g., from peristalsis, or from the passage of material through the lumen. In response to experiencing this tension, legs (3898) of staples (3890) deflect from the vertex to define a larger angle between the pair of legs (3898). Consequently, the width of staples (3890) increase, with the width being defined as the linear distance between the pair of legs (3898).

In other versions, staples (3890) initially have a straight or substantially straight shape and are bent when loaded within instrument (10). For instance, staples (3890) may be bent into a "V" shape when loaded within annular deck member (320). In this manner, staples (3890) are under tension when deployed, but then after deployment, staples (3890) return to their relaxed state and thus expand radially by expanding to a straighter shape. In this version, staples (3890) automatically expand after being deployed without needing any tissue force placed upon staples (3890) to achieve expansion of staples (3890). As will be described further below, other "V" shape staples having other features that promote expandability can be used with instrument (10) and stapling head assembly (4300) in place of staples (3890).

2. Exemplary Expandable Staples with "V" Shaped Crown and Spring Feature

FIG. 82 depicts an exemplary staple (3990), which can replace staple (3890) or (90) in the plurality of staples. Staple (3990) includes crown (3996) and a pair of legs (3998). Crown (3996) includes two straight portions (3997) and a spring feature (3995). Spring feature (3995) in the present example is located between each of straight portions (3997) and is formed with a curved shape. In the unexpanded state as shown in FIG. 82, staple (3990) defines an angle ($\alpha$) between straight portions (3997), and staple (3990) defines a distance (d) between legs (3998). After deployment and after staple (3990) expands the same or similar to the expansion described above with respect to staple (3890), staple (3990) expands about spring feature (3995) such that angle ($\alpha$) increases, which also corresponds with an increase in distance (d). This produces a broader "V" shape for staples (3990) that resembles staples (3990) becoming closer to linear shaped.

In the present example, staple (3990) starts initially as straight or substantially straight and adopts its "V" shape with incorporated spring feature (3995) during loading with instrument (10) such that staples (3990) are held within instrument (10) under tension. Moreover, staples (3990) are formed of fully or partially resilient material such that after being deployed, spring feature (3995) assists in automatically expanding staples (3990) as they return to their relaxed state. During this expansion, staples (3990) increase in width (d) between legs (3998), which widens the diameter of the anastomosis.

In some other versions, staple (3990) is formed such that in its relaxed state staple (3990) has the "V" shape with spring feature (3995). In these versions, spring feature (3995) promotes expansion of staple (3990) based on tissue forces described above acting on staple (3990). For instance, spring feature (3995) is coplanar with crown (3996) and legs (3998) extend generally orthogonal to a plane defined by crown (3996) and spring feature (3995). After deployment of staple (3990), tension from radial tissue forces act on staple (3990) and such forces are generally orthogonal to axes defined by legs (3998) when legs (3998) are in the unformed state. In this manner, spring feature (3995) is configured and oriented so that when radial tissue forces act on staple (3990), expansion of staple (3990) occurs as described above. In view of the teachings herein, other ways to configure staple (3990) with spring feature (3995) will be apparent to those of ordinary skill in the art.

3. Exemplary Expandable Staples with "V" Shaped Crown and Weakened Region

FIGS. 83A and 83B illustrate another exemplary staple (4090) which can replace staple (3890) or (90) in the plurality of staples. Staple (4090) includes crown (4096) and a pair of legs (4098). Crown (4096) includes two straight portions (4097) and a weakened region (4095). Weakened region (4095) in the present example is located between each of straight portions (4097) and is formed as a notch or cut-away portion of crown (4096). This configuration for weakened region (4095) provides for a thinner portion of crown (4096) at the junction or vertex of straight portions (4097) where there is less material present. This in turn allows for staple (4090) to be more responsive to expand when lower tissue forces act on staple (4090).

In the undeployed state as shown in FIG. 83A, staple (4090) defines an angle ($\alpha 1$) between straight portions (4097), and staple (4090) defines a distance (d1) between legs (4098). After deployment as shown in FIG. 83B, and after staple (4090) is subject to tension from tissue forces as described above, staple (4090) expands about weakened region (4095) such that angle ($\alpha 1$) increases, which also corresponds with an increase in distance (d1). This produces a broader "V" shape for staples (4090) that resembles staples (4090) becoming closer to linear shaped. In the present example, staple (4090) with weakened region (4095) is configured such that it plastically deforms when the tissue forces act on staple (4090) as described above. In this manner, the increased diameter at the anastomosis can be maintained.

As shown in FIGS. 83A and 83B, weakened region (4095) is coplanar with crown (4096). Additionally, legs (4098) extend generally orthogonal to a plane defined by crown (4096) and weakened region (4095). After deployment of staples (4090), tension from radial tissue forces act on staple (4090) and such forces are generally orthogonal to axes defined by legs (4098) when in the unformed state. In this manner, weakened region (4095) is configured and oriented so that when radial tissue forces act on staple (4090), expansion of staple (4090) occurs as described above. In view of the teachings herein, other ways to configure staple (4090) with weakened region (4095) will be apparent to those of ordinary skill in the art.

FIG. 84 illustrates another exemplary staple (4190) which can replace staple (3890) or (90) in the plurality of staples. Staple (4190) includes crown (4196) and a pair of legs (4198). Crown (4196) includes two straight portions (4197) and a weakened region (4195). Weakened region (4195) in the present example is located between each of straight portions (4197) and is formed as a reduced diameter section of crown (4196). This configuration for weakened region (4195) provides for a smaller portion of crown (4196) at the junction or vertex of straight portions (4197) where there is less material present. This in turn allows for staple (4190) to be more responsive to expand when lower tissue forces act on staple (4190).

In the undeployed state as shown in FIG. 84, staple (4190) defines an angle ($\alpha 2$) between straight portions (4197), and staple (4190) defines a distance (d2) between legs (4198). After deployment, and after staple (4190) is subject to tension from tissue forces as described above, staple (4190) expands about weakened region (4195) such that angle ($\alpha 2$) increases, which also corresponds with an increase in distance (d2). This produces a broader "V" shape for staples (4190) that resembles staples (4190) becoming closer to linear shaped. In the present example, staple (4190) with weakened region (4195) is configured such that it plastically deforms when the tissue forces act on staple (4190) as described above. In this manner, the increased diameter at the anastomosis can be maintained.

As shown in FIG. 84, weakened region (4195) is coplanar with crown (4196). Additionally, legs (4198) extend generally orthogonal to a plane defined by crown (4196) and spring feature (4195). After deployment of staples (4190), tension from radial tissue forces act on staple (4190) and such forces are generally orthogonal to axes defined by legs (4197) when in the unformed state. In this manner, weakened region (4195) is configured and oriented so that when radial tissue forces act on staple (4190), expansion of staple (4190) occurs as described above. In view of the teachings herein, other ways to configure staple (4190) with weakened region (4195) will be apparent to those of ordinary skill in the art.

Figure 85:
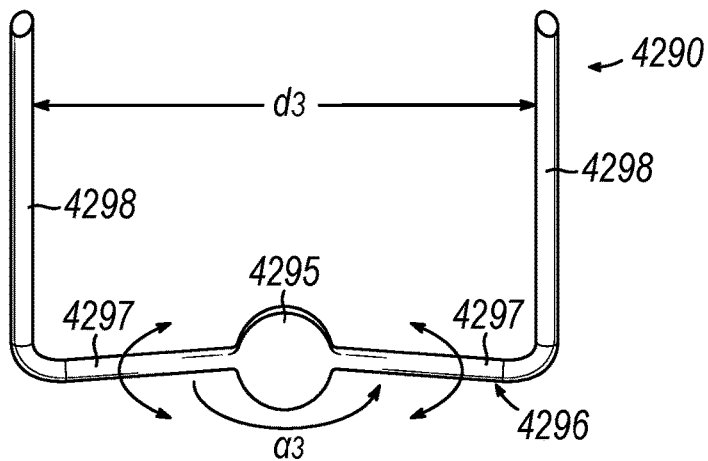
FIG. 85 depicts a front view of an exemplary "V" shaped staple having a flat area feature.

FIG. 85 illustrates another exemplary staple (4290) which can replace staple (3890) or (90) in the plurality of staples. Staple (4290) includes crown (4296) and a pair of legs (4298). Crown (4296) includes two straight portions (4297) and a weakened region (4295). Weakened region (4295) in the present example is located between each of straight portions (4297) and is formed as a flat area or portion of crown (4296). This configuration for weakened region (4295) provides for a more pliable portion of crown (4296) at the junction or vertex of straight portions (4297) where there is thinner material present. This in turn allows for staple (4290) to be more responsive to expand when lower tissue forces act on staple (4290).

In the undeployed state as shown in FIG. 85, staple (4290) defines an angle (α3) between straight portions (4297), and staple (4290) defines a distance (d3) between legs (4298). After deployment, and after staple (4290) is subject to tension from tissue forces as described above, staple (4290) expands about weakened region (4295) such that angle (α3) increases, which also corresponds with an increase in distance (d3). This produces a broader "V" shape for staples (4290) that resembles staples (4290) becoming closer to linear shaped. In the present example, staple (4290) with weakened region (4295) is configured such that it plastically deforms when the tissue forces act on staple (4290) as described above. In this manner, the increased diameter at the anastomosis can be maintained.

As shown in FIG. 85, legs (4298) extend generally orthogonal to a plane defined by crown (4296). Similarly, weakened region (4295), and its flat area, extend generally orthogonal to the plane defined by crown (4296). In use after deployment of staples (4290), tension from radial tissue forces act on staple (4290) and such forces are generally orthogonal to axes defined by legs (4298) when in the unformed state. Accordingly, in this manner, weakened region (4295) is configured and oriented so that when radial tissue forces act on staple (4290), expansion of staple (4290) occurs as described above. In view of the teachings herein, other ways to configure staple (4290) with spring feature (4295) will be apparent to those of ordinary skill in the art.

Staples (4090, 4190, 4290) above are described as being pre-formed with a "V" shape and a weakened region (4095, 4195, 4295) where these staples maintain their "V" shape in a relaxed state and expand when subjected to tissue forces. However, in some other versions, staples (4090, 4190, 4290) can be configured similar to staple (3990), where staples (4090, 4190, 4290) are initially straight or substantially straight and when loaded within instrument (10), staples (4090, 4190, 4290) are bent to the "V" shape and held under tension. After deployment, staples (4090, 4190, 4290) automatically expand to their relaxed straighter configuration.

4. Exemplary Expandable Staples with "V" Shaped Crown and Hinge Feature

Figure 86:
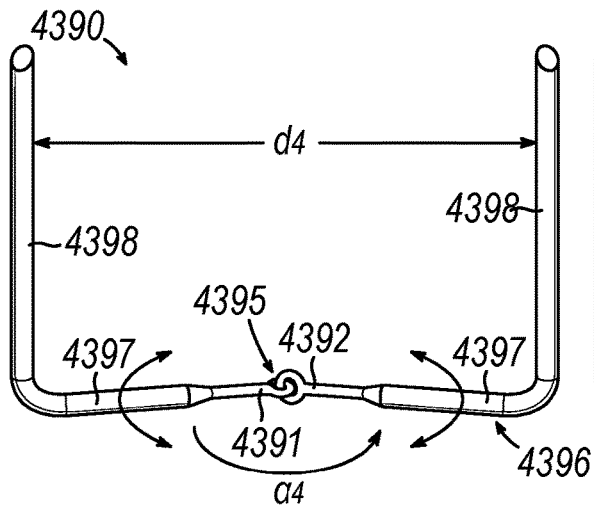
FIG. 86 depicts a front view of an exemplary "V" shaped staple having a hinge feature.

FIG. 86 depicts an exemplary staple (4390), which can replace staple (3890) or (90) in the plurality of staples. Staple (4390) includes crown (4396) and a pair of legs (4398). Crown (4396) includes two straight portions (4397) and a hinge feature (4395). Hinge feature (4395) in the present example is located between each of straight portions (4397) and is formed as two interlocking rings or loops (4391, 692). In the undeployed state as shown in FIG. 86, staple (4390) defines an angle (α4) between straight portions (4397), and staple (4390) defines a distance (d4) between legs (4398). After deployment and after staple (4390) is subject to tension from tissue forces as described above, staple (4390) expands about hinge feature (4395) such that angle (α4) increases, which also corresponds with an increase in distance (d4). This produces a broader "V" shape for staples (4390) that resembles staples (4390) becoming closer to linear shaped.

In the present example, hinge feature (4395) is configured such that it is operable to change the orientation of staple (4390) depending on the forces staple (4390) is subjected to. Also in the present example, hinge feature (4395) is configurable such that a tension within hinge feature (4395) can be such that a threshold amount of force must be imparted upon hinge feature (4395) to cause staple (4390) to change configuration as described above. For instance, in one version the amount of contact between interlocking rings (4391, 4392) can be configured to provide greater or lesser friction among these components, thereby making hinge feature (4395) more or less responsive to a given force applied on staple (4390). Other ways to configure the tension with hinge feature (4395) will be apparent to those of ordinary skill in the art in view of the teachings herein.

Staple (4390) can be considered to define a first portion that includes one leg (4398) and one portion (4397) of crown (4396), and a second portion that includes the other leg (4398) and the other portion (4397) of crown (4396). In this manner, first and second portions of staple (4390) are connected at hinge feature (4395) and are operable to move relative to one another about hinge feature (4395) depending on the forces being exerted on the first and second portions of staple (4390). In some instances, a force may be exerted evenly on staple (4390) such that each of the first and second portions of staple (4390) experience the same force and move relative to one another in a similar fashion. In some other instances, a different degree of force may act on each of the first and second portions of staple (4390). In such examples, the degree of movement of the first and the second portions of staple (4390) may differ. For example, the portion of staple (4390) experiencing the larger force may move a greater distance radially compared to the other portion of staple (4390) experiencing the lower force.

As shown in FIG. 86, hinge feature (4395) is coplanar with crown (4396). Additionally, legs (4398) extend generally orthogonal to a plane defined by crown (4396) and hinge feature (4395). In use after deployment of staples (4390), tension from radial tissue forces act on staple (4390) and such forces are generally orthogonal to axes defined by legs (4398) when in the unformed state. Accordingly, in this manner, hinge feature (4395) is configured and oriented so that when radial tissue forces act on staple (4390), expansion of staple (4390) occurs as described above. While the above examples describe expansion of staple (4390), in some instances, hinge feature (4395) also allows for staple (4390) to move or change orientation from an expanded state to a more retracted or compact state. This could be the case when forces acting on staple (4390) subside. Of course, in such examples hinge feature (4395) can be configured to allow for expansion only without the ability to contract or close down to a smaller width. In view of the teachings herein, other ways to configure staple (4390) with hinge feature (4395) will be apparent to those of ordinary skill in the art.

Figure 87:
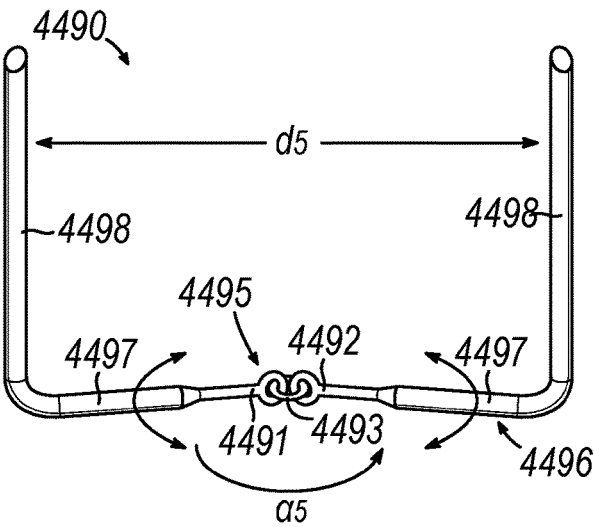
FIG. 87 depicts a front view of an exemplary "V" shaped staple having an alternate hinge feature.

FIG. 87 depicts an exemplary staple (4490), which can replace staple (3890) or (90) in the plurality of staples. Staple (4490) includes crown (4496) and a pair of legs (4498). Crown (4496) includes two straight portions (4497) and a hinge feature (4495). Hinge feature (4495) in the present example is located between each of straight portions (4497) and is formed as two interlocking rings or loops (4491, 792) with an intermediate member or link (4493). In the undeployed state as shown in FIG. 87, staple (4490) defines an angle ($\alpha 5$) between straight portions (4497), and staple (4490) defines a distance (d5) between legs (4498). After deployment and after staple (4490) is subject to tension from tissue forces as described above, staple (4490) expands about hinge feature (4495) such that angle ($\alpha 5$) increases, which also corresponds with an increase in distance (d5). This produces a broader "V" shape for staples (4490) that resembles staples (4490) becoming closer to linear shaped.

In the present example, hinge feature (4495) is configured such that it is operable to change the orientation of staple (4490) depending on the forces staple (4490) is subjected to. Also in the present example, hinge feature (4495) is configurable such that a tension within hinge feature (4495) can be such that a threshold amount of force must be imparted upon hinge feature (4495) to cause staple (4490) to change configuration as described above. For instance, in one version the amount of contact between interlocking rings (4491, 4492) and intermediate member (4493) can be configured to provide greater or lesser friction among these components, thereby making hinge feature (4495) more or less responsive to a given force applied on staple (4490). Other ways to configure the tension with hinge feature (4495) will be apparent to those of ordinary skill in the art in view of the teachings herein.

Staple (4490) can be considered to define a first portion that includes one leg (4498) and one portion (4497) of crown (4496), and a second portion that includes the other leg (4498) and the other portion (4497) of crown (4496). In this example each of these first and second portions connect with intermediate member (4493). In this manner, first and second portions of staple (4490) are connected at hinge feature (4495) and are operable to move relative to one another about hinge feature (4495) depending on the forces being exerted on the first and second portions of staple (4490). In some instances, a force may be exerted evenly on staple (4490) such that each of the first and second portions of staple (4490) experience the same force and move relative to one another in a similar fashion. In some other instances, a different degree of force may act on each of the first and second portions of staple (4490). In such examples, the degree of movement of the first and the second portions of staple (4490) may differ. For example, the portion of staple (4490) experiencing the larger force may move a greater distance radially compared to the other portion of staple (4490) experiencing the lower force.

As shown in FIG. 87, hinge feature (4495) is coplanar with crown (4496). Additionally, legs (4498) extend generally orthogonal to a plane defined by crown (4496) and hinge feature (4495). In use after deployment of staples (4490), tension from radial tissue forces act on staple (4490) and such forces are generally orthogonal to axes defined by legs (4498) when in the unformed state. Accordingly, in this manner, hinge feature (4495) is configured and oriented so that when radial tissue forces act on staple (4490), expansion of staple (4490) occurs as described above. While the above examples describe expansion of staple (4490), in some instances, hinge feature (4495) also allows for staple (4490) to move or change orientation from an expanded state to a more retracted or compact state. This could be the case when forces acting on staple (4490) subside. Of course, in such examples hinge feature (4495) can be configured to allow for expansion only without the ability to contract or close down to a smaller width. In view of the teachings herein, other ways to configure staple (4490) with hinge feature (4495) will be apparent to those of ordinary skill in the art.

5. Exemplary Expandable Staples with "V" Shaped Crown and Cable

Figure 88:
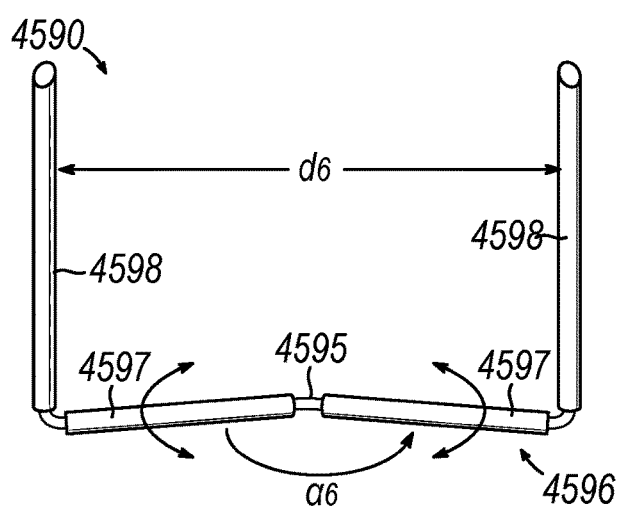
FIG. 88 depicts a front view of an exemplary "V" shaped staple having a cable connecting portions of a crown of the staple.

FIG. 88 depicts an exemplary staple (4590), which can replace staple (3890) or (90) in the plurality of staples. Staple (4590) includes crown (4596) and a pair of legs (4598). Crown (4596) includes two straight portions (4597) and a cable (4595). Cable (4595) in the present example extends from one leg (4598), through straight portions (4597), to the other leg (4598). In the present example, cable (4595) is configured as a unitary cable structure, while in other examples cable feature (4595) is configured as multiple discrete sections of cable structure that join or connect two portions of staple (4590). In the present example, cable (4595) is present where each leg (4598) meets or connects with a respective straight portion (4597). In some other versions, cable (4595) is omitted here such that cable (4595) is present only in the middle portion of staple (4590) connecting straight portions (4597).

In the undeployed state as shown in FIG. 88, staple (4590) defines an angle ($\alpha 6$) between straight portions (4597), and staple (4590) defines a distance (d6) between legs (4598). After deployment and after staple (4590) is subject to tension from tissue forces as described above, staple (4590) expands in width by bending cable (4595) such that angle ($\alpha 6$) increases, which also corresponds with an increase in distance (d6). This produces a broader "V" shape for staples (4590) that resembles staples (4590) becoming closer to linear shaped.

In the present example, cable (4595) is configured such that it is operable to change the orientation of staple (4590) depending on the forces staple (4590) is subjected to. Also in the present example, cable (4595) is configurable such that a tension within cable (4595) can be such that a threshold amount of force must be imparted upon cable (4595) to cause staple (4590) to change configuration as described above. For instance, in one version the amount of contact between cable (4595) and straight portions (4597) through which cable (4595) passes can be configured to provide greater or lesser friction among these components, thereby making staple (4590) more or less responsive to a given force applied on staple (4590). Other ways to configure the tension with cable (4595) will be apparent to those of ordinary skill in the art in view of the teachings herein. For instance, the rigidity of cable (4595) can be configured based on the material, construction, or diameter of cable (4595).

Staple (4590) can be considered to define a first portion that includes one leg (4598) and one portion (4597) of crown (4596), and a second portion that includes the other leg (4598) and the other portion (4597) of crown (4596). In this manner, first and second portions of staple (4590) are connected by cable (4595) and are operable to move relative to one another about cable (4595) depending on the forces being exerted on the first and second portions of staple (4590). In some instances, a force may be exerted evenly on staple (4590) such that each of the first and second portions of staple (4590) experience the same force and move relative to one another in a similar fashion. In some other instances, a different degree of force may act on each of the first and second portions of staple (4590). In such examples, the degree of movement of the first and the second portions of staple (4590) may differ. For example, the portion of staple (4590) experiencing the larger force may move a greater distance radially compared to the other portion of staple (4590) experiencing the lower force.

As shown in FIG. 88, cable (4595) is coplanar with crown (4596). Additionally, legs (4598) extend generally orthogonal to a plane defined by crown (4596) and cable (4595). In use after deployment of staples (4590), tension from radial tissue forces act on staple (4590) and such forces are generally orthogonal to axes defined by legs (4598) when in the unformed state. Accordingly, in this manner, cable (4595) is configured and oriented so that when radial tissue forces act on staple (4590), expansion of staple (4590) occurs as described above. While the above examples describe expansion of staple (4590), in some instances, cable (4595) also allows for staple (4590) to move or change orientation from an expanded state to a more retracted or compact state. This could be the case when forces acting on staple (4590) subside. Of course, in such examples cable (4595) can be configured to allow for expansion only without the ability to contract or close down to a smaller width. In view of the teachings herein, other ways to configure staple (4590) with cable (4595) will be apparent to those of ordinary skill in the art.

B. Exemplary Staple Patterns for Staples with "V" Shaped Crowns

Another variable for consideration with expandable staples is staple pattern. The staple pattern pertains to the arrangement and spacing of the staples. FIGS. 89A-89E illustrate staple patterns that may be used or adapted for use in a circular staple configuration and with expandable staples, such as staples (3890, 3990, 4090, 4190, 4290, 4390, 4490, 4590) described above.

Figure 89A:
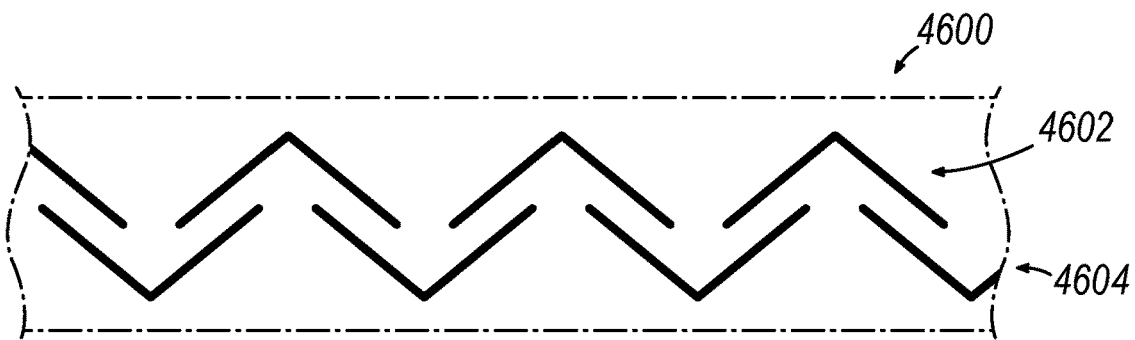
FIGS. 89A-89E depicts top views of exemplary staple patterns.

FIG. 89A illustrates an exemplary staple pattern (4600) for "V" shaped staples with equal length arms. As used herein, the "arms" of a "V" shaped staple is understood to refer to the distance along the crown portion from a given staple leg to the vertex. While FIG. 89A depicts staple pattern (4600) in a linear pattern, this pattern (4600) is adaptable into a wrap-around staple pattern for a circular stapler application. For instance, with a circular stapler, the staples may differ in size and/or shape between the inner row and outer row, although they could be of the same size and/or shape in some versions.

With staple pattern (4600), there is a first row or outer row (4602) of staples and a second row or inner row (4604) of staples. As shown, the staples of first row (4602) are opposite facing and offset from the staples of second row (4604). This offset appears as a lateral offset in pattern (4600), and this offset appears as a circumferential offset when pattern (4600) is in a circular or wrap-around staple pattern as seen in FIGS. 77-81. Furthermore, in the present example the opposite facing arrangement is shown with the staples in outer row (4602) have the vertex oriented to point outward, while the staples in inner row (4604) have the vertex oriented to point inward.

As evident from FIGS. 77-81 and FIG. 89A, with pattern (4600), the staples can move from their initial "V" shape to an expanded "V" shape without the staples interfering with one another. As shown in FIGS. 77-81, pattern (4600) allows for outward radial expansion of a circular staple pattern when the staples undergo expansion as described above.

Figure 89B:

FIG. 89B illustrates another exemplary staple pattern (4700) for "V" shaped staples with equal length arms. FIG. 89B depicts staple pattern (4700) as a linear pattern; however, this pattern (4700) is adaptable into a wrap-around staple pattern for a circular stapler application similar to pattern (4600) as described above.

With staple pattern (4700), there is a first row or outer row (4702) of staples and a second row or inner row (4704) of staples. As shown, the staples of first row (4702) are opposite facing and offset from the staples of second row (4704). This offset appears as a lateral offset in pattern (4700), and this offset appears as a circumferential offset when pattern (4700) is in a circular or wrap-around staple pattern. Furthermore, in the present example the opposite facing arrangement is shown with the staples in outer row (4702) have the vertex oriented to point inward, while the staples in inner row (4704) have the vertex oriented to point outward. With pattern (4700), the staples can move from their initial "V" shape to an expanded "V" shape without the staples interfering with one another. Furthermore, pattern (4700) allows for outward radial expansion of a circular staple pattern when the staples undergo expansion as described above.

Figure 89C:
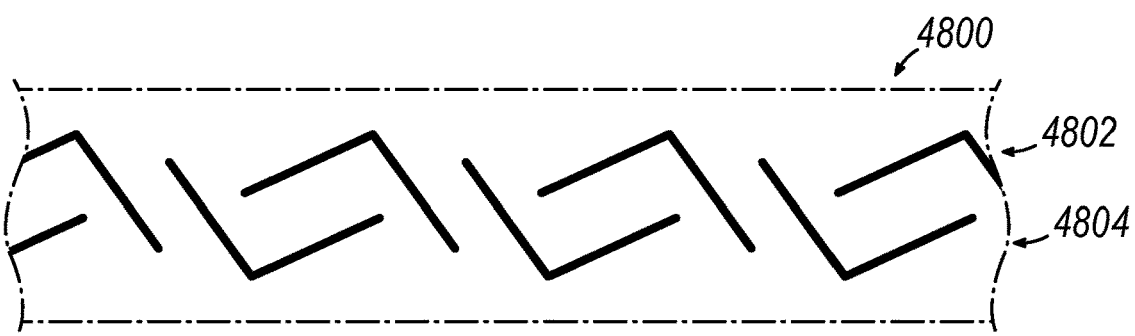

FIG. 89C illustrates another exemplary staple pattern (4800) for "V" shaped staples with equal length arms. FIG. 89C depicts staple pattern (4800) as a linear pattern; however, this pattern (4800) is adaptable into a wrap-around staple pattern for a circular stapler application similar to pattern (4600) as described above.

With staple pattern (4800), there is a first row or outer row (4802) of staples and a second row or inner row (4804) of staples. As with pattern (4600), with pattern (4800), the staples of outer row (4802) have their vertex generally pointing outward while the staples of inner row (4804) have their vertex generally pointing inward. Moreover, pattern (4800) has staple rows (4802, 4804) with staples that are canted in order to stagger the anchor points between the staple and the tissue to not be parallel to the staple line. This canted arrangement for staples also increases the rigid-body rotation of the staples independent of their flexure. In this manner, pattern (4800) provides for a stapling arrangement with less stress on the tissue for a given amount of elongation of the staple line compared to at least some other stapling patterns. As with the other patterns, with pattern (4800) the staples can move from their initial "V" shape to an expanded "V" shape without the staples interfering with one another. Furthermore, pattern (4800) allows for outward radial expansion of a circular staple pattern when the staples undergo expansion as described above.

Figure 89D:

FIG. 89D illustrates another exemplary staple pattern (4900) for "V" shaped staples with unequal length arms. FIG. 89D depicts staple pattern (4900) as a linear pattern; however, this pattern (4900) is adaptable into a wrap-around staple pattern for a circular stapler application similar to pattern (4600) as described above.

With staple pattern (4900), there is a first row or outer row (4902) of staples and a second row or inner row (4904) of staples. As shown, the staples of first row (4902) are opposite facing and offset from the staples of second row (4904). This offset appears as a lateral offset in pattern (4900), and this offset appears as a circumferential offset when pattern (4900) is in a circular or wrap-around staple pattern. Furthermore, in the present example the opposite facing arrangement is shown with the staples in outer row (4902) have the vertex oriented to point outward, while the staples in inner row (4704) have the vertex oriented to point inward. With pattern (4900), the staples can move from their initial "V" shape to an expanded "V" shape without the staples interfering with one another. Furthermore, pattern (4900) allows for outward radial expansion of a circular staple pattern when the staples undergo expansion as described above.

Figure 89E:
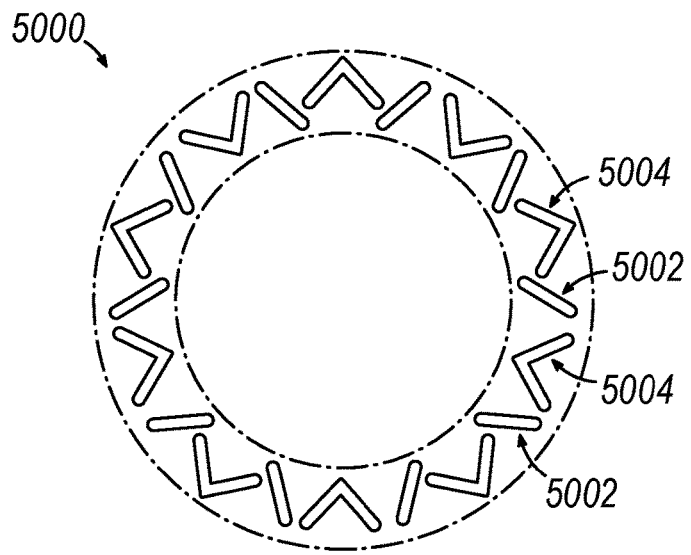

FIG. 89E illustrates another exemplary circular staple pattern (5000) for alternating angled staples (5002) with straight crowns and staples (5004) with "V" shaped crowns. With staple pattern (5000), staples (5004) with "V" shaped crowns alternate circumferentially with the vertex a staple (5004) pointing outwardly and then the adjacent staple (5004) oriented with the vertex pointing inwardly. Furthermore, between each staple (5004) is one of staples (5002). Staples (5002) alternate circumferentially in their angle direction as shown. With this arrangement, the combined staples (5002, 5004) define a pattern (5000) that forms a "W" shape repeating circumferentially. With pattern (5000), staples (5004) can move from their initial "V" shape to an expanded "V" shape without interfering with staples (5002) having the straight crowns. Furthermore, pattern (5000) allows for outward radial expansion of a circular staple pattern when the staples undergo expansion as described above.

C. Exemplary Stapling Head Assembly with Staples Having Crown Elongation Features FIGS. 90A-92B illustrate exemplary expandable staples that incorporate one or more features into the crown portion that enable the staples to elongate or expand after being deployed and when the staples are subjected to tissue forces.

1. Exemplary Staples with Bent Crowns

Figure 90A:
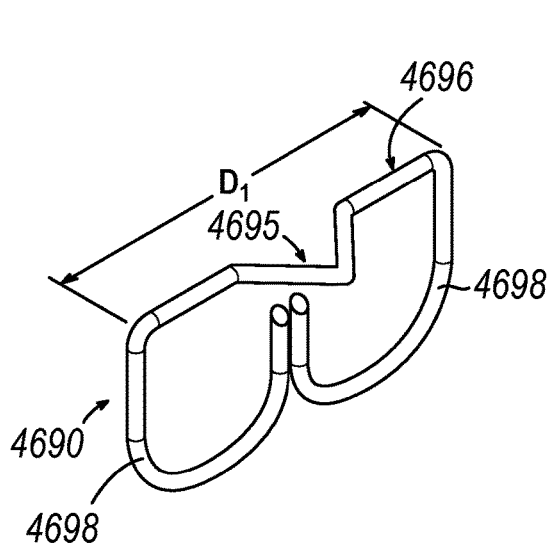
FIG. 90A depicts a perspective view of an exemplary staple having a crown with an expandable angled bend, shown in a relaxed state.
Figure 90B:
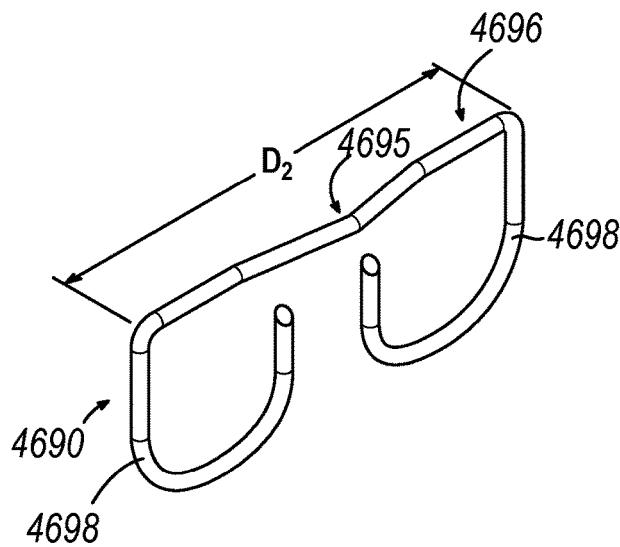
FIG. 90B depicts a perspective view of the staple of FIG. 90A, shown in an expanded state.

FIGS. 90A and 90B depict staple (4690) that is expandable and includes elongation feature (4695). In the present example, staple (4690) comprises legs (4698) that are shown formed into a "B" shape for fastening tissue and oriented in a coplanar fashion. Staple (4690) further comprises crown (4696) that incorporates elongation feature (4695). In the present example, elongation feature (4695) comprises a bend having an angled or "V" shape that is located along a middle portion of crown (4696). In the illustrated example, elongation feature (4695) extends along a plane that is generally orthogonal to the plane encompassing legs (4698). With this configuration, elongation feature (4695) maintains legs (4698) in a coplanar orientation while enabling staple (4690) to expand laterally such that its width increases during staple expansion as shown by staple width (D1) in the initial state shown in FIG. 90A compared to staple width (D2) in the expanded state shown in FIG. 90B.

Staple (4690) transitions or moves from its initial state shown in FIG. 90A to its expanded state shown in FIG. 90B based on tissue forces acting on staple (4690) after staples (4690) have been deployed in making the anastomosis. For instance, after the anastomosis tissue may try to expand due to peristalsis or based on objects passing through the lumen created by the anastomosis. In response, a force is exerted on staples (4690) that pulls legs (4698) apart from one another. With elongation feature (4695) of crown (4696), staples (4690) can expand in width by the bend of elongation feature (4695) straightening out due to the tissue forces acting on staple (4690). This in turn can also promote maintaining the formed state of legs (4698) to ensure adequate tissue fastening. While elongation feature (4695) is shown and described as an angled bend having a "V" shape, in view of the teachings herein, other configurations for elongation feature (4695) will be apparent to those of ordinary skill in the art.

2. Exemplary Staples with Crown Sliding Feature

Figure 91A:
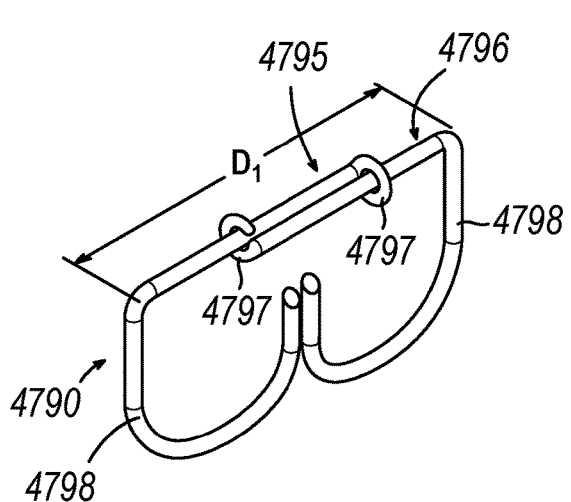
FIG. 91A depicts a perspective view of an exemplary staple having a crown with an expandable sliding feature, shown in a relaxed state.
Figure 91B:
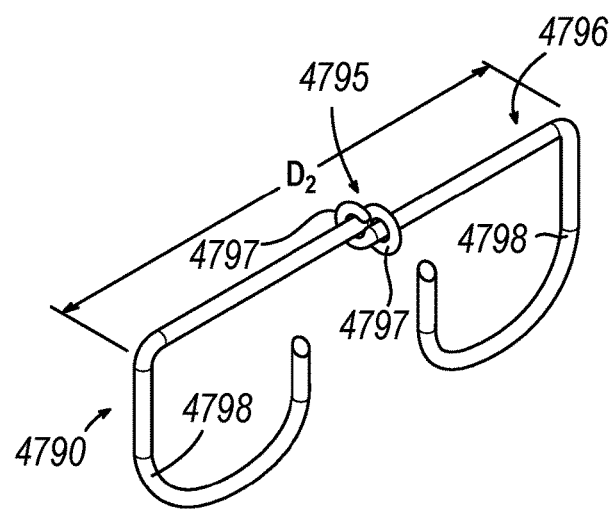
FIG. 91B depicts a perspective view of the staple of FIG. 91A, shown in an expanded state.

FIGS. 91A and 91B depict staple (4790) that is expandable and includes elongation feature (4795). In the present example, staple (4790) comprises legs (4798) that are shown formed into a "B" shape for fastening tissue and oriented in a coplanar fashion. Staple (4790) further comprises crown (4796) that incorporates elongation feature (4795). In the present example, elongation feature (4795) comprises a sliding or slidable feature that is located along a middle portion of crown (4796) and includes two linking members (4797) that in the present example are formed by bends in the staple wire. Linking members (4797) extend parallel to one another and are slidable relative to each other based on tissue forces acting on staple (4790). With this configuration, elongation feature (4795) maintains legs (4798) in a coplanar orientation while enabling staple (4790) to expand laterally such that its width increases during staple expansion as shown by staple width (D1) in the initial state shown in FIG. 91A compared to staple width (D2) in the expanded state shown in FIG. 91B.

Staple (4790) transitions or moves from its initial state shown in FIG. 91A to its expanded state shown in FIG. 91B based on tissue forces acting on staple (4790) after staples (4790) have been deployed in making the anastomosis. For instance, after the anastomosis, tissue may try to expand due to peristalsis or based on objects passing through the lumen created by the anastomosis. In response, force is exerted on staples (4790) that pulls legs (4798) apart from one another. With elongation feature (4795) of crown (4796), staples (4790) can expand in width by the slidable nature of linking members (4797) when the tissue forces act on staple (4790). For instance, FIG. 91A illustrates staple (4790) in its initial state, while FIG. 91B illustrates staple (4790) in its expanded state. This in turn can also promote maintaining the formed state of legs (4798) to ensure adequate tissue fastening, while still allowing for staple expansion. In view of the teachings herein, other configurations for elongation feature (4795) will be apparent to those of ordinary skill in the art.

3. Exemplary Staples with Crown Coil Feature

Figure 92A:
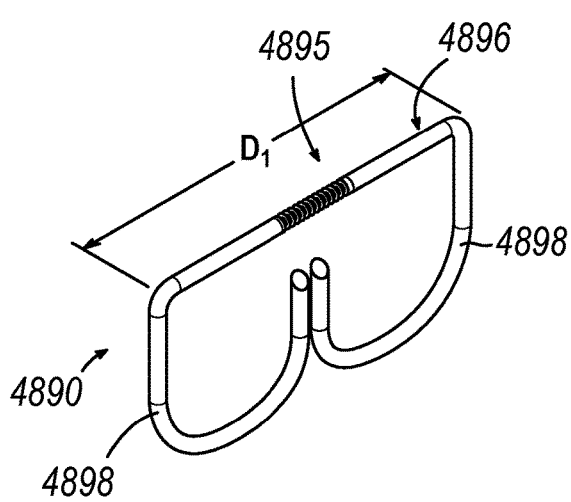
FIG. 92A depicts a perspective view of an exemplary staple having a crown with an expandable coil feature, shown in a relaxed state.
Figure 92B:
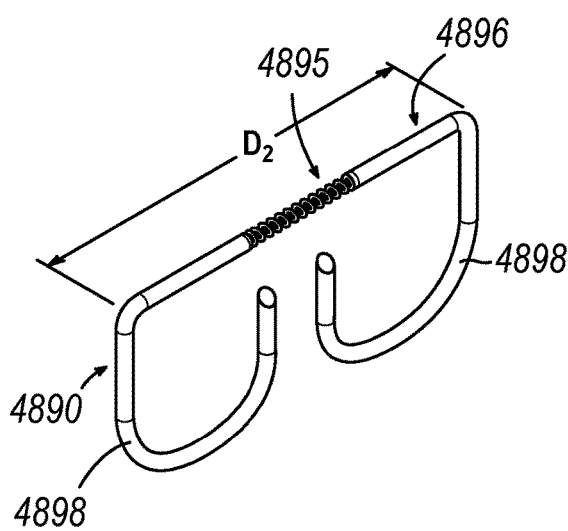

FIGS. 92A and 92B depict staple (4890) that is expandable and includes elongation feature (4895). In the present example, staple (4890) comprises legs (4898) that are shown formed into a "B" shape for fastening tissue and oriented in a coplanar fashion. Staple (4890) further comprises crown (4896) that incorporates elongation feature (4895). In the present example, elongation feature (4895) comprises a coil feature that is located along a middle portion of crown (4896) and formed within a portion of crown (4896). With this configuration, elongation feature (4895) maintains legs (4898) in a coplanar orientation while enabling staple (4890) to expand laterally such that its width increases during staple expansion as shown by staple width (D1) in the initial state shown in FIG. 92A compared to staple width (D2) in the expanded state shown in FIG. 92B.

Staple (4890) transitions or moves from its initial state shown in FIG. 92A to its expanded state shown in FIG. 92B based on tissue forces acting on staple (4890) after staples (4890) have been deployed in making the anastomosis. For instance, after the anastomosis, tissue may try to expand due to peristalsis or based on objects passing through the lumen created by the anastomosis. In response, force is exerted on staples (4890) that pulls legs (4898) apart from one another. With elongation feature (4895) of crown (4896), staples (4890) can expand in width by plastically deforming the coil feature when the tissue forces act on staple (4890). For instance, FIG. 92A illustrates staple (4890) in its initial state, while FIG. 92B illustrates staple (4890) in its expanded state. This in turn can also promote maintaining the formed state of legs (4898) to ensure adequate tissue fastening, while still allowing for staple expansion. In view of the teachings herein, other configurations for elongation feature (4895) will be apparent to those of ordinary skill in the art.

D. Exemplary Stapling Head Assembly with Staples Having Curved Crowns

In some other versions of instrument (10), stapling head assemblies (300, 4300) can be adapted for use with alternate configured staples. For instance, in one example, assemblies (300, 4300) can be adapted for use with staples having curved crowns. In view of the teachings herein, such adaptations of stapling head assemblies (300, 4300) will be apparent to those of ordinary skill in the art. The following sections will describe various exemplary staples having curved crowns.

FIGS. 93-96 depicts an exemplary staple (4990) comprising legs (4998) and a crown (4996). As shown, legs (4998) are formed and fasten two tissue structures (T1, T2) together. Crown (4996) is formed of two straight portions (4997) connected by alternating and repeating curved portions (4995). In the present example, additional straight portions (4999) connect repeating curved portions (4995). In some other versions, straight portions (4999) may be omitted. As seen in FIG. 94, additional straight portions (4999), when present, provide a way to increase the height (H) of staple (4990). With staples (4990), it can also be understood that two connected curved portions (4995), whether connected by straight portion (4999) or not, can form and "S" shape. In this manner, staple (4990) can also be considered as having crown (4996) with a repeating "S" shape.

FIGS. 95 and 96 depict a respective side view and front view of staple (4990) with tissues (T1, T2). These figures show an unbent portion of one of legs (4998) and its connection with crown (4996). These figures further show the formed or bent portions of legs (4998) wrapped around the tissue assembly. With crown (4996) on one side of tissues (T1, T2) contacting tissue (T1), and formed leg (4998) on the opposite side of tissues (T1, T2) contacting tissue (T2), staple (4990) securely fastens tissues (T1, T2) together as shown.

Figure 97:
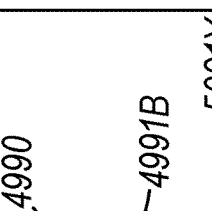

Referring to FIG. 97, various states or conditions are depicted for staples that include curved-shaped crowns. For instance, staple (4990) is shown in a compression state and two expansion states: an extension state and a flexion state. In one versions of staple (4990), the compression state represents the initial formed staple configuration where staple (4990) is not subjected to tissue forces. This can be considered the relaxed state for staple (4990) in such a version. In another version of staple (4990), the compression state can represent a formed staple configuration where staple (4990) is under a compressive tension. For instance, in such a version, staple (4990) may be loaded into instrument (10) under this compressive tension such that after deployment, staple (4990) automatically adopts the extension state without the need for tissue forces acting on staple (4990). In the version where the compression state coincides with a relaxed state, staple (4990) expands to the extension state based on tissue forces acting on staple (4990) as described above, and in response staple (4990) expands as shown in the extension state.

Another expansion state depicted in FIG. 97 for staple (4990) is the flexion state. Once staple (4990) has been deployed and undergone extension due to either relieving pre-formed tension or reacting to tissue forces acting on staple (4990) as mentioned above, based on tissue forces acting on staple (4990), staple (4990) can move to the flexion state. In the present example, the multiple curved-shape portions of crown (4996) provide for a curved flexion state as shown. This can be beneficial when considering the desire to expand the diameter of the anastomosis as it can aid in allowing expansion while not putting excessive tension on the stapled tissue thereby promoting the integrity of the seal at the anastomosis.

FIG. 97 additionally depicts an exemplary staple pattern (4991) for use with staples (4990). Staple pattern (4991) comprises an inner ring of staples (4991A) and an outer ring of staples (4991B) each formed using staples (4990) as shown. In use after deployment, staples (4990) arranged in staple pattern (4991), provides for an anastomosis where staples (4990) can expand and flex to produce an anastomosis having an initial diameter and a subsequent diameter that is larger than the initial diameter. This allows the lumen created by the anastomosis to achieve a size that is closer to the original size of the severed lumens joined by the anastomosis.

FIG. 97 depicts additional exemplary staples (5090, 5190, 5290) each comprising respective legs and a respective crown (5096, 5196, 5296). In these examples, the legs of staples (5090, 5190, 5290) are configured the same as legs (4998) of staple (4990). Accordingly, the description of legs (4998) applies equally to staples (5090, 5190, 5290) with the legs configured to fasten two tissue structures (T1, T2) together as described above.

With staple (5090), crown (5096) is formed of two straight portions (5097) connected by alternating and repeating curved portions (5095) that form a "W" shape. In the present example, additional straight portions (5099) connect repeating curved portions (5095) providing an increase in the height of staple (5090).

With staple (5190), crown (5196) is formed of two offset straight portions (5197) connected by alternating and repeating curved portions (5195) with additional straight portions (5199) connecting repeating curved portions (5195). Staple (5190) is similar in configuration to staple (4990), with the offset of straight portions (5197) being a difference. With staple (4990), straight portions (4997) are oriented along the same axis that intersects a centerline of the height defined by crown (4996). However, with staple (5190), straight portions (5197) are offset with one positioned above a centerline of the height defined by crown (5196), and one positioned below the centerline of the height defined by crown (5196).

With staple (5290), crown is formed of two offset straight portions (5297) connected by alternating and repeating curved portions (5295). Staple (5290) is similar in configuration to staple (4990), with the offset of straight portions (5297) being a difference. With staple (4990), straight portions (4997) are oriented along the same axis that intersects a centerline of the height defined by crown (4996). However, with staple (5290), straight portions (5297) are offset with one positioned above a centerline of the height defined by crown (5296), and one positioned below the centerline of the height defined by crown (5296). This configuration is similar to staple (5190); however, the difference between staples (5190) and staple (5290) is that the offset of straight portions (5297) is opposite to the arrangement shown for straight portions (5197) of staple (5190). For instance, where a straight portion (5197) of staple (5190) may be above a centerline of the staple height defined by crown (5196), with staple (5290) the corresponding straight portion (5297) would be below a centerline of the staple height defined by crown (5296).

Referring to FIG. 97, various states or conditions are depicted for staples (5090, 5190, 5290) that include curved-shaped crowns. For instance, staples (5090, 5190, 5290) are shown in a compression state and two expansion states: an extension state and a flexion state. In one versions of staples (5090, 5190, 5290), the compression state represents the initial formed staple configuration where staples (5090, 5190, 5290) are not subjected to tissue forces. This can be considered the relaxed state for staples (5090, 5190, 5290) in such versions. In another version of staples (5090, 5190, 5290), the compression state can represent a formed staple configuration where staples (5090, 5190, 5290) are under a compressive tension. For instance, in such versions, staples (5090, 5190, 5290) may be loaded into instrument (10) under this compressive tension such that after deployment, staples (5090, 5190, 5290) automatically adopt the extension state without the need for tissue forces acting on staples (5090, 5190, 5290). In the version where the compression state coincides with a relaxed state, staples (5090, 5190, 5290) expand to the extension state based on tissue forces acting on staples (5090, 5190, 5290) as described above, and in response staples (5090, 5190, 5290) expand as shown in the extension state.

Another expansion state depicted in FIG. 97 for staples (5090, 5190, 5290) is the flexion state. Once staples (5090, 1490, 1590) have been deployed and undergone extension due to either relieving pre-formed tension or reacting to tissue forces acting on staples (5090, 5190, 5290) as mentioned above, based on tissue forces acting on staples (5090, 5190, 5290), staples (5090, 5190, 5290) can move to the flexion state. In the present example, the multiple curved-shape portions of crowns (5096, 5196, 5296) provide for a curved flexion state as shown. This can be beneficial when considering the desire to expand the diameter of the anastomosis as it can aid in allowing expansion while not putting excessive tension on the stapled tissue thereby promoting the integrity of the seal at the anastomosis.

FIG. 97 additionally depicts exemplary staple patterns (5091X, 5091Y, 5191, 5291) for use with respective staples (5090, 5190, 5290). Staple patterns (5091X, 5091Y, 5191, 5291) each comprise an inner ring of staples (5091XA, 5091YA, 5191A, 5291A) and an outer ring of staples (5091YB, 5091YB, 5191B, 5291B) each formed using respective staples (5090, 5190, 5290) as shown. In use after deployment, staples (5090, 5190, 5290) arranged in respective staple patterns (5091X, 5091Y, 5191, 5291), provide for an anastomosis where staples (5090, 5190, 5290) can expand and flex to produce an anastomosis having an initial diameter and a subsequent diameter that is larger than the initial diameter. This allows the lumen created by the anastomosis to achieve a size that is closer to the original size of the severed lumens joined by the anastomosis.

E. Exemplary Nested "S" and "C" Shaped Expandable Staples

Figure 98A:
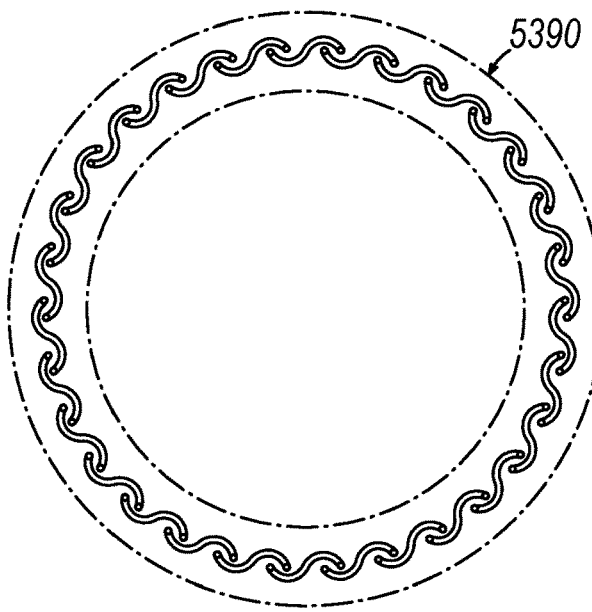
Figure 98B:
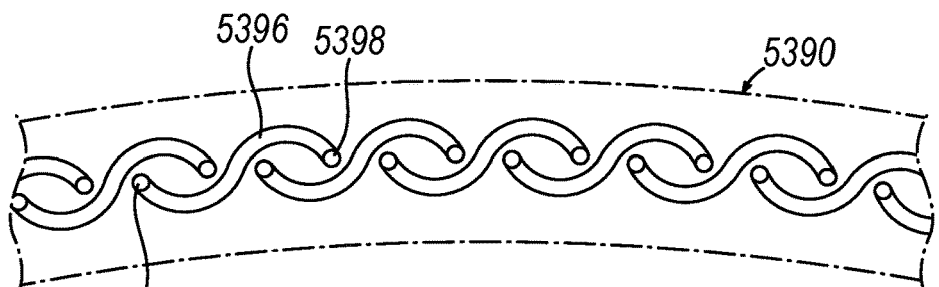

FIGS. 98A-98D depict another exemplary expandable staple (5390). Staples (5390) are configured with "S" shaped crowns (5396) and straight legs (5398). As shown in FIGS. 98A and 98B, staples (5390) are configured in a horizontal nested pattern with each "S" shaped staple (5390) overlapping adjacent staples (5390). In this manner, the resultant staple pattern closes any gaps in the circular staple pattern with a single row of staples (5390).

Figure 98C:
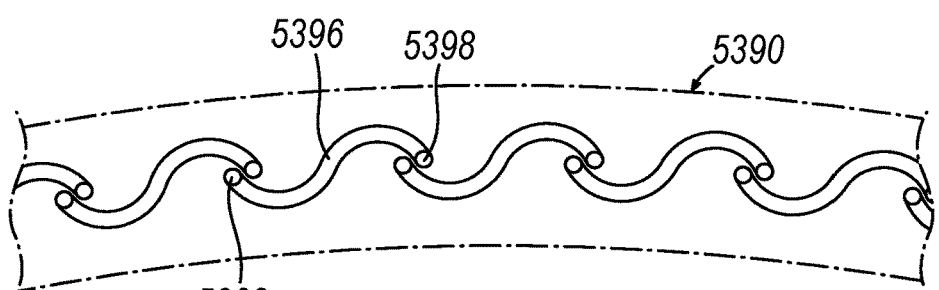
Figure 98D:
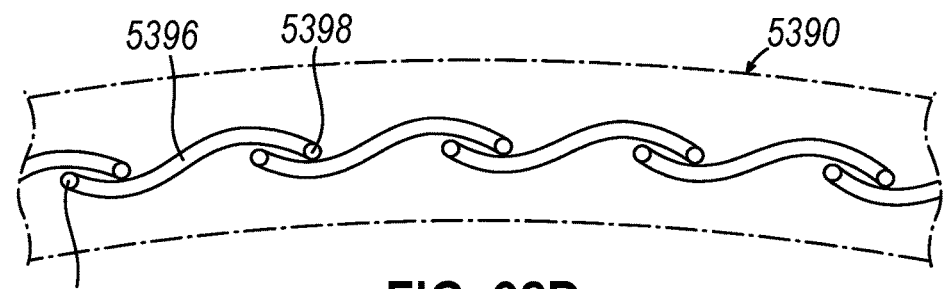

While FIGS. 98A and 98B illustrate a relaxed state of the nested arrangement of staples (5390), FIG. 98C depicts an expanded state where the nested arrangement of staples (5390) allows for expansion of the staple line in response to tissue expansion forces acting on staples (5390). More specifically, as tissue forces act on staples (5390) in their nested arrangement, staples (5390) reorient their relative position such that the nesting arrangement becomes less such that the overlapping of staples (5390) decreases when the pattern expands. Furthermore, in some versions as shown in FIG. 98D, staples (5390) can also provide for expansion by staples (5390) themselves expanding in similar ways as described above. In this manner, expansion of the staple line creating the anastomosis can be achieved in two ways: by the nesting pattern expanding, and/or by staples (5390) themselves expanding.

Figure 99:
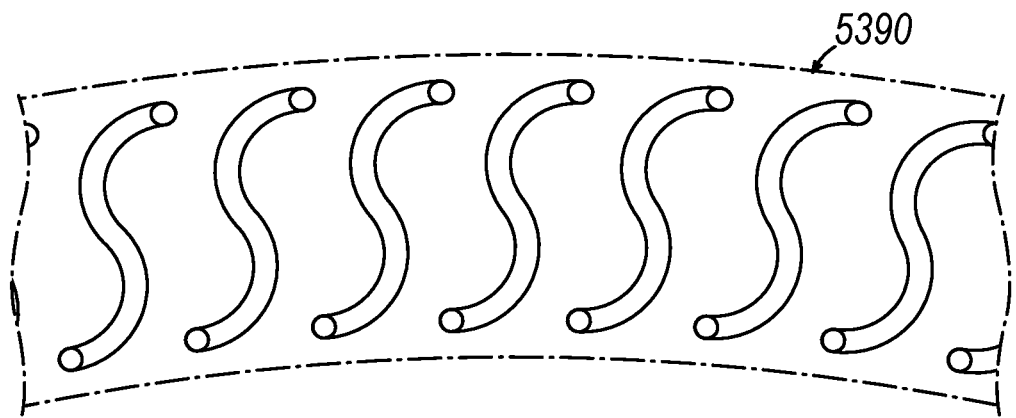

FIG. 99 depicts another exemplary orientation for staples (5390), where "S" shaped staples (5390) are oriented in a slightly angled and nested arrangement or configuration. Similar to the configuration shown in FIGS. 98A-D, staples (5390) configured in this manner may similarly allow for expansion where staples (5390) reorient their nested positions and the nesting degree in response to tissue forces acting on staples (5390). By way of example only, and not limitation, the nesting arrangement shown in FIG. 99 may adopt further spacing between staples (5390) when moving from the relaxed state shown in FIG. 99 to an expanded state. Still yet, in some versions when moving to the expanded state staples (5390) may pivot or rotate to some degree—taking on a more horizontal arrangement—when subjected to tissue expansive forces. Additionally, like shown in FIG. 98D, in some versions where staples (5390) are configured as shown in FIG. 99, staples (5390) themselves may also expand becoming more linear in their crown shape as seen in FIG. 98D.

Figure 100:
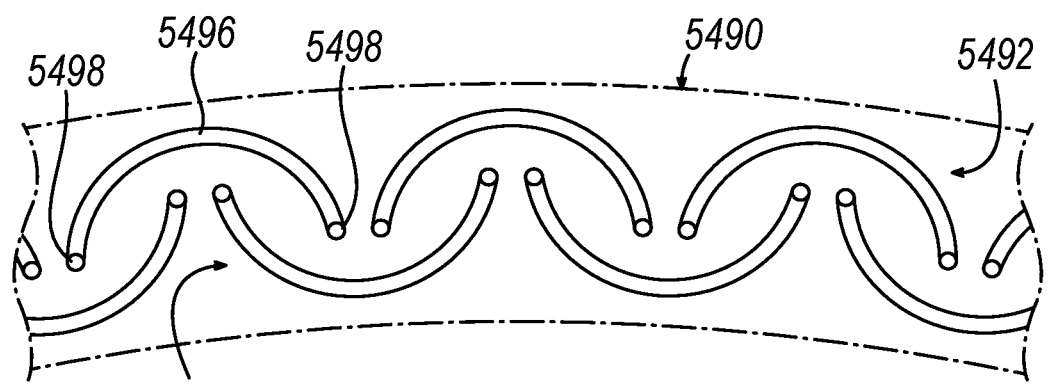

FIG. 100 depicts another exemplary expandable staple (5490). Staples (5490) are configured with "C" shaped crowns (5496) and straight legs (5498). Staples (5490) are configured in a horizontal nested pattern with an outer row (5492) of staples (5490) opening inward toward a center of the circular staple pattern, and an inner row (5494) of staples (5490) opening outward away from a center of the circular staple pattern. In this manner, each "C" shaped staple (5490) overlaps adjacent staples (5490) with the resultant staple pattern eliminating gaps in the circular staple pattern.

FIG. 100 illustrates a relaxed state of the nested arrangement of staples (5490); however, the nested arrangement of staples (5490) allows for expansion of the staple line in response to tissue expansion forces acting on staples (5490). More specifically, as tissue forces act on staples (5490) in their nested arrangement, staples (5490) reorient their relative position such that the nesting arrangement becomes less such that the overlapping of staples (5490) decreases when the pattern expands. Furthermore, in some versions, staples (5490) can also provide for expansion by staples (5490) themselves expanding in similar ways as described above where the "C" shaped crowns (5496) adopt a less curvature shape thereby also increasing their width as described above with respect to other staple versions. In this manner, expansion of the staple line creating the anastomosis using the arrangement shown in FIG. 100 can be achieved in two ways: by the nesting pattern expanding, and/or by staples (5490) themselves expanding.

VII. Exemplary Features for Forming Expandable Patterns of Staples

As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to enable the annular arrays of formed staples (90) to expand radially, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and/or anvil (400) with features that enable formation of such patterns of formed staples (90). In addition, or alternatively, it may be desirable to configure stapling head assembly (300) and/or anvil (400) with features that enable increased densities of formed staples (90) while minimizing the outer diameter of anvil (400) (e.g., by maintaining the outer diameter of anvil (400) or by decreasing the outer diameter of anvil (400)). Exemplary versions of such features are described in greater detail below.

A. Exemplary Deck Member with Staple Openings in Repeating "X" Patterns

FIG. 101 depicts an exemplary deck member (5510) for use with instrument (10) described above. Deck member (5510) is similar to deck member (320) described above except as otherwise described below. In this regard, deck member (5510) may be fixedly secured to a distal end of a body member (not shown) of a stapling head assembly (not shown), such as body member (310) of stapling head assembly (300), and may be configured to permit a knife member (not shown), such as knife member (340), to translate longitudinally through deck member (5510) to actuate between a proximal retracted position and a distal extended position in a manner similar to that described above in connection with FIGS. 1-7E.

As shown, deck member (5510) includes a distally presented stapling surface in the form of a deck surface (5512) extending radially between a generally circular radially inner edge (5514) and a generally circular radially outer edge (5516). Deck member (5510) has a central opening (5518) defined by radially inner edge (5514) and having an inner diameter that is just slightly larger than the outer diameter defined by knife member (340). Deck member (5510) is thus configured to permit knife member (340) to translate longitudinally through the central opening concurrently with longitudinal translation of staple driver member (350). In particular, knife member (340) is configured to actuate relative to deck member (5510) between a proximal retracted position and a distal extended position, where cutting edge (342) is proximal to deck surface (5512) in the proximal retracted position and distal to deck surface (5512) in the distal extended position.

Deck surface (5512) of the present version has two concentric annular arrays of linear staple openings (5520a, 5520b, 5520c, 5520d) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (5520a, 5520b, 5520c, 5520d) is configured to slidably receive and provide a pathway for a corresponding staple driver to drive a corresponding staple (90a, 90b, 90c, 90d) (FIGS. 102A-102C) distally through deck member (5510) and into a corresponding staple forming pocket when a stapling head assembly (not shown) similar to stapling head assembly (300) is actuated. In some versions, each staple opening (5520a, 5520b, 5520c, 5520d) may have a width of approximately 0.100 inch.

In the present version, staple openings (5520a, 5520b, 5520c, 5520d) are arranged in a radially inner annular array of circumferentially-alternating first and second staple openings (5520a, 5520b) and a radially outer annular array of circumferentially-alternating third and fourth staple openings (5520c, 5520d). More particularly, radially inner staple openings (5520a, 5520b) are arranged with uniform circumferential spacing about a longitudinal axis (L) of central opening (5518), with the midpoints of each radially inner staple opening (5520a, 5520b) positioned at a first radial distance from longitudinal axis (L) such that the midpoints of radially inner staple openings (5520a, 5520b) collectively define a first reference circle (C1). As shown, each radially inner staple opening (5520a, 5520b) is oriented non-tangentially relative to first circle (C1). In this regard, first staple openings (5520a) each extend along a respective first axis (A1) oriented at a first oblique angle ($\alpha$1) relative to a corresponding reference line (T1) that extends tangentially to first circle (C1) through the respective midpoint, and second staple openings (5520b) each extend along a respective second axis (A2) oriented at a second oblique angle ($\alpha$2) relative to a corresponding reference line (T2) that extends tangentially to first circle (C1) through the respective midpoint. In the example shown, first angle ($\alpha$1) is acute such that each first staple opening (5520a) extends generally radially outwardly in a clockwise direction, while second angle ($\alpha$2) is obtuse such that each second staple opening (5520b) extends generally radially inwardly in a clockwise direction. In some versions, first and second angles ($\alpha$1, $\alpha$2) may be supplementary to each other. For example, first angle ($\alpha$1) may be approximately 30° and second angle ($\alpha$2) may be approximately 150°. In any event, each first staple opening (5520a) and a corresponding clockwise-adjacent second staple opening (5520b) may collectively define a first internal angle ($\beta$1) which opens toward inner edge (5514), while each second staple opening (5520b) and a corresponding clockwise-adjacent first staple opening (5520a) may collectively define a second internal angle ($\beta$2) which opens toward outer edge (5516).

Likewise, radially outer staple openings (5520c, 5520d) are arranged with uniform circumferential spacing about longitudinal axis (L) of central opening (5518), with the midpoints of each radially outer staple opening (5520c, 5520d) positioned at a second radial distance from longitudinal axis (L) greater than the first radial distance, such that the midpoints of radially outer staple openings (5520c, 5520d) collectively define a second reference circle (C2) that is radially outward relative to first reference circle (C1). As shown, each radially outer staple opening (5520c, 5520d) is oriented non-tangentially relative to second circle (C2). In this regard, third staple openings (5520c) each extend along a respective third axis (A3) oriented at a third oblique angle ($\alpha$3) relative to a corresponding reference line (T3) that extends tangentially to second circle (C2) through the respective midpoint, and fourth staple openings (5520d) each extend along a respective fourth axis (A4) oriented at a fourth oblique angle ($\alpha$4) relative to a corresponding reference line (T4) that extends tangentially to second circle (C2) through the respective midpoint. In the example shown, third angle ($\alpha$3) is obtuse such that each third staple opening (5520c) extends generally radially inwardly in a clockwise direction, while fourth angle ($\alpha$4) is acute such that each fourth staple opening (5520d) extends generally radially outwardly in a clockwise direction. In some versions, third and fourth angles (α3, α4) may be supplementary to each other. For example, third angle (α3) may be approximately 150° and fourth angle (α4) may be approximately 30°. In any event, each third staple opening (5520c) and a corresponding clockwise-adjacent fourth staple opening (5520d) may collectively define a third internal angle (β3) which opens toward outer edge (5516), while each fourth staple opening (5520d) and a corresponding clockwise-adjacent third staple opening (5520c) may collectively define a fourth internal angle (β4) which opens toward inner edge (5514).

In the example shown, radially inner staple openings (5520a, 5520b) are each generally aligned with a corresponding radially outer staple opening (5520c, 5520d) along their respective axes (A1, A2, A3, A4). More particularly, first staple openings (5520a) are each generally aligned with a corresponding fourth staple opening (5520d) along their respective first and fourth axes (A1, A4), and second staple openings (5520b) are each generally aligned with a corresponding third staple opening (5520c) along their respective second and third axes (A2, A3). For example, the first axis (A1) of a first staple opening (5520a) may be colinear with the fourth axis (A4) of the corresponding axially-aligned fourth staple opening (5520d), and the second axis (A2) of a second staple opening (5520b) may be colinear with the third axis (A3) of the corresponding axially-aligned third staple opening (5520c). In this regard, first angle (α1) may be substantially equal to fourth angle (α4), and second angle (α2) may be substantially equal to third angle (α3).

In the example shown, radially inner staple openings (5520a, 5520b) are also each generally aligned with a corresponding radially outer staple opening (5520c, 5520d) in a radial direction. More particularly, first staple openings (5520a) are each generally aligned with a corresponding third staple opening (5520c) in a radial direction, and second staple openings (5520b) are each generally aligned with a corresponding fourth staple opening (5520d) in a radial direction.

Due to the relative positions and orientations of staple openings (5520a, 5520b, 5520c, 5520d), the annular arrays of staple openings (5520a, 5520b, 5520c, 5520d) may define a plurality of cross-shaped staple opening patterns and, more particularly, X-shaped staple opening patterns. In this regard, each first staple opening (5520a), corresponding clockwise-adjacent second staple opening (5520b), corresponding radially-aligned third staple opening (5520c), and corresponding axially-aligned fourth staple opening (5520d) may collectively define a respective X-shaped staple opening pattern. More particularly, the colinear first and fourth axes (A1, A4) of such first and fourth staple openings (5520a, 5520d) may intersect with the colinear second and third axes (A2, A3) of such second and third staple openings (5520b, 5520c) at a location between such staple openings (5520a, 5520b, 5520c, 5520d). In the example shown, the width of each X-shaped staple opening pattern in the circumferential direction is greater than the distance between adjacent pairs of X-shaped staple opening patterns in the circumferential direction. In some versions, the crossing point of each X-shaped staple opening pattern (e.g., the intersection between the corresponding colinear first and fourth axes (A1, A4) and the corresponding colinear second and third staple openings (5520b, 5520c)) may be offset from (e.g., radially outward of) a circumferential midline between inner and outer edges (5514, 5516) such that the crossing points are positioned closer to outer edge (5516) than inner edge (5514). In addition, or alternatively, the lengths of the radially inner staple openings (5520a, 5520b) may be greater than the lengths of the radially outer staple openings (5520c, 5520d). In any event, the X-shaped staple opening patterns may enable the annular arrays of formed staples (90a, 90b, 90c, 90d) driven from deck member (5510) to expand radially while maintaining a secure seal as described in greater detail below.

Referring now to FIGS. 102A-102C, the annular arrays of formed staples (90a, 90b, 90c, 90d) driven from deck member (5510) to secure tubular anatomical structures (20, 40) at anastomosis (70) may define a plurality of X-shaped staple patterns corresponding to the X-shaped staple opening patterns defined by the annular arrays of staple openings (5520a, 5520b, 5520c, 5520d). In this regard, formed staples (90a, 90b, 90c, 90d) may initially be positioned and oriented in manners corresponding to the respective staple openings (5520a, 5520b, 5520c, 5520d) so as to define the same internal angles (β1, β2, β3, β4) while anastomosis (70) is maintained in a radially unexpanded state, as shown in FIG. 102A. Formed staples (90a, 90b, 90c, 90d) may each be reoriented to accommodate expansion of at least a portion of anastomosis (70) (e.g., the inner diameter of the anastomosis (70) defined by the severed edge (60)) to one or more radially expanded states without stretching the puncture openings in tubular anatomical structures (20, 40) through which formed staples (90a, 90b, 90c, 90d) extend, as shown in FIGS. 102B and 102C. For example, formed staples (90a, 90b, 90c, 90d) may each be generally pivoted about their respective radially inner and/or outer ends such that first and second formed staples (90a, 90b) are rotated toward each other, thereby decreasing the first and second internal angles (β1, β2), and such that third and fourth formed staples (90c, 90d) are rotated toward each other, thereby decreasing the third and fourth internal angles (β3, β4), to accommodate expansion of anastomosis (70) in a first radial direction to a first radially expanded state (FIG. 102B). Similarly, formed staples (90a, 90b, 90c, 90d) may each be generally pivoted about their respective radially inner and/or outer ends such that first and second formed staples (90a, 90b) are rotated away from each other, thereby increasing the first and second internal angles (β1, β2), and such that third and fourth formed staples (90c, 90d) are rotated away from each other, thereby increasing the third and fourth internal angles (β3, β4), to accommodate expansion of anastomosis (70) in a second radial direction to a second radially expanded state (FIG. 102C).

B. Exemplary Deck Member with X-Shaped Staple Openings in Uniform Orientations

FIGS. 103-105 depict an exemplary deck member (5610) for use with instrument (10) described above. Deck member (5610) is similar to deck member (320) described above except as otherwise described below. In this regard, deck member (5610) may be fixedly secured to a distal end of a body member (not shown) of a stapling head assembly (not shown), such as body member (310) of stapling head assembly (300), and may be configured to permit a knife member (not shown), such as knife member (340), to translate longitudinally through deck member (5610) to actuate between a proximal retracted position and a distal extended position in a manner similar to that described above in connection with FIGS. 1-7E.

As shown, deck member (5610) includes a distally presented stapling surface in the form of a deck surface (5612) extending radially between a generally circular radially inner edge (5614) and a generally circular radially outer edge (5616). Deck member (5610) has a central opening (5618) defined by radially inner edge (5614) and having an inner diameter that is just slightly larger than the outer diameter defined by knife member (340). Deck member (5610) is thus configured to permit knife member (340) to translate longitudinally through the central opening concurrently with longitudinal translation of staple driver member (350). In particular, knife member (340) is configured to actuate relative to deck member (5610) between a proximal retracted position and a distal extended position, where cutting edge (342) is proximal to deck surface (5612) in the proximal retracted position and distal to deck surface (5612) in the distal extended position.

Deck surface (5612) of the present version has a single annular array of X-shaped staple openings (5620) arranged to align with corresponding arrays of X-shaped staple drivers (not shown) such as X-shaped staple driver assemblies (5830) described below, and with corresponding arrays of staple forming pockets (not shown) similar to staple forming pockets (414) of anvil (400) described above. Each staple opening (5620) is configured to slidably receive and provide a pathway for a corresponding staple driver to drive a corresponding staple assembly (5640) (FIGS. 106-107) distally through deck member (5610) and into a corresponding staple forming pocket when a stapling head assembly (not shown) similar to stapling head assembly (300) is actuated. In the example shown, each staple opening (5620) includes overlapping first and second linear staple opening portions (5622, 5624) which are oriented perpendicularly to each other, and which intersect each other at or near their respective midpoints to define a crossing point of the respective staple opening (5620).

In the present version, staple openings (5620) are arranged with uniform circumferential spacing about a longitudinal axis (L) of central opening (5618), with the midpoints of each staple opening portion (5622, 5624) (and thus the crossing points of each staple opening (5620)) positioned at a same radial distance from longitudinal axis (L) such that the midpoints of each staple opening portion (5622, 5624) (and thus the crossing points of staple openings (5620)) collectively define a reference circle (C). As shown, each staple opening portion (5622, 5624) is oriented non-tangentially relative to circle (C). In this regard, first staple opening portions (5622) each extend along a respective first axis (A1) oriented at a first oblique angle ($\alpha$1) relative to a corresponding reference line (T1) that extends tangentially to circle (C) through the respective midpoint, and second staple opening portions (5624) each extend along a respective second axis (A2) oriented at a second oblique angle ($\alpha$2) relative to a corresponding reference line (T2) that extends tangentially to circle (C) through the respective midpoint. In the example shown, first angle ($\alpha$1) is acute such that each first staple opening portion (5622) extends generally radially outwardly in a clockwise direction, while second angle ($\alpha$2) is obtuse such that each second staple opening portion (5624) extends generally radially inwardly in a clockwise direction. In some versions, first and second angles ($\alpha$1, $\alpha$2) may be supplementary to each other. For example, first angle ($\alpha$1) may be approximately 45° and second angle ($\alpha$2) may be approximately 135°. In any event, each first staple opening portion (5622) and corresponding second staple opening portion (5624) may collectively define a first internal angle ($\beta$1) which opens toward inner edge (5614) and a second internal angle ($\beta$2) which opens toward outer edge (5616).

In the example shown, the width of each X-shaped staple opening (5620) in the circumferential direction is greater than the distance between adjacent pairs of X-shaped staple openings (5620) in the circumferential direction. In some versions, the crossing point of each X-shaped staple opening (5620) may be offset from (e.g., radially outward of) a circumferential midline between inner and outer edges (5614, 5616) such that the crossing points are positioned closer to outer edge (5616) than inner edge (5614). In addition, or alternatively, the lengths of the portions of staple openings (5620) that are radially inward of the crossing points may be greater than the lengths of the portions of staple openings (5620) that are radially outward of the crossing points. In any event, the X-shaped staple openings (5620) may enable the annular array of formed staple assemblies (5640) driven from deck member (5610) to expand radially while maintaining a secure seal as described in greater detail below.

Referring now to FIGS. 106-107, each X-shaped staple assembly (5640) of the present example includes a first staple (5641a) and a second staple (5641b). As shown, each staple (5641a, 5641b) includes a crown (5642) extending between first and second ends (5643, 5644), and further includes first and second legs (5645, 5646) extending upwardly and generally perpendicularly from respective ends (5643, 5644) of crown (5642) to respective sharp tips (5647, 5648) configured to puncture tissue, such as tubular anatomical structures (20, 40). In the example shown, the first and second staples (5641a, 5641b) of each staple assembly (5640) overlap each other at or near the corresponding midpoints of the respective crowns (5642). In this regard, the crown (5642) of each first staple (5641a) is upwardly bent at or near the midpoint thereof to define a recess (5649) for receiving the crown (5642) of the corresponding overlapping second staple (5641b) such that each first staple (5641a) may be seated on the corresponding second staple (5641b). In some versions, the recess (5649) of each first staple (5641a) may be configured to pivotably receive the crown (5642) of the corresponding second staple (5641b) to permit relative pivoting of first and second staples (5641a, 5641b) about their respective midpoints (e.g., the midpoints of their respective crowns (5642)).

As shown in FIGS. 108A-108B, each staple assembly (5640) may be formed by a corresponding staple forming pocket into either a two-dimensional formed state (FIG. 108A) or a three-dimensional formed state (FIG. 108B). In the two-dimensional formed state shown in FIG. 108A, the crown (5642) and bent legs (5645, 5646) of each staple (5641a, 5641b) each reside in a corresponding plane, such that the tips (5647, 5648) of each staple (5641a, 5641b) confront each other within the corresponding plane. In this regard, legs (5645, 5646) of each staple (5641a, 5641b) may have lengths that are sufficiently short to prevent the corresponding tips (5647, 5648) from colliding with each other when staple assembly (5640) is in the two-dimensional formed state. In the three-dimensional formed state shown in FIG. 108B, the bent legs (5645, 5646) of each staple (5641a, 5641b) are deflected off-plane from the corresponding crown (5642). Bent legs (5645, 5646) may have non-uniform lengths to provide a three-dimensional pressure gradient in a radially outward direction (e.g., from a tightest point to a loosest point) to ensure proper healing conditions and a secure seal. In some versions, the three-dimensional formed state of staples (5641a, 5641b) may be provided in accordance with one or more teachings of U.S. Pub. No. 2018/0132849, entitled "Staple Forming Pocket Configurations for Circular Surgical Stapler Anvil," published May 17, 2018, now abandoned, incorporated by reference above, and/or U.S. Pub. No. 2020/0038017, entitled "Surgical End Effectors with Staple Cartridges," published Feb. 6, 2020, issued as U.S. Pat. No. 11,406,379 on Aug. 9, 2022, the disclosure of which is incorporated by reference herein.

Referring now to FIGS. 109A-109B, the annular arrays of formed staple assemblies (5640) driven from deck member (5610) to secure tubular anatomical structures (20, 40) at anastomosis (70) may define a plurality of X-shaped staple patterns corresponding to X-shaped staple openings (5620). In this regard, staples (5641a, 5641b) of formed staple assemblies (5640) may initially be positioned and oriented in manners corresponding to the respective staple opening portions (5622, 5624) so as to define the same internal angles ($\beta 1$, $\beta 2$) while anastomosis (70) is maintained in an unexpanded state, as shown in FIG. 109A. Formed staples (5641a, 5641b) may each be reoriented to accommodate expansion of at least a portion of anastomosis (70) (e.g., the inner diameter of the anastomosis (70) defined by the severed edge (60)) to one or more expanded states without stretching the puncture openings in tubular anatomical structures (20, 40) through which formed staples (5641a, 5641b) extend, as shown in FIG. 109B. For example, formed staples (5641a, 5641b) may each be generally pivoted about their respective radially inner and/or outer ends such that their respective radially inner ends are rotated away from each other and their respective radially outer ends are rotated toward each other, thereby increasing the first and second internal angles ($\beta 1$, $\beta 2$), to accommodate expansion of anastomosis (70) in a first radial direction to a first expanded state (FIG. 109B). Similarly, formed staples (5641a, 5641b) may each be generally pivoted about their respective radially inner and/or outer ends such that their respective radially inner ends are rotated toward each other and their respective radially outer ends are rotated toward each other, thereby decreasing the first and second internal angles ($\beta 1$, $\beta 2$), to accommodate expansion of anastomosis (70) in a second radial direction to a second expanded state (not shown).

C. Exemplary Deck Member with X-Shaped Staple Openings in Alternating Orientations FIG. 110 depicts an exemplary deck member (5710) for use with instrument (10) described above. Deck member (5710) is similar to deck member (5610) described above except as otherwise described below. In this regard, deck member (5710) includes a deck surface (5712) extending radially between a generally circular radially inner edge (5714) and a generally circular radially outer edge (5716). Deck member (5710) has a central opening (5718) defined by radially inner edge (5714) and having an inner diameter that is just slightly larger than the outer diameter defined by knife member (340). Deck member (5710) is thus configured to permit knife member (340) to translate longitudinally through the central opening concurrently with longitudinal translation of staple driver member (350). In particular, knife member (340) is configured to actuate relative to deck member (5710) between a proximal retracted position and a distal extended position, where cutting edge (342) is proximal to deck surface (5712) in the proximal retracted position and distal to deck surface (5712) in the distal extended position.

Deck surface (5712) of the present version has a single annular array of circumferentially-alternating non-tangential and tangential X-shaped staple openings (5620, 5720) arranged to align with corresponding arrays of X-shaped staple drivers (not shown) such as X-shaped staple driver assemblies (5830) described below, and with corresponding arrays of staple forming pockets (not shown) similar to staple forming pockets (414) of anvil (400) described above. Each staple opening (5720) is configured to slidably receive and provide a pathway for a corresponding staple driver to drive a corresponding staple assembly (5640) distally through deck member (5710) and into a corresponding staple forming pocket when a stapling head assembly (not shown) similar to stapling head assembly (300) is actuated. In the example shown, each staple opening (5720) includes overlapping first and second linear staple opening portions (5722, 5724) which are oriented perpendicularly to each other, and which intersect each other at or near their respective midpoints to define a crossing point of the respective staple opening (5720).

In the present version, staple openings (5620, 5720) are arranged with uniform circumferential spacing about a longitudinal axis (L) of central opening (5718), with the midpoints of each staple opening portion (5622, 5624, 5722, 5724) (and thus the crossing points of each staple opening (5620, 5720)) positioned at a same radial distance from longitudinal axis (L) such that the midpoints of each staple opening portion (5622, 5624, 5722, 5724) (and thus the crossing points of staple openings (5620, 5720)) collectively define a reference circle (C). As shown, each staple opening portion (5622, 5624) is oriented non-tangentially relative to circle (C) in the manner described above. Each first staple opening portion (5722) is oriented tangentially relative to circle (C), while each second staple opening portion (5724) is oriented radially relative to circle (C). In this manner, staple openings (5620, 5720) may have substantially the same shape as each other, while the orientations of staple openings (5620, 5720) may alternate relative to each other circumferentially about longitudinal axis (L), which may result in varying the positions at which staples (5641a, 5641b) of staple assembly (5640) are compressed and/or an increased complexity of any potential leak path between staples (5641a, 5641b). In any event, the X-shaped staple openings (5620, 5720) may enable the annular array of formed staple assemblies (5640) driven from deck member (5710) to expand radially while maintaining a secure seal in a manner similar to that described above in connection with FIGS. 109A-109B.

D. Exemplary X-Shaped Staple Driver Assembly

FIG. 111 depicts an exemplary X-shaped staple driver assembly (5830) for use with deck member (5610) and/or deck member (5710) described above. Staple driver assembly (5830) is similar to staple drivers (352) described above except as otherwise described below. In this regard, staple driver assemblies (5830) may be arranged to correspond with the arrangement of X-shaped staple openings (5620, 5720) of deck member (5610) and/or deck member (5710), and with staple forming pockets (not shown) of an anvil (not shown), similar to staple forming pockets (414) of anvil (400) described above. Staple driver assembly (5830) may further be configured to drive a corresponding X-shaped staple assembly (5640, 5840) distally into a corresponding staple forming pocket when a stapling head assembly (not shown) such as stapling head assembly (300) is actuated.

Staple driver assembly (5830) of the present version includes integrated first and second staple drivers (5832a, 5832b) which are oriented perpendicularly to each other, and which intersect each other at or near their respective midpoints for driving respective staples (5841a, 5841b) of staple assembly (5840). In this regard, each staple driver (5832a, 5832b) includes at least one longitudinal groove (5834) configured to cradle the crown (5842) of the corresponding staple (5841a, 5841b) of staple assembly (5840).

It will be appreciated that staple drivers (5832a, 5832b) may be unitarily secured to each other. It will be further appreciated that the term "assembly" as used herein is not intended to be limited to discrete assembled components. Rather the term "assembly" includes components that may be formed separately and assembled and components that may be formed integrally as a single part. Thus, the term "assembly" is not intended to limit the invention described herein.

E. Exemplary Deck Member with Two Arrays of X-Shaped Staple Openings

FIG. 112 depicts an exemplary deck member (5910) for use with instrument (10) described above. Deck member (5910) is similar to deck member (5610) described above except as otherwise described below. In this regard, deck member (5910) includes a deck surface (5912) extending radially between a generally circular radially inner edge (5914) and a generally circular radially outer edge (5916). Deck member (5910) has a central opening (5918) defined by radially inner edge (5914) and having an inner diameter that is just slightly larger than the outer diameter defined by knife member (340). Deck member (5910) is thus configured to permit knife member (340) to translate longitudinally through the central opening concurrently with longitudinal translation of staple driver member (350). In particular, knife member (340) is configured to actuate relative to deck member (5910) between a proximal retracted position and a distal extended position, where cutting edge (342) is proximal to deck surface (5912) in the proximal retracted position and distal to deck surface (5912) in the distal extended position.

Deck surface (5912) of the present version has two concentric annular arrays of X-shaped staple openings (5620a, 5620b) arranged to align with corresponding arrays of X-shaped staple drivers (not shown) such as X-shaped staple driver assemblies (5830) described above, and with corresponding arrays of staple forming pockets (not shown) similar to staple forming pockets (414) of anvil (400) described above. In the example shown, each staple opening (5620a, 5620b) includes overlapping first and second linear staple opening portions (5622a, 5622b, 5624a, 5624b) which are oriented perpendicularly to each other, and which intersect each other at or near their respective midpoints to define a crossing point of the respective staple opening (5620a, 5620b).

In the present version, staple openings (5620a, 5620b) are arranged in a radially inner annular array of staple openings (5620a) and a radially outer annular array of staple openings (5620b). More particularly, radially inner staple openings (5620a) are arranged with uniform circumferential spacing about a longitudinal axis (L) of central opening (5918), with the midpoints of each staple opening portion (5622a, 5624a) (and thus the crossing points of each radially inner staple opening (5620a)) positioned at a first radial distance from longitudinal axis (L) such that the midpoints of each staple opening portion (5622a, 5624a) collectively define a first reference circle (C1). Likewise, radially outer staple openings (5620b) are arranged with uniform circumferential spacing about longitudinal axis (L) of central opening (5918), with the midpoints of each staple opening portion (5622b, 5624b) (and thus the crossing points of each radially outer staple opening (5620b)) positioned at a second radial distance from longitudinal axis (L) greater than the first radial distance such that the midpoints of each staple opening portion (5622b, 5624b) collectively define a second reference circle (C2) that is radially outward relative to first reference circle (C1). As shown, each staple opening portion (5622a, 5622b, 5624a, 5624b) is oriented non-tangentially relative to circle (C) in a manner similar to that described above in connection with FIGS. 103-105. In the example shown, each radially outer staple opening (5620b) is positioned circumferentially between a corresponding pair of radially inner staple openings (5620a). In any event, the X-shaped staple openings (5620a, 5620b) may enable the annular arrays of formed staple assemblies (5640) driven from deck member (5910) to expand radially while maintaining a secure seal in a manner similar to that described above in connection with FIGS. 109A-109B.

F. Exemplary Deck Member with Alternating Linear and X-Shaped Staple Openings

FIG. 113 depicts an exemplary deck member (6010) for use with instrument (10) described above. Deck member (6010) is similar to deck member (5610) described above except as otherwise described below. In this regard, deck member (6010) includes a deck surface (6012) extending radially between a generally circular radially inner edge (6014) and a generally circular radially outer edge (6016). Deck member (6010) has a central opening (6018) defined by radially inner edge (6014) and having an inner diameter that is just slightly larger than the outer diameter defined by knife member (340). Deck member (6010) is thus configured to permit knife member (340) to translate longitudinally through the central opening concurrently with longitudinal translation of staple driver member (350). In particular, knife member (340) is configured to actuate relative to deck member (6010) between a proximal retracted position and a distal extended position, where cutting edge (342) is proximal to deck surface (6012) in the proximal retracted position and distal to deck surface (6012) in the distal extended position.

Deck surface (6012) of the present version has a single annular array of circumferentially-alternating X-shaped and linear staple openings (5620, 6020) arranged to align with corresponding arrays of circumferentially-alternating X-shaped and linear staple drivers (not shown) such as X-shaped staple driver assemblies (5830) and linear staple driver assemblies (352) described above, and with corresponding arrays of staple forming pockets (not shown) similar to staple forming pockets (414) of anvil (400) described above. Each staple opening (6020) is configured to slidably receive and provide a pathway for a corresponding staple driver to drive a corresponding staple assembly (5640) distally through deck member (6010) and into a corresponding staple forming pocket when a stapling head assembly (not shown) similar to stapling head assembly (300) is actuated.

In the present version, staple openings (5620, 6020) are arranged with uniform circumferential spacing about a longitudinal axis (L) of central opening (6018), with the midpoints of each staple opening portion (5622, 5624) (and thus the crossing points of each staple opening (5620)) and of each staple opening (6020) positioned at a same radial distance from longitudinal axis (L) such that the midpoints of each staple opening portion (5622, 5624) (and thus the crossing points of each staple opening (5620)) and of each staple opening (6020) collectively define a reference circle (C). As shown, each staple opening portion (5622, 5624) is oriented non-tangentially relative to circle (C) in the manner described above. Each staple opening (6020) is oriented tangentially relative to circle (C). In any event, the X-shaped staple openings (5620) may enable the annular array of formed staple assemblies (5640) driven from deck member (6010) to expand radially while maintaining a secure seal in a manner similar to that described above in connection with FIGS. 109A-109B.

G. Exemplary Deck Member with Alternating Deep and Shallow X-Shaped Staple Openings FIG. 114 depicts an exemplary deck member (6110) for use with instrument (10) described above. Deck member (6110) is similar to deck member (5610) described above except as otherwise described below. In this regard, deck member (6110) includes a deck surface (6112) extending radially between a generally circular radially inner edge (6114) and a generally circular radially outer edge (6116). Deck member (6110) has a central opening (6118) defined by radially inner edge (6114) and having an inner diameter that is just slightly larger than the outer diameter defined by knife member (340). Deck member (6110) is thus configured to permit knife member (340) to translate longitudinally through the central opening concurrently with longitudinal translation of staple driver member (350). In particular, knife member (340) is configured to actuate relative to deck member (6110) between a proximal retracted position and a distal extended position, where cutting edge (342) is proximal to deck surface (6112) in the proximal retracted position and distal to deck surface (6112) in the distal extended position.

Deck surface (6112) of the present version has a single annular array of circumferentially-alternating deep X-shaped and shallow X-shaped staple openings (6120, 6121) arranged to align with a corresponding array of circumferentially-alternating deep X-shaped and shallow X-shaped staple drivers (not shown) similar to X-shaped staple driver assemblies (5830) described above, and with a corresponding array of circumferentially-alternating deep X-shaped and shallow X-shaped staple forming pockets (not shown) similar to staple forming pockets (414) of anvil (400) described above. Each staple opening (6120, 6121) is configured to slidably receive and provide a pathway for a corresponding staple driver to drive a corresponding staple assembly (not shown) similar to staple assembly (5640) distally through deck member (6110) and into a corresponding staple forming pocket when a stapling head assembly (not shown) similar to stapling head assembly (300) is actuated. In the example shown, each staple opening (6120) includes overlapping first and second linear staple opening portions (6122, 6124) which are oriented obliquely to each other, and which intersect each other radially inwardly of their respective midpoints to define a crossing point of the respective staple opening (6120). Each staple opening (6121) includes overlapping first and second linear staple opening portions (6126, 6128) which are oriented obliquely to each other, and which intersect each other radially outwardly of their respective midpoints to define a crossing point of the respective staple opening (6121).

In the present version, staple openings (6120, 6121) are arranged with uniform circumferential spacing about a longitudinal axis (L) of central opening (6118), with the midpoints of each staple opening portion (6122, 6124, 6126, 6128) positioned at a same radial distance from longitudinal axis (L) such that the midpoints of each staple opening portion (6122, 6124, 6126, 6128) collectively define a reference circle (C). As shown, each staple opening portion (6122, 6124, 6126, 6128) is oriented non-tangentially relative to circle (C) in a manner similar to that described above in connection with FIGS. 103-105. In some versions, at least a portion of each deep X-shaped staple opening (6120) (e.g., a radially outer portion of its first staple opening portion (6122)) may be aligned in a radial direction with at least a portion of a corresponding clockwise-adjacent shallow X-shaped staple opening (6121) (e.g., a radially inner portion of its first staple opening portion (6126). In addition, or alternatively, at least a portion of each shallow X-shaped staple opening (6121) (e.g., a radially inner portion of its second staple opening portion (6128)) may be aligned in a radial direction with at least a portion of a corresponding clockwise-adjacent deep X-shaped staple opening (6120) (e.g., a radially outer portion of its second staple opening portion (6124)). It will be appreciated that such radial alignment(s) may increase the complexity of any potential leak path between staples of formed staple assemblies driven from deck member (6110). In any event, the X-shaped staple openings (6120, 6121) may enable the annular array of formed staple assemblies driven from deck member (6110) to expand radially while maintaining a secure seal in a manner similar to that described above in connection with FIGS. 109A-109B.

H. Exemplary Deck Member with Overlapping Deep X-Shaped Staple Openings

FIG. 115 depicts an exemplary deck member (6210) for use with instrument (10) described above. Deck member (6210) is similar to deck member (5610) described above except as otherwise described below. In this regard, deck member (6210) includes a deck surface (6212) extending radially between a generally circular radially inner edge (6214) and a generally circular radially outer edge (6216). Deck member (6210) has a central opening (6218) defined by radially inner edge (6214) and having an inner diameter that is just slightly larger than the outer diameter defined by knife member (340). Deck member (6210) is thus configured to permit knife member (340) to translate longitudinally through the central opening concurrently with longitudinal translation of staple driver member (350). In particular, knife member (340) is configured to actuate relative to deck member (6210) between a proximal retracted position and a distal extended position, where cutting edge (342) is proximal to deck surface (6212) in the proximal retracted position and distal to deck surface (6212) in the distal extended position.

Deck surface (6212) of the present version has a single annular array of deep X-shaped staple openings (6220) arranged to align with a corresponding array of deep X-shaped staple drivers (not shown) similar to X-shaped staple driver assemblies (5830) described above, and with a corresponding array of deep X-shaped staple forming pockets (not shown) similar to staple forming pockets (414) of anvil (400) described above. Each staple opening (6220) is configured to slidably receive and provide a pathway for a corresponding staple driver to drive a corresponding staple assembly (not shown) similar to staple assembly (5640) distally through deck member (6210) and into a corresponding staple forming pocket when a stapling head assembly (not shown) similar to stapling head assembly (300) is actuated. In the example shown, each staple opening (6220) includes overlapping first and second linear staple opening portions (6222, 6224) which are oriented obliquely to each other, and which intersect each other radially inwardly of their respective midpoints to define a crossing point of the respective staple opening (6220).

In the present version, staple openings (6220) are arranged with uniform circumferential spacing about a longitudinal axis (L) of central opening (6218), with the midpoints of each staple opening portion (6222, 6224) positioned at a same radial distance from longitudinal axis (L) such that the midpoints of each staple opening portion (6222, 6224) collectively define a reference circle (C). As shown, each staple opening portion (6222, 6224) is oriented non-tangentially relative to circle (C) in a manner similar to that described above in connection with FIGS. 103-105. In some versions, at least a portion of each staple opening (6220) (e.g., a radially outer portion of its first staple opening portion (6222)) may intersect at least a portion of the clockwise-adjacent staple opening (6120) (e.g., a radially outer portion of its second staple opening portion (6222). It will be appreciated that such intersecting may increase the complexity of any potential leak path between staples of formed staple assemblies driven from deck member (6210). In any event, the X-shaped staple openings (6220) may enable the annular array of formed staple assemblies driven from deck member (6210) to expand radially while maintaining a secure seal in a manner similar to that described above in connection with FIGS. 109A-109B.

I. Exemplary Deck Member with Staple Openings in Undulating Pattern

FIG. 116 depicts an exemplary deck member (6310) for use with instrument (10) described above. Deck member (6310) is similar to deck member (5510) described above except as otherwise described below. In this regard, deck member (6310) includes a deck surface (6312) extending radially between a generally circular radially inner edge (6314) and a generally circular radially outer edge (6316). Deck member (6310) has a central opening (6318) defined by radially inner edge (6314) and having an inner diameter that is just slightly larger than the outer diameter defined by knife member (340). Deck member (6310) is thus configured to permit knife member (340) to translate longitudinally through the central opening concurrently with longitudinal translation of staple driver member (350). In particular, knife member (340) is configured to actuate relative to deck member (6310) between a proximal retracted position and a distal extended position, where cutting edge (342) is proximal to deck surface (6312) in the proximal retracted position and distal to deck surface (6312) in the distal extended position.

Deck surface (6312) of the present version has three concentric annular arrays of linear staple openings (6320a, 6320b, 6320c, 6320d) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (6320a, 6320b, 6320c, 6320d) is configured to slidably receive and provide a pathway for a corresponding staple driver to drive a corresponding staple (90a, 90b, 90c, 90d) (FIGS. 117A-117B) distally through deck member (6310) and into a corresponding staple forming pocket when a stapling head assembly (not shown) similar to stapling head assembly (300) is actuated.

In the present version, staple openings (6320a, 6320b, 6320c, 6320d) are arranged in a radially inner annular array of first staple openings (6320a), a radially intermediate annular array of circumferentially-alternating second and third staple openings (6320b, 6320c), and a radially outer annular array of fourth staple openings (6320d). More particularly, radially inner staple openings (6320a) are arranged with uniform circumferential spacing about a longitudinal axis (not shown) of central opening (6318), with the midpoints of each radially inner staple opening (6320a) positioned at a first radial distance from the longitudinal axis such that the midpoints of radially inner staple openings (6320a) collectively define a first reference circle (C1). As shown, each radially inner staple opening (6320a) is oriented tangentially relative to first circle (C1). In this regard, first staple openings (6320a) each extend along a respective first axis (A1) colinear with a corresponding reference line (T1) that extends tangentially to first circle (C1) through the respective midpoint.

Likewise, radially intermediate staple openings (6320b, 6320c) are arranged with uniform circumferential spacing about the longitudinal axis of central opening (6318), with the midpoints of each radially intermediate staple openings (6320b, 6320c) positioned at a second radial distance from the longitudinal axis greater than the first radial distance, such that the midpoints of radially intermediate staple openings (6320b, 6320c) collectively define a second reference circle (C2) that is radially outward relative to the first reference circle (C1). As shown, each radially intermediate staple opening (6320b, 6320c) is oriented non-tangentially relative to second circle (C2). In this regard, second staple openings (6320b) each extend along a respective second axis (A2) oriented at a first oblique angle ($\alpha1$) relative to a corresponding reference line (T2) that extends tangentially to second circle (C2) through the respective midpoint, and third staple openings (6320c) each extend along a respective third axis (A3) oriented at a second oblique angle ($\alpha2$) relative to a corresponding reference line (T3) that extends tangentially to second circle (C2) through the respective midpoint. In the example shown, first angle ($\alpha1$) is acute such that each second staple opening (6320b) extends generally radially outwardly in a clockwise direction, while second angle ($\alpha2$) is obtuse such that each third staple opening (6320c) extends generally radially inwardly in a clockwise direction. In some versions, first and second angles ($\alpha1$, $\alpha2$) may be supplementary to each other. For example, first angle ($\alpha1$) may be approximately 30° and second angle ($\alpha2$) may be approximately 150°. In any event, each second staple opening (6320b) and a corresponding clockwise-adjacent third staple opening (6320c) may collectively define a first internal angle ($\beta1$) which opens toward inner edge (6314), while each third staple opening (6320c) and a corresponding clockwise-adjacent second staple opening (6320b) may collectively define a second internal angle ($\beta2$) which opens toward outer edge (6316).

Likewise, radially outer staple openings (6320d) are arranged with uniform circumferential spacing about the longitudinal axis of central opening (6318), with the midpoints of each radially outer staple opening (6320d) positioned at a third radial distance from the longitudinal axis greater than the second radial distance, such that the midpoints of radially outer staple openings (6320d) collectively define a third reference circle (C3) that is radially outward relative to the second reference circle (C2). As shown, each radially outer staple opening (6320d) is oriented tangentially relative to third circle (C3). In this regard, fourth staple openings (6320d) each extend along a respective fourth axis (A4) colinear with a corresponding reference line (T4) that extends tangentially to third circle (C3) through the respective midpoint.

In the example shown, radially inner staple openings (6320a) are each generally centered between a corresponding circumferentially-adjacent pair of radially outer staple openings (6320d) in the circumferential direction, and radially outer staple openings (6320d) are each generally centered between a corresponding circumferentially-adjacent pair of radially inner staple openings (6320a). Radially intermediate staple openings (6320b, 6320c) each extend radially and circumferentially between respective ends of corresponding circumferentially-adjacent radially inner and radially outer staple openings (6320a, 6320d). More particularly, second staple openings (6320b) each generally extend radially outwardly in the clockwise direction from a radially inner end near a clockwise end of the corresponding radially inner staple opening (6320a) toward a radially outer end near a counterclockwise end of the corresponding radially outer staple opening (6320d). Third staple openings (6320c) each generally extend radially inwardly in the clockwise direction from a radially outer end near a clockwise end of the corresponding radially outer staple opening (6320d) toward a radially inner end near a counterclockwise end of the corresponding radially inner staple opening (6320a).

Due to the relative positions and orientations of staple openings (6320a, 6320b, 6320c, 6320d), the annular arrays of staple openings (6320a, 6320b, 6320c, 6320d) may collectively define an undulating curvilinear staple opening pattern. In this regard, each first staple opening (6320a), corresponding clockwise-adjacent second staple opening (6320b), and corresponding counterclockwise-adjacent third staple opening (6320c) may collectively define a respective U-shaped staple opening pattern which faces radially outwardly (e.g., opens toward outer edge (6316)), while each fourth staple opening (6320d), corresponding counterclockwise-adjacent second staple opening (6320b), and corresponding clockwise-adjacent third staple opening (6320c) may collectively define a respective U-shaped staple opening pattern which faces radially inwardly (e.g., opens toward inner edge (6314)). The undulating staple opening pattern may enable the annular arrays of formed staples (90a, 90b, 90c, 90d) driven from deck member (6310) to expand radially while maintaining a secure seal as described in greater detail below.

Referring now to FIGS. 117A-117B, the annular arrays of formed staples (90a, 90b, 90c, 90d) driven from deck member (6310) to secure tubular anatomical structures (20, 40) at anastomosis (70) may define an undulating curvilinear staple pattern corresponding to the undulating staple opening pattern defined by the annular arrays of staple openings (6320a, 6320b, 6320c, 6320d). In this regard, formed staples (90a, 90b, 90c, 90d) may initially be positioned and oriented in manners corresponding to the respective staple openings (6320a, 6320b, 6320c, 6320d) so as to define the same internal angles ($\beta 1, \beta 2, \beta 3, \beta 4$) while anastomosis (70) is maintained in an unexpanded state, as shown in FIG. 117A. Formed staples (90a, 90b, 90c, 90d) may each be reoriented to accommodate expansion of at least a portion of anastomosis (70) (e.g., the inner diameter of the anastomosis (70) defined by the severed edge (60)) to one or more expanded states without stretching the puncture openings in tubular anatomical structures (20, 40) through which formed staples (90a, 90b, 90c, 90d) extend, as shown in FIG. 117B. For example, the radially intermediate formed staples (90b, 90c) may each be generally pivoted about their respective radially inner and/or outer ends such that their respective radially inner ends are rotated away from each other and their respective radially outer ends are rotated toward each other, thereby increasing the first internal angle ($\beta 1$) and decreasing the second internal angle ($\beta 2$), to accommodate expansion of anastomosis (70) in a first radial direction to a first expanded state (FIG. 117B). Similarly, the radially intermediate formed staples (90b, 90c) may each be generally pivoted about their respective radially inner and/or outer ends such that their respective radially inner ends are rotated toward each other and their respective radially outer ends are rotated away from each other, thereby decreasing the first internal angle ($\beta 1$) and increasing the second internal angle ($\beta 2$), to accommodate expansion of anastomosis (70) in a second radial direction to a second expanded state (not shown).

J. Exemplary Deck Member with Large Staple Openings in Undulating Pattern and with Nested Small Staple Openings FIG. 118 depicts an exemplary deck member (6410) for use with instrument (10) described above. Deck member (6410) is similar to deck member (6310) described above except as otherwise described below. In this regard, deck member (6410) includes a deck surface (6412) extending radially between a generally circular radially inner edge (6414) and a generally circular radially outer edge (6416). Deck member (6410) has a central opening (6418) defined by radially inner edge (6414) and having an inner diameter that is just slightly larger than the outer diameter defined by knife member (340). Deck member (6410) is thus configured to permit knife member (340) to translate longitudinally through the central opening concurrently with longitudinal translation of staple driver member (350). In particular, knife member (340) is configured to actuate relative to deck member (6410) between a proximal retracted position and a distal extended position, where cutting edge (342) is proximal to deck surface (6412) in the proximal retracted position and distal to deck surface (6412) in the distal extended position.

Deck surface (6412) of the present version has four concentric annular arrays of linear staple openings (6320a, 6320b, 6320c, 6320d, 6420a, 6420b, 6420c, 6420d) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (6320a, 6320b, 6320c, 6320d, 6420a, 6420b, 6420c, 6420d) is configured to slidably receive and provide a pathway for a corresponding staple driver to drive a corresponding staple (90a, 90b, 90c, 90d) (FIGS. 117A-117B) distally through deck member (6410) and into a corresponding staple forming pocket when a stapling head assembly (not shown) similar to stapling head assembly (300) is actuated. In the example shown, staple openings (6320a, 6320b, 6320c, 6320d, 6420a, 6420b, 6420c, 6420d) include relatively large staple openings (6320a, 6320b, 6320c, 6320d) and relatively small staple openings (also referred to herein as auxiliary staple openings) (6420a, 6420b, 6420c, 6420d).

In the present version, the relatively large staple openings (6320a, 6320b, 6320c, 6320d) are arranged to define an undulating curvilinear staple opening pattern as described above. The relatively small staple openings (6420a, 6420b, 6420c, 6420d) are arranged circumferentially about the longitudinal axis (L) of central opening (6418), with the midpoints of each small staple opening (6420a, 6420b, 6420c, 6420d) positioned at a fourth radial distance from longitudinal axis (L) between the first and second radial distances such that the midpoints of small staple openings (6420a, 6420b, 6420c, 6420d) collectively define a fourth reference circle (C4) radially between the first and second circles (C1, C2). In some versions, fourth circle (C4) may be offset from (e.g., radially inward of) a circumferential midline between inner and outer edges (6414, 6416). As shown, each small staple opening (6420a, 6420b, 6420c, 6420d) is oriented non-tangentially relative to fourth circle (C4), with each first and fourth staple opening (6420a, 6420d) extending generally radially outwardly in a clockwise direction and with each second and third staple opening (6420b, 6420c) extending generally radially inwardly in a clockwise direction. Each first staple opening (6420c) and a corresponding clockwise-adjacent second staple opening (6420b) are captured within the first internal angle ($\beta 1$) and nested within the U-shaped staple pattern defined by the corresponding large staple openings (6320b, 6320c, 6320d), while each third staple opening (6420c) and a corresponding clockwise-adjacent fourth staple opening (6420d) are captured within the second internal angle ($\beta 2$) and nested within the U-shaped staple pattern defined by the corresponding large staple openings (6320a, 6320b, 6320c).

In the example shown, at least a portion of each first small staple opening (6420a) (e.g., a radially outer portion thereof) may be aligned in a radial direction with at least a portion of a corresponding radially-adjacent fourth large staple opening (6320d) (e.g., a counterclockwise portion thereof), and at least a portion of each first small staple opening (6420a) (e.g., a radially inner portion thereof) may be aligned in a radial direction with at least a portion of a corresponding counterclockwise-adjacent second large staple opening (6320b) (e.g., a clockwise portion thereof).

In addition, or alternatively, at least a portion of each second small staple opening (6420b) (e.g., a radially outer portion thereof) may be aligned in a radial direction with at least a portion of a corresponding radially-adjacent fourth large staple opening (6320d) (e.g., a clockwise portion thereof), and at least a portion of each second small staple opening (6420b) (e.g., a radially inner portion thereof) may be aligned in a radial direction with at least a portion of a corresponding clockwise-adjacent third large staple opening (6320c) (e.g., a counterclockwise portion thereof).

In addition, or alternatively, at least a portion of each third small staple opening (6420c) (e.g., a radially inner portion thereof) may be aligned in a radial direction with at least a portion of a corresponding radially-adjacent first large staple opening (6320a) (e.g., a counterclockwise portion thereof), and at least a portion of each third small staple opening (6420c) (e.g., a radially outer portion thereof) may be aligned in a radial direction with at least a portion of a corresponding counterclockwise-adjacent third large staple opening (6320c) (e.g., a clockwise portion thereof).

In addition, or alternatively, at least a portion of each fourth small staple opening (6420d) (e.g., a radially inner portion thereof) may be aligned in a radial direction with at least a portion of a corresponding radially-adjacent first large staple opening (6320a) (e.g., a clockwise portion thereof), and at least a portion of each fourth small staple opening (6420d) (e.g., a radially outer portion thereof) may be aligned in a radial direction with at least a portion of a corresponding counterclockwise-adjacent second large staple opening (6320b) (e.g., a counterclockwise portion thereof).

It will be appreciated that such radial alignment(s) may increase the complexity of any potential leak path between formed staples (90a, 90b, 90c, 90d) driven from deck member (6410). In any event, the undulating staple opening pattern may enable the annular array of formed staples (90a, 90b, 90c, 90d) driven from deck member (6410) to expand radially while maintaining a secure seal in a manner similar to that described above in connection with FIGS. 117A-117B.

K. Exemplary Deck Member with Staple Openings in Nested Undulating Patterns

FIG. 119 depicts an exemplary deck member (6510) for use with instrument (10) described above. Deck member (6510) is similar to deck member (5510) described above except as otherwise described below. In this regard, deck member (6510) includes a deck surface (6512) extending radially between a generally circular radially inner edge (6514) and a generally circular radially outer edge (6516). Deck member (6510) has a central opening (6518) defined by radially inner edge (6514) and having an inner diameter that is just slightly larger than the outer diameter defined by knife member (340). Deck member (6510) is thus configured to permit knife member (340) to translate longitudinally through the central opening concurrently with longitudinal translation of staple driver member (350). In particular, knife member (340) is configured to actuate relative to deck member (6510) between a proximal retracted position and a distal extended position, where cutting edge (342) is proximal to deck surface (6512) in the proximal retracted position and distal to deck surface (6512) in the distal extended position.

Deck surface (6512) of the present version has two concentric star-shaped arrays of linear staple openings (6520a, 6520b, 6520c, 6520d) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (6520a, 6520b, 6520c, 6520d) is configured to slidably receive and provide a pathway for a corresponding staple driver to drive a corresponding staple (90a, 90b, 90c, 90d) (FIGS. 120A-120C) distally through deck member (6510) and into a corresponding staple forming pocket when a stapling head assembly (not shown) similar to stapling head assembly (300) is actuated. In some versions, each staple opening (6520a, 6520b, 6520c, 6520d) may have a width of approximately 0.100 inch.

In the present version, staple openings (6520a, 6520b, 6520c, 6520d) are arranged in a radially inner star-shaped array of circumferentially-alternating pairs of inline first and second staple openings (6520a, 6520b) and a radially outer star-shaped array of circumferentially-alternating pairs of inline third and fourth staple openings (6520c, 6520d). More particularly, each pair of first staple openings (6520a) extends radially outwardly in a clockwise direction along a respective first axis (A1), each pair of second staple openings (6520b) extends radially inwardly in a clockwise direction along a respective second axis (A2), each pair of third staple openings (6520c) extends radially outwardly in a clockwise direction along a respective third axis (A3), and each pair of fourth staple openings (6520d) extends radially inwardly in a clockwise direction along a respective fourth axis (A4). Each pair of first staple openings (6520a) and a corresponding clockwise-adjacent pair of second staple openings (6520b) may collectively define a first internal angle ($\beta 1$) which opens toward inner edge (6514), while each pair of second staple openings (6520b) and a corresponding clockwise-adjacent pair of first staple openings (6520a) may collectively define a second internal angle ($\beta 2$) which opens toward outer edge (6516). In some versions, the first and third axes (A1, A3) are parallel to each other and the second and fourth axes (A2, A4) are parallel to each other such that each pair of third staple openings (6520c) and a corresponding clockwise-adjacent pair of fourth staple openings (6520d) may also collectively define the first internal angle ($\beta 1$), while each pair of fourth staple openings (6520d) and a corresponding clockwise-adjacent pair of third staple openings (6520c) may also collectively define the second internal angle ($\beta 2$). In the example shown, the first and second internal angles ($\beta 1$, $\beta 2$) are each bifurcated by a corresponding radial reference line (R1, R2) such that staple openings (6520a, 6520b, 6520c, 6520d) are arranged symmetrically (e.g., mirrored) about each radial line (R1, R2). In some versions, the axes (A1, A2, A3, A4) may each be oriented at an angle of approximately 25° or approximately 155° relative to a corresponding reference line (not shown) that is tangential to inner edge (6514) or outer edge (6516) and perpendicular to the corresponding radial line (R1, R2).

In the example shown, radially inner staple openings (6520a, 6520b) are each generally aligned with a corresponding radially outer staple opening (6520c, 6520d) in a radial direction. More particularly, first staple openings (6520a) are each generally aligned with a corresponding third staple opening (6520c) in a radial direction, and second staple openings (6520b) are each generally aligned with a corresponding fourth staple opening (6520d) in a radial direction. While two concentric star-shaped arrays of linear staple openings (6520a, 6520b, 6520c, 6520d) are shown, it will be appreciated that one or more additional concentric star-shaped staple opening arrays may be included.

Due to the relative positions and orientations of staple openings (6520a, 6520b, 6520c, 6520d), the star-shaped arrays of staple openings (6520a, 6520b, 6520c, 6520d) may define a pair of nested undulating curvilinear staple opening patterns. In this regard, each pair of first staple openings (6520a) and corresponding clockwise-adjacent pair of second staple openings (6520b) may collectively define a respective V-shaped staple opening pattern which faces radially inwardly (e.g., opens toward inner edge (6514)), while each pair of second staple openings (6520b) and corresponding clockwise-adjacent pair of first staple openings (6520a) may collectively define a respective V-shaped staple opening pattern which faces radially outwardly (e.g., opens toward outer edge (6516)). Similarly, each pair of third staple openings (6520c) and corresponding clockwise-adjacent pair of fourth staple openings (6520d) may collectively define a respective V-shaped staple opening pattern which faces radially inwardly (e.g., opens toward inner edge (6514)) and captures the V-shaped staple opening pattern defined by the corresponding pairs of first and second staple openings (6520a, 6520b), while each pair of fourth staple openings (6520d) and corresponding clockwise-adjacent pair of third staple openings (6520c) may collectively define a respective V-shaped staple opening pattern which faces radially outwardly (e.g., opens toward outer edge (6516)) and is captured by the V-shaped staple opening pattern defined by the corresponding pairs of first and second staple openings (6520a, 6520b). The nested undulating staple opening patterns may enable the annular arrays of formed staples (90a, 90b, 90c, 90d) driven from deck member (6510) to expand radially while maintaining a secure seal as described in greater detail below.

Referring now to FIGS. 120A-120C, the star-shaped arrays of formed staples (90a, 90b, 90c, 90d) driven from deck member (6510) to secure tubular anatomical structures (20, 40) at anastomosis (70) may define a pair of nested undulating curvilinear staple patterns corresponding to the nested undulating curvilinear staple opening patterns defined by the star-shaped arrays of staple openings (6520a, 6520b, 1520c, 1520d). In this regard, formed staples (90a, 90b, 90c, 90d) may initially be positioned and oriented in manners corresponding to the respective staple openings (6520a, 6520b, 6520c, 6520d) so as to define the same internal angles ($\beta1$, $\beta2$) while anastomosis (70) is maintained in an unexpanded state, as shown in FIG. 120A. Formed staples (90a, 90b, 90c, 90d) may each be reoriented to accommodate expansion of at least a portion of anastomosis (70) (e.g., the inner diameter of the anastomosis (70) defined by the severed edge (60)) to one or more expanded states without stretching the puncture openings in tubular anatomical structures (20, 40) through which formed staples (90a, 90b, 90c, 90d) extend, as shown in FIGS. 120B and 120C. For example, the radially inner formed staples (90a, 90b) may each be generally pivoted about their respective radially inner and/or outer ends such that their respective radially inner ends are rotated toward each other and the radially outer formed staples (90c, 90d) may each be generally pivoted about their respective radially inner and/or outer ends such that their respective radially inner ends are rotated toward each other, thereby decreasing the first and second internal angles ($\beta1$, $\beta2$), to accommodate expansion of anastomosis (70) in a first radial direction to a first expanded state (FIG. 120B). Similarly, the radially inner formed staples (90a, 90b) may each be generally pivoted about their respective radially inner and/or outer ends such that their respective radially inner ends are rotated away from each other and the radially outer formed staples (90c, 90d) may each be generally pivoted about their respective radially inner and/or outer ends such that their respective radially inner ends are rotated away from each other, thereby increasing the first and second internal angles ($\beta1$, $\beta2$), to accommodate expansion of anastomosis (70) in a second radial direction to a second expanded state (FIG. 120C).

L. Exemplary Deck Member with Staple Openings in Alternating Triangular Patterns FIG. 121 depicts an exemplary deck member (6610) for use with instrument (10) described above. Deck member (6610) is similar to deck member (5510) described above except as otherwise described below. In this regard, deck member (6610) includes a deck surface (6612) extending radially between a generally circular radially inner edge (6614) and a generally circular radially outer edge (6616). Deck member (6610) has a central opening (6618) defined by radially inner edge (6614).

Deck surface (6612) of the present version has three concentric annular arrays of linear staple openings (6620a, 6620b, 6620c, 6620d) arranged in a radially inner annular array of first staple openings (6620a), a radially intermediate annular array of circumferentially-alternating second and third staple openings (6620b, 6620c), and a radially outer annular array of fourth staple openings (6620d). As shown, each radially inner and outer staple opening (6620a, 6620d) is oriented tangentially relative to a corresponding reference circle (not shown). Each radially intermediate staple opening (6620b, 6620c) is oriented non-tangentially relative to a respective reference circle (not shown), such that each second staple opening (6620b) extends generally radially inwardly in a clockwise direction and each third staple opening (6620c) extends generally radially outwardly in a clockwise direction.

Due to the relative positions and orientations of staple openings (6620a, 6620b, 6620c, 6620d), the annular arrays of staple openings (6620a, 6620b, 6620c, 6620d) may define a plurality of alternating, generally triangular staple opening patterns. In this regard, each first staple opening (6620a), corresponding clockwise-adjacent second staple opening (6620b), and corresponding counterclockwise-adjacent third staple opening (6620c) may collectively define a respective triangular staple opening pattern, while each fourth staple opening (6620d), corresponding counterclockwise-adjacent second staple opening (6620b), and corresponding clockwise-adjacent third staple opening (6620c) may collectively define a respective triangular staple opening pattern. The alternating triangular staple opening patterns may enable the annular arrays of formed staples (90a, 90b, 90c, 90d) driven from deck member (6610) to expand radially while maintaining a secure seal, such as by creating a spring element in the staple line by providing a compressible member via rotation of the structural elements, thereby leveraging the triangular staple opening patterns to create compliance and an optimal staple pressure field. In this regard, the alternating triangular staple opening patterns may allow for three distinct pressure zones (e.g., inner, middle, and outer), and may also allow for rotation of arm elements of the triangle to "oblique" the triangle, creating compliance.

M. Exemplary Deck Member with Staple Openings in Repeating Parallelogram Patterns FIG. 122 depicts an exemplary deck member (6710) for use with instrument (10) described above. Deck member (6710) is similar to deck member (5510) described above except as otherwise described below. In this regard, deck member (6710) includes a deck surface (6712) extending radially between a generally circular radially inner edge (6714) and a generally circular radially outer edge (6716). Deck member (6710) has a central opening (6718) defined by radially inner edge (6714).

Deck surface (6712) of the present version has three concentric annular arrays of linear staple openings (6720a, 6720b, 6720c) arranged in a radially inner annular array of first staple openings (6720a), a radially intermediate annular array of second staple openings (6720b), and a radially outer annular array of third staple openings (6720c). As shown, each radially inner and outer staple opening (6720a, 6720c) is oriented tangentially relative to a corresponding reference circle (not shown). Each radially intermediate staple opening (6720b) is oriented non-tangentially relative to a respective reference circle (not shown), such that each second staple opening (6720b) extends generally radially outwardly in a clockwise direction.

Due to the relative positions and orientations of staple openings (6720a, 6720b, 6720c), the annular arrays of staple openings (6720a, 6720b, 6720c) may define a plurality of repeating, generally parallelogram-shaped staple opening patterns. In this regard, each first staple opening (6720a), corresponding clockwise-adjacent and counterclockwise-adjacent second staple openings (6720b), and corresponding radially-adjacent third staple opening (6720c) may collectively define a respective parallelogram-shaped staple opening pattern. The repeating parallelogram-shaped staple opening patterns may enable the annular arrays of formed staples (90a, 90b, 90c) driven from deck member (6710) to expand radially while maintaining a secure seal, such as by creating a spring element in the staple line by providing a compressible member via rotation of the structural elements, thereby leveraging the repeating parallelogram-shaped staple opening patterns to create compliance and an optimal staple pressure field. In this regard, the repeating parallelogram-shaped staple opening patterns may allow for a rotatable element of the parallelogram to create compliance, and may also allow for the pressure field to be controlled by varying the formed staple height which, in combination with uneven formed leg lengths, may allow for different pressure zones radially in the staple line.

N. Exemplary Deck Member with Staple Openings in Alternating "V" Patterns

FIG. 123 depicts an exemplary deck member (6810) for use with instrument (10) described above. Deck member (6810) is similar to deck member (5510) described above except as otherwise described below. In this regard, deck member (6810) includes a deck surface (6812) extending radially between a generally circular radially inner edge (6814) and a generally circular radially outer edge (6816). Deck member (6810) has a central opening (6818) defined by radially inner edge (6814).

Deck surface (6812) of the present version has two concentric annular arrays of linear staple openings (6820a, 6820b, 6820c, 6820d) arranged in a radially inner annular array of circumferentially-alternating first and second staple openings (6820a, 6820b) and a radially outer annular array of circumferentially-alternating third and fourth staple openings (6820c, 6820d). As shown, each radially inner and outer staple opening (6820a, 6820b, 6820c, 6820d) is oriented non-tangentially relative to a respective reference circle (not shown), such that each first staple opening (6820a) extends generally radially outwardly in a clockwise direction, each second staple opening (6820b) extends generally radially inwardly in a clockwise direction, each third staple opening (6820c) extends generally radially outwardly in a clockwise direction, and each fourth staple opening (6820d) extends generally radially inwardly in a clockwise direction.

Due to the relative positions and orientations of staple openings (6820a, 6820b, 6820c, 6820d), the annular arrays of staple openings (6820a, 6820b, 6820c, 6820d) may define a plurality of generally V-shaped staple opening patterns. In this regard, each first staple opening (6820a) and corresponding counterclockwise-adjacent second staple opening (6820b) may collectively define a respective V-shaped staple opening pattern with a first internal angle (β1) opening toward outer edge (6816), while each third staple opening (6820c) and corresponding clockwise-adjacent fourth staple opening (6820d) may collectively define a respective V-shaped staple opening pattern with a second internal angle (β2) opening toward inner edge (6814). In some versions, the first internal angle (β1) may be different from (e.g., greater than or less than) the second internal angle (β2). In addition, or alternatively, deck member (6810) may be used to deploy three dimensional staples (not shown) to spread the compression zone for each staple. In any event, the V-shaped staple opening patterns may enable the annular arrays of formed staples (90a, 90b, 90c, 90d) driven from deck member (6810) to expand radially while maintaining a secure seal.

O. Exemplary Deck Member with Staple Openings in Alternating "U" Patterns

FIG. 124 depicts an exemplary deck member (6910) for use with instrument (10) described above. Deck member (6910) is similar to deck member (5510) described above except as otherwise described below. In this regard, deck member (6910) includes a deck surface (6912) extending radially between a generally circular radially inner edge (6914) and a generally circular radially outer edge (6916). Deck member (6910) has a central opening (6918) defined by radially inner edge (6914).

Deck surface (6912) of the present version has three concentric annular arrays of linear staple openings (6920a, 6920b, 6920c, 6920d) arranged in a radially inner annular array of first staple openings (6920a), a radially intermediate annular array of circumferentially-alternating second and third staple openings (6920b, 6920c), and a radially outer annular array of fourth staple openings (6920d). As shown, each radially inner and outer staple opening (6920a, 6920d) is oriented tangentially relative to a corresponding reference circle (not shown). Each radially intermediate staple opening (6920b, 6920c) is oriented non-tangentially relative to a respective reference circle (C), such that each second staple opening (6920b) extends generally radially inwardly in a clockwise direction and each third staple opening (6920c) extends generally radially outwardly in a clockwise direction. In the example shown, each radially inner staple opening (6920a) is positioned slightly radially inwardly relative to circle (C) such that each radially inner staple opening (6920a) is positioned closer to the radially inner ends of second and third staple openings (6920b, 6920c) than their radially outer ends, while each radially outer staple opening (6920d) is positioned slightly radially outwardly relative to circle (C) such that each radially outer staple opening (6920*d*) is positioned closer to the radially outer ends of second and third staple openings (6920*b*, 6920*c*) than their radially inner ends.

Due to the relative positions and orientations of staple openings (6920*a*, 6920*b*, 6920*c*, 6920*d*), the annular arrays of staple openings (6920*a*, 6920*b*, 6920*c*, 6920*d*) may define a plurality of generally U-shaped staple opening patterns. In this regard, each first staple opening (6920*a*), corresponding counterclockwise-adjacent second staple opening (6920*b*), and corresponding clockwise-adjacent third staple opening (6920*c*) may collectively define a respective U-shaped staple opening pattern, while each fourth staple opening (6920*d*), corresponding clockwise-adjacent second staple opening (6920*b*), and corresponding counterclockwise-adjacent third staple opening (6920*c*) may collectively define a respective U-shaped staple opening pattern. The U-shaped staple opening patterns may enable the annular arrays of formed staples (90*a*, 90*b*, 90*c*, 90*d*) driven from deck member (6910) to expand radially while maintaining a secure seal.

VIII. Exemplary Alternative Features for Circular Surgical Fastening Instruments As noted above, the inner diameter of anastomosis (70) formed by instrument (10) is defined by the outer diameter of knife member (340). Because knife member (340) is smaller than the inner diameters of tubular anatomical structures (20, 40), the resulting diameter of anastomosis (70) is generally smaller than that of each tubular anatomical structure (20, 40). Additionally, the configuration of formed staples (90) may inhibit the ability of anastomosis (70) to expand radially.

In some procedures, it may be desirable to form an anastomosis (70) of enlarged diameter and/or to enable the annular arrays of formed staples (90) (or other fastener configurations) to expand radially, thereby minimizing strictures, enabling better peristalsis, and minimizing local tension in and resulting damage to the joined portions of tubular anatomical structures (20, 40). Accordingly, in some such instances, it may be desirable to configure stapling head assembly (300) and anvil (400) with features that enable formation of such an anastomosis and/or patterns of formed staples (90). In addition, or alternatively, it may be desirable to configure stapling head assembly (300) and/or anvil (400) with features that enable increased densities of formed staples (90) while minimizing the outer diameter of anvil (400) (e.g., by maintaining the outer diameter of anvil (400) or by decreasing the outer diameter of anvil (400)). In some instances, it may be desirable to configure anvil (400) with features that enable radial contraction of anvil (400) during proximal retraction of anvil (400) through anastomosis (70). Exemplary versions of such features are described in greater detail below.

A. Exemplary Flexible Barbed Ring

FIGS. 125A-127 depict an exemplary fastening ring element in the form of a flexible barbed ring (7010) for use with instrument (10) described above. In this regard, barbed ring (7010) may be used in addition, or alternatively, to staples (90). For example, barbed ring (7010) may be driven through the tissue of tubular anatomical structures (20, 40) by instrument (10), such that barbed ring (7010) secures the ends of tissue together, thereby coupling tubular anatomical structure (20) with tubular anatomical structure (40). To that end, barbed ring (7010) may be constructed of a biocompatible material, such as a bioabsorbable or implantable polymeric or metallic material.

As shown, barbed ring (7010) includes a generally annular body (7012) extending about a longitudinal axis (L) and an annular array of barbs (7014) extending upwardly (e.g., distally) from body (7012). Barbed ring (7010) includes a central opening (7016) having an inner diameter that is just slightly larger than the outer diameter defined by knife member (340) (FIG. 126). Body (7012) includes circumferentially-alternating barb platforms (7020) and flexible spring elements in the form of generally U-shaped and/or V-shaped bridges (7022). In this regard, barb platforms (7020) and bridges (7022) may be integrally formed together with each other as a unitary (e.g., monolithic) piece. In the present version, each bridge (7022) extends between a corresponding circumferentially-adjacent pair of barb platforms (7020) and is at least partially defined by a pair of radially-inwardly extending slots (7024, 7026) and a radially-outwardly extending slot (7028) positioned circumferentially therebetween. As shown, each bridge (7022) may be relatively thin and thus exhibit relatively reduced rigidity, at least by comparison to barb platforms (7020). In any event, a pair of radially inner living hinges (7030, 7032) are defined at or near respective radially inner ends of each bridge (7022), and a radially outer living hinge (7034) is defined at or near a radially outer apex of each bridge (7022). In the example shown, an annular groove (7036) (FIG. 126) extends upwardly from a lower surface of body (7012) at or near a circumferential midline of body (7012), the purpose of which is described below.

In the present version, barbs (7014) are arranged with uniform circumferential spacing about longitudinal axis (L). Each barb (7014) extends upwardly from and is fixedly coupled to a corresponding barb platform (7020). In this regard, each barb (7014) and corresponding barb platform (7020) may be integrally formed together with each other as a unitary (e.g., monolithic) piece. As best shown in FIGS. 126-127, each barb (7014) includes a sharp upper conical tip (7040) and a plurality of downwardly-facing annular ridges (7042) stacked on top of each other below conical tip (7040) for promoting advancement of barbs (7014) through tissue (e.g., in an upward direction) and resisting retraction of barbs (7014) out of tissue (e.g., in a downward direction).

In the example shown, barbed ring (7010) is configured to radially expand from a radially unexpanded state (FIG. 125A) to a radially expanded state (FIG. 125B) to accommodate expansion of anastomosis (70) in a radial direction. For example, each barb (7014) may be generally pivotable relative to a corresponding circumferentially-adjacent barb (7014) about any one or more of the respective living hinges (7030, 7032, 7034) positioned therebetween to permit tissue expansion between circumferentially-adjacent pairs of barbs (7014). In addition, or alternatively, the relatively thin bridges (7022) may be radially expandable in response to loads applied thereto (e.g., either naturally or manually) to assist with transitioning barbed ring (7010) from the radially unexpanded state toward the radially expanded state.

As shown in FIG. 126, barbed ring (7010) may be deployable from a fastening head assembly (7050) which may be incorporated into instrument (10) in place of fastening head assembly (300). For example, fastening head assembly (7050) may be coupled to a distal end of shaft assembly (200). In any event, fastening head assembly (7050) of the present example includes a ring driver member (7052) and knife member (340) described above and fixedly secured to ring driver member (7052). Knife member (340) defines an outer diameter that is just smaller than the diameter defined by the radially inner-most surfaces of ring driver member (7052). Ring driver member (7052) is configured to drive barbed ring (7010) distally relative to a casing (7053) when fastening head assembly (7050) is actuated (or "fired"). In this regard, ring driver member (7052) includes a generally cylindrical sidewall (7054) and an annular protrusion (7056) extending upwardly from an upper surface of sidewall (7054) at or near a circumferential midline of sidewall (7054) for receipt within groove (7036) of barbed ring (7010) to thereby stabilize barbed ring (7010) on ring driver member (7052) before and/or during actuation of fastening head assembly (7050). In any event, fastening head assembly (7050) may be distally actuatable (e.g., relative to casing (110) of handle assembly (100)) for driving knife member (340) and ring driver member (7052) distally together.

As shown in FIG. 127, barbed ring (7010) may be driven at least partially through the tissue of tubular anatomical structures (20, 40), such as via distal translation of ring driver member (7052), until conical tips (7040) of barbs (7014) are positioned at or above an upper surface of tissue of tubular anatomical structure (20) and an upper surface of body (7012) is in contact or near contact with a lower surface of tissue of tubular anatomical structure (40). Knife member (340) may be translated distally to cut the tissue of tubular anatomical structures (20, 40) in a manner similar to that described above in connection with FIGS. 7A-7E. In any event, ridges (7042) may grip the tissue of tubular anatomical structures (20, 40) to resist retraction of barbs (7014) from the tissue of tubular anatomical structures (20, 40), thereby coupling tubular anatomical structure (20) with tubular anatomical structure (40) at anastomosis (70), and barbed ring (7010) may be radially expandable to accommodate radial expansion of anastomosis (70) in the manner described above.

B. First Exemplary Staple Chain

FIGS. 128A-129 depict an exemplary staple chain (7110) for use with instrument (10) described above. In this regard, staple chain (7110) may be used in addition, or alternatively, to staples (90). For example, staple chain (7110) may be driven through the tissue of tubular anatomical structures (20, 40) by instrument (10), such that staple chain (7110) secures the ends of tissue together, thereby coupling tubular anatomical structure (20) with tubular anatomical structure (40).

As shown, staple chain (7110) includes a plurality of staples (7112) pivotably coupled to each other. Each staple (7112) includes a crown (7114) extending between first and second ends (7116, 7118), and further includes a single leg (7120) extending upwardly and generally perpendicularly from first end (7116) of crown (7114) to a sharp tip (7122) configured to puncture tissue, such as tubular anatomical structures (20, 40). In the example shown, each staple (7112) also includes an eyelet (7124) positioned at or near second end (7118) of crown (7114) and having an eyelet bore (7126). Each bore (7126) has a cross dimension (e.g., diameter) substantially equal to or slightly greater than that of the respective leg (7120), and is oriented such that a longitudinal axis (L) of each bore (7126) is generally parallel to the respective leg (7120). In this manner, the bore (7126) of each staple (7112) may be configured to pivotably receive the leg (7120) of an adjacent staple (7112) to thereby define staple chain (7110). In some versions, each staple (7112) may be manufactured via a continuous wire-forming process, and a plurality of staples (7112) may be subsequently pivotably coupled to each other to form staple chain (7110). For example, the leg (7120) of each staple (7112) may be inserted into the bore (7126) of the adjacent staple (7112) during loading of staples (7112) into a staple cartridge (not shown). While three staples (7112) are shown, it will be appreciated that any suitable number of staples (7112) may be included in staple chain (7110).

In the example shown, staples (7112) of staple chain (7110) are coupled to each other in an open-ended linkage with the midpoints of their respective crowns (7114) arranged along a reference line (not shown) to define a longitudinal array of staples (7112). Moreover, the orientations of staples (7112) alternate longitudinally, with one staple (7112) of each longitudinally-adjacent pair of staples (7112) extending at least partially in a first lateral direction and the other staple (7112) of each longitudinally-adjacent pair of staples (7112) extending at least partially in a second lateral direction opposite the first direction to define an undulating (e.g., "zig-zag") pattern. In some versions, a plurality of staple chains (7110) may be arranged circumferentially, with the midpoints of the crowns (7114) of their respective staples (7112) arranged along one or more reference circles (not shown) to define one or more annular arrays of staples (7112). In other versions, staples (7112) of staple chain (7110) may be coupled to each other in a closed loop and thereby form a fastening ring element, with the midpoints of their respective crowns (7114) arranged along a reference circle (not shown) to define an annular array of staples (7112). Moreover, the orientations of staples (7112) may alternate circumferentially, with one staple (7112) of each circumferentially-adjacent pair of staples (7112) extending radially inwardly in a first circumferential direction (e.g., clockwise or counterclockwise) and the other staple (7112) of each circumferentially-adjacent pair of staples (7112) extending radially outwardly in the first circumferential direction to define an undulating (e.g., "zig-zag") staple pattern.

As shown, each staple (7112) may be formed by a corresponding staple forming pocket from a respective initial (e.g., unformed) state (FIG. 128A) into a respective formed state (FIGS. 128B-128C). In the formed state, the crown (7114) and bent leg (7120) of each staple (7112) each reside in a corresponding plane, such that the tip (7122) of each staple (7112) generally confronts the respective eyelet (7124). In the example shown, each bent leg (7120) is substantially curved within the corresponding plane. Alternatively, each bent leg (7120) may be substantially flat within the corresponding plane. In any event, each bent leg (7120) remains pivotably received within the bore (7126) of the adjacent formed staple (7112).

In the example shown, staple chain (7110) is configured to longitudinally expand from a longitudinally unexpanded state (FIGS. 128A-128B) to a longitudinally expanded state (FIG. 128C). In some versions, such as those described above in which staples (7112) are arranged in one or more annular arrays, one or more staple chains (7110) may be configured to individually or collectively radially expand from a radially unexpanded state to a radially expanded state to accommodate expansion of anastomosis (70) in a radial direction. For example, each staple (7112) may be generally pivotable relative to a corresponding circumferentially-adjacent staple (7112) about the corresponding longitudinal axis (L) to permit tissue expansion between circumferentially-adjacent pairs of staples (7112). In some versions, a maximum achievable diameter of the circular array(s) of staples (7112) of staple chain (7110) may restrict over-expansion of anastomosis (70) by defining a maximum tissue expansion limit and thereby prevent dehiscence, and/or may provide increased strength to anastomosis (70) when staple chain (7110) is in its expanded state.

C. Second Exemplary Staple Chain

FIGS. 130-131 depict another exemplary staple chain (7210) for use with instrument (10) described above. Staple chain (7210) is similar to staple chain (7110) described above except as otherwise described below. In this regard, staple chain (7210) may be driven through the tissue of tubular anatomical structures (20, 40) by instrument (10), such that staple chain (7210) secures the ends of tissue together, thereby coupling tubular anatomical structure (20) with tubular anatomical structure (40).

As shown, staple chain (7210) includes a plurality of staples (7212) pivotably coupled to each other. Each staple (7212) includes a crown (7214) extending between first and second ends (7216, 7218), and further includes a pair of legs (7220) extending upwardly and generally perpendicularly from respective ends (7216, 7218) of crown (7214) to respective sharp tips (7222) configured to puncture tissue, such as tubular anatomical structures (20, 40). In the example shown, each staple (7212) is fixedly coupled to a corresponding backspan (7230). In this regard, each backspan (7230) includes a crown plate (7232) extending between first and second ends (7234, 7236). As shown, first and second staple leg bores (7238, 7239) extend through crown plate (7232) at or near respective ends (7234, 7236) thereof. Each staple leg bore (7238, 7239) has a cross dimension (e.g., diameter) substantially equal to or slightly less than that of the legs (7220) of the respective staple (7212). In this manner, the staple leg bores (7238, 7239) of each backspan (7230) may be configured to fixedly receive the legs (7220) of the respective staple (7212), such as via a press fit. As shown, each backspan (7230) further includes first and second eyelets (7240, 7242) positioned at or near respect ends (7234, 7236) of crown plate (7232) and having first and second eyelet bores (7244, 7246), respectively. Each eyelet bore (7244, 7246) has a cross dimension (e.g., diameter) substantially equal to or slightly greater than a thickness of the other eyelet (7240, 7242), and is oriented such that a longitudinal axis (L2) of each second bore (7246) is generally parallel to the respective legs (7220) and such that a longitudinal axis (L1) of each first bore (7244) is generally perpendicular to the longitudinal axis (L2) of the respective second bore (7246) and generally perpendicular to a longitudinal axis of the respective crown plate (7232). In this manner, the second bore (7246) of each backspan (7230) may be configured to pivotably receive the first eyelet (7240) of an adjacent backspan (7230) to thereby define staple chain (7210). In some versions, each backspan (7230) may be formed via a stamping process, and a corresponding staple (7212) may subsequently be threaded through the staple leg bores (7238, 7239) of the backspan (7230) and press fit thereto to define a respective staple assembly. A plurality of such staple assemblies may be subsequently pivotably coupled to each other to form staple chain (7210). While three staples (7212) and corresponding backspans (7230) are shown, it will be appreciated that any suitable number of staples (7212) and corresponding backspans (7230) may be included in staple chain (7210).

In the example shown, staples (7212) of staple chain (7210) are coupled to each other in an open-ended linkage with the midpoints of their respective crowns (7214) arranged along a reference line (not shown) to define a longitudinal array of staples (7212). Moreover, the orientations of staples (7212) alternate longitudinally, with one staple (7212) of each longitudinally-adjacent pair of staples (7212) extending at least partially in a first lateral direction and the other staple (7212) of each longitudinally-adjacent pair of staples (7212) extending at least partially in a second lateral direction opposite the first direction to define an undulating (e.g., "zig-zag") pattern. In some versions, a plurality of staple chains (7210) may be arranged circumferentially, with the midpoints of the crowns (7214) of their respective staples (7212) arranged along one or more reference circles (not shown) to define one or more annular arrays of staples (7212). In other versions, staples (7212) of staple chain (7210) may be coupled to each other in a closed loop and thereby form a fastening ring element, with the midpoints of their respective crowns (7214) arranged along a reference circle (not shown) to define an annular array of staples (7212). Moreover, the orientations of staples (7212) may alternate circumferentially, with one staple (7212) of each circumferentially-adjacent pair of staples (7212) extending radially inwardly in a first circumferential direction (e.g., clockwise or counterclockwise) and the other staple (7212) of each circumferentially-adjacent pair of staples (7212) extending radially outwardly in the first circumferential direction to define an undulating (e.g., "zig-zag") staple pattern.

While not shown, each staple (7212) may be formed by a corresponding staple forming pocket from a respective initial (e.g., unformed) state into a respective formed state, in a manner generally similar to that described above in connection with FIGS. 128A-128C. In the formed state, the crown (7214) and bent legs (7220) of each staple (7212) each reside in a corresponding plane, such that the tips (7222) of each staple (7212) generally confront each other. In any event, each first eyelet (7240) remains pivotably received within the second bore (7246) of the adjacent backspan (7230).

While not shown, staple chain (7210) is configured to longitudinally expand from a longitudinally unexpanded state to a longitudinally expanded state, in a manner generally similar to that described above in connection with FIGS. 128A-128C. In some versions, such as those described above in which staples (7212) are arranged in one or more annular arrays, one or more staple chains (7210) may be configured to individually or collectively radially expand from a radially unexpanded state to a radially expanded state to accommodate expansion of anastomosis (70) in a radial direction. For example, each staple (7212) may be generally pivotable relative to a corresponding circumferentially-adjacent staple (7212) about the corresponding second longitudinal axis (L2) to permit tissue expansion between circumferentially-adjacent pairs of staples (7212). In some versions, a maximum achievable diameter of the circular array(s) of staples (7212) of staple chain (7210) may restrict over-expansion of anastomosis (70) by defining a maximum tissue expansion limit and thereby prevent dehiscence, and/or may provide increased strength to anastomosis (70) when staple chain (7210) is in its expanded state.

D. First Exemplary Deck Member for Deploying Staple Chain

FIG. 132 depicts an exemplary deck member (7310) for use with instrument (10) described above. Deck member (7310) is similar to deck member (320) described above except as otherwise described below. In this regard, deck member (7310) may be fixedly secured to a distal end of a body member (not shown) of a stapling head assembly (not shown), such as body member (310) of stapling head assembly (300), and may be configured to permit a knife member (not shown), such as knife member (340), to translate longitudinally through deck member (7310) to actuate between a proximal retracted position and a distal extended position in a manner similar to that described above in connection with FIGS. 1-7E.

As shown, deck member (7310) includes a distally presented stapling surface in the form of a deck surface (7312) extending radially between a generally circular radially inner edge (7314) and a generally circular radially outer edge (7316). Deck member (7310) has a central opening (7318) defined by radially inner edge (7314) and having an inner diameter that is just slightly larger than the outer diameter defined by knife member (340). Deck member (7310) is thus configured to permit knife member (340) to translate longitudinally through the central opening concurrently with longitudinal translation of staple driver member (350). In particular, knife member (340) is configured to actuate relative to deck member (7310) between a proximal retracted position and a distal extended position, where cutting edge (342) is proximal to deck surface (7312) in the proximal retracted position and distal to deck surface (7312) in the distal extended position.

Deck surface (7312) of the present version has two concentric annular arrays of linear staple openings (7320*a*, 7320*b*, 7320*c*) arranged to align with corresponding arrays of staple drivers (not shown) similar to staple drivers (352) of staple driver member (350) and with corresponding arrays of staple forming pockets (not shown) similar to staple forming pockets (414) of anvil (400) described above. Each staple opening (7320*a*, 7320*b*, 7320*c*) is configured to slidably receive and provide a pathway for a corresponding staple driver to drive a corresponding staple (90, 7112, 7212) distally through deck member (7310) and into a corresponding staple forming pocket when a stapling head assembly (not shown) similar to stapling head assembly (300) is actuated.

In the example shown, linear staple openings (7320*a*, 7320*b*, 7320*c*) are arranged in a radially inner annular array of circumferentially-alternating first and second staple openings (7320*a*, 7320*b*) and a radially outer annular array of third staple openings (7320*c*). As shown, each radially outer staple opening (7320*c*) is oriented tangentially relative to a corresponding reference circle (not shown) along which the midpoints of radially outer staple openings (7320*c*) are circumferentially spaced apart. Each radially outer staple opening (7320*c*) is isolated relative to the remaining staple openings (7320*a*, 7320*b*, 7320*c*) such that each radially outer staple opening (7320*c*) is configured for receipt and deployment of a respective staple (90). As shown, each radially inner staple opening (7320*a*, 7320*b*) is oriented non-tangentially relative to a corresponding reference circle (not shown) along which the midpoints of radially inner staple openings (7320*a*, 7320*b*) are circumferentially spaced apart, such that each first staple opening (7320*a*) extends generally radially inwardly in a clockwise direction and each second staple opening (7320*b*) extends generally radially outwardly in a clockwise direction. Each first staple opening (7320*a*) is in communication with the clockwise-adjacent second staple opening (7320*b*) at or near the respective radially inner ends thereof and is also in communication with the counterclockwise-adjacent second staple opening (7320*b*) at or near the respective radially outer ends thereof to define a continuous, undulating staple opening pattern. In this manner, radially inner staple openings (7320*a*, 7320*b*) are collectively configured for receipt and deployment of one or more respective staple chains (7110, 7210) having either a closed loop or open-ended configuration, as described above in connection with FIGS. 128A-131.

E. Second Exemplary Deck Member for Deploying Staple Chain

FIG. 133 depicts another exemplary deck member (7410) for use with instrument (10) described above. Deck member (7410) is similar to deck member (7310) described above except as otherwise described below. In this regard, deck member (7410) includes a deck surface (7412) extending radially between a generally circular radially inner edge (7414) and a generally circular radially outer edge (7416). Deck member (7410) has a central opening (7418) defined by radially inner edge (7414).

Deck surface (7412) of the present version has three concentric annular arrays of linear staple openings (7320*a*, 7320*b*, 7320*c*, 7420) arranged in a radially intermediate annular array of circumferentially-alternating first and second staple openings (7320*a*, 7320*b*), a radially outer annular array of third staple openings (7320*c*), and a radially inner annular array of fourth staple openings (7420). As shown, each radially inner staple opening (7420) is oriented tangentially relative to a corresponding reference circle (not shown) along which the midpoints of radially inner staple openings (7420) are circumferentially spaced apart. Each radially inner staple opening (7420) is isolated relative to the remaining staple openings (7320*a*, 7320*b*, 7320*c*, 7420) such that each radially inner staple opening (7420) is configured for receipt and deployment of a respective staple (90).

F. Third Exemplary Deck Member for Deploying Staple Chain

FIGS. 134-135 depict another exemplary deck member (7510) for use with instrument (10) described above. Deck member (7510) is similar to deck member (7310) described above except as otherwise described below. In this regard, deck member (7510) includes a deck surface (7512) extending radially between a generally circular radially inner edge (7514) and a generally circular radially outer edge (7516). Deck member (7510) has a central opening (7518) defined by radially inner edge (7514).

Deck surface (7512) of the present version has two concentric annular arrays of linear staple openings (7520*a*, 7520*b*, 7520*c*) arranged in a radially inner annular array of circumferentially-alternating first and second staple openings (7520*a*, 7520*b*) and a radially outer annular array of third staple openings (7520*c*). As shown, each radially outer staple opening (7520*c*) is oriented tangentially relative to a corresponding reference circle (not shown) along which the midpoints of radially outer staple openings (7520*c*) are circumferentially spaced apart. Each radially inner staple opening (7520*a*, 7520*b*) is oriented non-tangentially relative to a corresponding reference circle (not shown) along which the midpoints of radially inner staple openings (7520*a*, 7520*b*) are circumferentially spaced apart, such that each first staple opening (7520*a*) extends generally radially outwardly in a clockwise direction and each second staple opening (7520*b*) extends generally radially inwardly in a clockwise direction. As shown, each radially outer staple opening (7520*c*) is in communication with the circumferentially-adjacent radially inner staple openings (7520*a*, 7520*b*) at or near the respective radially outer ends thereof, and each first staple opening (7520*a*) is in communication with the counterclockwise-adjacent second staple opening (7520*b*) at or near the respective radially inner ends thereof to define a continuous, repeating plateau-shaped staple opening pattern. In this manner, staple openings (7520*a*, 7520*b*, 7520*c*) are collectively configured for receipt and deployment of one or more respective staple chains (7110, 7210) having either a closed loop or open-ended configuration, as described above in connection with FIGS. 128A-131. In other versions, each first staple opening (7520*a*) may be isolated relative to the counterclockwise-adjacent second staple opening (7520b) to define a divided, repeating plateau-shaped staple opening pattern.

G. Fourth Exemplary Deck Member for Deploying Staple Chain

FIG. 136 depicts another exemplary deck member (7610) for use with instrument (10) described above. Deck member (7610) is similar to deck member (7510) described above except as otherwise described below. In this regard, deck member (7610) includes a deck surface (7612) extending radially between a generally circular radially inner edge (7614) and a generally circular radially outer edge (7616). Deck member (7610) has a central opening (7618) defined by radially inner edge (7614).

Deck surface (7612) of the present version has three concentric annular arrays of linear staple openings (7520a, 7520b, 7520c, 7620) arranged in a radially intermediate annular array of circumferentially-alternating first and second staple openings (7520a, 7520b), a radially outer annular array of third staple openings (7520c), and a radially inner annular array of fourth staple openings (7620). As shown, each radially inner staple opening (7620) is oriented tangentially relative to a corresponding reference circle (not shown) along which the midpoints of radially inner staple openings (7620) are circumferentially spaced apart. Each radially inner staple opening (7620) is isolated relative to the remaining staple openings (7520a, 7520b, 7520c, 7620) such that each radially inner staple opening (7620) is configured for receipt and deployment of a respective staple (90).

H. Fifth Exemplary Deck Member for Deploying Staple Chain

FIG. 137 depicts another exemplary deck member (7710) for use with instrument (10) described above. Deck member (7710) is similar to deck member (7310) described above except as otherwise described below. In this regard, deck member (7710) includes a deck surface (7712) extending radially between a generally circular radially inner edge (7714) and a generally circular radially outer edge (7716). Deck member (7710) has a central opening (7718) defined by radially inner edge (7714).

Deck surface (7712) of the present version has a single annular array of linear staple openings (7720a, 7720b, 7720c, 7720d) oriented non-tangentially relative to a corresponding reference circle (not shown) along which the midpoints of staple openings (7720a, 7720b, 7720c, 7720d) are circumferentially spaced apart, such that each first and third staple opening (7720a, 7720c) extends generally radially inwardly in a clockwise direction and each second and fourth staple opening (7720b, 7720d) extends generally radially outwardly in a clockwise direction. Each first staple opening (7720a) is in communication with the clockwise-adjacent second staple opening (7720b) at or near the respective radially inner ends thereof and is also in communication with the counterclockwise-adjacent second staple opening (7720b) at or near the respective radially outer ends thereof to define a continuous, undulating staple opening pattern. In this manner, first and second staple openings (7720a, 7720b) are collectively configured for receipt and deployment of one or more respective staple chains (7110, 7210) having either a closed loop or open-ended configuration, as described above in connection with FIGS. 128A-131. Similarly, each third staple opening (7720c) is in communication with the clockwise-adjacent fourth staple opening (7720d) at or near the respective radially inner ends thereof and is also in communication with the counterclockwise-adjacent fourth staple opening (7720d) at or near the respective radially outer ends thereof to define a continuous, undulating staple opening pattern overlapping that defined by first and second staple openings (7720a, 7720b). In this manner, third and fourth staple openings (7720c, 7720d) are collectively configured for receipt and deployment of one or more respective staple chains (7110, 7210) having either a closed loop or open-ended configuration, as described above in connection with FIGS. 128A-131.

As shown, each first staple opening (7720a) intersects a corresponding fourth staple opening (7720d) at or near respective midpoints thereof, while each second staple opening (7720b) intersects a corresponding third staple opening (7720c) at or near respective midpoints thereof. In some versions, first and second staple openings (7720a, 7720b) may have lower ends positioned at a first depth below deck surface (7712), and third and fourth staple openings (7720c, 7720d) may have lower ends positioned at a second depth below deck surface (7712) different from (e.g., greater or less than) the first depth for allowing the staple chain(s) (7110, 7210) received within first and second staple openings (7720a, 7720b) to overlap the staple chain(s) (7110, 7210) received within third and fourth staple openings (7720c, 7720d).

I. Exemplary Deck Member for Deploying Expandable Support Ring

FIG. 138 depicts another exemplary deck member (7810) for use with instrument (10) described above. Deck member (7810) is similar to deck member (7310) described above except as otherwise described below. In this regard, deck member (7810) includes a deck surface (7812) extending radially between a generally circular radially inner edge (7814) and a generally circular radially outer edge (7816). Deck member (7810) has a central opening (7818) defined by radially inner edge (7814).

Deck surface (7812) of the present version has a single annular array of linear staple openings (7820) oriented non-tangentially relative to a corresponding reference circle (not shown) along which the midpoints of staple openings (7820) are circumferentially spaced apart, such that each staple opening (7820) extends generally radially inwardly in a clockwise direction. Each staple opening (7820) is isolated relative to the remaining staple openings (7820) such that each staple opening (7820) is configured for receipt and deployment of a respective staple (90). It will be appreciated that the non-tangential orientations of staple openings (7820) may enable the annular arrays of formed staples (90) driven from deck member (7810) to expand radially while maintaining a secure seal.

In the example shown, an exemplary support ring (7830) is positioned on deck surface (7812). Support ring (7830) of the present version includes a flexible wire (7832) extending between first and second looped ends (7834, 7836) and having a spiraled configuration to generally define a radially inner circumferential row and a radially outer circumferential row. In some versions, a groove (not shown) may be provided in deck surface (7812) for receiving support ring (7830). In any event, support ring (7830) may extend across each staple opening (7820) above a corresponding staple (90) positioned therein. In this manner, support ring (7830) may be captured by staples (90) during deployment of staples (90) from deck member (7810) and may thereby be deployed together with staples (90) for providing a redundant seal between circumferentially-adjacent staples (90). Support ring (7830) may be configured to radially expand from the illustrated radially unexpanded state to a radially expanded state (not shown) to accommodate expansion of anastomosis (70) in a radial direction.

While support ring (7830) of the present version is a unitary piece, support ring (7830) may alternatively include a plurality of separate pieces coupled together or spaced apart from each other. Such versions of support ring (7830) may provide increased flexibility as well as the ability of support ring (7830) to pass through the digestive tract of a patient and out of the patient's body after healing has occurred. In addition, or alternatively, support ring (7830) may be used in conjunction with three dimensional staples (not shown) to even out pressure from opposite sides of support ring (7830).

J. Exemplary Deck Member for Deploying Non-Uniform 3D Staples

FIG. 139 depicts another exemplary deck member (7910) for use with instrument (10) described above. Deck member (7910) is similar to deck member (7310) described above except as otherwise described below. In this regard, deck member (7910) includes a deck surface (7912) extending radially between a generally circular radially inner edge (7914) and a generally circular radially outer edge (7916). Deck member (7910) has a central opening (7918) defined by radially inner edge (7914).

Deck surface (7912) of the present version has a single annular array of linear staple openings (7920) oriented non-tangentially relative to a corresponding reference circle (not shown) along which the midpoints of staple openings (7920) are circumferentially spaced apart, such that each staple opening (7920) extends generally radially outwardly in a clockwise direction. Each staple opening (7920) is isolated relative to the remaining staple openings (7920) such that each staple opening (7920) is configured for receipt and deployment of a respective staple (90). It will be appreciated that the non-tangential orientations of staple openings (7920) may enable the annular arrays of formed staples (90) driven from deck member (7910) to expand radially while maintaining a secure seal.

In some versions, deck member (7910) may be used to deploy three dimensional staples (not shown) to spread the compression zone for each staple. To enable proper pressure field in the tissue, non-uniform formed lengths of such three dimensional staples may be used, with the radially outer staple leg of each three dimensional staple being less formed than the respective radially inner staple leg. In this manner, a variable three dimensional pressure gradient may be provided radially outwardly across the staple line from tightest to loosest, thereby promoting proper healing conditions as well as a secure seal.

K. First Exemplary Radially Contractable Anvil

FIGS. 140A-141 depict an exemplary anvil (8010) for use with instrument (10) described above. Anvil (8010) is similar to anvil (400) described above except as otherwise described below. In this regard, anvil (8010) may be configured to removably couple with a shaft assembly (not shown), such as shaft assembly (200), adjacent to a stapling head assembly (not shown), such as stapling head assembly (300), and may be configured to cooperate with the stapling head assembly to clamp, cut, and/or staple tissue in a manner similar to that described above in connection with FIGS. 1-7E.

As shown, anvil (8010) of the present example comprises a segmented anvil head (8012), an anvil core (8014), and a translatable member in the form of an anvil cap (8016). Anvil core (8014) includes a shank (8020) defining a bore (8021), and further includes a plurality of (e.g., four) distal, generally T-shaped ramps (8022) extending radially outwardly from shank (8020) and circumferentially spaced apart from each other at uniform intervals. Each ramp (8022) includes a radially outer cam surface (8024) tapered radially inwardly in a distal direction, the purpose of which is described below. Head (8012) includes a plurality of (e.g., four) head segments (8030) movable relative to each other, with each head segment (8030) having a generally T-shaped slot (8032) configured to slidably receive a corresponding ramp (8022) such that each head segment (8030) may be translatable along the corresponding ramp (8022). More particularly, the slot (8032) of each head segment (8030) includes a radially inner cam surface (8034) tapered radially inwardly in a distal direction for cammingly engaging the radially outer cam surface (8024) of the corresponding ramp (8022). In some versions, each radially inner cam surface (8034) may be tapered radially inwardly in a distal direction at a substantially same angle as that at which the corresponding radially outer cam surface (8024) is tapered. In this manner, distal movement of each head segment (8030) relative to the corresponding ramp (8022) may be converted into radially inward movement of the head segment (8030), such that each head segment (8030) is obliquely translatable relative to core (8014) between a radially extended state (FIG. 140A) and a radially unextended state (FIG. 140B). As shown, each head segment (8030) further includes a proximal stapling surface (8036) that defines a plurality of staple forming pockets (8038) (e.g., collectively arranged in two concentric annular arrays) configured to deform staples (90) driven therein.

Anvil cap (8016) includes a stem (8040) and a distal cover (8042) extending radially outwardly therefrom. Stem (8040) is slidably received within bore (8021) of shank (8020), such that cap (8016) is longitudinally translatable relative to core (8014) between a proximal state (FIG. 140A) in which cover (8042) securely clamps head segments (8030) against the corresponding ramps (8022) in their radially extended states, and a distal state (FIG. 140B) in which cover (8042) permits head segments (8030) to translate obliquely along the corresponding ramps (8022) toward their radially unextended states. In the example shown, cap (8016) is resiliently biased toward the distal state by an energy storage device in the form of a compression spring (8044) positioned between a proximal end of stem (8040) and a proximal end of bore (8021). Cap (8016) is also selectively lockable in the proximal state by a latching mechanism, which includes a detent (8046) configured to be selectively received by and removed from a corresponding recess (8048) provided in stem (8040) via an opposing pair of release buttons (8049).

During operation, cap (8016) may initially be locked in the proximal state to secure head segments (8030) in their radially extended states during driving of staples (90) through the tissue of tubular anatomical structures (20, 40) into staple forming pockets (8038), as shown in FIG. 140A. Cap (8016) may subsequently be urged to the distal state. For example, the operator may press release buttons (8049) radially inwardly using a grasper (not shown), as indicated by arrows (A1, A2) in FIG. 140B, to remove detent (8046) from recess (8048) and thereby allow spring (8044) to urge cap (8016) to the distal state. Head segments (8030) may then be moved to their radially unextended states for assisting with retraction of anvil (8010) proximally through anastomosis (70). For example, head segments (8030) may be pushed distally by anastomosis (70) during proximal retraction of anvil (8010), thereby causing head segments (8030) to translate radially inwardly along the corresponding ramps (8022), as indicated by arrow (A3) in FIG. 140B.

L. Second Exemplary Radially Contractable Anvil

FIGS. 142A-142B depict another exemplary anvil (8110) for use with instrument (10) described above. Anvil (8110)

is similar to anvil (8010) described above except as otherwise described below. In this regard, anvil (8110) comprises a segmented anvil head (8112), an anvil core (8114), and a translatable member in the form of a push sleeve (8116).

In the example shown, anvil core (8114) includes a shank (8120) defining a bore (8121), and further includes a distal nose (8122) extending radially outwardly from shank (8120). Head (8112) includes a plurality of (e.g., four) head segments (8130) movable relative to each other, with each head segment (8130) being pivotably coupled to nose (8122) via a respective pivot pin (8132) such that each head segment (8130) may be pivotable relative to core (8114) about the respective pivot pin (8132) between a radially unextended state (FIG. 142A) and a radially extended state (FIG. 142B). In the present version, each head segment (8130) is resiliently biased toward the radially unextended state by a corresponding energy storage device in the form of a torsion spring (8134). As shown, each head segment (8130) further includes a proximal stapling surface (8136) that defines a plurality of staple forming pockets (8138) (e.g., collectively arranged in two concentric annular arrays) configured to deform staples (90) driven therein.

Anvil push sleeve (8116) includes a cylindrical body (8140) defining a bore (8142) slidably received about shank (8120), such that push sleeve (8116) is longitudinally translatable relative to core (8114) between a proximal state (FIG. 142A) in which a distal end of push sleeve (8116) is disengaged from head segments (8130) to permit head segments (8130) to remain in their radially unextended states, and a distal state (FIG. 142B) in which a distal end of push sleeve (8116) engages portions of head segments (8130) radially inward of the corresponding pivot pins (8132) to pivot head segments (8130) toward their radially extended states.

During operation, push sleeve (8116) may initially be in the proximal state to permit head segments (8130) to remain in their radially unextended states via the resilient biasing of spring (8134), as shown in FIG. 142A. Push sleeve (8116) may subsequently be pushed to the distal state. For example, the operator may retract trocar (330) and anvil (8110) proximally to compress the tissue of tubular anatomical structures (20, 40) between anvil (8110) and stapling head assembly (300), which may cause a proximal end of push sleeve (8116) to engage a radially inner ledge (8150) of stapling head assembly (300) and thereby push sleeve (8116) to the distal state to move head segments (8130) to their radially extended states for driving staples (90) into staple forming pockets (8138), as shown in FIG. 142B. Push sleeve (8116) may then be returned to the proximal state. For example, the operator may extend trocar (330) and anvil (8110) distally to disengage push sleeve (8116) from head segments (8130) and thereby allow springs (8134) to urge head segments (8130) to their radially unextended states for assisting with retraction of anvil (8110) proximally through anastomosis (70), as shown in FIG. 142A.

M. Third Exemplary Radially Contractable Anvil

FIGS. 143A-144 depict another exemplary anvil (8210) for use with instrument (10) described above. Anvil (8210) is similar to anvil (8110) described above except as otherwise described below. In this regard, anvil (8210) comprises a segmented anvil head (8212), an anvil core (8214), and a translatable member in the form of a push sleeve (8216).

In the example shown, anvil core (8214) includes a shank (8220) defining a bore (8221). Head (8212) includes a plurality of (e.g., four) head segments (8230) movable relative to each other, such that each head segment (8230) may be radially translatable relative to core (8214) between a radially unextended state (FIG. 143A) and a radially extended state (FIG. 143B). In some versions, each head segment (8230) may be resiliently biased toward the radially unextended state by a corresponding energy storage device, such as a spring (not shown). As shown, each head segment (8230) further includes a proximal stapling surface (8236) that defines a plurality of staple forming pockets (8238) (e.g., collectively arranged in two concentric annular arrays) configured to deform staples (90) driven therein.

Anvil push sleeve (8216) includes a cylindrical body (8240) defining a bore (8242) slidably received about shank (8220), such that push sleeve (8216) is longitudinally translatable relative to core (8214) between a proximal state (FIG. 143A) in which a distal end of push sleeve (8216) is disengaged from head segments (8230) to permit head segments (8230) to remain in their radially unextended states, and a distal state (FIG. 143B) in which a distal end of push sleeve (8216) operatively engages an internal pin or wedged feature (not shown) of head segments (8230) to push head segments (8230) toward their radially extended states.

During operation, push sleeve (8216) may initially be in the proximal state to permit head segments (8230) to remain in their radially unextended states, as shown in FIG. 143A. Push sleeve (8216) may subsequently be pushed to the distal state. For example, the operator may retract trocar (330) and anvil (8210) proximally to compress the tissue of tubular anatomical structures (20, 40) between anvil (8210) and stapling head assembly (300), as indicated by arrow (A4) in FIG. 143A, which may cause a proximal end of push sleeve (8216) to engage radially inner ledge (8150) of stapling head assembly (300) and thereby push sleeve (8216) to the distal state to move head segments (8230) to their radially extended states for driving staples (90) into staple forming pockets (8238), as indicated by arrows (A5, A6) in FIG. 143B. Push sleeve (8216) may then be returned to the proximal state. For example, the operator may extend trocar (330) and anvil (8210) distally to disengage push sleeve (8216) from head segments (8230) and thereby allow head segments (8230) to be returned to their radially unextended states for assisting with retraction of anvil (8210) proximally through anastomosis (70), as shown in FIG. 143A.

N. Fourth Exemplary Radially Contractable Anvil

FIGS. 145A-146B depict another exemplary anvil (8310) for use with instrument (10) described above. Anvil (8310) is similar to anvil (8010) described above except as otherwise described below. In this regard, anvil (8310) comprises a segmented anvil head (8312), an anvil core (8314), and a translatable member in the form of a push sleeve (8316). Anvil (8310) of the present version further includes a rotatable member in the form of a star-shaped disc (8318).

In the example shown, anvil core (8314) includes a shank (8320) defining a bore (8321). Head (8312) includes a plurality of (e.g., four) head segments (8330) movable relative to each other, with each head segment (8330) being translatably coupled to shank (8320) such that each head segment (8330) may be radially translatable relative to core (8314) between a radially unextended state (FIGS. 145A and 146A) and a radially extended state (FIGS. 145B and 146B). In some versions, each head segment (8330) may be resiliently biased toward the radially unextended state by a corresponding energy storage device, such as a spring (not shown). As shown, each head segment (8330) further includes a proximal stapling surface (8336) that defines a plurality of staple forming pockets (8338) (e.g., collectively arranged in two concentric annular arrays) configured to deform staples (90) driven therein.

Anvil push sleeve (8316) includes a cylindrical body (8340) defining a bore (8342) slidably received about shank (8320), such that push sleeve (8316) is longitudinally translatable relative to core (8314) between a proximal state (FIG. 145A) in which a distal cam surface of push sleeve (8316) is operatively disengaged from head segments (8330) to permit head segments (8330) to remain in their radially unextended states, and a distal state (FIG. 145B) in which the distal cam surface of push sleeve (8316) operatively engages head segments (8330) to push head segments (8330) toward their radially extended states. In this regard, disc (8318) includes a hub (8362) defining a bore (8364) rotatably received about shank (8320, such that disc (8318) is rotatable relative to core (8314) between a first state (FIG. 146A) in which arms (8366) extending radially outwardly from hub (8362) are disengaged from head segments (8330) to permit head segments (8330) to remain in their radially unextended states, and a second state (FIG. 146B) in which arms (8366) engage radially inner surfaces of head segments (8330) to push head segments (8330) toward their radially extended states. It will be appreciated that engagement between the distal cam surface of push sleeve (8316) and a proximal cam surface of disc (8318) may transition disc (8318) between the first and second states.

During operation, push sleeve (8316) may initially be in the proximal state and disc (8318) may initially be in the first state to permit head segments (8330) to remain in their radially unextended states, as shown in FIGS. 145A and 146A. Push sleeve (8316) may subsequently be pushed to the distal state to transition disc (8318) to the second state. For example, the operator may retract trocar (330) and anvil (8310) proximally to compress the tissue of tubular anatomical structures (20, 40) between anvil (8310) and stapling head assembly (300), as indicated by arrow (A7) in FIG. 145A, which may cause a proximal end of push sleeve (8316) to engage radially inner ledge (8150) of stapling head assembly (300) and thereby push sleeve (8316) to the distal state to transition disc (8318) to the second state, as indicated by arrow (A8) in FIG. 145B and arrow (A9) in FIG. 146B, and thus move head segments (8330) to their radially extended states for driving staples (90) into staple forming pockets (8338), as indicated by arrows (A10, A11) in FIG. 145B and arrows (A12, A13, A14, A15) in FIG. 146B. Push sleeve (8316) may then be returned to the proximal state to permit disc (8318) to return to the first state. For example, the operator may extend trocar (330) and anvil (8310) distally to disengage push sleeve (8316) from head segments (8330) and thereby allow head segments (8330) to be returned to their radially unextended states for assisting with retraction of anvil (8310) proximally through anastomosis (70), as shown in FIGS. 145A and 146A.

O. Fifth Exemplary Radially Contractable Anvil

FIG. 147 depicts another exemplary anvil (8410) for use with instrument (10) described above. Anvil (8410) is similar to anvil (8310) described above except as otherwise described below. In this regard, anvil (8410) comprises a segmented anvil head (not shown), an anvil core (8414), and a rotatable member in the form of a slotted disc (8418).

In the example shown, anvil core (8414) includes a shank (8420) defining a bore (8421) and a distal plate (8422) extending radially outwardly from shank (8420) and having a plurality of (e.g., six) bores (8424) extending radially therethrough for slidably receiving respective anvil head segment actuating rods (8430) such that each rod (8430) may be radially translatable relative to core (8414) between a radially unextended state (not shown) and the illustrated radially extended state. While not shown, a corresponding anvil head segment may be fixedly coupled to a radially outer end of each rod (8430), and may include a proximal stapling surface that defines a plurality of staple forming pockets configured to deform staples (90) driven therein.

As shown, disc (8418) includes a hub (8462) defining a bore (8464) rotatably received about shank (8420), such that disc (8418) is rotatable relative to core (8414) between a first state (not shown) in which curved slots (8466) extending along disc (8418) guide respective pins (8468) extending distally from corresponding rods (8430) radially inwardly to pull rods (8430) toward their radially unextended states, and the illustrated second state in which curved slots (8466) guide the respective pins (8468) radially outwardly to push rods (8430) toward their radially extended states.

During operation, disc (8418) may initially be in the first state to pull rods (8430) and the accompanying anvil head segments to their radially unextended states. Disc (8418) may subsequently be transitioned to the second state, as indicated by arrow (A16) in FIG. 147, to thereby move rods (8430) and the accompanying anvil head segments to their radially extended states for driving staples (90) into the staple forming pockets, as indicated by arrows (A17, A18, A19, A20, A21, A22) in FIG. 147. Disc (8418) may then be returned to the first state to return pull rods (8430) and the accompanying anvil head segments to their radially unextended states for assisting with retraction of anvil (8410) proximally through anastomosis (70).

P. Sixth Exemplary Radially Contractable Anvil

FIGS. 148A-148D depict another exemplary anvil (8510) for use with instrument (10) described above. Anvil (8510) is similar to anvil (8010) described above except as otherwise described below. In this regard, anvil (8510) comprises a segmented anvil head (8512) and an anvil core (8514).

In the example shown, anvil core (8514) includes a shank (8520) defining a bore (8521), and further includes a distal nose (8522) extending radially outwardly from shank (8520). Head (8512) includes a plurality of head segments (8530) movable relative to each other, with each head segment (8530) being flexibly coupled to nose (8522) such that each head segment (8530) may be movable relative to core (8514) between a radially unextended state (FIGS. 148C-148D) and a radially extended state (FIGS. 148A-148B). In the present version, each head segment (8530) is resiliently biased toward the radially unextended state via pre-tensioning of each head segment (8530). In other versions, each head segment (8530) may be resiliently biased toward the radially unextended state by a corresponding energy storage device, such as a spring (not shown). In any event, a breakable washer or other suitable breakaway component (not shown) may secure head segments (8530) in their radially extended states. As shown, each head segment (8530) further includes a proximal stapling surface (8536) that defines a plurality of staple forming pockets (not shown) configured to deform staples (90) driven therein. In this regard, the bending stiffness of head (8512) may be selected such that the force from tissue or staples (90) may not cause deflection of head (8512) or any head segment (8530) thereof when head segments (8530) are in the radially extended states. In addition, or alternatively, a support cap (not shown) may surround head segments (8530) to provide a hard stop to assist in preventing such deflection. In some versions, the breakaway washer or other suitable breakaway component described above may occupy any slots or other spaces between circumferentially-adjacent head segments (8530) when head segments (8530) are in the radially extended states to provide further rigidity to head (8512).

During operation, the breakaway washer or other suitable breakaway component may initially be intact to secure head segments (8530) in their radially extended states while anvil (8510) is positioned within tubular anatomical structure (20), secured to trocar (330), and retracted with trocar (330) proximally to compress the tissue of tubular anatomical structures (20, 40) between anvil (8510) and stapling head assembly (300) for driving staples (90) into the staple forming pockets, as shown in FIGS. 148A-148B. The breakaway washer or other suitable breakaway component may subsequently be broken (e.g., by knife member (340)), thereby permitting head segments (8530) to resiliently assume their radially unextended (and unstressed) states, as indicated by arrows (A23, A24) in FIG. 148C. In the example shown, anvil (8510) is also driven distally by the operator away from stapling head assembly (300) to facilitate release of the tissue between anvil (8510) and stapling head assembly (300). The operator then retracts anvil (8510), trocar (330), and stapling head assembly (300) proximally, with anvil (8510) still secured to trocar (330), such that anvil (8510) is retracted proximally through anastomosis (70) with head segments (8530) remaining in their radially unextended states, as indicated by arrow (A25) in FIG. 148D.

Q. First Exemplary Segmented Anvil Head with S-Shaped Slots

FIG. 149 depicts an exemplary segmented anvil head (8610) for use with instrument (10) described above. Anvil head (8610) is similar to anvil head (8012) described above except as otherwise described below. In this regard, anvil head (8610) includes a plurality of head segments (8630) movable relative to each other and each having a proximal stapling surface (8636) that defines a plurality of staple forming pockets (8638a, 8638b) (e.g., collectively arranged in two concentric annular arrays) configured to deform staples (90) driven therein.

In the example shown, each head segment (8630) is separated from the circumferentially-adjacent head segments (8630) by corresponding S-shaped slots (8639). As shown, each S-shaped slot may be isolated relative to staple forming pockets (8638a, 8638b) and may thereby avoid interfering with the formation of staples (90) driven therein. In the present version, four S-shaped slots (8639) are circumferentially spaced apart from each other at uniform intervals to thereby define four substantially identical head segments (8630). It will be appreciated that any suitable number of S-shaped slots (8639) may be provided in any suitable arrangement to define a corresponding number of head segments (8630). For example, any number of head segments (8630) greater than two may be provided.

R. Second Exemplary Segmented Anvil Head with S-Shaped Slots

FIG. 150 depicts an exemplary segmented anvil head (8710) for use with instrument (10) described above. Anvil head (8710) is similar to anvil head (8610) described above except as otherwise described below. In this regard, anvil head (8710) includes a plurality of head segments (8730) movable relative to each other and each having a proximal stapling surface (8736) that defines a plurality of staple forming pockets (8738a, 8738b) (e.g., collectively arranged in two concentric annular arrays) configured to deform staples (90) driven therein.

In the example shown, each head segment (8730) is separated from the circumferentially-adjacent head segments (8730) by corresponding S-shaped slots (8739). As shown, each S-shaped slot may be isolated relative to staple forming pockets (8738a, 8738b) and may thereby avoid interfering with the formation of staples (90) driven therein. In the present version, fourteen S-shaped slots (8739) are circumferentially spaced apart from each other at uniform intervals to thereby define fourteen substantially identical head segments (8730).

IX. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of creating an anastomosis using a stapling assembly including (i) a body extending distally along a longitudinal axis and (ii) a deck member defining a deck surface, wherein the deck surface includes a first array of staple openings comprising a herringbone pattern, wherein each staple opening of the first array of staple openings has a same size, the method comprising: (a) positioning an anvil within a first lumen of a patient; (b) positioning the stapling assembly within a second lumen of the patient; (c) releasably coupling the anvil with the stapling assembly; (d) compressing tissue of the first and second lumens between the anvil and the deck member; and (e) actuating a plurality of staple drivers to drive a first plurality of staples distally and parallel to the longitudinal axis from the first array of staple openings into the tissue to define the anastomosis.

Example 2

The method of Example 1, wherein the deck member is defined by an outer arched perimeter and an inner arched perimeter fixed to the body, wherein at least one non-tangential staple opening in the first array of staple openings extends along a longitudinal axis in a non-tangential relationship with a closest tangent line of the inner arched perimeter or the outer arched perimeter.

Example 3

The method of any one or more of Examples 1 through 2, wherein the deck surface has a deck surface centerline that surrounds the longitudinal axis, wherein the deck surface further includes (A) a first deck surface portion extending along a first angular range of the deck surface about the longitudinal axis, wherein the first array of staple openings is disposed on the first deck surface portion, (B) a second deck surface portion extending along a second angular range of the deck surface about the longitudinal axis, and (C) a second array of staple openings disposed on the second deck surface portion, wherein each staple opening of the second array of staple openings is oriented tangentially or parallel relative to the deck surface centerline, wherein the act of actuating the plurality of staple drivers includes driving a second plurality of staples distally and parallel to the longitudinal axis from the second array of staple openings into the tissue to further define the anastomosis.

Example 4

The method of Example 3, wherein each staple opening of the second array of staple openings has the same size as each staple opening of the first array of staple openings.

Example 5

The method of any one or more of Examples 1 through 4, wherein each staple of the first plurality of staples comprises a first leg, a second leg, and an angled crown such that each staple defines a "V" shape extending from the first leg to the second leg when viewed from a top or a bottom.

Example 6

The method of Example 5, wherein the crown of each staple of the first plurality of staples comprises a weakened portion to promote bending for expandability when the respective staple is exposed to tension due to tissue forces.

Example 7

The method of any one or more of Examples 1 through 6, wherein the deck surface further includes a second plurality of staple openings, wherein the second plurality of staple openings includes a first pair of staple openings extending along a first axis and a second pair of staple openings extending along a second axis, wherein the first and second axes intersect each other to collectively define at least one cross shape.

Example 8

The method of Example 7, wherein the deck member is annular, wherein the second plurality of staple openings are circumferentially arranged along a reference circle.

Example 9

The method of any one or more of Examples 1 through 8, wherein the deck member includes an alignment feature, the method further comprising aligning the alignment feature with a staple line transecting the second lumen prior to the act of releasably coupling the anvil with the stapling assembly, wherein the act of actuating the plurality of staple drivers is performed while the staple line transecting the second lumen is located within the alignment feature.

Example 10

The method of Example 9, wherein the alignment feature comprises a groove in the deck surface.

Example 11

The method of any one or more of Examples 1 through 10, wherein the deck member includes an exterior perimeter having a first shape and an interior perimeter enclosed by the exterior perimeter and having a second shape different than the first shape.

Example 12

The method of Example 11, wherein the staple assembly further includes a knife member, wherein a distal end of the knife member includes a cutting edge defining an edge plane that intersects the longitudinal axis, wherein the cutting edge has a non-circular shape in the edge plane.

Example 13

The method of any one or more of Examples 1 through 12, wherein each staple of the first plurality of staples is coupled to an adjacent staple of the first plurality of staples.

Example 14

The method of Example 13, wherein each staple of the first plurality of staples is pivotably coupled to the adjacent staple of the first plurality of staples.

Example 15

The method of any one or more of Examples 1 through 14, further comprising retracting the anvil proximally through the anastomosis, wherein the act of retracting includes expanding the first plurality of staples radially outwardly relative to the longitudinal axis.

Example 16

A method of creating an anastomosis using a stapling assembly including (i) a housing extending distally along a central axis, (ii) a deck member having a plurality of staple openings, wherein the deck member includes an exterior perimeter having a first shape and an interior perimeter enclosed by the exterior perimeter and having a second shape different than the first shape, and (iii) a knife member at least partially disposed within the housing, wherein a distal end of the knife member includes a cutting edge defining an edge plane that intersects the central axis, wherein the cutting edge has a non-circular shape in the edge plane, the method comprising: (a) positioning an anvil within a first lumen of a patient; (b) positioning the stapling assembly within a second lumen of the patient; (c) releasably coupling the anvil with the stapling assembly; (d) compressing tissue of the first and second lumens between the anvil and the deck member; (e) driving the knife member distally to sever the tissue via the cutting edge; and (f) actuating a plurality of staple drivers to drive a plurality of staples distally from the plurality of staple openings into the tissue to define the anastomosis.

Example 17

The method of Example 16, wherein each staple of the plurality of staples comprises a first leg, a second leg, and an angled crown such that each staple defines a "V" shape extending from the first leg to the second leg when viewed from a top or a bottom.

Example 18

The method of any one or more of Examples 16 through 17, wherein the plurality of staple openings includes a first pair of staple openings extending along a first axis and a second pair of staple openings extending along a second axis, wherein the first and second axes intersect each other to collectively define at least one cross shape.

Example 19

A method of creating an anastomosis, the method comprising: (a) positioning a distal component of a surgical fastening instrument within a first lumen of a patient; (b) positioning a fastening assembly of the surgical fastening instrument within a second lumen of the patient, the fastening assembly including a deck member; (c) releasably coupling the distal component with the fastening assembly; (d) compressing tissue of the first and second lumens between the distal component and the deck member; and (e) actuating at least one fastener driver to drive a fastening ring element distally from the deck member into the tissue to define the anastomosis, wherein the fastening ring element includes a plurality of fastening elements coupled to each other in a closed loop.

Example 20

The method of Example 19, wherein the plurality of fastening elements includes at least one of a plurality of staples coupled to each other in the closed loop or a plurality of barbs coupled to each other in the closed loop.

X. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Additionally, any one or more of the teachings herein may be combined with any one or more of the teachings of U.S. patent application Ser. No. 17/401,428, entitled "Staple Forming Features for Circular Surgical Stapler," filed on Aug. 13, 2021, issued as U.S. Pat. No. 11,998,209 on Jun. 4, 2024; U.S. patent application Ser. No. 17/401,430, entitled "Non-Circular End Effector Features for Circular Surgical Stapler," filed on Aug. 13, 2021, issued as U.S. Pat. No. 11,944,310 on Apr. 2, 2024; U.S. patent application Ser. No. 17/401,439, entitled "Circular Surgical Stapler End Effector Having Staple Line Alignment Feature," filed on Aug. 13, 2021, issued as U.S. Pat. No. 12,201,301 on Jan. 21, 2025; U.S. patent application Ser. No. 17/401,444, entitled "Circular Surgical Stapler for Forming Pattern of Non-Tangential Staples," filed on Aug. 13, 2021, issued as U.S. Pat. No. 11,653,926 on May 23, 2023; U.S. patent application Ser. No. 17/401,451, entitled "Circular Surgical Stapler Having Staples with Expandable Crowns," filed on Aug. 13, 2021, issued as U.S. Pat. No. 11,911,039 on Feb. 27, 2024; and U.S. patent application Ser. No. 17/401,460, entitled "Circular Surgical Stapler for Forming Cross-Pattern of Staples," filed on Aug. 13, 2021, issued as U.S. Pat. No. 11,666,339 on Jun. 6, 2023. The disclosure of each of these US patent documents is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of creating an anastomosis using a stapling assembly including (i) a body extending distally along a longitudinal axis and (ii) a deck defining a deck surface, wherein the deck surface surrounds the longitudinal axis and includes a first array of staple openings comprising a herringbone pattern, wherein each staple opening of the first array of staple openings has a same size, the method comprising:
   (a) positioning an anvil within a first lumen of a patient;
   (b) positioning the stapling assembly within a second lumen of the patient;
   (c) releasably coupling the anvil with the stapling assembly;
   (d) compressing tissue of the first and second lumens between the anvil and the deck; and
   (e) actuating a plurality of staple drivers to drive a first plurality of staples distally away from the body and parallel to the longitudinal axis from the first array of staple openings into the tissue to define the anastomosis.

2. The method of claim 1, wherein the deck is defined by an outer arched perimeter and an inner arched perimeter fixed to the body, wherein at least one non-tangential staple opening in the first array of staple openings extends along a longitudinal axis in a non-tangential relationship with a closest tangent line of the inner arched perimeter or the outer arched perimeter.

3. The method of claim 1, wherein the deck surface has a deck surface centerline that surrounds the longitudinal axis, wherein the deck surface further includes (A) a first deck surface portion extending along a first angular range of the deck surface about the longitudinal axis, wherein the first array of staple openings is disposed on the first deck surface portion, (B) a second deck surface portion extending along a second angular range of the deck surface about the longitudinal axis, and (C) a second array of staple openings disposed on the second deck surface portion, wherein each staple opening of the second array of staple openings is oriented tangentially or parallel relative to the deck surface centerline, wherein the act of actuating the plurality of staple drivers includes driving a second plurality of staples distally and parallel to the longitudinal axis from the second array of staple openings into the tissue to further define the anastomosis.

4. The method of claim 3, wherein each staple opening of the second array of staple openings has the same size as each staple opening of the first array of staple openings.

5. The method of claim 1, wherein each staple of the first plurality of staples comprises a first leg, a second leg, and an angled crown such that each staple defines a "V" shape extending from the first leg to the second leg when viewed from a top or a bottom.

6. The method of claim 5, wherein the crown of each staple of the first plurality of staples comprises a weakened portion to promote bending for expandability when the respective staple is exposed to tension due to tissue forces.

7. The method of claim 1, wherein the deck surface further includes a second plurality of staple openings, wherein the second plurality of staple openings includes a first pair of staple openings extending along a first axis and a second pair of staple openings extending along a second axis, wherein the first and second axes intersect each other to collectively define at least one cross shape.

8. The method of claim 7, wherein the deck is annular, wherein the second plurality of staple openings are circumferentially arranged along a reference circle.

9. The method of claim 1, wherein the deck includes an alignment feature, the method further comprising aligning the alignment feature with a staple line transecting the second lumen prior to the act of releasably coupling the anvil with the stapling assembly, wherein the act of actuating the plurality of staple drivers is performed while the staple line transecting the second lumen is located within the alignment feature.

10. The method of claim 9, wherein the alignment feature comprises a groove in the deck surface.

11. The method of claim 1, wherein the deck includes an exterior perimeter having a first shape and an interior perimeter enclosed by the exterior perimeter and having a second shape different than the first shape.

12. The method of claim 11, wherein the staple assembly further includes a knife, wherein a distal end of the knife includes a cutting edge defining an edge plane that intersects the longitudinal axis, wherein the cutting edge has a non-circular shape in the edge plane.

13. The method of claim 1, further comprising retracting the anvil proximally through the anastomosis, wherein the act of retracting includes expanding the first plurality of staples radially outwardly relative to the longitudinal axis.

14. A method of creating an anastomosis using a stapling assembly including (i) a housing extending distally along a central axis, (ii) a deck having a plurality of staple openings, wherein the deck includes an exterior perimeter having a first shape and an interior perimeter enclosed by the exterior perimeter and having a second shape different than the first shape, wherein the interior perimeter surrounds the central axis and (iii) a knife at least partially disposed within the housing, wherein a distal end of the knife includes a cutting edge defining an edge plane that intersects the central axis, wherein the cutting edge has a non-circular shape in the edge plane, the method comprising:
   (a) positioning an anvil within a first lumen of a patient;
   (b) positioning the stapling assembly within a second lumen of the patient;
   (c) releasably coupling the anvil with the stapling assembly;
   (d) compressing tissue of the first and second lumens between the anvil and the deck;
   (e) driving the knife distally to sever the tissue via the cutting edge; and
   (f) actuating a plurality of staple drivers to drive a plurality of staples distally from the plurality of staple openings away from the housing and into the tissue to define the anastomosis.

15. The method of claim 14, wherein each staple of the plurality of staples comprises a first leg, a second leg, and an angled crown such that each staple defines a "V" shape extending from the first leg to the second leg when viewed from a top or a bottom.

16. The method of claim 14, wherein the plurality of staple openings includes a first pair of staple openings extending along a first axis and a second pair of staple openings extending along a second axis, wherein the first and second axes intersect each other to collectively define at least one cross shape.

17. The method of claim 1, wherein the act of releasably coupling the anvil with the stapling assembly is performed after the acts of positioning the anvil within the first lumen of the patient and positioning the stapling assembly within the second lumen of the patient.

18. A method of creating an anastomosis using a stapling assembly including (i) a housing extending distally along a central axis, (ii) a deck having a plurality of staple openings, wherein the deck includes an exterior perimeter having a first shape and an interior perimeter enclosed by the exterior perimeter and having a second shape different than the first shape, and (iii) a knife at least partially disposed within the housing, wherein a distal end of the knife includes a cutting edge defining an edge plane that intersects the central axis, wherein the cutting edge has a non-circular shape in the edge plane, the method comprising:
(a) positioning an anvil within a first lumen of a patient;
(b) positioning the stapling assembly within a second lumen of the patient;
(c) releasably coupling the anvil with the stapling assembly;
(d) compressing tissue of the first and second lumens between the anvil and the deck;
(e) driving the knife distally to sever the tissue via the cutting edge; and
(f) actuating a plurality of staple drivers to drive a plurality of staples distally from the plurality of staple openings into the tissue to define the anastomosis,
wherein the first shape includes a first elongate shape, wherein the second shape includes a second elongate shape, wherein the first elongate shape includes a pair of arcuate end portion and defines a longitudinal axis that extends through the arcuate end portions and intersects the central axis.

* * * * *